US009709567B2

(12) United States Patent
Jayaraman et al.

(10) Patent No.: US 9,709,567 B2
(45) Date of Patent: Jul. 18, 2017

(54) COMPOSITIONS AND METHODS FOR DIAGNOSING AND/OR TREATING INFLUENZA INFECTION

(71) Applicant: Massachusetts Institute of Technology, Cambridge, MA (US)

(72) Inventors: Akila Jayaraman, Waltham, MA (US); Karthik Viswanathan, Waltham, MA (US); Rahul Raman, Waltham, MA (US); Zachary H. Shriver, Cambridge, MA (US); Ram Sasisekharan, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/009,270

(22) Filed: Jan. 28, 2016

(65) Prior Publication Data

US 2016/0266117 A1    Sep. 15, 2016

Related U.S. Application Data

(62) Division of application No. 12/829,931, filed on Jul. 2, 2010, now Pat. No. 9,278,998.

(60) Provisional application No. 61/222,889, filed on Jul. 2, 2009.

(51) Int. Cl.
*G01N 33/569* (2006.01)
*C07K 14/005* (2006.01)

(52) U.S. Cl.
CPC ..... *G01N 33/56983* (2013.01); *C07K 14/005* (2013.01); *C12N 2760/16122* (2013.01); *G01N 2333/11* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 4,166,452 A | 9/1979 | Generales, Jr. | |
| 4,692,411 A | 9/1987 | Ghose | |
| 4,816,567 A | 3/1989 | Cabilly et al. | |
| 5,500,161 A | 3/1996 | Andrianov et al. | |
| 5,698,390 A | 12/1997 | Houghton et al. | |
| 9,278,998 B2 | 3/2016 | Jayaraman et al. | |
| 2005/0009008 A1 | 1/2005 | Robinson et al. | |
| 2008/0032921 A1 | 2/2008 | Alexander et al. | |
| 2008/0241918 A1 | 10/2008 | Sasisekharan et al. | |
| 2009/0081193 A1 | 3/2009 | Sasisekharan et al. | |
| 2009/0124567 A1 | 5/2009 | Chen et al. | |
| 2009/0269342 A1 | 10/2009 | Sasisekharan et al. | |
| 2010/0004195 A1 | 1/2010 | Sasisekharan et al. | |
| 2010/0125043 A1 | 5/2010 | Sasisekharan et al. | |
| 2011/0033490 A1 | 2/2011 | Jayaraman et al. | |

FOREIGN PATENT DOCUMENTS

| | | |
|---|---|---|
| WO | WO-91/11465 A1 | 8/1991 |
| WO | WO-02/00885 A2 | 1/2002 |
| WO | WO-2005/020889 A2 | 3/2005 |
| WO | WO-2006/108226 A1 | 10/2006 |
| WO | WO-2007/100584 A2 | 9/2007 |
| WO | WO-2007/130327 A2 | 11/2007 |
| WO | WO-2007/130330 A2 | 11/2007 |
| WO | WO-2008/005777 A2 | 1/2008 |
| WO | WO-2008/040060 A1 | 4/2008 |
| WO | WO-2008/054535 A2 | 5/2008 |
| WO | WO-2008/061243 A2 | 5/2008 |
| WO | WO-2008/073161 A2 | 6/2008 |
| WO | WO-2008/094197 A2 | 8/2008 |
| WO | WO-2008/094200 A2 | 8/2008 |
| WO | WO-2008/148104 A1 | 12/2008 |
| WO | WO-2009/009876 A1 | 1/2009 |
| WO | WO-2009/012489 A1 | 1/2009 |
| WO | WO-2009/089119 A2 | 7/2009 |
| WO | WO-2010/006452 A1 | 1/2010 |

OTHER PUBLICATIONS

Allison, The mode of action of immunological adjuvants, Dev. Biol. Stand., 92:3-11, (1998).
Altschul, et al., Basic local alignment search tool, J. Mol. Biol., 215(3): 403-410 (1990).
Altschul, et al., Gapped BLAST and PSI-BLAST: a new generation of protein database search programs, Nucleic Acids Res. 25:3389-3402, (1997).
Author Not Known, New influenza A (H1N1) virus: global epidemiological situation, Jun. 2009, World Health Organization, Wkly. Epidemiol. Rec., 84(25):249-57 (2009).
Author Not Known, Sheet labeled "Align H1 with wt H3 sequence," 1 page, (printed Apr. 11, 2013).
Author Not Known, Sheet labeled "Wang aligned with wt H3 sequence," 1 page (printed Apr. 11, 2013).
Baylor et al., Aluminum salts in vaccines—US perspective, Vaccine, 20:S18 (2002).
Cao et al., Enhancement of the protective effect of inactivated influenza virus vaccine by cytokines, Vaccine, 10:238 (1992).

(Continued)

*Primary Examiner* — Shanon A Foley
*Assistant Examiner* — Myron Hill
(74) *Attorney, Agent, or Firm* — Choate, Hall & Stewart LLP; Brenda Herschbach Jarrell; Cassandra Gianna Luca

(57) ABSTRACT

The present invention provides HA polypeptides (e.g., H1 HA polypeptides) that bind to umbrella-topology glycans, and reagents and methods relating thereto. The present invention provides binding agents that bind to HA polypeptides (e.g., H1 HA polypeptides), and reagents and methods relating thereto. The present invention provides interfering agents that inhibit the binding of HA polypeptides (e.g., H1 HA polypeptides) to HA receptors, and reagents and methods relating thereto. The present invention provides compositions and methods for treating, preventing, and/or diagnosing influenza infection utilizing HA polypeptides, HA polypeptide binding agents, HA polypeptide interfering agents, and/or vaccine compositions comprising any of the foregoing.

5 Claims, 46 Drawing Sheets

(56) References Cited

OTHER PUBLICATIONS

Chandrasekaran et al., Glycan topology determines human adaptation of avian H5N1 virus hemagglutinin, Nature Biotechnology 26(1): 107-113 (2008).
Childs, R.A., et al., Receptor-binding specificity of pandemic influenza A (H1N1) 2009 virus determined by carbohydrate microarray, Nature Biotechnology, 27(9):797-799 (2009).
Connor et al., "Receptor Specificity in Human, Avian, and Equine H2 and H3 Influenza Virus Isolates," Virology, 205:17, 1994.
Cooper et al., "Safety and immunogenicity of CPG 7909 injection as an adjuvant to Fluarix influenza vaccine," Vaccine, 22:3136, 2004.
Dunham et al., Different evolutionary trajectories of European avian-like and classical swine H1N1 Influenza A Viruses, Journal of Virology, 83(11): 5485-5494 (2009).
Eisen et al., "Binding of the influenza A Virus to Cell-Surface Receptors: Structures of Five Hemagglutinin-Sialyloligosaccharide Complexes Determined by X-Ray Crystallography" Virology, 232:19, 1997.
Extended European Search Report for PCT/US2010/040978, 7 pages (Jan. 18, 2013).
Fishwild et al., "High-avidity human IgG kappa monoclonal antibodies from a novel stain of minilocus transgenic mice", Nat. Biotechnol., 14(7):845-51, 1996.
Gamblin et al., "The Structure and Receptor Binding Properties of the 1918 Influenza Hemagglutinin" Science, 303:1838, 2004.
Garten, et al., Antigenic and genetic characteristics of swine-origin 2009 A(H1N1) influenza viruses circulating in human, Science 325: 197-201 (2009).
GenBank Accession No. AAB52910.0, Influenza A virus (A/mallard/Alberta/35/1976(H1Ni)) (Mar. 21, 2006).
Ghochikyan, A. et al., Prototype Alzheimer's disease epitope vaccine induced strong Th2-type anti-Abeta antibody response with Alum to Quil A adjuvant switch, Vaccine, 24(13):2275-82 (2006).
Ha et al., "X-ray structure of the hemagglutinin of a potential H3 avian progenitor of the 1968 Hong Kong pandemic influenza virus," Virology, 309:209, 2003.
Ha et al., X-ray structures of H5 avian and H9 swine influenza virus hemagglutinins bound to avian and human receptor analogs, Proc. Natl Acad Sci USA, 98:11181 (2001).
Hoogenboom et al., Construction and Expression of Antibody-tumor Necrosis Factor Fusion Proteins, Mol. Immunol., 28(9):1027-37 (1991).
International Search Report for PCT/US2010/040978, 4 pages (Dec. 22, 2010).
Jayasena, S.D., "Aptamers: An Emerging Class of Molecules That Rival Antibodies in Diagnostics," Clin. Chem., 45:1628-1650, 1999.
Karasin, A.I. et al., Identification of human H1N2 and human-swine reassortant H1N2 and H1N1 influenza A viruses among pigs in Ontario, Canada (2003 to 2005), J. Clin. Microbiol., 44(3):1123-6 (2006).
Katz et al., "A nonionic block co-polymer adjuvant (CRL1005) enhances the immunogenicity and protective efficacy of inactivated influenza vaccine in young and aged mice," Vaccine, 18:2177, 2000.
Kreuter et al., "Long-Term Studies of Microencapsulated and Adsorbed Influenza Vaccine Nanoparticles," J. Pharm. Sci., 70:367, 1981.
Kumari, K. et al., Receptor binding specificity of recent human H3N2 influenza viruses, Virol. J., 4:42 (2007).
Lonberg and Huszar, "Human antibodies from transgenic mice", Int. Rev. Immunol., 13(1): 65-93, 1995.
Lonberg et al., "Antigen-specific human antibodies from mice comprising four distinct genetic modifications", Nature 368(6474):856-9, 1994.
Losman et al., "Baboon Anti-Idiotype Antibodies Mimic A Carcinoembryonic Antigen Epitope," Int. J. Cancer, 46:310, 1990.
Maines, T.R., et al., Transmission and Pathogenesis of Swine-Origin 2009 A(H1N1) Influenza Viruses in Ferrets and Mice, Science, 325(5939):484-487 (2009).
Marks et al., "By-passing immunization: building high affinity human antibodies by chain shuffling", Biotechnology (NY), 10(7):779-83, 1992.
Marks, J.D. et al., By-passing immunization. Human antibodies from V-gene libraries displayed on phage, J. Mol. Biol., 222(3):581-97 (1991).
Mbwuike et al., "Enhancement of the protective efficacy of inactivated influenza A virus vaccine in aged mice by IL-2 liposomes," Vaccine, 8:347, 1990.
Milstein and Cuello, "Hybrid hybridomas and their use in immunohistochemistry," Nature 305(5934):537-40, 1983.
Mostow et al., "Application of the Single Radial Diffusion Test for Assay of Antibody to Influenza Type A Viruses," J. Clin. Microbiol., 2:531, 1975.
Obenauer, et al., Large-scale sequence analysis of avian influenza isolates, Science 311: 1576-1580 (2006).
Payne et al., "Poly[di(carboxylataphenoxy)phosphazene] (PCPP) is a potent immunoadjuvant for an influenza vaccine," Vaccine, 16:92, 1998.
Phillips et al., Enhanced antibody response to lipsome-associated protein antigens: preferential stimulation of IgG2a/b production, Vaccine, 10(3):151-158, (1992).
Reisfeld and Sell, "Human tumour-associated antigens: targets for monoclonal antibody-mediated cancer therapy," Cancer Surv., 4(1):271-90, 1985.
Ribi, E. et al., Moduclation of Humoral and Cell-Mediated Immune Response, Immunobiology and Immunopharmacology of Bacterial Endotoxins, 407-420 (1986).
Riechmann et al., Reshaping human antibodies for therapy, Nature, 332(6162):323-7 (1988).
Rogers & Paulson, "Receptor Determinants of Human and Animal Influenza Virus Isolates: Differences in Receptor Specificity of the H3 Hemagglutinin Based on Species of Origin," Virology, 127:361, 1983.
Rogers, et al., "Single amino acid substitutions in influenza haemagglutinin change receptor binding specificity," *Nature*, 304:76, (1983).
Russell et al., "H1 and H7 influenza haemagglutinin structures extend a structural classification of haemagglutinin subtypes," *Virology*, 325:287, (2004).
Russell, et al., "Avian and human receptor binding by hemagglutinins of influenza A viruses," *Glycoconj J.*, 23:85, (2006).
Sauter et al., "Binding of Influenza Virus Hemagglutinin to Analogs of Its Cell-Surface Receptor, Sialic Acid: Analysis by Proton Nuclear Magnetic Resonance Spectroscopy and X-ray Crystallography," Biochemistry, 31:9609, 1992.
Schild et al., "Single-radial-haemolysis: a new method for the assay of antibody to influenza haemagglutinin," Bull. World Health Organ., 52:43-50 & 223-31, 1975.
Skehel & Wiley, "Receptor Binding and Membrane Fusion in Virus Entry: The Influenza Hemagglutinin," Annu Rev Biochem, 69:531, 2000.
Soundararajan et al., Extrapolating from sequence—the 2009 H1N1 'swine' influenza virus, Nature Biotechnology 27:510, (2009).
Srinivasan, A., et al., Quantitative biochemical rationale for differences in transmissibility of 1918 pandemic influenza A viruses, PNAS, 105(8):2800-2805 (2008).
Stevens et al., "Structure of the Uncleaved Human H1 Hemagglutinin from the Extinct 1918 Influenza Virus," Science, 303:1866, 2004.
Stevens, et al., "Structure and Receptor Specificity of the Hemagglutinin from an H5N1 Influenza Virus" *Science* 312:404, (2006).
Stevens, J.M., et. al., Glycan microarray technologies: tools to survey host specificity of influenza viruses, Nature Reviews Microbiology, 4:857-864 (2006).
Tuerk, C., and Gold, L., "Systematic Evolution of Ligands by Exponential Enrichment: RNA Ligands to Bacteriophage T4 DNA Polymerase," Science 249:505-510, 1990.
Tumpey et al., "Characterization of the Reconstructed 1918 Spanish Influenza Pandemic Virus," Science, 310:77, 2005.
Tumpey, et al., A Two-amino acid change in the hemagglutinin of the 1918 Influenza virus abolishes transmission, Science, 315:655-659 (2007).

(56) References Cited

OTHER PUBLICATIONS

Unkeless et al., Structure and function of human and murine receptors for IgG, Ann. Rev. Immunol., 6:251-281 (1988).

Van Hoeven, N. et al., Human HA and polymerase subunit PB2 proteins confer transmission of an avian influenza virus through the air, Proc. Natl. Acad. Sci. U S A., 106(9):3366-71 (2009).

Verhoeyen et al., Reshaping Human Antibodies: Grafting an Antilysozyme Activity, Science, 239(4847):1534-6 (1988).

Wang, S. et al., Hemagglutinin (HA) proteins from H1 and H3 serotypes of influenza A viruses require different antigen designs for the induction of optimal protective antibody responses as studied by codon-optimized HA DNA vaccines, J. Virol., 80(23):11628-37 (2006).

Written Opinion for PCT/US2010/040978, 7 pages (Dec. 22, 2010).

Xu et al., Distinct glycan topology for avian and human sialopentasaccharide receptor analogues upon binding different hemagglutinins: a molecular dynamics perspective, J. Mol. Bioi., 387:465-491 (2009).

Yang, H. et al., Structure and Receptor binding properties of a pandemic H1N1 virus hemagglutinin, Version 2, PLoS. Curr. (2010).

FIG. 1A

```
H1_Av   AYVSVGSSKYNRRFAPEIAARPEVRGQAGRMNYYWTLLDQGDTITFEACGNLIAPWYAFALNKGSD--------SGIITS-DAPVH-NCDIRCQTPHGALNSSLPFQNVHPLT
H1_Hu1  AYVSVGSSKYNRRFTPEIAARPKVRDQAGRMNYYWTLLEPGDTITFEACGNLIAPWYAFALNRGSG--------SGIITS-DAPVH-DCNTKCQTPHGAINSSLPFQNIHPVT
H1_Hu2  AYVSVTSSHYSRRFTPEIAKRPKVRDQEGRINYYWTLLECGTIIFEANGNLIAPWFALSRGFG---------SGIITS-NAPMD-ECDAKCQTPQGAINSSLPFQNVHPVT
H2_Av   TVTSVGTSTLNKRSTPEIATRPKVNGQGGRMEFSWTLLETWDVINFESTGNLIAPEYGFKISKRGS-------SGIMKT-EKTLE-NCETKCQTPLGAINTTLPFHNIHPLT
H2_Hu   TVYSVGTISTLNKRSTPDIATRPKYNGLGSRMEFSWTLLDWWSTINFESTGNLIAPEYGFKISKRGS-------SGIMKT-ECTLE-NCETKCQTPLGAINTTLPFHNVHPLT
H3_Av   GRVTVSTRRSQQTIPNIGSRPWRGQPGRISIYWTIVKPGBVIVINSNGNLIAPRGYFKMRTG---------KSSIMRS-DAPID-TCISECITPNGSIPNDKPFQNVNKHT
H3_Hu1  GRVTVSTRRSQQTIPNIGSRPWVRGLSSRISIYWTIVKPGDVLVINSNGNLIAPRGYFKMRTG---------KSSIMRS-DAPID-TCISECITPNGSIPNDKPFQNVNKIT
H3_Hu2  GRITVSTKRSQQTVIPNIGYRPVRDISSRISIYWTIVKPGDILLINSGNLIAPRGYFKIRSG---------KSSIMRS-DAPIG-KCNSECITPNGSIPNDKPFQNVRIT
H4_Av   GRVTVSTKTSQTSVPNIGSRPWVRGQSGRISFYWTIVDPGDIIVENTFGNLIAPRGHYKLNSQK--------KSTILNT-AVPIG-SCVSKCHTDRGSITTKPFQNISRIS
H5_Av1  TYISVGTSTLNQRLVPRIATRSKVNGQSGRMEFFWTILKPNDAINFESNGNFIAPFYAYKIVKKGD-------STIMKS-ELEYG-NCNTKCQTPMGAINSSMPFHNIHPLT
H5_Av2  TYISVGTSTLNQRLVPKIATRSKVNGQNGRMEFFWTILKPNDAINFESNGNFIAPFYAYKFVSINSK------SAIMKS-ELEYG-NCNTKCQTPMGAINSSMPFHNIHPLT
H6_Av   RVYRMGTESMNFAKGPEISARPVNGQRGRIDYWSVLKPGETINVESNGNLIAPWYAYKFVSINSK-------GAVFKS-NLPIE-NCDATCQTIAGVLRTNKTFQNVSPLW
H7_Av   KLITVESSNYQQSFVPSPGAREKVDGQSGRIDFHWMLMLNPNDTITFSFNGAFIAPDRASFLR---------GKSMGIQS-GVQVDDNCEGDCYHSGGTISNLPFQNINSRA
H8_Av   TLSSVTNTINRSFQPNIGPRPLVRGQQGRMDYWGILHKRGETLKIRTNGNLIAPEGYLLKGESY--------GRIIQNEDIPIG-NCNTKCQTYAGAINSSKPFQNASRHY
H9_Av   TTTSVTTEDLNRIFKPVIGPRPLVIGPRPIVNGLQGRINYYWSVLKPGQTLRVRSNGNLIAPWGHVLSGGSH--------GRILKT-DINSG-NCVVQCQTE

| | 324 | 333 | |
|---|---|---|---|
| H1_Av | IGECPKYVKSTKLRMATGLRNVPSIQ---- | SRGLFGAIAGFIEGGWTGMIDGWYGYHHQNEQGSGYAADQKSTQNAIDGITSKVNSVIEKMNTQFTAVGKEFNLERRIENLN | |
| H1_Hu1 | IGECPKYVRSTKLRMATGLRNIPSIQ---- | SRGLFGAIAGFIEGGWTGMIDGWYGYHHQNEQGSGYAADQKSTQNAIDGITNKVNSVIEKMNTQFTAVGKEFNLERRIENLN | |
| H1_Hu2 | IGECPKYVRSAKLRMVTGLRNIPSIQ---- | SRGLFGAIAGFIEGGWTGMVDGWYGYHHQNEQGSGYAADQKSTQNAINGITNKVNSVIEKMNT

FIG. 2A

```
                     98                                                                 136                                  153
                      :                                                                  :                                    :
H1 Subtype
ADA76    SYIIETSNSENGTCYPGEFIDYEELREQLSSISSFEKFEIFPKASSWPNHETTKGVTAACSYSGASSFYRNLLWLTKKGTSY
ASI30    SYIVETSNSDNGTCYPGDFIDYEELREQLSSVSSFEKFEIFPKTSSWPNHETTRGVTAACPYAGASSFYRNLLWLVKKGNSY
APR34    SYIVETPNSENGICYPGDFIDYEELREQLSSVSSFERFEIFPKESSWPNHNTNG-VTAACSHEGKSSFYRNLLWLTEKEGSY
ASC18    SYIVETSNSENGTCYPGDFIDYEELREQLSSVSSFEKFEIFPKTSSWPNHETTKGVTAACSYAGASSFYRNLLWLTKKGSSY
AT91     SYIAETPNPENGTCYPGYFADYEELREQLSSVSSFERFEIFPKESSWPNHTVTKGVTAACSYSCHNGKSSFYRNLLWLTKKNGLY
ANY18    SYIVETSNSENGTCYPGDFIDYEELREQLSSVSSFEKFEIFPKTSSWPNHETTKGVTAACSYAGASSFYRNLLWLTKKGSSY H3 Subtype
ADU63    DLFVERSNAFS-NCYPYDIPDYASLRSIVASSGTLEFITEG----FTWTGVTQNGGSACKRGPANGFFSRLNWLTKSESAY
AAI68    DLFVERSKAFS-NCYPYDVPDYASLRSIVASSG---TLEFITEGETWTG-VTQNGGSNACKRGPGSGFFSRLNWLTKSGSTY
AM99     DLFVERSKAYS-NCYPYDVPDYASLRSIVASSGTLEFNNES----FNWTGVAONGTSSSCKRRSIKSFFSRLNWLHOLKYRY H5 Subtype
ADS97    SYIVEKDNPVNGLCYPENFNDYEELKHLLSSTNHFEKIRIIPR-SSWSNHDASSGVSSACPYNGRSSFFRNVVLIKKNNAY
Viet04   SYIVEKANPVNDLCYPGDFNDYEELKHLLSRINHFEKIQIIPK-SSWSSHEASLGVSSACPYQGKSSFFRNVVLIKKNSTY
```

```
                                        183    190                                                   222 226
H1 Subtype                                :      :                                                      :   :
ADA76   PKLSKSYTNNKGKEVLVLWGVHHPPSVSEQQSLYQNADAYVSVGSSKYNRRFAPEIAARPEVRGQAGRMNYYWTLLDQGDTI
ASI30   PKLSKSYVNNKGKEVLVLWGVHHPPTSTDQQSLYQNADAYVSVGSSKYDRRFTPEIAARPKVRSQAGRMNYYWTLLEPGDTI
APR34   PKLKNSYVNKKGKEVLVLWGIHHPPNSKEQQNLYQNENAYVSVVTSNYNRRFTPEIAERPNVRDQAGRMNYYWTLLKPGDTI
ASC18   PKLSKSYVNNKGKEVLVLWGVHHPPTGIDQQSLYQNADAYVSVGSSKYNRRFTPEIAARPKVRDQAGRMNYYWTLLEPGDTI
AT91    PNVSKSYVNNKEKEVLVLWGVHHPSNISDQRAIYHTENAYVSVVSSHYSRRFTPEIAKRPKVRDQEGRINYYWTLLEPGDTI
ANY18   PKLSKSYVNNKGKEVLVLWGVHHPPTGTDQQSLYQNADAYVSVGSSKYNRRFTPEIAARPKVRDQAGRMNYYWTLLEPGDTI H3 Subtype
ADU63   PVLNVTMPNNDNFDKLYIWGVHHPSTNQEQTNLYVQASGRVTVSTRRSQQTIIPNIGSRPWVRGQPGRISIYWTIVKPGDVL
AAI68   PVLNVTMPNNDNFDKLYIWGIHHPSTNQEQTSLYVQASGRVTVSTRRSQQTIIPNIGSRPWVRGLSSRISIYWTIVKPGDVL
AM99    PALNVTMPNNDKFDKLYIWGVHHPSTDSDQTSLYTQASGRVTVSTKRSQQTVIPNIGSRPWVRGISSRISIYWTIVKPGDIL H5 Subtype
ADS97   PTIKRSYNNTNQEDLLILWGIHHPNDAAEQTKLYQNPTTYVSVGTSTLNQRSVPEIATRPKVNGQSGRMEFFWTILKPNDAI
Viet04  PTIKRSYNNTNQEDLLYLWGIHHPNDAAEQTKLYQNPTTYISVGTSTLNQRLVPRIATRSKVNGQSGRMEFFWTILKPNDAI

| | |
|---|---|
| CA_04_09 | MKAILVVLLYTFATANADTLCIGYHANNSTDTVDTVLEKNVTVTHSVNLLEDKHNGKLCKLCKLRGVAPLHLGKCNIAGWILGNPECESLSTASSWSYI |
| CA_04_09_Mut1 | MKAILVVLLYTFATANADTLCIGYHANNSTDTVDTVLEKNVTVTHSVNLLEDKHNGKLCKLCKLRGVAPLHLGKCNIAGWILGNPECESLSTASSWSYI |
| CA_04_09_Mut2 | MKAILVVLLYTFATANADTLCIGYHANNSTDTVDTVLEKNVTVTHSVNLLEDKHNGKLCKLCKLRGVAPLHLGKCNIAGWILGNPECESLSTASSWSYI |
| SC_1_18 | MEARLIVILCAFAATNADTICIGYHANNSTDTVDTVLEKNVTVTHSVNLLEDSHNGKLCKLKGIAPLQLGKCNIAGWILGNPECDLLTASSWSYI |
| Solis_3_06 | MKVKLLVLLCTFTATYADTICIGYHANNSTDTVDTVLEKNVTVTHSVNLLEDSHNGKLCLLKGIAPLQLGNCSVAGWILGNPECELLISRESWSYI |
| Bris_59_07 | MKVKLLVLLCTFTATYADTICIGYHANNSTDTVDTVLEKNVTVTHSVNLLENSHNGKLCLLKGIAPLQLGNCSVAGWILGNPECELLISKESWSYI |

| | 136        145  153 156 |
|---|---|
| CA_04_09 | VETPSSDNGTCYPGDFIDYEELREQLSSVSSFERFEIFPKTSSWPNHDSNKGVTAACPHAGAKSFYKNLIWLVKKGNSYPKLSKSYINDKGKEVLV |
| CA_04_09_Mut1 | VETPSSDNGTCYPGDFIDYEELREQLSSVSSFERFEIFPKTSSWPNHDSNKGVTAACPHAGAKSFYKNLIWLVKKGNSYPKLSKSYINDKGKEVLV |
| CA_04_09_Mut2 | VETPSSDNGTCYPGDFIDYEELREQLSSVSSFERFEIFPKTSSWPNHDSNKGVTAACPHAGAKSFYKNLIWLVKKGNSYPKLSKSYINDKGKEVLV |
| SC_1_18 | VETSNSENGTCYPGDFIDYEELREQLSSVSSFEKFEIFPKTSSWPNHETTKGVTAACSYAGASSFYRNLLWLLLKKGSSYPKLSKSYVNNKEKVLV |
| Solis_3_06 | VEKPNPENGTCYPGHFADYEELREQLSSVSSFERFEIFPKESSWPNHTTT-GVSASCSHNGESSFYRNLIWLTGKNGLYPNLSKSYANNKEKVLV |
| Bris_59_07 | VEKPNPENGTCYPGHFADYEELREQLSSVSSFERFEIFPKESSWPNHTVT-GVSASCSHNGESSFYRNLIWLIGKNGLYPNLSKSYANNKEKVLV |

| | 183 186  190   196               219 222 227 |
|---|---|
| CA_04_09 | LWGIHHPSTSRDQQSLYQNADTYVFVGSSRYSKKFKPEIAIRPKVRDQEGRMNYYWTLVEPGDKITFEATGNLVPRYAFAMERNAGSGIIISDTP |
| CA_04_09_Mut1 | LWGIHHPSTSADQQSLYQNADTYVFVGSSRYSKKFKPEIAKRPKVRDQEEGRMNYYWTLVEPGDKITFEATGNLVPRYAFAMERNAGSGIIISDTP |
| CA_04_09_Mut2 | LWGIHHPSTSPTSADQQSLYQNADTYVFVGSSRYSKKFKPEIAIRPKVRDQAGRMNYYWTLVEPGDKITFEATGNLVPRYAFAMERNAGSGIIISDTP |
| SC_1_18 | LWGVHHPPTGTDQQSLYQNADAYVSVGSSKYNRRFTPEIAARPKVRDQNGRMNYYWTLLEPGDTIFEATGNLIAPWYAFALNRGSGSGIITSDAP |
| Solis_3_06 | LWGVHHPNIGDQRALYHKENAYVSVSVSSHYSRKFTPEIAKRPKEVRDQEGRINYYWTLLEPGDTIFEANGNLIAPRYAFALSRGFGSGIINSNAP |
| Bris_59_07 | LWGVHHPNIGDQKALYHTENAVVSVSVSSHYSRKFTPEIAKRPKVRDQEGRINYYWTLLEPGDTIFEANGNLIAPRYAFALSRGFGSGIINSNAP |

FIG. 4A (continued)

```
CA_04_09        VHDCNTTCQTPKGAINTSLPFQNIHPITIGKCPKYVKSTKLRLATGLRNIPSIQSRGLFGAIAGFIEGGWTGMVDGWYGYHHQNEQGSGYAADLKS
CA_04_09_Mut1   VHDCNTTCQTPKGAINTSLPFQNIHPITIGKCPKYVKSTKLRLATGLRNIPSIQSRGLFGAIAGFIEGGWTGMVDGWYGYHHQNEQGSGYAADLKS
CA_04_09_Mut2   VHDCNTTCQTPKGAINTSLPFQNIHPITIGKCPKYVKSTKLRLATGLRNIPSIQSRGLFGAIAGFIEGGWTGMVDGWYGYHHQNEQGSGYAADLKS
SC_1_18         VHDCNTKCQTPHGAINSSLPFQNIHPVTIGECPKYVRSTKLRMATGLRNIPSIQSRGLFGAIAGFIEGGWTGMIDGWYGYHHQNEQGSGYAADQKS
Solis_3_06      MDECDAKCQTPQGAINSSLPFQNVHPVTIGECPKYVRSAKLRMVTGLRNIPSIQSRGLFGAIAGFIEGGWTGMVDGWYGYHHQNEQGSGYAADQKS
Bris_59_07      MDKCDAKCQTPQGAINSSLPFQNVHPVTIGECPKYVRSAKLRMVTGLRNIPSIQSRGLFGAIAGFIEGGWTGMVDGWYGYHHQNEQGSGYAADQKS CA_04_09        TQNAIDEITNKVNSVIEKMNTQFTAVGKEFNHLEKRIENLNKKVDDGFLDIWTYNAELLVLLENERTLDYHDSNVKNLYEKVRSQLKNNAKEIGNG
CA_04_09_Mut1   TQNAIDEITNKVNSVIEKMNTQFTAVGKEFNHLEKRIENLNKKVDDGFLDIWTYNAELLVLLENERTLDYHDSNVKNLYEKVRSQLKNNAKEIGNG
CA_04_09_Mut2   TQNAIDEITNKVNSVIEKMNTQFTAVGKEFNHLEKRIENLNKKVDDGFLDIWTYNAELLVLLENERTLDYHDSNVKNLYEKVRSQLKNNAKEIGNG
SC_1_18         TQNAIDGITNKVNSVIEKMNTQFTAVGKEFNNLERRIENLNKKVDDGFLDIWTYNAELLVLLENERTLDFHDSNVKNLYEKVKSQLKNNAKEIGNG
Solis_3_06      TQNAINGITNKVNSVIERMNTQFTAVGKEFNKLERRMENLNKKVDDGFIDIWTYNAELLVLLENERTLDFHDSNVKNLYEKVKSQLKNNAKEIGNG
Bris_59_07      TQNAINGITNKVNSVIERMNTQFTAVGKEFNKLERRMENLNKKVDDGFIDIWTYNAELLVLLENERTLDFHDSNVKNLYEKVKSQLKNNAKEIGNG CA_04_09        CFEFYHKCDNTCMESVKNGTYDYPKYSEEAKLNREEIDGVKLESTRIYQILAIYSTVASSLVLVVSLGAISFWMCSNGSLQCRICI
CA_04_09_Mut1   CFEFYHKCDNTCMESVKNGTYDYPKYSEEAKLNREEIDGVKLESTRIYQILAIYSTVASSLVLVVSLGAISFWMCSNGSLQCRICI
CA_04_09_Mut2   CFEFYHKCDNTCMESVKNGTYDYPKYSEEAKLNREEIDGVKLESTRIYQILAIYSTVASSLVLVVSLGAISFWMCSNGSLQCRICI
SC_1_18         CFEFYHKCDDACMESVRNGTYDYPKYSEESKLNREEIDGVKLESMGVYQILAIYSTVASSLVLVVSLGAISFWMCSNGSLQCRICI
Solis_3_06      CFEFYHKCNDECMESVKNGTYDYPKYSEESKLNREKIDGVKLESMGVYQILAIYSTVASSLVLVVSLGAISFWMCSNGSLQCRICI
Bris_59_07      CFEFYHKCNDECMESVKNGTYDYPKYSEESKLNREKIDGVKLESMGVYQILAIYSTVASSLVLVVSLGAISFWMCSNGSLQCRICI
```

FIG. 4B

```
AAichi_9_09  DTICIGYHANNSTDTVDTVLEKNVTVTHSVNLLENSHNGKICLLKGIAPLQLGNCSVAGWILGNPECELLISKESWSYIVEKPNPENGTCYPGHFADYEELREQLSSVSS
ABris_59_07  DTICIGYHANNSTDTVDTVLEKNVTVTHSVNLLENSHNGKICLLKGIAPLQLGNCSVAGWILGNPECELLISKESWSYIVEKPNPENGTCYPGHFADYEELREQLSSVSS
ACal_04_09   DTLCIGYHANNSTDTVDTVLEKNVTVTHSVNLLEDKHNGKLCKLRGVAPLHLGKCNIAGWILGNPECESLTASSWSYIVETPSSDNGTCYPGDFIDYEELREQLSSVSS
                                                                                                               219 222
                       136 138        145         153 156                          183      190       196
AAichi_9_09  FERFEIFPKESSWPNHTV--GVSASCSHNGESFYRNLLWILTGKNGLYPNLSKSYVANNKEKEVLVLWGVHHPPNIAQKALYETENAYVSVVSSHYSRKFTPEIAKRPKV
ABris_59_07  FERFEIFPKESSWPNHTV--GVSASCSHNGESFYRNLLWILTGKNGLYPNLSKSYVANNKEKEVLVLWGVHHPPNIGDKALYETENAYVSVVSSHYSRKFTPEIAKRPKV
ACal_04_09   FERFEIFPKESSWPNHDSNKGVTAACPHAGAKSFYKNLIWLVKKGNSYPKLSKSYINDKGKEVLVLWGIHHPSSADQQSLYQNADTVFVGSSRYSKKKFKPEIAIRPKV 225 227
AAichi_9_09  RDQEGRINYYWTLLEPGDTIIFEANGNLIAPRYAFALSRGFGSGIINSNAPMDKCDAKCQTPQGAINSSLPFQNVHPVTIGECPKYVRSAKLRMVTGLRNIPSIQSR
ABris_59_07  RDQEGRINYYWTLLEPGDTIIFEANGNLIAPRYAFALSRGFGSGIINSNAPMDKCDAKCQTPQGAINSSLPFQNVHPVTIGECPKYVRSAKLRMVTGLRNIPSIQSR
ACal_04_09   RDQEGRMNYYWTLVEPGDKITFEATGNLVVPRYAFAMERNAGSGIIISDTPVHDCNTTCQTPKGAINTSLPFQNIHPTTIGKCPKYVKSTKLRLATGLRNIPSIQSR
```

FIG. 4C

```
SC_1_18    MEARLLVLLCAFAATNADTICIGYHANNSTDTVDTVLEKNVTVTHSVNLLEDSHNGKLCKLKGTAPLQLGKCNIAGMLLGNPECDLLLTASSWSYIVETSNSNGTCYPGD
SwIA_15_30 MKAILLLVLLCAFAATNADTLCIGYHANNSTDTVDTVLEKNVTVTHSVNLLEDSHNGKLCKLKCRIGGIAPLQLGKCNIAGXXLGNPECDLLLTVSSWSYIVETSNGNGTCYPGD
Cal_04_09  MKAIIVLLYTFATANADTLCIGYHANNSTDTVDTVLEKNVTVTHSVNLLEDKHNGKLCKLKRGVAPIHLGKCNIAGWILGNPECESLSTASSWSYIVETPSSDNGTCYPGD
                                                                                                  183   190    196
                                                     136     145    153    156
SC_1_18    FIDYEELREQLSSVSSFERFEIFPKTSSWPNHETTKGVTRCSYAGASFYRNLLIKLLRKGSSYPKLSKSYVNNKGKEVLVLWGVEHPTGTDQQSEYQNADAYVSGSSK
SwIA_15_30 FIDYEELREQLSSVSSFERFEIFPKTSSWPNHETTRGVTRCPYAGASFYRNLLIMLMKKENSYPKLSKSYVNNKGKEVLVLWGVEHPPTSDQQSEYQNADAYVSGSSK
Cal_04_09  FIDYEELREQLSSVSSFERFEIFPKTSSWPNEHDSNKGVTRCPHAGASFYKNLIAWLMKGNSYPRLSKSYINDKGKEVLVLWGIEHPTSADQSEYQNADTIVFGSSR
           219   225
SC_1_18    YNRRFTPELAARPKVRDQGRMNYYWTLLEPGDTITFEATGNLIAPWIAFALNRGSGGIITSDAPVHDCNTKCQTPHGAINSSLPFQNIHPVTIGECPKYVSTKLRMAT
SwIA_15_30 YDRRFTPELAARPKVRQQGRMNYYWTLLEPGDTITFEATGNIVAPRVAFALNRGSESGIITSDAPVHDCDTKCQTPHGAINSSLPFQNIHPVTIGBCPKYVKSTKLRMVT
Cal_04_09  YSKKFKPELAERPKVRDQGRMNYYWLVEPGDKITFEATGNLVPRYAEAMERNAGSGIISDTPVHDCNTTCQTPKGAINTSLPFQNIHPTIGKCPKYVKSTKLRLAT
SC_1_18    GLRNIPSIQSRGLFGAIAGFIEGGWTGMIDGWYGYHHQNEQGSGYAADQKSTQNAIDGITNKVNSVIEKMNTQFTAVGKEFNNLERRIENLNKKVDDGFLDIWTYNAELLV
SwIA_15_30 GLRNIPSIQSRGLFGAIAGFIEGGWTGMIDGWYGYHHQNGGSGYAADQKSTQNAIDGITNKVNSVIEKMNTQFTVVGKEFNNLERRIKNLNKKVDDGFLDWWTYNAEMLV
Cal_04_09  GLRNIPSIQSRGLFGAIAGFIEGGWTGMVDGWYGYHHQNEQGSGYAADQKSTQNAIDKVTNKVNSVIEKMNTQFTAVGKEFNLKRIENLNKKVDDGFLDIWTYNAELLV
SC_1_18    LLENERTLDHDSNVRNLYEKVKSQLKNNAKEIGNGCFEFYHKCDDACMESVRNGTYDYPKYSEESKLNREIDGVKLESMGVYQILAIYSTVASSIVLLVSLGAISFWMC
SwIA_15_30 LLENERTLDFHDSNVKNLYEKARSQLRNNAKEIGNGCFEFYHKCDDACMESVRNGTYDYPKYSEESKLNREEIDGVKLESMVYQILAIYSTVASSIVLLVSLGAISFWMC
Cal_04_09  LLENERTLDYHDSNVKNLYEKVRSQLKNNAKEIGNGCFEFYHKCDNTCMESVKNGTYDYPKYSEEAKLNREIDGVKLESTRIYQILAIYSTVASSIVLLVSLGAISFWMC
SC_1_18    SNGSLQCRICI 566
SwIA_15_30 SNGSLQCRICI 566
Cal_04_09  SNGSLQCRICI 566
```

Conformational sampling of α2–6 linkage

| | Umbrella-like (%) : Cone-like (%) |
|---|---|
| ω = −60° | 60 : 20 |
| ω = +60° | 10 : 40 |
| ω = 180° | 30 : 30 |

FIG. 5C-6

Conformational sampling of α2–3 linkage

| Cone-like | 100% |
|---|---|
| Umbrella-like | 0% |

FIG. 5C-5

α2–3 and α2–6 motif in Cone topology

- Typical of short oligosaccharide or oligosaccharide branch attached to a Core Structure

- Short branch of N-linked Core

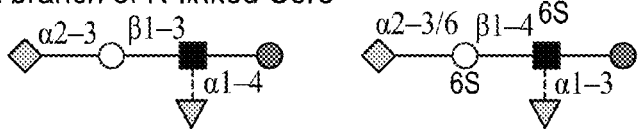

- Short branch of O-linked Core

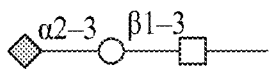

- The Cone topology can also be adopted by longer α2–3 and α2–6 oligosaccharide branch attached to Core Structure ◆ Neu5Ac    ▽ Fuc ○ Gal       ● Glc       ⊛ Man ☐ GalNAc    ■ GlcNAc Dotted Gray lines, 4S and 6S indicate potential sites for fucosylation and sulfation modifications

FIG. 7

Key: ■ GlcNAc □ GalNAc ○ Gal ● Glc ◆ Neu5Ac ▽ Fucose ☐ Terminal HexNAc

Long α2–6 umbrella-like topology glycan decoys

N-linked glycans:

α2–6 Type 2 extension branch attached to trimannosyl core

α2–6 LacDiNAc extension branch attached to trimannosyl core

**Long α2–6 *umbrella*-like topology glycans that are not decoys**

N-linked glycans:

α2–6 linkage on GlcNAc of Type 1/Type 2 extension

**Long α2–6 *umbrella*-like topology glycan decoys**
O-linked glycans:
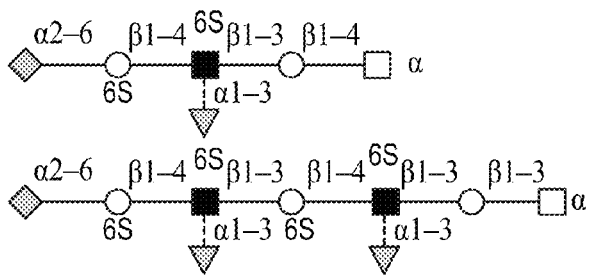
*α2–6 Type 2 extension branch in a Core 1 type structure*
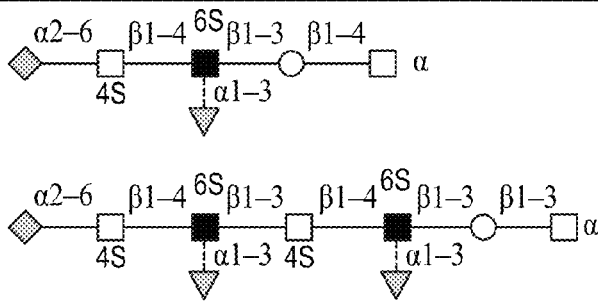
*α2–6 LacDiNAc extension branch in a Core 1 type structure*
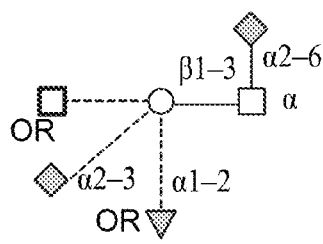
*α2–6 attached to core GalNAc in Core 1 type structure*
FIG. 8A-3

**Long α2–6 *umbrella*-like topology glycan decoys**
O-linked glycans:
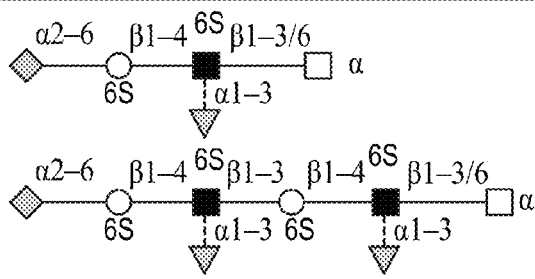
*α2–6 Type 2 extension branch in a Core 2 or 3 or 4 type structure*
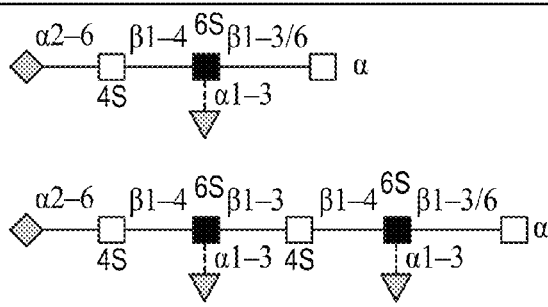
*α2–6 LacDiNAc extension branch in a Core 2 or 3 or 4 type structure*
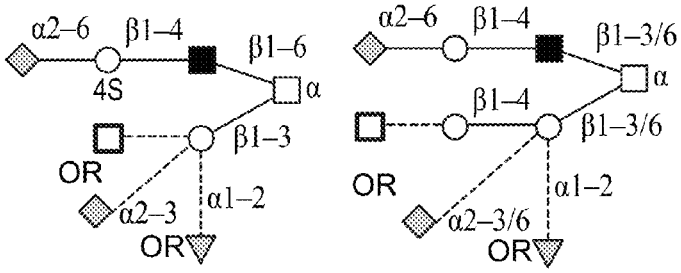
*α2–6 attached to branched Core 2 and Core 4 structures*
FIG. 8A-4

**Long α2–6 *umbrella*-like topology glycan that are not decoys**

Glycolipids:

*Glucosylceramide Core Ganglio type*

*Glucosylceramide Core Globo type*

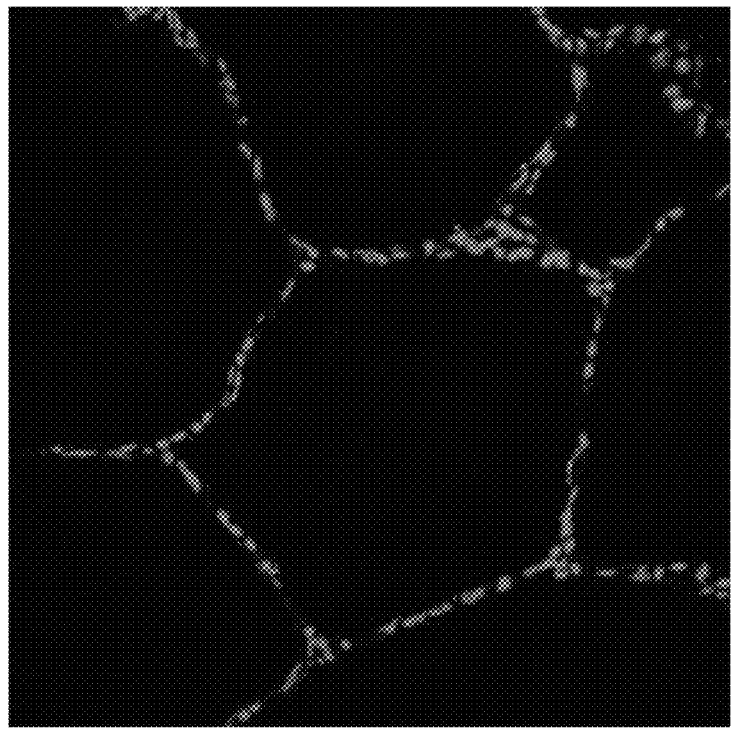
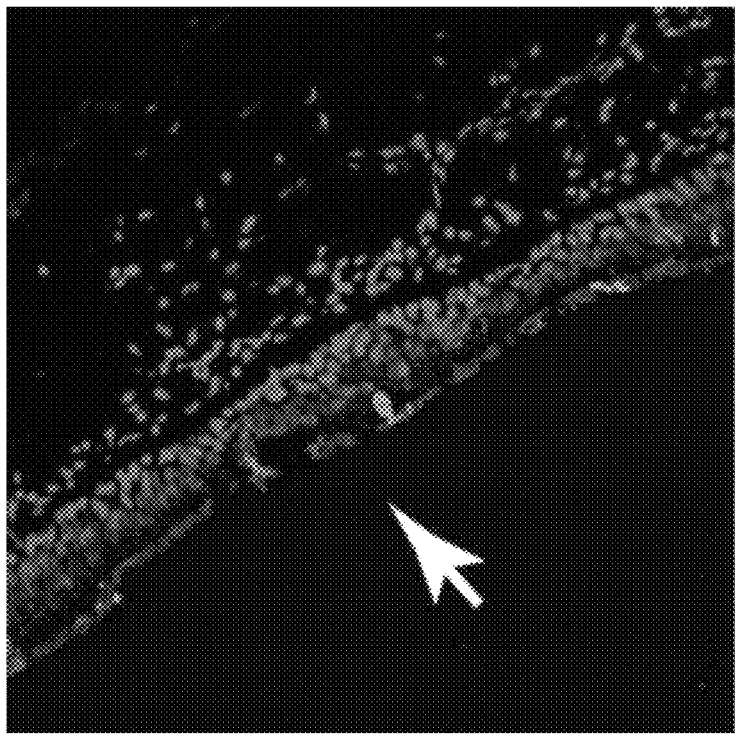
FIG. 10

| H1N1 Strains | Cluster 1 ||| Cluster 2 ||||| Cluster 3 || Cluster 4 ||||| Cluster 5 |||||
|---|---|---|---|---|---|---|---|---|---|---|---|---|---|---|---|---|---|---|---|---|
| | 136 | 138 | 226 | 137 | 153 | 155 | 194 | 183 | 145 | 222 | 225 | 190 | 189 | 187 | 186 | 219 | 227 | 192 | 193 | 156 | 159 | 196 |
| Solls_3_06 | S | S | Q | A | W | T | L | H | S | K | D | D | G | N | P | K | E | R | A | G | G | H |
| Bris_59_07 | S | S | Q | A | W | T | L | H | S | K | D | D | G | N | P | K | E | K | A | G | G | H |
| NewCal_20_99 | S | S | Q | A | W | T | L | H | S | K | D | N | G | N | P | K | E | R | A | G | G | H |
| TX_36_91 | T | S | Q | T | W | T | – | H | S | K | D | D | R | N | S | K | E | R | A | E | G | H |
| SC18 | T | A | Q | A | W | T | L | H | S | K | D | D | T | T | P | A | A | Q | S | K | S | Q |
| TX/15 | T | A | Q | A | W | V | L | H | K | K | D | D | A | T | S | – | E | Q | S | K | N | Q |
| MX/4482 | T | A | Q | A | W | V | L | H | K | K | D | D | A | T | S | – | E | Q | S | K | N | Q |
| CA/04 | T | A | Q | A | W | V | L | H | K | K | D | D | A | T | S | – | E | Q | S | K | N | Q |
| | Neu5Ac-1 |||||||| Gal-2 || GlcNAc-3 ||||| Gal-4, Glc-5,.... |||||

FIG. 11

| Glycan | Expanded nomenclature |
|---|---|
| 3'SLN | Neu5Acα2-3Galβ1-4GlcNAcβ1- |
| 6'SLN | Neu5Acα2-6Galβ1-4GlcNAcβ1- |
| 3'SLN-LN | Neu5Acα2-3Galβ1-4GlcNAcβ1-3Galβ1-4GlcNAcβ1- |
| 6'SLN-LN | Neu5Acα2-6Galβ1-4GlcNAcβ1-3Galβ1-4GlcNAcβ1- |
| 3'SLN-LN-LN | Neu5Acα2-3Galβ1-4GlcNAcβ1-3Galβ1-4GlcNAcβ1-3Galβ1-4GlcNAcβ1- |

Key: Neu5Ac: N-acetyl D-neuraminic acid; Gal: D-galatose; GlcNAc: N-acetyl D-glucosamine. α / β: anomeric configuration of the pyranose sugars. All the sugars are linked via a spacer to biotin (-Sp-LC-LC-Biotin as described in http://www.functionalglycomics.org/static/consortium/resources/resourcecored5.shtml)

CA04M2 (Ser186→Pro/Ala189→Thr/Glu227→Ala)

COMPOSITIONS AND METHODS FOR DIAGNOSING AND/OR TREATING INFLUENZA INFECTION

RELATED APPLICATIONS

This patent application is a continuation of U.S. non-provisional patent application Ser. No. 12/829,931, filed Jul. 2, 2010, ("the '931 application") which claims priority under 35 U.S.C. §119(e) to U.S. provisional patent application No. 61/222,889, filed Jul. 2, 2009 ("the '889 application"). The entire contents of both the '931 and '889 applications are incorporated herein by reference.

GOVERNMENT SUPPORT

This invention was made with Government support under Grant Nos. R01 GM057073 and U54 GM062116 awarded by the National Institutes of Health. The Government has certain rights in the invention.

SEQUENCE LISTING

In accordance with 37 C.F.R. §1.52(e)(5), a Sequence Listing in the form of a text file (entitled "Sequence_Listing," created on Oct. 20, 2010 and 205 kilobytes) is incorporated herein by reference in its entirety.

BACKGROUND OF THE INVENTION

On Jun. 11, 2009 the World Health Organization raised the global pandemic alert level to phase 6, the pandemic phase, in response to the emergence and global spread of a novel influenza A (H1N1) virus henceforth referred to as 2009 A/H1N1 virus containing a unique combination of genes of swine origin (Garten et al., "Antigenic and Genetic Characteristics of Swine-Origin 2009 A(H1N1) Influenza Viruses Circulating in Humans" *Science*, May 22, 2009, Science Express Online; incorporated herein by reference). The emergence of this new strain can be traced back to March-April 2009 when there were reports of increased numbers of patients with influenza-like illness and associated hospitalizations and deaths in several areas of Mexico. In the period Mar.-Jun. 19, 2009, there have been over 44,000 laboratory-confirmed human cases of influenza 2009 A/H1N1 infections reported in 85 countries on 6 continents.

Given the rapid outbreak of this virus, there have been uncertainties associated with its virulence, transmissibility and its origins. Recent studies using epidemiological models to interpret data on outbreaks of the 2009 H1N1 virus have indicated that its transmissibility is on the lower end of what was estimated for the 1918 H1N1 pandemic. In most of the cases of human infection with the 2009 H1N1 viruses, the symptoms have been relatively mild, however, there have been over 150 deaths reported. Additionally, a substantial portion (~40%) of infected individuals experience gastrointestinal distress and vomiting, a percentage that is higher than what is typically observed for seasonal flu.

SUMMARY OF THE INVENTION

The present invention provides compositions and methods for the treatment, prevention, and/or diagnosis of infection with an H1N1 influenza virus. In some embodiments, the invention provides compositions and methods for treatment, prevention, and/or diagnosis of infection with an H1N1 influenza virus that has acquired significant human infectivity.

Among other things, the present invention defines H1N1 HA variants with enhanced human binding and/or infectivity as compared with H1N1 influenza strains. Such variants may be utilized, among other things, as components of vaccines and/or therapeutics to treat, reduce, and/or prevent human infection by and H1N1 virus, and particularly by a variant with enhanced human binding and/or infectivity. Alternatively or additionally, such variants may be utilized as standards in systems for detecting occurrence of and/or infection with an H1N1 variant with enhanced human infectivity.

In some aspects, the present invention provides agents that bind specifically to an H1N1 HA polypeptide, for example for use in detecting H1N1 infection. In some embodiments, the present invention provides agents that bind specifically to an H1N1 variant with enhanced human binding and/or infectivity. In some embodiments, the present invention provides agents that discriminate between H1N1 variants with enhanced human infectivity and H1N1 variants without enhanced human infectivity.

In some aspects, the present invention provides agents that interfere (and/or compete) with binding interactions between an H1N1 HA polypeptide and one or more glycans, for example umbrella-topology glycans. In some embodiments, the present invention provides agents that interfere (and/or compete with) binding interactions between an H1N1 HA polypeptide and one or more α2-6 sialylated glycans. In some embodiments, the present invention provides agents that interfere (and/or compete) with binding interactions between an H1N1 HA polypeptide and one or more 6'SLN-LN glycans. In some embodiments, the H1N1 HA polypeptide whose binding interaction is interfered with is an H1N1 variant with enhanced human binding and/or infectivity.

As already noted, in some embodiments, the present invention provides systems for performing surveillance to detect presence of and/or infection with H1N1 influenza. In some embodiments, the present invention provides systems for performing surveillance to detect presence of and/or infection with an H1N1 influenza variant with enhanced human binding and/or infectivity.

In some embodiments, the present invention provides strategies for vaccinating and/or treating populations (e.g., human populations) against infection with H1N1 influenza strains. In some embodiments, the present invention provides strategies for vaccinating and/or treating populations (e.g., human populations) against infection with an H1N1 influenza variant with enhanced human binding and/or infectivity.

In some embodiments, the present invention provides strategies for stratifying patient populations, e.g., identifying subjects previously exposed to one or more viruses showing similarity with 2009 A/H1N1. In this manner, it is envisioned that patient populations can be identified that are at reduced or increased risk for contracting 2009 A/H1N1 virus and/or potentially have a delayed immune response due to the lack of previous humoral immunity to one or more viruses showing similarity to 2009 A/H1N1.

BRIEF DESCRIPTION OF THE DRAWING

Figure 1A:
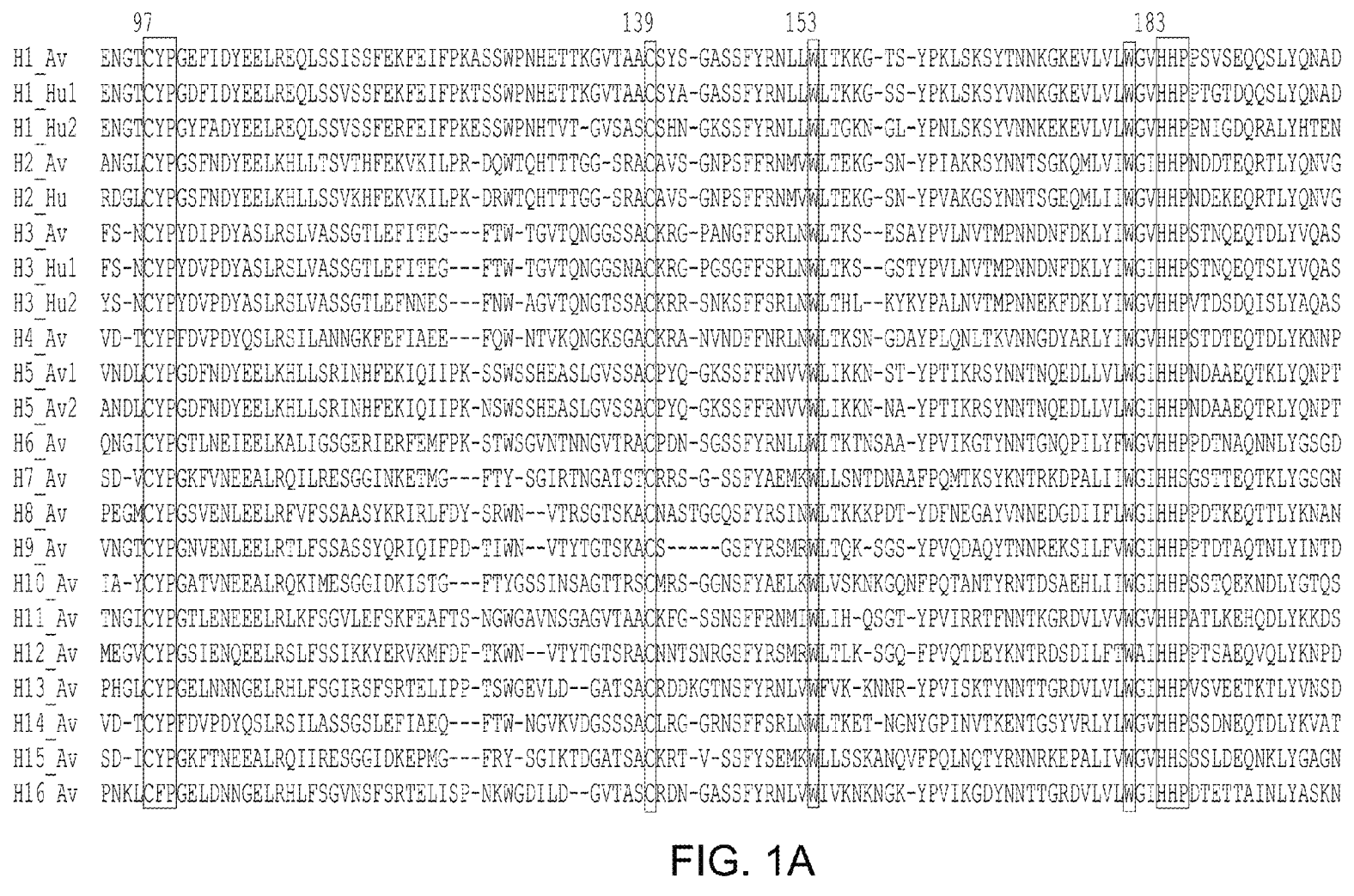

FIGS. 1A-C. Alignment of exemplary sequences of wild type HAs. Sequences were obtained from the NCBI influenza virus sequence database (http://www.ncbi.nlm.nih.gov/ genomes/FLU/FLU.html). FIGS. 1A, 1B, and 1C represent the sequence alignment of the amino acid residues of the following wild type HAs: H1_Av (SEQ ID NO: 1). H1_Hu1 (SEQ ID NO: 2). H1_Hu2 (SEQ ID NO: 3). H2_Av (SEQ ID NO: 4). H2_Hu (SEQ ID NO: 5). H3_Av (SEQ ID NO: 6). H3_Hu1 (SEQ ID NO: 7). H3_Hu2 (SEQ ID NO: 8). H4_Av (SEQ ID NO: 9). H5_Av1 (SEQ ID NO: 10). H5_Av2 (SEQ ID NO: 11). H6_Av (SEQ ID NO: 12). H7_Av (SEQ ID NO: 13). H8_Av (SEQ ID NO: 14). H9_Av (SEQ ID NO: 15). H10_Av (SEQ ID NO: 16). H11_Av (SEQ ID NO: 17). H12_Av (SEQ ID NO: 18). H13_Av (SEQ ID NO: 19). H14_Av (SEQ ID NO: 20). H15_Av (SEQ ID NO: 21). H16_Av (SEQ ID NO: 22).

FIGS. 2A-B. Sequence alignment of HA glycan binding domains. FIGS. 2A and 2B represent the sequence alignment of the amino acid residues of HA glycan binding domains: ADA76, ASI30, APR34, ASC18, AT91, ANY18, ADU63, AAI68, AM99, ADS97, and Viet04. Residues at positions 98, 136, 153, 155, 183, and 194 are conserved amino acids involved in binding to sialic acid. Residues at positions 190 and 226 are particular amino acids involved in binding to Neu5Acα2-3/6Gal motifs. Residues at positions 186 and 228 are amino acids that influence positioning of Q226 (137, 138) and E190 (186, 228). Residues at positions 189, 193, 222, and 225 are amino acids involved in binding to other monosaccharides (or modifications) attached to Neu5Acα2-3/6Gal motif. The sequence for ASI30, APR34, ADU63, ADS97 and Viet04 were obtained from their respective crystal structures. The other sequences were obtained from SwissProt (http://us.expasy.org). Abbreviations: ADA76, A/duck/Alberta/35/76 (H1N1) (SEQ ID NO: 23); ASI30, A/Swine/Iowa/30 (H1N1) (SEQ ID NO: 24); APR34, A/Puerto Rico/8/34 (H1N1) (SEQ ID NO: 25); ASC18, A/South Carolina/1/18 (H1N1) (SEQ ID NO: 26); AT91, A/Texas/36/91 (H1N1) (SEQ ID NO: 27); ANY18, A/New York/1/18 (H1N1) (SEQ ID NO: 28); ADU63, A/Duck/Ukraine/1/63 (H3N8) (SEQ ID NO: 29); AAI68, A/Aichi/2/68 (H3N2) (SEQ ID NO: 30); AM99, A/Moscow/10/99 (H3N2) (SEQ ID NO: 31); ADS97, A/Duck/Singapore/3/97 (H5N3) (SEQ ID NO: 32); Viet04, A/Vietnam/1203/2004 (H5N1) (SEQ ID NO: 33).

Figure 3A:
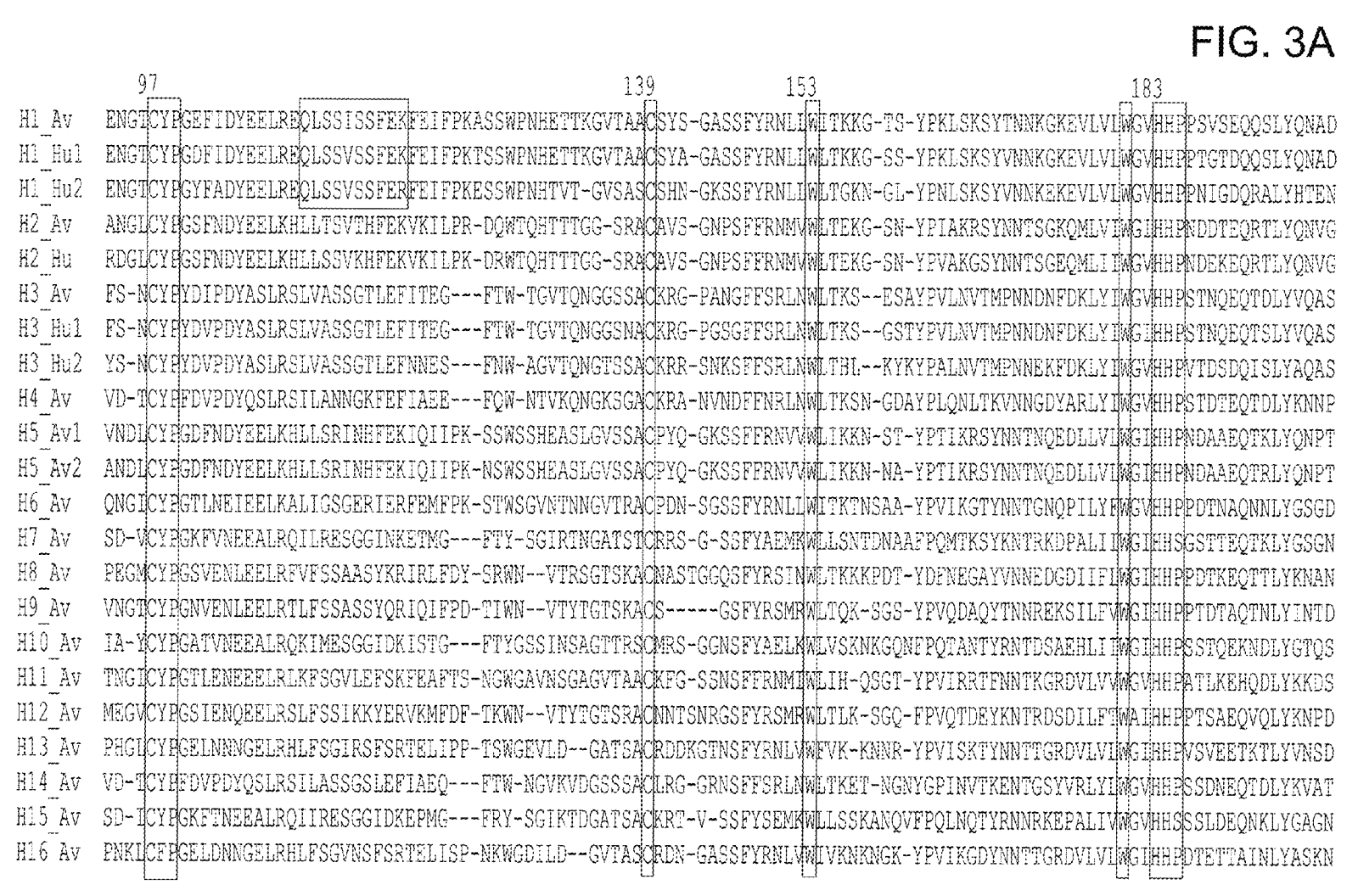

FIGS. 3A-B. Sequence alignment illustrating conserved subsequences characteristic of H1 HAs. FIG. 3A presents the same alignment that was presented in FIG. 1A, except that FIG. 3A indicates the presence of an additional conserved subsequence. FIG. 3B presents the same alignment that was presented in FIG. 1C, except that FIG. 3B indicates the presence of an additional conserved subsequence.

FIGS. 4A-C. (FIG. 4A) Sequence alignment of 2009 A/H1N1 HA (CA_04_09) and its mutant forms (Mut_1) and Mut_2) along with human adapted HAs (SC_1_18, Solls_3_06, Bris_50_07). Residues marked contribute directly or indirectly to α2-6 binding. Residues 186 (P), 189 (T), and 227 (A) for CA_04_09_Mut2 and 219 (K) for CA_04_09 Mut1 are residues that are altered in H1N1 variants with enhanced human binding and/or infectivity as compared with 2009 A/H1N1 HA (CA_04_09). CA_04_09 (SEQ ID NO: 34). CA_04_09 Mut1 (SEQ ID NO: 35). CA_04_09 Mut2 (SEQ ID NO: 36). SC_1_18 (SEQ ID NO: 37). Solls_3_06 (SEQ ID NO: 38). Bris_59_07 (SEQ ID NO: 39). (FIG. 4B) Sequence alignment of influenza H1N1 HA from a 2009 seasonal strain (Aichi_9_09), 2007-2008 seasonal strain (Bris_59_07) and a "swine flu" strain (Cal_04_09). A/Aichi_9_09 (SEQ ID NO: 40)=A/Aichi/9/2009; ABris_59_07 (SEQ ID NO: 41)=A/Brisbane/59/2007; ACal_04_09 (SEQ ID NO: 42)=A/California/04/2009. Residues that are directly or indirectly involved in α2-6 binding are marked. (FIG. 4C) Sequence alignment of influenza H1N1 HA from 1918 pandemic (SC_1_18), 1930 swine isolate (SwIA_15_30) and a "swine flu" strain (Cal_04_09). SC_1_18 (SEQ ID NO: 43)=A/South Carolina/1/1918; SwIA_15_30 (SEQ ID NO: 44)=A/Swine/IA/15/1930; ACal_04_09 (SEQ ID NO: 45)=A/California/04/2009. Residues that are directly or indirectly involved in α2-6 binding are marked.

FIGS. 5A-C. Frameworks for understanding glycan receptor specificity. α2-3- and/or α2-6-linked glycans can adopt different topologies. According to the present invention, the ability of an HA polypeptide to bind to certain of these topologies confers upon it the ability to mediate infection of different hosts, for example, humans. As illustrated in FIG. 5A of this figure, the present invention defines two particularly relevant topologies, a "cone" topology and an "umbrella" topology. The cone topology can be adopted by α2-3- and/or α2-6-linked glycans, and is typical of short oligosaccharides or branched oligosaccharides attached to a core (although this topology can be adopted by certain long oligosaccharides). The umbrella topology can only be adopted by α2-6-linked glycans (presumably due to the increased conformational plurality afforded by the extra C5-C6 bond that is present in the α2-6 linkage), and is predominantly adopted by long oligosaccharides or branched glycans with long oligosaccharide branches, particularly containing the motif Neu5Acα2-6Galβ1-3/4GlcNAc-. As described herein, ability of HA polypeptides to bind the umbrella glycan topology, confers binding to human receptors and/or ability to mediate infection of humans. FIG. 5B-1 and FIG. 5B-2 specifically show the topology of α2-3 and α2-6 as governed by the glycosidic torsion angles of the trisaccharide motifs—Neu5Acα2-3Galβ1-3/4GlcNAc and Neu5Acα2-6Galβ1-4GlcNAc respectively. A parameter (θ)—angle between C2 atom of Neu5Ac and C1 atoms of the subsequent Gal and GlcNAc sugars in these trisaccharide motifs was defined to characterize the topology. Superimposition of the θ contour and the conformational maps of the α2-3 and α2-6 motifs shows that α2-3 motifs adopt 100% cone-like topology and α2-6 motifs sampled both cone-like and umbrella-like topologies (See, FIG. 5C-1, FIG. 5C-2, FIG. 5C-3, FIG. 5C-4, FIG. 5C-5 and FIG. 5C-6, discussed further below). In the cone-like topology sampled by α2-3 and α2-6, GlcNAc and subsequent sugars are positioned along a region spanning a cone. Interactions of HA with cone-like topology primarily involve contacts of amino acids at the numbered positions (based on H3 HA numbering) with Neu5Ac and Gal sugars. On the other hand, in umbrella-like topology, which is unique to α2-6, \ GlcNAc and subsequent sugars bend towards the HA binding site (as observed in HA-α2-6 co-crystal structures). Longer α2-6 oligosaccharides (e.g., at least a tetrasaccharide) would favor this conformation since it is stabilized by intra-sugar van der Waals contact between acetyl groups of GlcNAc and Neu5Ac. HA interactions with umbrella-like topology involve contacts of amino acids at the numbered positions (based on H3 HA numbering) with GlcNAc and subsequent sugars in addition to contacts with Neu5Ac and Gal sugars. FIGS. 5C-1, FIG. 5C-2, FIG. 5C-3 and FIG. 5C-4 together depict conformational sampling of cone- and umbrella-like topology by α2-3 and α2-6. Specifically, FIG. 5C-1, FIG. 5C-2, FIG. 5C-3 and FIG. 5C-4 show the conformational (φ,ψ), maps of Neu5Acα2-3Gal, Neu5Acα2-6Gal, Galβ1-3GlcNAc, and Galβ1-4GlcNAc linkages, respectively. These maps obtained from Glyco-Maps DB (http://www.glycosciences.de/modeling/glycomapsdb/) were generated using ab initio MD simulations using MM3 force field. Energy distribution is coded starting from dark shading (representing highest energy) to light shading representing lowest energy. Encircled regions 1-5 represent (φ,ψ) values observed for the α2-3 and α2-6 oligosaccharides in the HA-glycan co-crystal structures. The trans conformation (encircled region 1) of Neu5Acα2-3Gal predominates in HA binding pocket with the exception of the co-crystal structure of A/Aichi/2/68 H3N2 HA with α2-3 where this conformation is gauche (encircled region 2). On the other hand, the cis conformation of Neu5Acα2-6Gal (encircled region 3) predominates in HA binding pocket. The cone-like topology is sampled by encircled regions 1 and 2 and the umbrella-like topology is sampled by encircled region 3. FIG. 5C-5 and FIG. 5C-6 show conformational sampling of cone-like and umbrella-like topologies by α2-3 and α2-6 motifs, respectively. Regions marked in dark shading in the conformational maps were used as the outer boundaries to calculate the θ parameter (angle between C2 atom of Neu5Ac and C1 atoms of subsequent Gal and GlcNAc sugars) for a given set of (φ,ψ) values. Based on the energy cutoff, the value of θ>110° was used to characterize cone-like topology and θ<100° was used to characterize umbrella-like topology. Superimposition of the θ contour with the conformational energy map indicated that α2-3 motif adopts 100% cone-like topology since it was energetically unfavorable to adopt umbrella-like topology. On the other hand, the α2-6 motif sampled both the cone-like and umbrella-like topologies and this sampling was classified based on the ω angle (O—C6-C5-H5) of Neu5Acα2-6Gal linkage.

FIG. 6. Interactions of HA residues with cone vs. umbrella glycan topologies. Analysis of HA-glycan co-crystals reveals that the position of Neu5Ac relative to the HA binding site is almost invariant. Contacts with Neu5Ac involve highly conserved residues such as F98, S/T136, W153, H183 and L3194. Contacts with other sugars involve different residues, depending on whether the sugar linkage is α2-3 or α2-6 and whether the glycan topology is cone or umbrella. For example, in the cone topology, the primary contacts are with Neu5Ac and with Gal sugars. E190 and Q226 play particularly important roles in this binding. This Figure also illustrates other positions (e.g., 137, 145, 186, 187, 193, 222) that can participate in binding to cone structures. In some cases, different residues can make different contacts with different glycan structures. The type of amino acid in these positions can influence ability of an HA polypeptide to bind to receptors with different modification and/or branching patterns in the glycan structures. In the umbrella topology, contacts are made with sugars beyond Neu5Ac and Gal. This Figure illustrates residues (e.g., 137, 145, 156, 159, 186, 187, 189, 190, 192, 193, 196, 222, 225, 226) that can participate in binding to umbrella structures. In some cases, different residues can make different contacts with different glycan structures. The type of amino acid in these positions can influence ability of an HA polypeptide to bind to receptors with different modification and/or branching patterns in the glycan structures. In some embodiments, a D residue at position 190 and/or a D residue at position 225 contribute(s) to binding to umbrella topologies.

FIG. 7. Exemplary cone topologies. This Figure illustrates certain exemplary (but not exhaustive) glycan structures that adopt cone topologies.

FIGS. 8A-B. Exemplary umbrella topologies. (FIG. 8A-1 to FIG. 8A-7) Certain exemplary (but not exhaustive) N- and O-linked glycan structures that can adopt umbrella topologies. (FIG. 8B) Certain exemplary (but not exhaustive) O-linked glycan structures that can adopt umbrella topologies.

FIGS. 9A-B. Dose dependent direct receptor binding of CA/04 (FIG. 9A) and SC18 (FIG. 9B) HAs. A streptavidin plate array comprising of representative biotinylated α2-3 and α2-6 sialylated glycans (shown in legend) were used for the assay. LN corresponds to lactosamine (Galβ1-4GlcNAc) and 3'SLN and 6'SLN respectively correspond to Neu5Acα2-3 and Neu5Acα2-6 linked to LN. The assay was carried out as described previously (Srinivasan et al., *Proc Natl Acad Sci USA* 105:2800, 2008) for an entire range of HA concentration from 0.01-40 μg/ml by pre-complexing HA:primary antibody:secondary antibody in the ratio 4:2:1 to enhance the multivalent presentation of HA. The pattern of binding selectively to 6'SLN-LN is similar for both the HAs. Note that no detectable binding signals are observed for CA/04 HA below 2 μg/ml concentrations whereas SC18 HA shows substantial binding at these concentrations indicating a much higher binding affinity than CA/04 HA.

FIG. 10: Human lung tissue binding of CA/04 HA. Shown in the top is the binding of CA/04 HA at 20 μg/ml concentration to apical surface (white arrow) of human tracheal tissue sections. Note the binding of HA to the apical surface of tracheal tissue which is known to predominantly express α2-6 sialylated glycans. Shown in the bottom is the minimal binding of HA at 20 μg/ml concentration to the alveolar tissue section. The sialic acid specific binding of HA to the tracheal tissue section was confirmed by the minimal binding of HA to the tissue section pre-treated with 0.2 U of Sialidase A (recombinantly expressed in *Arthrobacter ureafaciens*). The binding of the recombinantly expressed HA to the human tissues was carried out as described previously (Chandrasekaran, et al., *Nat Biotechnol* 26:107, 2008; incorporated herein by reference) by precomplexing HA: primary antibody:secondary antibody in the ratio 4:2:1 to enhance multivalent presentation of HA.

FIG. 11. Glycan binding residues of H1N1 HAs. The residues are organized into network forming clusters. The sugar unit (numbered as shown in FIG. 12), which makes contact with the clusters, is shown in the last row. The unique amino acids in 2009 H1N1 HAs are "K", shown in column 145. The key for the virus strains SolIS_3_06 (A/Solomon Islands/3/06); Bris_59_07 (A/Brisbane/59/07); NewCal_20_99 (A/New Caledonia/20/99); TX/15 (A/Texas/15/2009); MX/4482 (A/Mexico/4482/2009).

FIG. 12: Structural model of CA/04 HA bound to α2-6 oligosaccharide. The contacts of CA/04 HA with an α2-6 oligosaccharide (Neu5Acα2-6Galβ1-4GlcNAcβ1-3Galβ1-4Glc) were analyzed by constructing a structural model as described previously (Soundararajan, et al., *Nat Biotechnol* 27, 510, 2009; incorporated herein by reference). Shown in the figure is the cartoon representation of the glycan binding site of CA/04 HA where the side chains of the key amino acids are shown in stick representation. The α2-6 oligosaccharide is shown as a stick representation (bold) and labeled starting from non-reducing end Neu5Ac-1 to reducing end Glc-5. The potential destabilization of the interaction network due to the Ile219/Glu227 combination is highlighted in dotted circle.

FIGS. 13A-D: Fixing the mismatched interaction in RBS of CA04 HA. (FIG. 13A) Structural complex of RBS of CA04 HA with human receptor (mismatched Ile219-Glu227 contacts highlighted in circle). (FIG. 13B) RBS of CA04M1 complexed with human receptor where Lys219 makes ionic contacts with Glu227. (FIG. 13C) RBS of CA04M2 complexed with the human receptor. (FIG. 13D) RBS of SC18

HA complexed with human receptor. The hydrophobic interactions between Ile219, Pro186, and Ala227 and interactions between Ser187, Thr189, and Asp190 in RBS of CA04M2 HA are similar to that between analogous residues in SC18 HA. The structural complexes are shown in stereo with RBS represented as a cartoon schematic with side chains of key amino acids. The substituted amino acids are shown. Stick representation of human receptor is shown with carbon atoms.

FIG. 14: Nomenclature of glycans used in the glycan array

FIGS. 15A-D: Glycan receptor-binding properties of CA04M1 and CA04M2 HAs. (FIG. 15A) Dose dependent direct glycan array binding of CA04M1. (FIG. 15B) Dose-dependent direct glycan array binding of CA04M2. (FIG. 15C) Binding curves of CA04, CA04M1, CA04M2 and SC18 HAs to 6'SLN-LN. The experimental data (disconnected markers indicated using "Data") is shown along with the theoretical binding curve (line indicated using "Model") generated as described in Example 4. The $K_d'$ of SC18 HA is around 6 pM (in the same range as that of CA04M2 HA) and hence is indicated using the same label. (FIG. 15D) Human tracheal tissue binding of CA04, CA04M1, and CA04M2 HA (staining of HA against propidium iodide). The apical surface of the tracheal tissue sections is indicated using a white arrow. The sialic acid specific binding of HA to the tracheal tissue sections was confirmed by loss of staining upon pre-treatment of the tissue sections with Sialidase A (from *Arthrobacter ureafaciens*) and enzyme that cleaves terminal sialic acid from both avian and human receptors.

DESCRIPTION OF HA SEQUENCE ELEMENTS

HA Sequence Element 1

HA Sequence Element 1 is a sequence element corresponding approximately to residues 97-185 (where residue positions are assigned using H3 HA as reference) of many HA proteins found in natural influenza isolates. This sequence element has the basic structure:

C(Y/F)PX$_1$CX$_2$WX$_3$WX$_4$HHP, wherein:

X$_1$ is approximately 30-45 amino acids long;
X$_2$ is approximately 5-20 amino acids long;
X$_3$ is approximately 25-30 amino acids long; and
X$_4$ is approximately 2 amino acids long.

In some embodiments, X$_1$ is about 35-45, or about 35-43, or about 35, 36, 37, 38, 38, 40, 41, 42, or 43 amino acids long. In some embodiments, X$_2$ is about 9-15, or about 9-14, or about 9, 10, 11, 12, 13, or 14 amino acids long. In some embodiments, X$_3$ is about 26-28, or about 26, 27, or 28 amino acids long. In some embodiments, X$_4$ has the sequence (G/A) (I/V). In some embodiments, X$_4$ has the sequence GI; in some embodiments, X$_4$ has the sequence GV; in some embodiments, X$_4$ has the sequence AI; in some embodiments, X$_4$ has the sequence AV. In some embodiments, HA Sequence Element 1 comprises a disulfide bond. In some embodiments, this disulfide bond bridges residues corresponding to positions 97 and 139 (based on the canonical H3 numbering system utilized herein).

In some embodiments, and particularly in H1 polypeptides, X$_1$ is about 43 amino acids long, and/or X$_2$ is about 13 amino acids long, and/or X$_3$ is about 26 amino acids long. In some embodiments, and particularly in H1 polypeptides, HA Sequence Element 1 has the structure:

CYPX$_{1A}$T(A/T)(A/S)CX$_2$WX$_3$WX$_4$HHP, wherein:

X$_{1A}$ is approximately 27-42, or approximately 32-42, or approximately 32-40, or approximately 26-41, or approximately 31-41, or approximately 31-39, or approximately 31, 32, 33, 34, 35, 36, 37, 38, 39, or 40 amino acids long, and X$_2$-X$_4$ are as above.

In some embodiments, and particularly in H1 polypeptides, HA Sequence Element 1 has the structure:

CYPX$_{1A}$T(A/T)(A/S)CX$_2$W(I/L)(TN)X$_{3A}$WX$_4$HHP, wherein:

X$_{1A}$ is approximately 27-42, or approximately 32-42, or approximately 32-40, or approximately 32, 33, 34, 35, 36, 37, 38, 39, or 40 amino acids long,
X$_{3A}$ is approximately 23-28, or approximately 24-26, or approximately 24, 25, or 26 amino acids long, and X$_2$ and X$_4$ are as above.

Figure 5A:
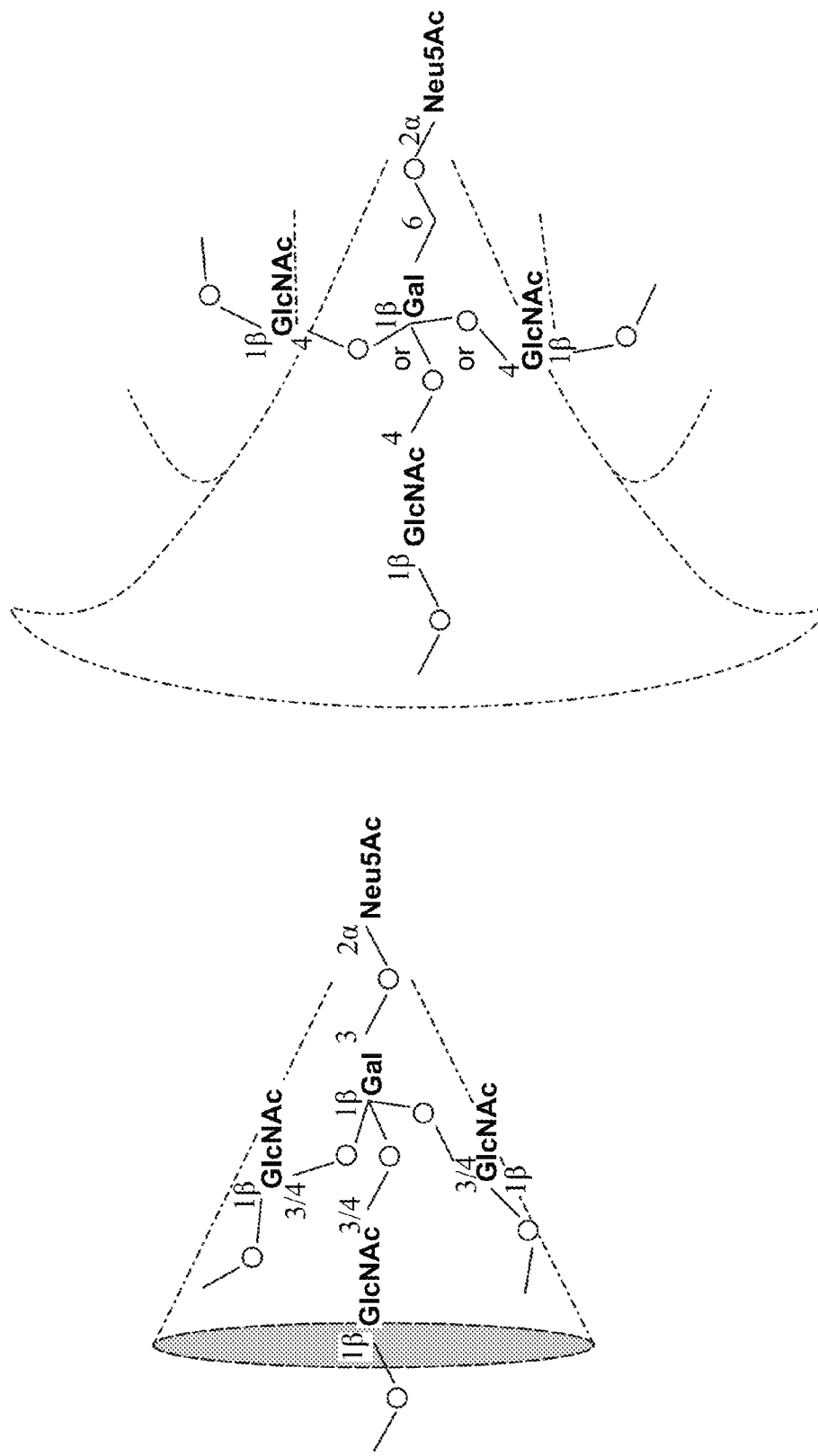
Figures 1, 5B:
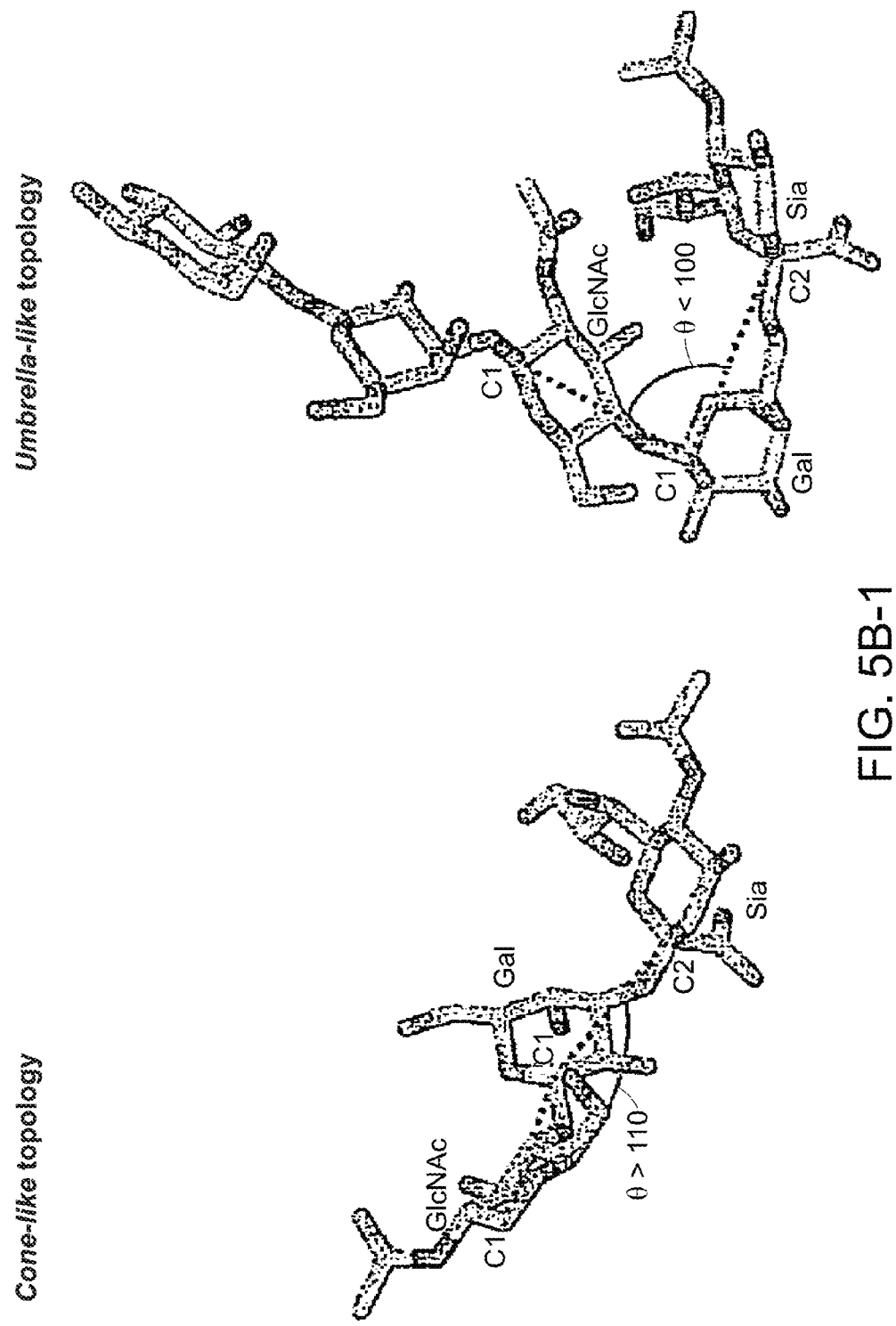
Figures 2, 5B:
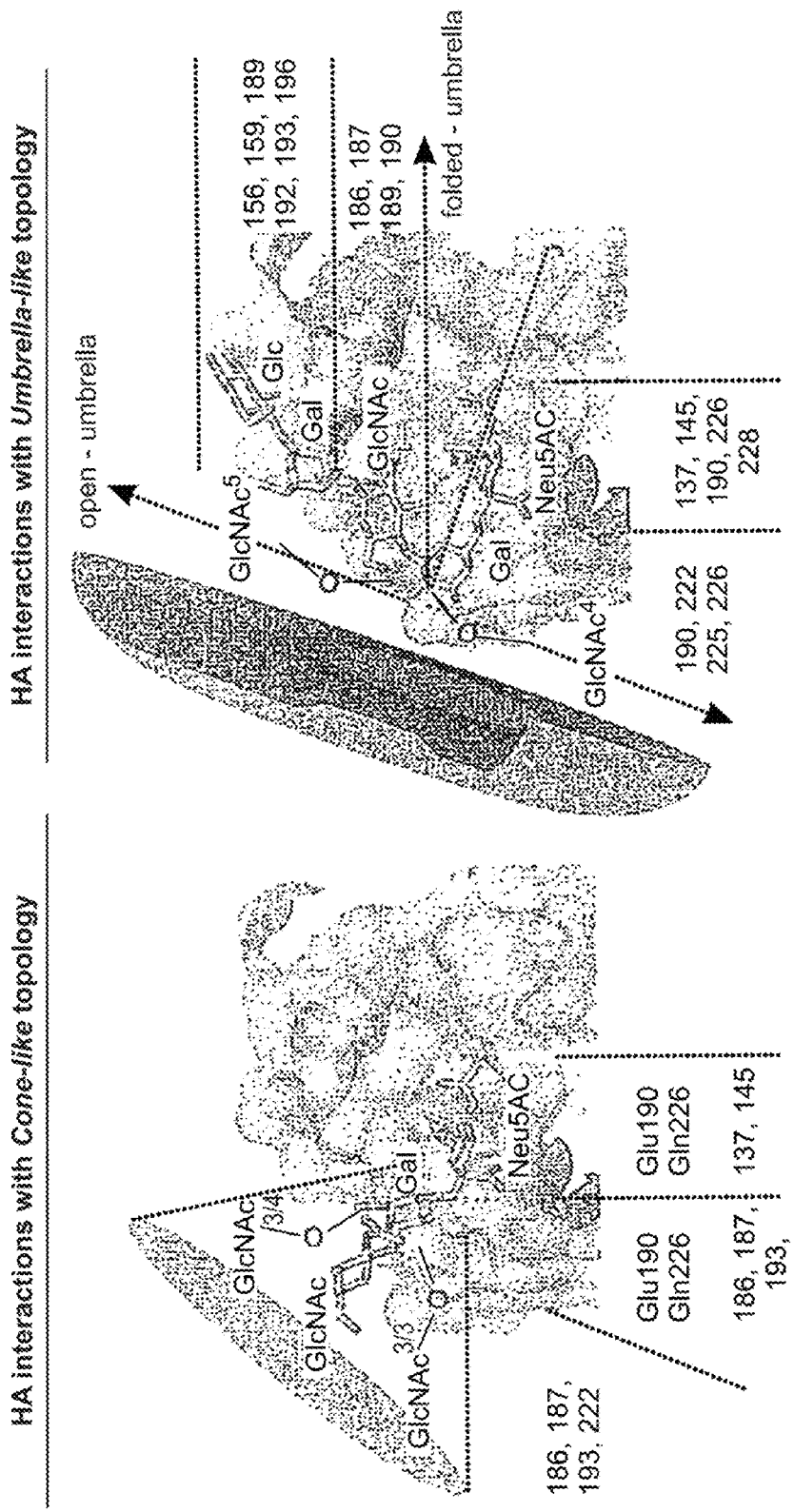
Figures 2, 5C:
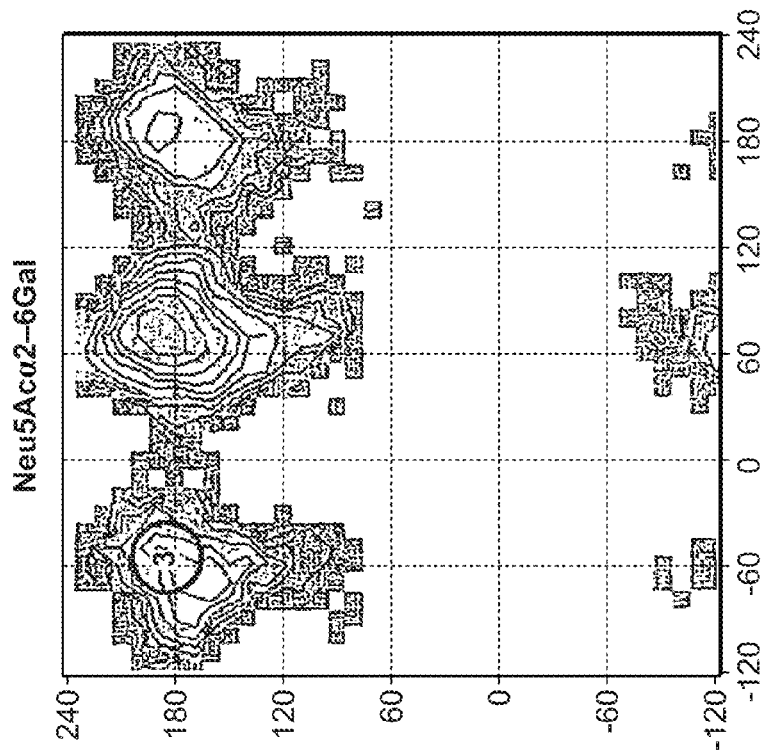
Figures 1, 5C:
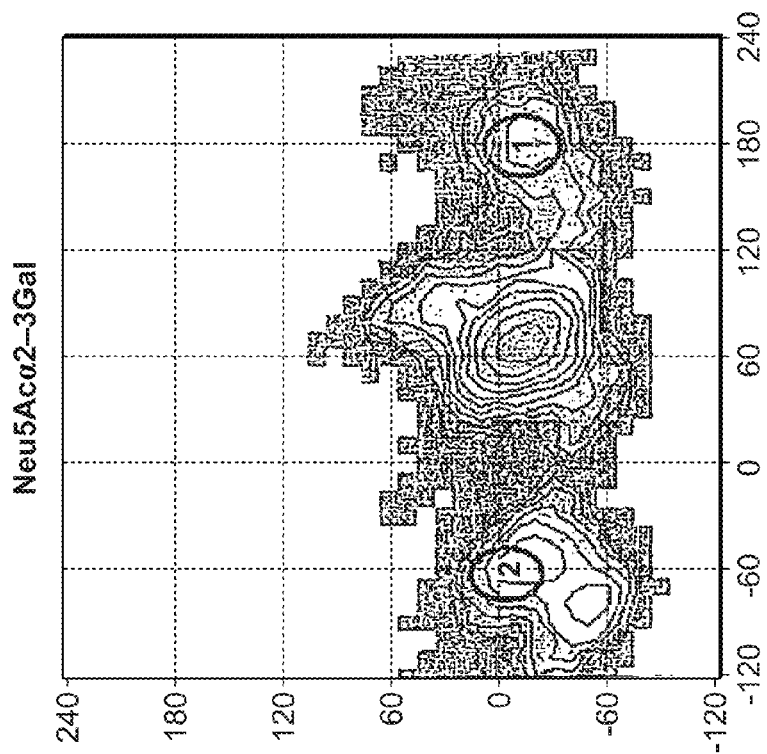
Figures 4, 5C:
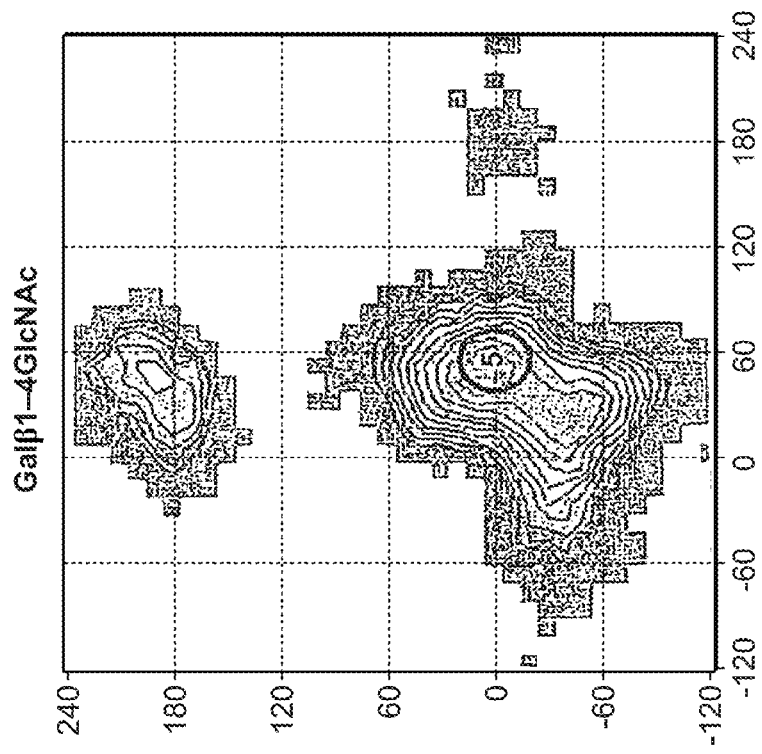
Figures 3, 5C:
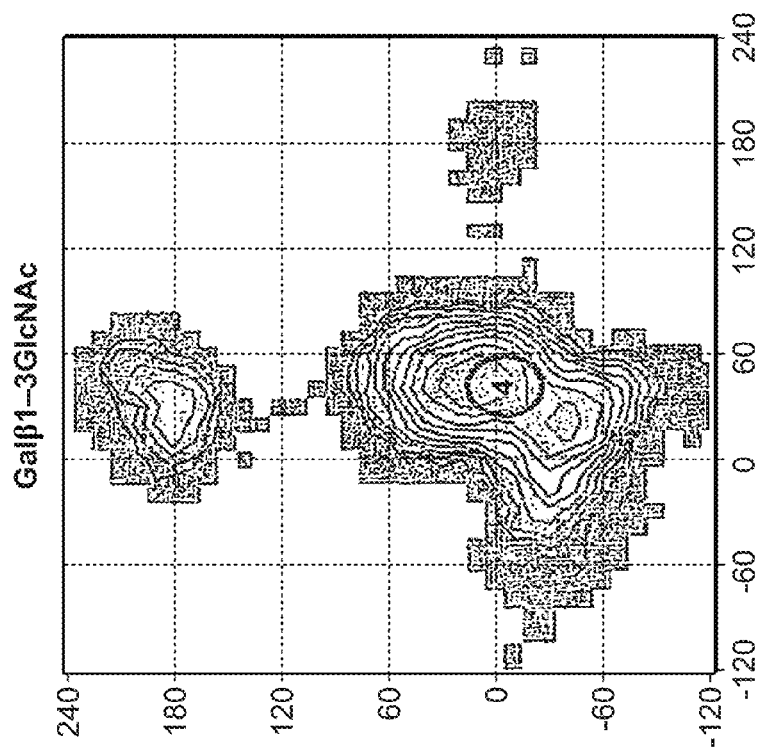

In some embodiments, and particularly in H1 polypeptides, HA Sequence Element 1 includes the sequence:

QLSSISSFEK, typically within X$_1$, (including within X$_{1A}$) and especially beginning about residue 12 of X$_1$ (as illustrated, for example, in FIGS. 1-3).

In some embodiments, and particularly in H3 polypeptides, X$_1$ is about 39 amino acids long, and/or X$_2$ is about 13 amino acids long, and/or X$_3$ is about 26 amino acids long.

In some embodiments, and particularly in H3 polypeptides, HA Sequence Element 1 has the structure:

CYPX$_{1A}$S(S/N)(A/S)CX$_2$WX$_3$WX$_4$HHP, wherein:

X$_{1A}$ is approximately 27-42, or approximately 32-42, or approximately 32-40, or approximately 23-38, or approximately 28-38, or approximately 28-36, or approximately 28, 29, 30, 31, 32, 33, 34, 35, 36, 37, 38, 39, or 40 amino acids long, and X$_2$-X$_4$ are as above.

In some embodiments, and particularly in H3 polypeptides, HA Sequence Element 1 has the structure:

CYPX$_{1A}$S(S/N)(A/S)CX$_2$WL(T/H)X$_{3A}$WX$_4$HHP,
wherein:

X$_{1A}$ is approximately 27-42, or approximately 32-42, or approximately 32-40, or approximately 32, 33, 34, 35, 36, 37, 38, 39, or 40 amino acids long,
X$_{3A}$ is approximately 23-28, or approximately 24-26, or approximately 24, 25, or 26 amino acids long, and X$_2$ and X$_4$ are as above.

In some embodiments, and particularly in H3 polypeptides, HA Sequence Element 1 includes the sequence:

(L/I)(V/I)ASSGTLEF, typically within X$_1$ (including within X$_{1A}$), and especially beginning about residue 12 of X$_1$ (as illustrated, for example, in FIGS. 1 and 2).

In some embodiments, and particularly in H5 polypeptides, $X_1$ is about 42 amino acids long, and/or $X_2$ is about 13 amino acids long, and/or $X_3$ is about 26 amino acids long.

In some embodiments, and particularly in H5 polypeptides, HA Sequence Element 1 has the structure:

CYPX$_{1A}$SSACX$_2$WX$_3$WX$_4$HHP, wherein:

$X_{1A}$ is approximately 27-42, or approximately 32-42, or approximately 32-40, or approximately 23-38, or approximately 28-38, or approximately 28-36, or approximately 28, 29, 30, 31, 32, 33, 34, 35, 36, 37, 38, 39, or 40 amino acids long, and $X_2$-$X_4$ are as.

In some embodiments, and particularly in H5 polypeptides, HA Sequence Element 1 has the structure:

CYPX$_{1A}$SSACX$_2$WLIX$_{3A}$WX$_4$HHP, wherein:

$X_{1A}$ is approximately 27-42, or approximately 32-42, or approximately 32-40, or approximately 32, 33, 34, 35, 36, 37, 38, 39, or 40 amino acids long, and $X_{3A}$ is approximately 23-28, or approximately 24-26, or approximately 24, 25, or 26 amino acids long, and $X_2$ and $X_4$ are as above.

In some embodiments, and particularly in H5 polypeptides, HA Sequence Element 1 is extended (i.e., at a position corresponding to residues 186-193) by the sequence:

NDAAEXX(K/R)

In some embodiments, and particularly in H5 polypeptides, HA Sequence Element 1 includes the sequence:

YEELKHLXSXXNHFEK, typically within $X_1$, and especially beginning about residue 6 of $X_1$ (as illustrated, for example, in FIGS. 1 and 2).

HA Sequence Element 2

HA Sequence Element 2 is a sequence element corresponding approximately to residues 324-340 (again using a numbering system based on H3 HA) of many HA proteins found in natural influenza isolates. This sequence element has the basic structure:

GAIAGFIE

In some embodiments, HA Sequence Element 2 has the sequence:

PX$_1$GAIAGFIE, wherein:

$X_1$ is approximately 4-14 amino acids long, or about 8-12 amino acids long, or about 12, 11, 10, 9 or 8 amino acids long. In some embodiments, this sequence element provides the HA0 cleavage site, allowing production of HA1 and HA2.

In some embodiments, and particularly in H1 polypeptides, HA Sequence Element 2 has the structure:

P(I/V)QSRX$_{1A}$GAIAGFIE, wherein:

$X_{1A}$ is approximately 3 amino acids long; in some embodiments, $X_{1A}$ is G (L/I) F.

In some embodiments, and particularly in H3 polypeptides, HA Sequence Element 2 has the structure:

PXKXTRX$_{1A}$GAIAGFIE, wherein:

$X_{1A}$ is approximately 3 amino acids long; in some embodiments, $X_{1A}$ is G (L/I) F.

In some embodiments, and particularly in H5 polypeptides, HA Sequence Element 2 has the structure:

PQRXXXRXXXRX$_{1A}$GAIAGFIE, wherein:

$X_{1A}$ is approximately 3 amino acids long; in some embodiments, $X_{1A}$ is G (L/I) F.

DEFINITIONS

Affinity: As is known in the art, "affinity" is a measure of the tightness with a particular ligand (e.g., an HA polypeptide) binds to its partner (e.g., and HA receptor). In some embodiments, affinity refers to strength of binding of one entity to another. Affinities can be measured in different ways.

Amino acid: As used herein, term "amino acid," in its broadest sense, refers to any compound and/or substance that can be incorporated into a polypeptide chain. In some embodiments, an amino acid has the general structure H$_2$N—C(H)(R)—COOH. In some embodiments, an amino acid is a naturally occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), substitutions, and/or those modified through chemical reactions and/or biosynthetically. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by influenza. In some embodiments, an animal may be a transgenic animal, genetically engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding: It will be understood that the term "binding", as used herein, typically refers to a non-covalent association between or among agents. In many embodiments herein, binding is addressed with respect to particular glycans (e.g., umbrella topology glycans or cone topology glycans). It will be appreciated by those of ordinary skill in the art that such binding may be assessed in any of a variety of contexts. In some embodiments, binding is assessed with respect to free glycans. In some embodiments, binding is assessed with respect to glycans attached (e.g., covalently linked to) a carrier. In some such embodiments, the carrier is a polypeptide. In some embodiments, binding is assessed with respect to glycans attached to an HA receptor. In such embodiments, reference may be made to receptor binding or to glycan binding. In some embodiments, binding is specific in that a binding agent discriminates between its target binding partner and other potential binding partners in its environment.

Binding agent: In general, the term "binding agent" is used herein to refer to any entity that binds to an agent of interest. For example, an HA binding agent binds to one or more HA polypeptides (and/or to variants, fragments, and/or characteristic portions thereof), as described herein. Binding agents may be of any chemical type. In some embodiments, binding agents are polypeptides (including, e.g., antibodies or antibody fragments). In some embodiments, binding agents are small molecules. In some embodiments, binding agents are nucleic acids. In some embodiments, binding agents are aptamers. In some embodiments, binding agents are polymers; in some embodiments, binding agents are non-polymeric. In some embodiments, binding agents are carbohydrates. In some embodiments, binding agents are lectins. In some embodiments, H1 HA binding agents bind to H1 HA polypeptides. In some embodiments, binding agents bind to H1 HA polypeptide variants with enhanced human binding and/or infectivity. In some embodiments, a binding agent provided herein is an umbrella topology blocking agent. In some embodiments, a binding agent provided herein is an umbrella topology specific blocking agent.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, 10, 15, 20 or more amino acids are required to be characteristic of a protein. In general, a characteristic portion is one that, in addition to the sequence identity specified above, shares at least one functional characteristic with the relevant intact protein.

Characteristic sequence: A "characteristic sequence" is a sequence that is found in all members of a family of polypeptides or nucleic acids, and therefore can be used by those of ordinary skill in the art to define members of the family.

Figure 8A:
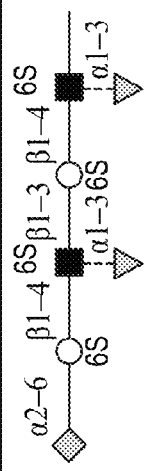
Figures 2, 8A:
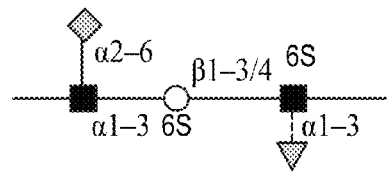
Figures 5, 8A:
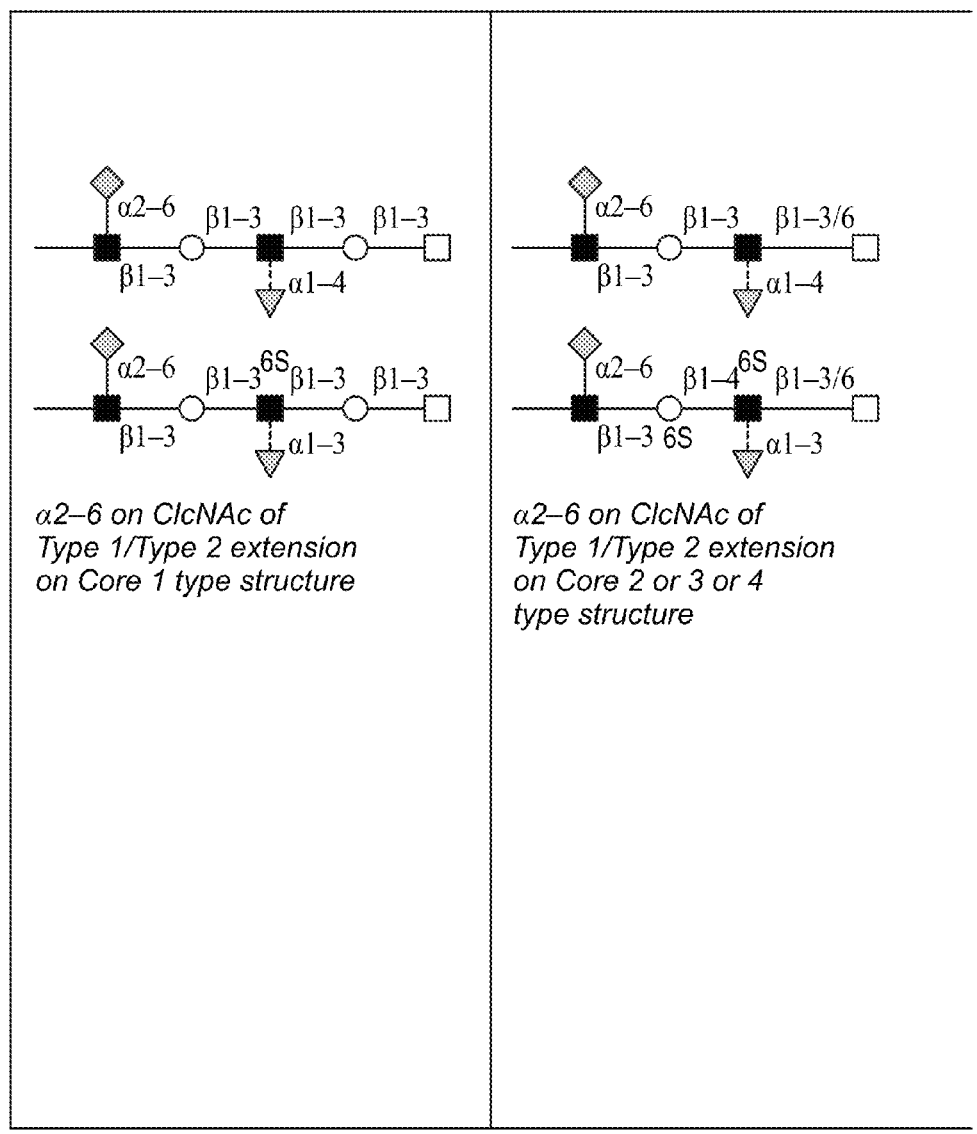
Figures 6, 8A:
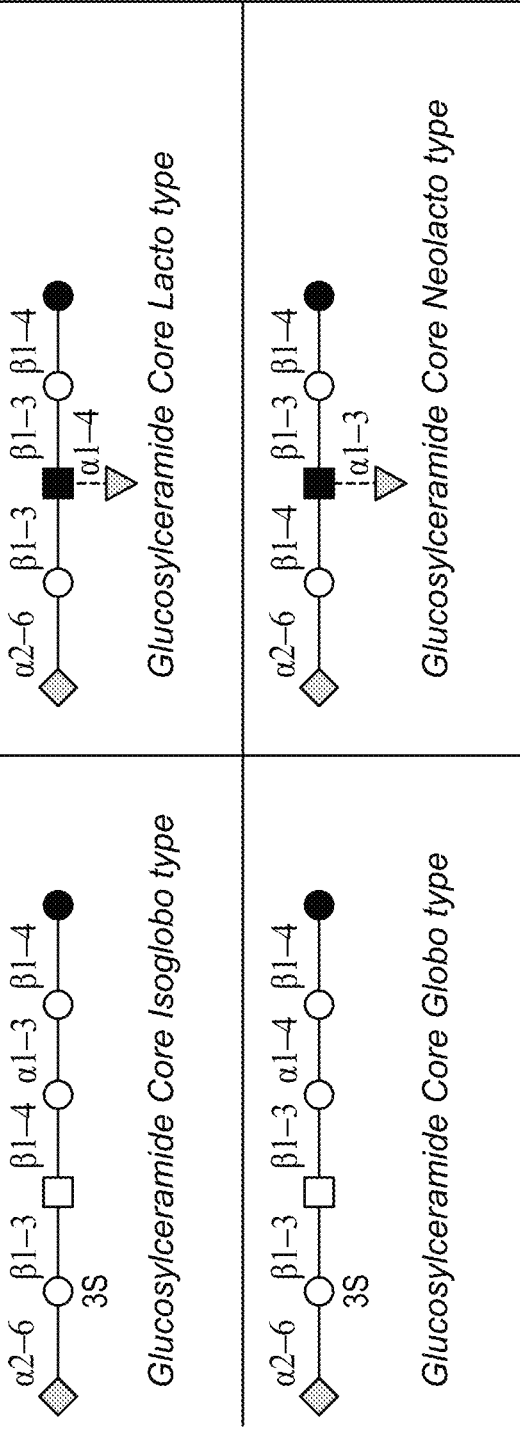
Figure 8A:
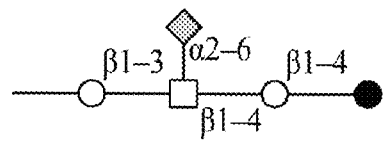
Figure 7:
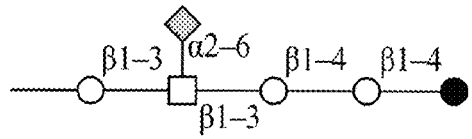
Figure 8B:
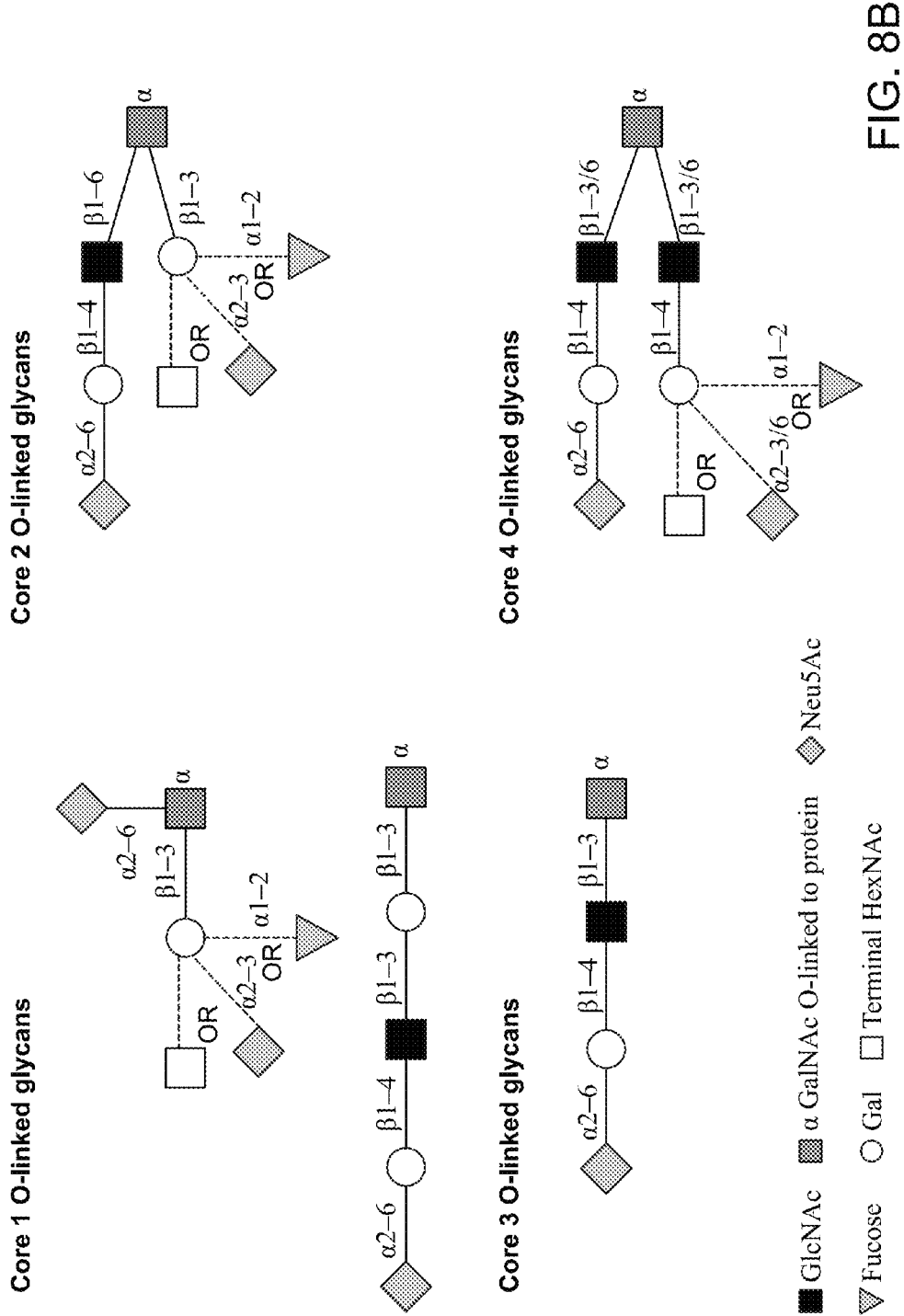

Cone topology: The phrase "cone topology" is used herein to refer to a 3-dimensional arrangement adopted by certain glycans and in particular by glycans on HA receptors. As illustrated in FIGS. 5 and 7, cone topology can be adopted by α2-3 sialylated glycans or by α2-6 sialylated glycans, and is typical of short oligonucleotide chains, though some long oligonucleotides can also adopt this conformation. The cone topology is characterized by the glycosidic torsion angles of Neu5Acα2-3Gal linkage which samples three regions of minimum energy conformations given by $\phi$ (C1-C2-O—C3/C6) value of around −60, 60 or 180 and $\psi$ (C2-O—C3/C6-H3/C5) samples −60 to 60. FIG. 7 presents certain representative (though not exhaustive) examples of glycans that adopt a cone topology.

Corresponding to: As used herein, the term "corresponding to" is often used to designate the position/identity of an amino acid residue in an HA polypeptide. Those of ordinary skill will appreciate that, for purposes of simplicity, a canonical numbering system (based on wild type H3 HA) is utilized herein (as illustrated, for example, in FIGS. 1-4), so that an amino acid "corresponding to" a residue at position 190, for example, need not actually be the $190^{th}$ amino acid in a particular amino acid chain but rather corresponds to the residue found at 190 in wild type H3 HA; those of ordinary skill in the art readily appreciate how to identify corresponding amino acids.

Degree of separation removed: As used herein, amino acids that are a "degree of separation removed" are HA amino acids that have indirect effects on glycan binding. For example, one-degree-of-separation-removed amino acids may either: (1) interact with the direct-binding amino acids; and/or (2) otherwise affect the ability of direct-binding amino acids to interact with glycan that is associated with host cell HA receptors; such one-degree-of-separation-removed amino acids may or may not directly bind to glycan themselves. Two-degree-of-separation-removed amino acids either (1) interact with one-degree-of-separation-removed amino acids; and/or (2) otherwise affect the ability of the one-degree-of-separation-removed amino acids to interact with direct-binding amino acids, etc.

Direct-binding amino acids: As used herein, the phrase "direct-binding amino acids" refers to HA polypeptide amino acids which interact directly with one or more glycans that is associated with host cell HA receptors.

Engineered: The term "engineered", as used herein, describes a polypeptide whose amino acid sequence has been selected by man. For example, an engineered HA polypeptide has an amino acid sequence that differs from the amino acid sequences of HA polypeptides found in natural influenza isolates. In some embodiments, an engineered HA polypeptide has an amino acid sequence that differs from the amino acid sequence of HA polypeptides included in the NCBI database.

Enhanced human binding and/or infectivity variant HA: As used herein, the phrase "enhanced human binding and/or infectivity variant HA" refers to a version of an HA polypeptide (e.g., of an H1 HA polypeptide) that binds to HA receptors found in human epithelial tissues, and particularly to human HA receptors having α2-6 sialylated glycans. In some embodiments, enhanced human binding and/or infectivity variant HAs bind to umbrella topology glycans. In some embodiments, enhanced human binding and/or infectivity variant HAs bind α2-6 sialylated glycans. In some embodiments, enhanced human binding and/or infectivity variant HAs bind long α2-6 sialylated glycans. In some embodiments, enhanced human binding and/or infectivity variant HAs bind 6'SLN-LN glycans. In some embodiments, "enhanced human binding" means that, for example, a variant HA polypeptide shows increased binding relative to that observed with its cognate wild type HA polypeptide (e.g., a control H1 HA polypeptide strain, such as those provided in Table 1). In some embodiments, "enhanced human binding" means that, for example, a variant HA polypeptide shows at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, at least 500-fold, or at least 1000-fold increased binding relative to that observed with its cognate wild type HA polypeptide (e.g., a control H1 HA polypeptide strain, such as those provided in Table 1). In some embodiments, "enhanced infectivity" means that, for example, influenza having a variant HA polypeptide shows increased infectivity of a subject relative to that observed with its cognate wild type HA polypeptide (e.g., a control H1 HA polypeptide strain, such as those provided in Table 1). In some embodiments, "enhanced infectivity" means that, for example, influenza having a variant HA polypeptide shows at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, at least 500-fold, or at least 1000-fold increased infectivity of a subject relative to that observed with its cognate wild type HA polypeptide (e.g., a control H1 HA polypeptide strain, such as those provided in Table 1). In some embodiments, "enhanced human binding" means that, relative to that observed with its cognate wild type HA polypeptide (e.g., a control H1 HA polypeptide strain, such as those provided in Table 1), a variant H1 HA polypeptide shows binding that is increased to substantially the same degree as H1 HA present in one or more of influenza strains A/South Carolina/1/1918, 2009 A/H1N1 (e.g., A/CA/4/2009), and A/Swine/Iowa/15/1930. In some embodiments, "enhanced infectivity" means that, relative to that observed with its cognate wild type HA polypeptide (e.g., a control H1 HA polypeptide strain, such as those provided in Table 1), influenza having a variant H1 HA polypeptide shows infectivity that is increased to substantially the same degree as H1 HA present in one or more of influenza strains A/South Carolina/1/1918, 2009 A/H1N1 (e.g., A/CA/4/2009), and A/Swine/Iowa/15/1930. In general, an enhanced human binding H1 HA polypeptide as described herein shows enhanced binding to umbrella-topology glycans (e.g., at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, at least 500-fold, or at least 1000-fold enhanced binding) and/or enhanced discrimination in binding to umbrella-topology glycans as compared with cone-topology glycans (e.g., at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, at least 500-fold, or at least 1000-fold enhanced binding) as compared with an H1 HA polypeptide found in 2009 A/H1N1 (see, e.g., Table 1). In some embodiments, an enhanced human binding H1 HA shows increased binding to α2-6 sialylated, e.g., long α-2-6 sialylated, e.g., 6'SLN-LN glycans, as compared with an H1 HA polypeptide found in 2009 A/H1N1 (see, e.g., Table 1). As will be appreciated by those of ordinary skill in the art, such enhanced binding and/or infectivity may be assessed using any of a variety of assays including, for example, those described herein.

H1 polypeptide: An "H1 polypeptide", as that term is used herein, is an HA polypeptide whose amino acid sequence includes at least one sequence element that is characteristic of H1 and distinguishes H1 from other HA subtypes. Representative such sequence elements can be determined by alignments such as, for example, those illustrated in FIGS. 1-4 and include, for example, those described herein with regard to H1-specific embodiments of HA Sequence Elements.

H3 polypeptide: An "H3 polypeptide", as that term is used herein, is an HA polypeptide whose amino acid sequence includes at least one sequence element that is characteristic of H3 and distinguishes H3 from other HA subtypes. Representative such sequence elements can be determined by alignments such as, for example, those illustrated in FIGS. 1 and 2 and include, for example, those described herein with regard to H3-specific embodiments of HA Sequence Elements.

H5 polypeptide: An "H5 polypeptide", as that term is used herein, is an HA polypeptide whose amino acid sequence includes at least one sequence element that is characteristic of H5 and distinguishes H5 from other HA subtypes. Representative such sequence elements can be determined by alignments such as, for example, those illustrated in FIGS. 1 and 2 and include, for example, those described herein with regard to H5-specific embodiments of HA Sequence Elements.

Hemagglutinin (HA) polypeptide: As used herein, the term "hemagglutinin polypeptide" (or "HA polypeptide') refers to a polypeptide whose amino acid sequence includes at least one characteristic sequence of HA. A wide variety of HA sequences from influenza isolates are known in the art; indeed, the National Center for Biotechnology Information (NCBI) maintains a database (www.ncbi.nlm.nih.gov/genomes/FLU/flu.html) that, as of the filing of the present application included 9796 HA sequences. Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides); or of HAs that mediate infection of particular hosts, e.g., avian, camel, canine, cat, civet, environment, equine, human, leopard, mink, mouse, seal, stone martin, swine, tiger, whale, etc. For example, in some embodiments, an HA polypeptide includes one or more characteristic sequence elements found between about residues 97 and 185, 324 and 340, 96 and 100, and/or 130-230 of an HA protein found in a natural isolate of an influenza virus. In some embodiments, an HA polypeptide has an amino acid sequence comprising at least one of HA Sequence Elements 1 and 2, as defined herein. In some embodiments, an HA polypeptide has an amino acid sequence comprising HA Sequence Elements 1 and 2, in some embodiments separated from one another by about 100 to about 200, or by about 125 to about 175, or about 125 to about 160, or about 125 to about 150, or about 129 to about 139, or about 129, about 130, about 131, about 132, about 133, about 134, about 135, about 136, about 137, about 138, or about 139 amino acids. In some embodiments, an HA polypeptide has an amino acid sequence that includes residues at positions within the regions 96-100 and/or 130-230 that participate in glycan binding. For example, many HA polypeptides include one or more of the following residues: Tyr98, Ser/Thr136, Trp153, His183, and Leu/Ile194. In some embodiments, an HA polypeptide includes at least 2, at least 3, at least 4, or at least all 5 of these residues.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Interfering agent: As used herein, the term "interfering agent" refers to any entity that binds to a designated target (e.g., to a particular HA polypeptide and/or to particular glycans, such as umbrella-topology glycans) as described herein. Interfering agents may be of any chemical type. In some embodiments, interfering agents are polypeptides (including, e.g., antibodies or antibody fragments); in some such embodiments, interfering agents are HA polypeptides; in other embodiments, interfering agents are polypeptides whose amino acid sequence does not include an HA characteristic sequence (i.e., "non-HA polypeptides"). In some embodiments, interfering agents are small molecules. In some embodiments, interfering agents are nucleic acids. In some embodiments, interfering agents are aptamers. In some embodiments, interfering agents are polymers; in some embodiments, interfering agents are non-polymeric. In some embodiments, interfering agents are carbohydrates. In some embodiments, interfering agents are lectins. In some embodiments, interfering agents as described herein bind to one or more HA polypeptides. In some embodiments, interfering agents bind to H1 HA polypeptides. In some embodiments, interfering agents bind to H1 HA polypeptide variants having enhanced human binding and/or infectivity. In some embodiments, interfering agents as described herein bind to sialylated glycans having an umbrella-like topology. In certain embodiments, interfering agents bind to umbrella-topology glycans with high affinity and/or specificity. In some embodiments, interfering agents show a binding preference for umbrella-topology glycans as compared with cone-topology glycans. In some embodiments, interfering agents compete with hemagglutinin for binding to glycans on hemagglutinin receptors. In some embodiments, interfering agents compete with hemagglutinin for binding to umbrella-topology glycans. In some embodiments, an interfering agent provided herein is an umbrella topology blocking agent. In some embodiments, an interfering agent provided herein is an umbrella topology specific blocking agent. In some embodiments, interfering agents bind to umbrella topology glycan mimics.

Isolated: The term "isolated", as used herein, refers to an agent or entity that has either (i) been separated from at least some of the components with which it was associated when initially produced (whether in nature or in an experimental setting); or (ii) produced by the hand of man. Isolated agents or entities may be separated from at least about 10%, about 20%, about 30%, about 40%, about 50%, about 60%, about 70%, about 80%, about 90%, or more of the other components with which they were initially associated. In some embodiments, isolated agents are more than 90%, 91%, 92%, 93%, 94%, 95%, 96%, 97%, 98%, 99% pure. In some embodiments, calculation of percent purity of isolated substances and/or entities does not include excipients (e.g., buffer, solvent, water, etc.)

Linkage Specific Blocking Agent (LSBA): As used herein, the term "linkage specific blocking agent" refers to an agent which binds to an HA receptor having an α2-6 sialylated glycan. In some embodiments, an LSBA selectively binds to an HA receptor having an α2-6 sialylated glycan with at least about 40, about 50, or about 75% of the affinity of that for an HA receptor having an α2-3 sialylated glycan. In some embodiments, an LSBA selectively binds to an HA receptor having an α2-6 sialylated glycan with at least about 2, about 4, about 5, or about 10 times greater affinity than that for an HA receptor having an α2-3 sialylated glycan. In some embodiments, an LSBA has an affinity for an α2-6 sialylated glycan that is at least 50, 100, 150, or 200% of its affinity for an α2-3 sialylated glycan. In some embodiments, an LSBA may compete with hemagglutinin for binding to an HA receptor. For example, an LSBA may selectively inhibit the binding of an influenza virus particle (e.g., human or avian influenza virus) to an HA receptor based on the linkage characteristics (e.g., α2-6 sialylated glycan or α2-3 sialylated glycan). In some embodiments, an LSBA is a polypeptide. In some such embodiments, an LSBA polypeptide has an amino acid sequence that is substantially identical or substantially homologous to that of a naturally-occurring polypeptide. In some embodiments, an LSBA polypeptide is an HA polypeptide. In some embodiments, an LSBA polypeptide is a naturally-occurring HA polypeptide, or a fragment thereof. In some embodiments, an LSBA polypeptide has an amino acid sequence that is not related to that of an HA polypeptide. In some embodiments, an LSBA polypeptide is an antibody or fragment thereof. In some embodiments, an LSBA polypeptide is a lectin (e.g., SNA-1). In some embodiments, an LSBA is not a polypeptide. In some embodiments, an LSBA is a small molecule. In some embodiments, an LSBA is a nucleic acid.

Long oligosaccharide: For purposes of the present disclosure, an oligosaccharide is typically considered to be "long" if it includes at least one linear chain that has at least four saccharide residues.

Non-natural amino acid: The phrase "non-natural amino acid" refers to an entity having the chemical structure of an amino acid (i.e.:

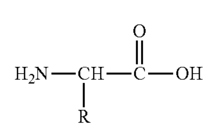

and therefore being capable of participating in at least two peptide bonds, but having an R group that differs from those found in nature. In some embodiments, non-natural amino acids may also have a second R group rather than a hydrogen, and/or may have one or more other substitutions on the amino or carboxylic acid moieties.

Polypeptide: A "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Preferentially: As used herein, a first entity "preferentially" binds to second entity as compared to a reference entity if the first entity demonstrates enhanced binding to the second entity than the reference entity. In some embodiments, a first entity will bind to a second entity with a binding affinity that is about 1.5-fold, about 2-fold, about 3-fold, about 4-fold, about 5-fold, about 6-fold, about 7-fold, about 8-fold, about 9-fold, about 10-fold, about 20-fold, about 50-fold, about 100-fold, about 500-fold, or about 1000-fold that of the reference entity.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, 92%, 93%, 94%, 95%, 96%, 97%, 98%, or 99% pure.

Short oligosaccharide: For purposes of the present disclosure, an oligosaccharide is typically considered to be "short" if it has fewer than 4, or certainly fewer than 3, residues in any linear chain.

Specificity: As is known in the art, "specificity" is a measure of the ability of a particular ligand (e.g., an HA polypeptide) to distinguish its binding partner (e.g., a human HA receptor, and particularly a human upper respiratory tract HA receptor) from other potential binding partners (e.g., an avian HA receptor).

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| | | | | | |
|---|---|---|---|---|---|
| Alanine | Ala | A | nonpolar | Neutral | 1.8 |
| Arginine | Arg | R | polar | Positive | −4.5 |
| Asparagine | Asn | N | polar | Neutral | −3.5 |
| Aspartic acid | Asp | D | polar | Negative | −3.5 |
| Cysteine | Cys | C | nonpolar | Neutral | 2.5 |
| Glutamic acid | Glu | E | polar | Negative | −3.5 |
| Glutamine | Gln | Q | polar | Neutral | −3.5 |
| Glycine | Gly | G | nonpolar | Neutral | −0.4 |
| Histidine | His | H | polar | Positive | −3.2 |
| Isoleucine | Ile | I | nonpolar | Neutral | 4.5 |
| Leucine | Leu | L | nonpolar | Neutral | 3.8 |
| Lysine | Lys | K | polar | Positive | −3.9 |
| Methionine | Met | M | nonpolar | Neutral | 1.9 |
| Phenylalanine | Phe | F | nonpolar | Neutral | 2.8 |
| Proline | Pro | P | nonpolar | Neutral | −1.6 |
| Serine | Ser | S | polar | Neutral | −0.8 |
| Threonine | Thr | T | polar | Neutral | −0.7 |
| Tryptophan | Trp | W | nonpolar | Neutral | −0.9 |
| Tyrosine | Tyr | Y | polar | Neutral | −1.3 |
| Valine | Val | V | nonpolar | Neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology*; Altschul, et al., "Gapped BLAST and PSI-BLAST: a new generation of protein database search programs," *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999; all of which are incorporated herein by reference. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.,* 215(3): 403-410, 1990; Altschul, et al., *Methods in Enzymology;* Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics*

*Methods and Protocols* (Methods in Molecular Biology, Vol. 132), Humana Press, 1999; all of which are incorporated herein by reference. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, and/or condition (e.g., influenza infection) has been diagnosed with and/or displays one or more symptoms of a disease, disorder, and/or condition.

Susceptible to: An individual who is "susceptible to" a disease, disorder, and/or condition (e.g., influenza infection) has not been diagnosed with a disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of and/or reduce incidence of one or more symptoms or features of influenza infection.

Therapeutically effective amount: As used herein, the term "therapeutically effective amount" means an amount of inventive composition that is sufficient, when administered to a subject suffering from or susceptible to a disease, disorder, and/or condition (e.g., influenza infection), to treat, diagnose, prevent, and/or delay the onset of the disease, disorder, and/or condition.

Treatment: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition (e.g., influenza infection). Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

Umbrella topology: The phrase "umbrella topology" is used herein to refer to a 3-dimensional arrangement adopted by certain glycans and in particular by glycans bound to HA receptors. The present invention encompasses the recognition that binding to umbrella topology glycans is characteristic of HA proteins that mediate infection of human hosts. As illustrated in FIG. 5, the umbrella topology is typically adopted only by α2-6 sialylated glycans, and is typical of long (e.g., greater than tetrasaccharide) oligosaccharides. In some embodiments, umbrella-topology glycans are glycans exhibiting a three-dimensional structure substantially similar to the structure presented in FIG. 5A (right panel). In some embodiments, umbrella-topology glycans are glycans which contact HA polypeptides via the amino acid residues shown in FIG. 5B-2 (right panel) and FIG. 6 (right panel). In some embodiments, umbrella-topology glycans are glycans which are able to contact and/or specifically bind to the amino acid binding pocket shown in FIG. 5B-2 (right panel). In some embodiments, glycan structural topology is classified based on parameter θ defined as angle between $C_2$ of Sia, $C_1$ of Gal, and $C_1$ of GlcNAc. Values of θ<100° represent cone-like topology adopted by α2-3 and short α2-6 glycans. Values of θ>110° represent umbrella-like topology, such as topology adopted by long α2-6 glycans (FIG. 6). An example of umbrella topology is given by ϕ angle of Neu5Acα2-6Gal linkage of around −60. FIG. 8 presents certain representative (though not exhaustive) examples of glycans that can adopt an umbrella topology. The long α2-6 motifs presented in FIG. 8 include Neu5Acα2-6 linked at the non-reducing end to a long chain (e.g., at least a trisaccharide) found as a part of biological N-linked glycans, O-linked glycans, and glycolipids. The boxed inset shows examples of the umbrella-topology long α2-6 glycan moieties that are found as a part of biological glycans that bind to high affinity with HA. In some embodiments, umbrella-topology glycans (e.g., at a site) comprise a greater proportion of long (e.g., multiple lactosamine units) α2-6 oligosaccharide branches than short α2-6 (e.g., single lactosamine) branches. In some embodiments, umbrella-topology glycans (e.g., at a site) comprise about 2-fold, about 3-fold, about 4-fold, about 5-fold, about 10-fold, about 20-fold, about 50-fold, or greater than about 50-fold more long α2-6 oligosaccharide branches than short α2-6 (e.g., single lactosamine) branches. In certain embodiments, the unique characteristic of HA interactions with umbrella-topology glycans and/or glycan decoys is the HA contact with a glycan comprising sialic acid (SA) and/or SA analogs at the non-reducing end. In some embodiments, chain length of the oligosaccharide is at least a trisaccharide (excluding the SA or SA analog). In some embodiments, a combination of the numbered residues shown in FIGS. 5A and 5B-2 (right-hand panels) is involved in contacts with umbrella-like topology. In certain embodiments, umbrella topology glycans are oligosaccharides of the following form:

Neu5Acα2-6Sug1-Sug2-Sug3 where:

(a) Neu5Ac α2-6 is typically (but not essentially) at the non-reducing end;

(b) Sug1:

(i) is a hexose (frequently Gal or Glc) or hexosamine (GlcNAc or GalNAc) in α or β configuration (frequently β- for N- and O-linked extension and α- in the case of GalNAcα- that is O-linked to glycoprotein);

(ii) no sugars other than Neu5Acα2-6 are attached to any of the non-reducing positions of Sug1 (except when Sug1 is GalNAcα- that is O-linked to the glycoprotein); and/or (iii) non-sugar moieties such as sulfate, phosphate, guanidium, amine, N-acetyl, etc. can be attached to non-reducing positions (typically 6 position) of Sug1 (e.g., to improve contacts with HA);

(c) Sug2 and/or Sug3 is/are:
(i) hexose (frequently Gal or Glc) or hexosamine (GlcNAc or GalNAc) in α or ρ configuration (frequently β); and/or
(ii) sugars (such as Fuc) or non-sugar moieties such as sulfate, phosphate, guanidium, amine, N-acetyl, etc. can be attached to non-reducing positions of Sug2, Sug3, and/or Sug4;
(d) Linkage between any two sugars in the oligosaccharide apart from Neu5Acα2-6 linkage can be 1-2, 1-3, 1-4, and/or 1-6 (typically 1-3 or 1-4); and/or
(e) Structure where Neu5Acα2-6 is linked GalNAcα that is O-linked to the glycoprotein and additional sugars are linked to the non-reducing end of GalNAcα for example
(i) Neu5Acα2-6(Neu5Acα2-3Galβ1-3)GalNAcα-
(ii) Neu5Acα2-6(Galβ1-3)GalNAcα-

Umbrella topology blocking agent (UTBA): As used herein, the term "umbrella topology blocking agent" refers to an agent which binds to an HA receptor having an umbrella topology glycan. In some embodiments, a UTBA binds to an HA receptor having an umbrella topology glycan found in human upper airways. A UBTA can bind to either an umbrella topology glycan and/or to a cone topology glycan. In some embodiments, a UTBA selectively binds to an umbrella topology glycan with 50, 100, 150, or 200% of its affinity for a cone topology glycan. In some embodiments a UTBA selectively binds to an umbrella topology glycan with 50-150% of its affinity for a cone topology glycan. In some embodiments, a UTBA binds to an umbrella topology glycan with about the same affinity as for a cone topology glycan. For example, in some embodiments, a UTBA binds an umbrella topology glycan (e.g., 6'SLN-LN) with about 50-200%, 50-150%, or about the same affinity to which it binds a cone topology glycan (e.g., 3' SLN-LN). In some embodiments, a UTBA selectively inhibits the binding of an influenza virus particle (e.g., a human or avian influenza virus) to the HA receptor based on the glycan topology of the receptor (e.g., umbrella or cone). In some embodiments, a UTBA is a polypeptide. In some such embodiments, a UTBA polypeptide has an amino acid sequence that is substantially identical or substantially homologous to that of a naturally-occurring polypeptide. In some embodiments, a UTBA polypeptide is an HA polypeptide. In some embodiments, a UTBA polypeptide is a naturally-occurring HA polypeptide, or a fragment thereof. In some embodiments, a UTBA polypeptide has an amino acid sequence that is not related to that of an HA polypeptide. In some embodiments, a UTBA polypeptide is an antibody or fragment thereof. In some embodiments, a UTBA polypeptide is a lectin (e.g., SNA-1). In some embodiments, a UTBA is not a polypeptide. In some embodiments, a UTBA is a small molecule. In some embodiments, a UTBA is a nucleic acid.

Umbrella topology glycan mimic: An "umbrella topology glycan mimic" is an agent, other than an umbrella topology glycan, that binds to binding agents as described herein. In some embodiments, umbrella topology glycan mimics are agents that bind to HA polypeptides. In some such embodiments, umbrella topology glycan mimics are agents that interact with HA polypeptide residues selected from the group consisting of residues 136, 137, 145, 153, 155, 156, 159, 186, 187, 189, 190, 192, 193, 194, 196, 222, 225, 226, 228 and combinations thereof. In some such embodiments, umbrella topology glycan mimics are agents that interact with HA polypeptide residues selected from the group consisting of residues. In some such embodiments, umbrella topology glycan mimics are agents that interact with HA polypeptide residues selected from the group consisting of residues 156, 159, 189, 192, 193, 196, and combinations thereof. In some such embodiments, umbrella topology glycan mimics are agents that interact with HA polypeptide residues selected from the group consisting of residues 186, 187, 189, 190, and combinations thereof. In some such embodiments, umbrella topology glycan mimics are agents that interact with HA polypeptide residues selected from the group consisting of residues 137, 145, 190, 226, 228, and combinations thereof. In some such embodiments, umbrella topology glycan mimics are agents that interact with HA polypeptide residues selected from the group consisting of residues 190, 222, 225, 226, and combinations thereof. In some such embodiments, umbrella topology glycan mimics are agents that interact with HA polypeptide residues selected from the group consisting of residues 136, 153, 155, 194, and combinations thereof. In some such embodiments, umbrella topology glycan mimics are agents that interact with HA polypeptide residues selected from the group consisting of residues 190 and 226. In some such embodiments, umbrella topology glycan mimics are agents that interact with HA polypeptide residues selected from the group consisting of residues 222, 225, and 226. In some such embodiments, umbrella topology glycan mimics are agents that interact with HA polypeptide residues selected from the group consisting of residues 190, 192, 193, and 225. In some such embodiments, umbrella topology glycan mimics are agents that interact with HA polypeptide residues selected from the group consisting of residues 186, 193, and 222. Note that amino acid positions stated above are based on H3 HA numbering. In certain embodiments, an HA topology glycan mimic is an agent that competes with umbrella topology glycans for interaction with an HA polypeptide.

Umbrella topology specific blocking agent (UTSBA): As used herein, the term "umbrella topology specific blocking agent" refers to an agent which binds to an HA receptor having an umbrella topology glycan found in human upper airways. A UTSBA selectively binds an umbrella topology glycan HA. For example, a UTSBA binds an umbrella topology glycan (e.g., 6'SLN-LN) with about at least 2, 4, 5, or 10 times greater affinity than it binds to a cone topology glycan (e.g., 3' SLN-LN). Typically, the affinity of a UTSBA for an umbrella topology glycan is greater than 1 nM. Typically the affinity of a UTSBA for a cone topology glycan is less is at least within 2 to 3 orders of magnitude of the binding affinity of umbrella topology glycans to human adapted HAs such as SC18, Mos99, Tx91, etc., and α2-6 binding plant lectins such as SNA-I. The binding affinity of UTSBA as measured by the dose-dependent direct binding assay would typically be at least 1 nM. Typically the affinity of a UTSBA for a cone topology glycan is at most 1 to 3 orders of magnitude less than the binding affinity of cone topology glycans to avian HAs such as Viet0405, Av18, etc. In some embodiments, a UTSBA selectively inhibits binding of an influenza virus particle (e.g., a human or avian influenza virus) to the HA receptor (e.g., an H1, H2 or H3 or a human-adapted H5, H7 or H9) based on glycan topology (e.g., umbrella or cone). In some embodiments, a UTSBA is a polypeptide. In some such embodiments, a UTSBA polypeptide has an amino acid sequence that is that is substantially identical or substantially homologous to that of a naturally-occurring polypeptide. In some embodiments, a UTSBA polypeptide is an HA polypeptide. In some embodiments, a UTSBA polypeptide is a naturally-occurring HA polypeptide, or a fragment thereof. In some embodiments, a UTSBA polypeptide has an amino acid sequence that is not related to that of an HA polypeptide. In some embodiments, a UTSBA polypeptide is an antibody or fragment thereof. In some embodiments, a UTSBA polypeptide is a lectin (e.g., SNA-1). In some embodiments, a UTSBA is not a polypeptide. In some embodiments, a UTSBA is a small molecule. In some embodiments, a UTSBA is a nucleic acid.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Variant: As used herein, the term "variant" is a relative term that describes the relationship between a particular polypeptide (e.g., HA polypeptide) of interest and a "parent" polypeptide to which its sequence is being compared. A polypeptide of interest is considered to be a "variant" of a parent polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, 20, 19, 18, 17, 16, 15, 14, 13, 10, 9, 8, 7, 6, and commonly are fewer than about 5, 4, 3, or 2 residues. In some embodiments, the parent polypeptide is one found in nature. For example, a parent HA polypeptide may be one found in a natural (e.g., wild type) isolate of an influenza virus (e.g., a wild type HA). In some embodiments, an H1 HA parent polypeptide may correspond to the H1 polypeptide characteristic of any of the influenza strains presented in Table 1. In some embodiments, a variant H1 HA polypeptide has at least 1, 2, 3, 4, 5, 6, 7, 8, 9, 10, 15, 20, 50, 100, or more than 100 substitutions, deletions, and/or additions relative to one or more of the H1 polypeptides characteristic of any of the influenza strains presented in Table 1.

Vector: As used herein, "vector" refers to a nucleic acid molecule capable of transporting another nucleic acid to which it has been linked. In some embodiment, vectors are capable of extra-chromosomal replication and/or expression of nucleic acids to which they are linked in a host cell such as a eukaryotic or prokaryotic cell. Vectors capable of directing the expression of operatively linked genes are referred to herein as "expression vectors."

Wild type: As is understood in the art, the phrase "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database, http://www.ncbi.nlm.nih.gov/genomes/FLU/FLU.html.

DETAILED DESCRIPTION OF CERTAIN PARTICULAR EMBODIMENTS OF THE INVENTION

Among other things, the present invention defines H1N1 HA variants with enhanced human binding and/or infectivity as compared with an H1 polypeptide found in H1N1 influenza strains (see, e.g., Table 1). Such variants may be utilized, among other things, as components of vaccines and/or therapeutics to treat, reduce, and/or prevent human infection by and H1N1 virus, and particularly by a variant with enhanced human binding and/or infectivity. Alternatively or additionally, such variants may be utilized as standards in systems for detecting occurrence of and/or infection with an H1N1 variant with enhanced human infectivity.

In some aspects, the present invention provides agents that bind specifically to an H1N1 HA polypeptides, for example for use in detecting H1N1 infection. In some embodiments, the present invention provides agents that bind specifically to an H1N1 variant with enhanced human infectivity. In some embodiments, the present invention provides agents that discriminate between H1N1 variants with enhanced human infectivity and H1N1 variants without enhanced human infectivity.

In some aspects, the present invention provides agents that interfere (and/or compete) with binding interactions between an H1N1 HA polypeptide and one or more glycans, for example umbrella-topology glycans. In some embodiments, the present invention provides agents that interfere (and/or compete with) binding interactions between an H1N1 HA polypeptide and one or more α2-6 sialylated glycans. In some embodiments, the present invention provides agents that interfere (and/or compete) with binding interactions between an H1N1 HA polypeptide and one or more 6'SLN-LN glycans. In some embodiments, the H1N1 HA polypeptide whose binding interaction is interfered with is an H1N1 variant with enhanced human infectivity.

Hemagglutinin (HA)

Influenza viruses are RNA viruses which are characterized by a lipid membrane envelope containing two glycoproteins, hemagglutinin (HA) and neuraminidase (NA), embedded in the membrane of the virus particular. There are 16 known HA subtypes and 9 NA subtypes, and different influenza strains are named based on the number of the strain's HA and NA subtypes. Based on comparisons of amino acid sequence identity and of crystal structures, the HA subtypes have been divided into two main groups and four smaller clades. The different HA subtypes do not necessarily share strong amino acid sequence identity, but the overall 3D structures of the different HA subtypes are similar to one another, with several subtle differences that can be used for classification purposes. For example, the particular orientation of the membrane-distal subdomains in relation to a central α-helix is one structural characteristic commonly used to determine HA subtype (Russell et al., *Virology*, 325:287, 2004).

HA exists in the membrane as a homotrimer of one of 16 subtypes, termed H1-H16. Only three of these subtypes (H1, H2, and H3) have thus far become adapted for human infection. One reported characteristic of HAs that have adapted to infect humans (e.g., of HAs from the pandemic H1N1 (1918) and H3N2 (1967-68) influenza subtypes) is their ability to preferentially bind to α2-6 sialylated glycans in comparison with their avian progenitors that preferentially bind to α2-3 sialylated glycans (Skehel & Wiley, *Annu Rev Biochem*, 69:531, 2000; Rogers, & Paulson, *Virology*, 127:361, 1983; Rogers et al., *Nature*, 304:76, 1983; Sauter et al., *Biochemistry*, 31:9609, 1992; Connor et al., *Virology*, 205:17, 1994; Tumpey et al., *Science*, 310:77, 2005; all of which are incorporated herein by reference). The present inventors, however, have discovered that ability to infect human hosts correlates less with binding to glycans of a particular linkage, and more with binding to glycans of a particular topology (see, e.g., US patent application publications 2009/0269342, 2010/0004195, and 2010/0125043, all of which are incorporated herein by reference). Thus, the present inventors have demonstrated that HAs that mediate infection of humans bind to umbrella topology glycans, often showing preference for umbrella topology glycans over cone topology glycans (even though cone-topology glycans may be or comprise α2-6 sialylated glycans).

Several crystal structures of HAs from H1 (human and swine), H3 (avian) and H5 (avian) subtypes bound to sialylated oligosaccharides (of both α2-3 and α2-6 linkages) are available and provide molecular insights into the specific amino acids that are involved in distinct interactions of the HAs with these glycans (Eisen et al., Virology, 232:19, 1997; Ha et al., Proc Natl Acad Sci USA, 98:11181, 2001; Ha et al., Virology, 309:209, 2003; Gamblin et al., Science, 303:1838, 2004; Stevens et al., Science, 303:1866, 2004; Russell et al., Glycoconj J 23:85, 2006; Stevens et al., Science, 312:404, 2006; all of which are incorporated herein by reference).

For example, the crystal structures of H5 (A/duck/Singapore/3/97) alone or bound to an α2-3 or an α2-6 sialylated oligosaccharide identifies certain amino acids that interact directly with bound glycans, and also amino acids that are one or more degree of separation removed (Stevens et al., Proc Natl Acad Sci USA 98:11181, 2001; incorporated herein by reference). In some cases, conformation of these residues is different in bound versus unbound states. For instance, Glu190, Lys193 and Gln226 all participate in direct-binding interactions and have different conformations in the bound versus the unbound state. The conformation of Asn186, which is proximal to Glu190, is also significantly different in the bound versus the unbound state.

HA Polypeptides

The present invention provides HA polypeptides. As used herein, the term "HA polypeptides" is understood to encompass fragments of HA polypeptides, portions (e.g., characteristic portions) of HA polypeptides, and/or variants of HA polypeptides. HA polypeptide fragments, portions of HA polypeptides, and variant HA polypeptides are described in further detail below, in the subsections below entitled "Portions and/or Fragments of HA Polypeptides" and "Variant HA Polypeptides."

The present invention particularly provides HA H1 polypeptides. As used herein, the term "H1 polypeptides" is understood to encompass fragments of H1 polypeptides, portions (e.g., characteristic portions) of H1 polypeptides, and/or polypeptides that are H1 variants. H1 polypeptide fragments, portions of H1 polypeptides, and H1 variant polypeptides are described in further detail below, in the subsections below entitled "Portions and/or Fragments of HA Polypeptides" and "Variant HA Polypeptides."

In some embodiments, HA polypeptides are isolated HA polypeptides with designated binding characteristics with respect to umbrella topology glycans. In some embodiments, HA polypeptides are engineered HA polypeptides with designated binding characteristics with respect to umbrella topology glycans.

In some embodiments, provided HA polypeptides with designated binding characteristics are H1 polypeptides. In some embodiments, provided HA polypeptides are H1 HA variant polypeptides that show enhanced human binding and/or infectivity as compared with a reference H1 HA polypeptide. In some embodiments, such H1 HA variant polypeptides are engineered. In some embodiments, such H1 HA variant polypeptides are isolated from influenza strains found in the environment. Exemplary H1 HA variant polypeptides with enhanced human binding and/or infectivity include, but are not limited to, H1 HA polypeptides (e.g., fragments thereof and/or characteristic portions thereof) present in influenza strains A/South Carolina/1/1918, 2009 A/H1N1 (e.g., A/CA/4/2009), A/Swine/Iowa/15/1930. In some embodiments, H1 HA variant polypeptides with enhanced human binding and/or infectivity, such as H1 HA polypeptides present in influenza strains A/South Carolina/1/1918, 2009 A/H1N1 (e.g., A/CA/4/2009), and A/Swine/Iowa/15/1930 are engineered to exhibit even more enhanced human binding and/or infectivity. In some embodiments, H1 HA polypeptides with enhanced human binding and/or infectivity specifically exclude H1 polypeptides found in influenza strains A/South Carolina/1/1918, 2009 A/H1N1 (e.g., A/CA/4/2009), A/Swine/Iowa/15/1930.

In some embodiments, reference H1 HA polypeptides include the HA protein from one or more of the strains presented in Table 1. In some embodiments, reference H1 HA polypeptides include any H1 HA found in a 2009 A/H1N1 "swine flu" isolate listed in one or both of the GISAID Influenza portal database (http://platform.gisaid.org/dante-cms/live/struktur.jdante?aid=1131) and/or the NCBI Flu database (http://www.ncbi.nlm.nih.gov/genomes/FLU/FLU.html).

TABLE 1

Sequences of Exemplary H1 HA Polypeptides found in 2009 A/H1N1

| Strain | H1 HA Sequence |
|---|---|
| A/California/04/2009 | MKAILVVLLYTFATANADTLCIGYHANNSTDTVDTVLEKNVT VTHSVNLLEDKHNGKLCKLRGVAPLHLGKCNIAGWILGNPEC ESLSTASSWSYIVETPSSDNGTCYPGDFIDYEELREQLSSVSSF ERFEIFPKTSSWPNHDSNKGVTAACPHAGAKSFYKNLIWLVK KGNSYPKLSKSYINDKGKEVLVLWGIHHPSTSADQQSLYQNA DTYVFVGSSRYSKKFKPEIAIRPKVRDQEGRMNYYWTLVEPG DKITFEATGNLVVPRYAFAMERNAGSGIIISDTPVHDCNTTCQ TPKGAINTSLPFQNIHPITIGKCPKYVKSTKLRLATGLRNIPSIQ SRGLFGAIAGFIEGGWTGMVDGWYGYHHQNEQGSGYAADL KSTQNAIDEITNKVNSVIEKMNTQFTAVGKEFNHLEKRIENLN KKVDDGFLDIWTYNAELLVLLENERTLDYHDSNVKNLYEKV RSQLKNNAKEIGNGCFEFYHKCDNTCMESVKNGTYDYPKYS EEAKLNREEIDGVKLESTRIYQILAIYSTVASSLVLVVSLGAISF WMCSNGSLQCRICI (SEQ ID NO: 46) |
| A/Texas/15/09 | MKAILVVLLYTFATANADTLCIGYHANNSTDTVDTVLEKNVT VTHSVNLLEDKHNGKLCKLRGVAPLHLGKCNIAGWILGNPEC ESLSTASSWSYIVETSSSDNGTCYPGDFIDYEELREQLSSMSSF |

TABLE 1-continued

Sequences of Exemplary H1 HA Polypeptides found in 2009 A/H1N1

| Strain | H1 HA Sequence |
|---|---|
| | ERFEIFPKTSSWPNHDSNKGVTAACPHAGAKSFYKNLIWLVK<br>KGNSYPKLSKSYINDKGKEVLVLWGIHHPSTSADQQSLYQNA<br>DAYVFVGSSRYSKKLKPEIAIRPKVRDQEGRMNYYWTLVEPG<br>DKITFEATGNLVVPRYAFAMERNAGSGIIISDTPVHDCNTTCQ<br>TPKGAINTSLPFQNIHPITIGKCPKYVKSTKLRLATGLRNVPSIQ<br>SRGLFGAIAGFIEGGWTGMVDGWYGYHHQNEQGSGYAADL<br>KSTQNAIDEITNKVNSVIEKMNTQFTAVGKEFNHLEKRIENLN<br>KKVDDGFLDIWTYNAELLVLLENERTLDYHDSNVKNLYEKV<br>RSQLKNNAKEIGNGCFEFYHKCDNTCMESVKNGTYDYPKYS<br>EEAKLNREEIDGVKLESTRIYQILAIYSTVASSLVLVVSLGAISF<br>WMCSNGSLQCRICI (SEQ ID NO: 47) |
| A/Mexico/4482/09 | MKAILVVLLYTFATANADTLCIGYHANNSTDTVDTVLEKNVT<br>VTHSVNLLEDKHNGKLCKLRGVAPLHLGKCNIAGWILGNPEC<br>ESLSTASSWSYIVETSSSDNGTCYPGDFIDYEELREQLSSVSSF<br>ERFEIFPKTSSWPNHDSNKGVTAACPHAGAKSFYKNLIWLVK<br>KGNSYPKLSKSYINDKGKEVLVLWGIHHPSTSADQQSLYQNA<br>DAYVFVGSSRYSKKFKPEIAIRPKVRDQEGRMNYYWTLVEPG<br>DKITFEATGNLVVPRYAFAMERNAGSGIIISDTPVHDCNTTCQ<br>TPKGAINTSLPFQNIHPITIGKCPKYVKSTKLRLATGLRNVPSIQ<br>SRGLFGAIAGFIEGGWTGMVDGWYGYHHQNEQGSGYAADL<br>KSTQNAIDEITNKVNSVIEKMNTQFTAVGKEFNHLEKRIENLN<br>KKVDDGFLDIWTYNAELLVLLENERTLDYHDSNVKNLYEKV<br>RSQLKNNAKEIGNGCFEFYHKCDNTCMESVKNGTYDYPKYS<br>EEAKLNREEIDGVKLESTRIYQILAIYSTVASSLVLVVSLGAISF<br>WMCSNGSLQCRICI (SEQ ID NO: 48) |

Sequences of H1 HA polypeptides found in influenza strains A/South Carolina/1/1918 and A/Swine/Iowa/15/1930 are found in Table 2.

TABLE 2

Sequences of Exemplary H1 HA Polypeptides from Pandemic H1 Influenza Strains

| Strain | H1 HA Sequence |
|---|---|
| A/South Carolina/1/1918 | MEARLLVLLCAFAATNADTICIGYHANNSTDTVDTVLEKNVT<br>VTHSVNLLEDSHNGKLCKLKGIAPLQLGKCNIAGWLLGNPEC<br>DLLLTASSWSYIVETSNSENGTCYPGDFIDYEELREQLSSVSSF<br>EKFEIFPKTSSWPNHETTKGVTAACSYAGASSFYRNLLWLTK<br>KGSSYPKLSKSYVNNKGKEVLVLWGVHHPPTGTDQQSLYQN<br>ADAYVSVGSSKYNRRFTPEIAARPKVRDQAGRMNYYWTLLE<br>PGDTITFEATGNLIAPWYAFALNRGSGSGIITSDAPVHDCNTK<br>CQTPHGAINSSLPFQNIHPVTIGECPKYVRSTKLRMATGLRNIP<br>SIQSRGLFGAIAGFIEGGWTGMIDGWYGYHHQNEQGSGYAA<br>DQKSTQNAIDGITNKVNSVIEKMNTQFTAVGKEFNNLERRIEN<br>LNKKVDDGFLDIWTYNAELLVLLENERTLDFHDSNVRNLYE<br>KVKSQLKNNAKEIGNGCFEFYHKCDDACMESVRNGTYDYPK<br>YSEESKLNREEIDGVKLESMGVYQILAIYSTVASSLVLLVSLG<br>AISFWMCSNGSLQCRICI (SEQ ID NO: 49) |
| A/Swine/IA/15/1930 | MKAILLVLLCAFAATNADTLCIGYHANNSTDTVDTVLEKNVT<br>VTHSVNLLEDSHNGKLCRLGGIAPLQLGKCNIAGXXLGNPEC<br>DLLLTVSSWSYIVETSNSDNGTCYPGDFIDYEELREQLSSVSSF<br>EKFEIFPKTSSWPNHETTRGVTAACPYAGASSFYRNLLWLVK<br>KENSYPKLSKSYVNNKGKEVLVLWGVHHPPTSTDQQSLYQN<br>ADAYVSVGSSKYDRRFTPEIAARPKVRGQAGRMNYYWTLLE<br>PGDTITFEATGNLVAPRYAFALNRGSESGIITSDAPVHDCDTK<br>CQTPHGAINSSLPFQNIHPVTIGECPKYVKSTKLRMVTGLRNIP<br>SIQSRGLFGAIAGFIEGGWTGLIDGWYGYHHQNGQGSGYAAD<br>QKSTQNAIDGITNKVNSVIEKMNTQFTVVGKEFNNLERRIKNL<br>NKKVDDGFLDVWTYNAEMLVLLENERTLDFHDSNVKNLYE<br>KARSQLRNNAKEIGNGCFEFYHKCDDACMESVRNGTYDYPK<br>YSEESKLNREEIDGVKLESMMVYQILAIYSTVASSLVLLVSLG<br>AISFWMCSNGSLQCRICI (SEQ ID NO: 50) |

In some embodiments, HA polypeptides (e.g., H1 polypeptides) are useful for developing and/or preparing influenza vaccines. In some embodiments, HA polypeptides (e.g., H1 polypeptides) are useful for developing and/or preparing influenza therapeutics. In some embodiments, HA polypeptides (e.g., H1 polypeptides) are useful for developing and/or preparing reagents useful for diagnosing influenza and/or determining whether a patient has been infected with an H1 HA influenza virus. In some embodiments, HA polypeptides (e.g., H1 polypeptides) are useful for surveillance of the emergence of a potential pandemic H1 HA influenza virus. Therapeutic, prophylactic, and diagnostic methods are described in further detail in the sections entitled "Detection of H1-Containing Influenzas" and "Treatment."

Variant HA Polypeptides

In certain embodiments, a provided HA polypeptide (e.g., H1 polypeptide) is a variant of a parent HA polypeptide in that its amino acid sequence is identical to that of the parent HA but for a small number of particular sequence alterations. In some embodiments, the parent HA is an HA polypeptide found in a natural isolate of an influenza virus (e.g., a wild type HA polypeptide). In some embodiments, the parent HA is one of the HAs set forth in Table 1. Any of the portions and/or fragments described herein can be fragments and/or characteristic portions of HA polypeptides, as described in the section below entitled "Portions and/or Fragments of HA Polypeptides."

In some embodiments, HA polypeptide variants have different glycan binding characteristics than their corresponding parent HA polypeptides. In some embodiments, HA variant polypeptides have greater affinity and/or specificity for umbrella glycans (e.g., as compared with for cone glycans) than do their cognate parent HA polypeptides. In certain embodiments, such HA polypeptide variants are engineered variants.

In some embodiments, HA variant polypeptides have a 2-fold, 3-fold, 4-fold, 5-fold, 10-fold, 15-fold, 20-fold, 50-fold, 100-fold, 500-fold, 1000-fold, or more than 1000-fold greater affinity and/or specificity for umbrella glycans (e.g., as compared with for cone glycans) than do their cognate parent HA polypeptides. In some embodiments, influenza virus expressing HA variant polypeptides has a 2-fold, 3-fold, 4-fold, 5-fold, 10-fold, 15-fold, 20-fold, 50-fold, 100-fold, 500-fold, 1000-fold, or more than 1000-fold enhanced human infectivity than does an influenza virus expressing their cognate parent HA polypeptides.

In some embodiments, HA polypeptide variants with altered glycan binding characteristics have sequence alternations in residues within or affecting the glycan binding site. In some embodiments, such substitutions are of amino acids that interact directly with bound glycan; in other embodiments, such substitutions are of amino acids that are one degree of separation removed from those that interact with bound glycan, in that the one degree of separation removed-amino acids either (1) interact with the direct-binding amino acids; (2) otherwise affect the ability of the direct-binding amino acids to interact with glycan, but do not interact directly with glycan themselves; or (3) otherwise affect the ability of the direct-binding amino acids to interact with glycan, and also interact directly with glycan themselves. HA polypeptide variants contain substitutions of one or more direct-binding amino acids, one or more first degree of separation-amino acids, one or more second degree of separation-amino acids, or any combination of these. In some embodiments, HA polypeptide variants may contain substitutions of one or more amino acids with even higher degrees of separation.

Figure 6:
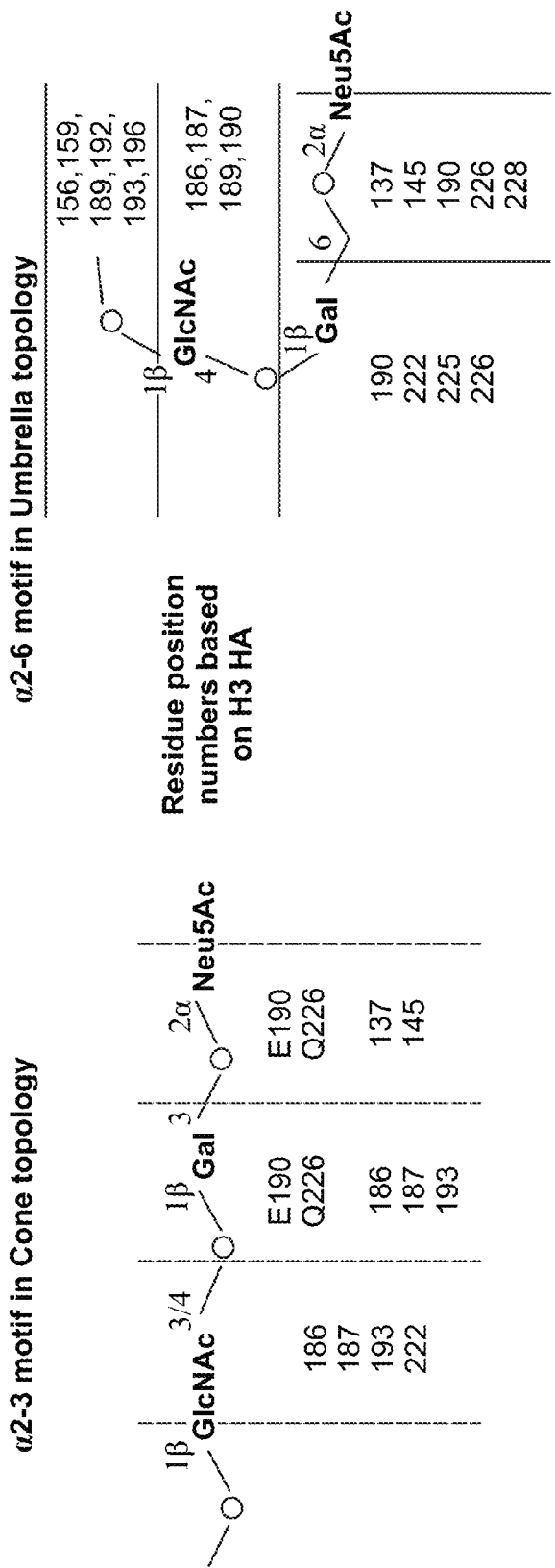
Figure 1:
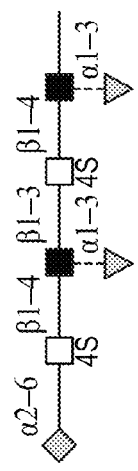

In some embodiments, HA polypeptide variants with altered glycan binding characteristics have sequence alterations in residues that make contact with sugars beyond Neu5Ac and Gal (see, for example, FIG. 6).

In some embodiments, HA polypeptide variants have at least one amino acid substitution, as compared with a wild type parent HA. In certain embodiments, HA polypeptide variants have 1, 2, 3, 4, 5, 6, 7, 8, 9, 10, 11, 12, 13, 14, 15, 16, 17, 18, 19, 20, or more than 20 amino acid substitutions as compared with a cognate wild type parent HA. In some embodiments, HA polypeptide variants have one or more amino acid substitutions separated by at least 1, at least 2, at least 3, at least 4, at least 5, at least 10, at least 20, at least 50, at least 100, at least 200, at least 300, at least 400, or at least 500 wild type amino acid residues. In some embodiments, about 70%, about 80%, about 90%, about 95%, about 96%, about 97%, about 98%, about 99%, about 100% of such amino acid substitutions are located within the glycan binding site. In some embodiments, at least 70%, at least 80%, at least 90%, at least 95%, at least 96%, at least 97%, at least 98%, or at least 99% of such amino acid substitutions are located within the glycan binding site.

In some embodiments, HA polypeptide variants have at least one amino acid addition and/or deletion, as compared with a wild type parent HA. In some embodiments, HA polypeptide variants have 1, 2, 3, 4, 5, 6, 7, 8, 9, 10, 11, 12, 13, 14, 15, 16, 17, 18, 19, 20, or more than 20 additions and/or deletions of residues. In some embodiments, HA polypeptide variants have one or more additions and/or deletions of residues separated by at least 1, at least 2, at least 3, at least 4, at least 5, at least 10, at least 20, at least 50, at least 100, at least 200, at least 300, at least 400, or at least 500 wild type amino acid residues. In some embodiments, about 70%, about 80%, about 90%, about 95%, about 96%, about 97%, about 98%, about 99%, about 100% of such amino acid additions and/or deletions are located within the glycan binding site. In some embodiments, at least 70%, at least 80%, at least 90%, at least 95%, at least 96%, at least 97%, at least 98%, or at least 99% of such amino acid additions and/or deletions are located within the glycan binding site.

In some embodiments, HA polypeptide variants are about 40%, about 50%, about 60%, about 70%, about 80%, about 90%, about 91%, about 92%, about 93%, about 94%, about 95%, about 96%, about 97%, about 98%, or about 99% identical to a cognate wild type parent HA.

In some embodiments, HA polypeptide variants are about 40%, about 50%, about 60%, about 70%, about 80%, about 90%, about 91%, about 92%, about 93%, about 94%, about 95%, about 96%, about 97%, about 98%, or about 99% identical to a contiguous stretch of about 10, about 20, about 30, about 40, about 50, about 100, about 150, about 200, about 250, about 300, about 350, about 400, about 450, about 500, or about 550 amino acids of a cognate wild type parent HA.

In some embodiments, HA polypeptide variants have sequence substitutions, additions, and/or deletions at positions corresponding to one or more of residues 98, 136, 137, 138, 145, 153, 155, 156, 159, 183, 186, 187, 189, 190, 192, 193, 194, 195, 196, 215, 219, 222, 225, 226, 227, and 228. In some embodiments, HA polypeptide variants have sequence substitutions, additions, and/or deletions at positions corresponding to one or more of residues 156, 159, 189, 192, 193, and 196; and/or at positions corresponding to one or more of residues 186, 187, 189, and 190; and/or at positions corresponding to one or more of residues 190, 222, 225, and 226; and/or at positions corresponding to one or more of residues 137, 145, 190, 226 and 228. In some embodiments, HA polypeptide variants have sequence substitutions, additions, and/or deletions at positions corresponding to one or more of residues 190, 225, 226, and 228. In some embodiments, HA polypeptide variants, particularly H1 polypeptide variants, have sequence substitutions, additions, and/or deletions corresponding to one or more of residues 145, 186, 189, 219, and/or 227.

In some embodiments, HA polypeptide variants, and particularly H1 polypeptide variants, have one or more amino acid substitutions, additions, and/or deletions relative to a wild type parent HA at residues selected from amino acids located in the region of the polypeptide that directly binds to the glycan, including but not limited to residues 136, 145 (e.g., Lys145), 153, 155, 156, 183, 186, 189, 190, 192, 193, 194, 196, 215, 222, 225, 226 and/or 227. In some embodiments, an HA polypeptide variant, and particularly an H1 polypeptide variant, has one or more amino acid substitutions, additions, and/or deletions relative to a wild type parent HA at residues selected from amino acids located adjacent to the region of the polypeptide that directly binds the glycan, including but not limited to residues Ala/Thr137, Ala/Ser138, Pro/Ser186, Ser/Thr/Asn187, Ala/Thr189, Ile/Lys219, Glu/Ala227, and/or Lys222. In some embodiments, amino acids located adjacent to the region of the polypeptide that directly binds the glycan influence the ability of amino acids located in the region of the polypeptide that directly binds the glycan to mediate an interaction between the HA polypeptide and the receptor. To give but a few examples, in some embodiments, Ala/Thr137 and/or Ala/Ser138 influence Thr/Ser136 and/or Gln226; Pro/Ser186, Ser/Thr/Asn187, and/or Ala/Thr189 influence Asp190; Ile/Lys219 and/or Glu/Ala227 influence Pro/Ser186; Glu227 influences Lys222; and/or Lys222 influences Asp225.

In certain embodiments, an HA polypeptide variant, and particularly an H1 polypeptide variant has one or more amino acid substitutions, additions, and/or deletions relative to a wild type parent HA at residues selected from amino acids that are one degree of separation removed from those that interact with bound glycan, in that the one degree of separation removed-amino acids either (1) interact with the direct-binding amino acids; (2) otherwise affect the ability of the direct-binding amino acids to interact with glycan, but do not interact directly with glycan themselves; or (3) otherwise affect the ability of the direct-binding amino acids to interact with glycan, and also interact directly with glycan themselves, including but not limited to residues Ala/Thr137, Ala/Ser138, Pro/Ser186, Ser/Thr/Asn187, Ala/Thr189, Ile/Lys219, Glu/Ala227, and/or Lys222.

In certain embodiments, an HA polypeptide variant, and particularly an H1 polypeptide variant, has an amino acid substitution, addition, and/or deletion relative to a wild type parent HA at residue 145. In certain embodiments, an HA polypeptide variant, and particularly an H1 polypeptide variant, has an amino acid substitution, addition, and/or deletion relative to a wild type parent HA at residue 186. In certain embodiments, an HA polypeptide variant, and particularly an H1 polypeptide variant, has an amino acid substitution, addition, and/or deletion relative to a wild type parent HA at residue 189. In certain embodiments, an HA polypeptide variant, and particularly an H1 polypeptide variant, has an amino acid substitution, addition, and/or deletion relative to a wild type parent HA at residue 219. In certain embodiments, an HA polypeptide variant, and particularly an H1 polypeptide variant, has an amino acid substitution, addition, and/or deletion relative to a wild type parent HA at residue 227.

In some embodiments, an HA polypeptide variant, and particularly an H1 polypeptide variant, has one or more amino acid substitutions, additions, and/or deletions relative to a wild type parent HA at residues selected from 145, 186, 189, 219, and 227. In some embodiments, an HA polypeptide variant, and particularly an H1 polypeptide variant, has one or more amino acid substitutions, additions, and/or deletions relative to a wild type parent HA at residues 186, 189, and 227. In some embodiments, an HA polypeptide variant, and particularly an H1 polypeptide variant, has one or more amino acid substitutions, additions, and/or deletions relative to a wild type parent HA at residues 186, 189, 225, and 227. In some embodiments, an HA polypeptide variant, and particularly an H1 polypeptide variant, has one or more amino acid substitutions, additions, and/or deletions relative to a wild type parent HA at residues 219 and 225.

In some embodiments, an HA polypeptide variant, and particularly an H1 variant has one or more of the following amino acid substitutions: Lys145Ser, Lys145Asn, Ile219Lys, Ser 186Pro, Ala189Thr, Gly227Ala. In some embodiments, an HA polypeptide variant, and particularly an H1 variant has one or more of the following amino acid substitutions: Lys145Ser, Lys145Asn, Ile219Lys, Ser 186Pro, Ala189Thr, Asp225Glu, Asp225Asn, or Asp225Gly, and/or Gly227Ala. In some embodiments, an HA polypeptide variant has at least one addition and/or deletion at one or more of amino acid positions 145, 186, 189, 219, and/or 227. In some embodiments, an HA polypeptide variant has at least one addition and/or deletion at one or more of amino acid positions 145, 186, 189, 219, 225, and/or 227. In some embodiments, an HA polypeptide variant has at least one addition and/or deletion at one or more of amino acid positions 137, 156, 186, 187, 189, 190, 193, 225, 226, 227, and/or 228.

In some embodiments, an HA polypeptide variant, and particularly an H1 variant has one or more of the following sets of amino acid substitutions:
Ile219Lys
Ser186Pro, Ala189Thr, Glu227Ala
Ser186Pro, Ala1 89Thr
Ser186Pro, Glu227Ala
Ala189Thr, Glu227Ala
Ile219Lys, Ser186Pro, Ala189Thr, Glu227Ala
Ile219Lys, Ser186Pro, Ala189Thr
Ile219Lys, Ser186Pro
Ile219Lys, Ser186Pro, Glu227Ala
Ile219Lys, Glu227Ala
Ile219Lys, Ala189Thr, Glu227Ala
Ile219Lys, Glu227Ala
Lys145Ser or Lys145Asn
Lys145Ser or Lys145Asn, Ser186Pro, Ala189Thr, Glu227Ala
Lys145Ser or Lys145Asn, Ile219Lys
Asp225Asn, Ile219Lys
Asp225Asn, Ser186Pro, Ala189Thr, Glu227Ala
Asp225Gly, Ile219Lys
Asp225Gly, Ser186Pro, Ala189Thr, Glu227Ala
Asp225Glu, Ile219Lys
Asp225Glu, Ser186Pro, Ala189Thr, Glu227Ala In some such embodiments, an HA polypeptide has at least one further substitution as compared with a wild type HA, such that affinity and/or specificity of the variant for umbrella glycans is increased. In other words, an HA polypeptide may comprise one or more of any of the sets of amino acid substitutions listed in this paragraph and one or more additional amino acid substitutions. To give but a few specific examples, an HA polypeptide may comprise one or more of any of the sets of amino acid substitutions listed in this paragraph and one or more additional amino acid substitutions, e.g., at positions 98, 136, 137, 138, 145, 153, 155, 156, 159, 183, 186, 187, 189, 190, 192, 193, 194, 195, 196, 215, 219, 222, 225, 226, 227, and 228, and/or combinations thereof In some embodiments, an HA polypeptide has at least one addition at and/or deletion of any of the amino acid positions and/or sets of amino acid positions described in this section.

In some embodiments, HA polypeptides (including HA polypeptide variants) have sequences that include S145, N145, L219, P186, T189, and/or A227. In some embodiments, HA polypeptides (including HA polypeptide variants) have sequences that include D190, D225, L226, and/or S228. In some embodiments, HA polypeptides have sequences that include D190 and D225; in some embodiments, HA polypeptides have sequences that include L226 and S228.

In some embodiments, HA polypeptide variants have an open binding site as compared with a parent HA, and particularly with a parent wild type HAs.

Portions and/or Fragments of HA Polypeptides

The present invention provides characteristic portions of HA polypeptides and nucleic acids that encode them. In general, a characteristic portion is one that contains a continuous stretch of amino acids, or a collection of continuous stretches of amino acids, that together are characteristic of the HA polypeptide. Each such continuous stretch generally will contain at least two amino acids. Furthermore, those of ordinary skill in the art will appreciate that typically at least 5, 10, 15, 20 or more amino acids are required to be characteristic of a H5 HA polypeptide. In general, a characteristic portion is one that, in addition to the sequence identity specified above, shares at least one functional characteristic with the relevant intact HA polypeptide. In some embodiments, characteristic portions of HA polypeptides share glycan binding characteristics with the relevant full-length HA polypeptides.

Any of the portions and/or fragments described herein can be variant HA polypeptide portions and/or fragments, as described in the section above entitled "Variant HA Polypeptides."

In some embodiments, an HA polypeptide fragment and/or characteristic portion of an HA polypeptide corresponds to a contiguous stretch of about 10, about 20, about 30, about 40, about 50, about 100, about 150, about 200, about 250, about 300, about 350, about 400, about 450, about 500, or about 550 amino acids of a cognate wild type parent HA. In some embodiments, such a contiguous stretch is present within the context of non-HA polypeptide sequence at the 5' end, at the 3' end, or at both the 5' and 3' ends of the contiguous stretch. In some embodiments, the non-HA polypeptide sequence is about 1 amino acid, about 2 amino acids, about 3 amino acids, about 4 amino acids, about 5 amino acids, about 6 amino acids, about 7 amino acids, about 8 amino acids, about 9 amino acids, about 10 amino acids, about 15 amino acids, about 20 amino acids, about 25 amino acids, about 50 amino acids, about 75 amino acids, about 100 amino acids, about 250 amino acids, about 500 amino acids, about 750 amino acids, about 1000 amino acids, about 2000 amino acids, about 3000 amino acids, about 4000 amino acids, about 5000 amino acids, about 6000 amino acids, about 7000 amino acids, about 8000 amino acids, about 9000 amino acids, about 10,000 amino acids, or more than about 10,000 amino acids in length.

In some embodiments, two or more HA polypeptides, fragments thereof, and/or characteristic portions thereof (e.g., each of which corresponds to a contiguous stretch of about 10, about 20, about 30, about 40, about 50, about 100, about 150, about 200, about 250, about 300, about 350, about 400, about 450, about 500, or about 550 amino acids of a cognate wild type parent HA) are fused together in tandem. In some embodiments, tandem HA polypeptides comprise 2, 3, 4, 5, 6, 7, 8, 9, 10, 15, 20, 30, 40, 50, 100, or more than 100 HA polypeptides, fragments thereof, and/or characteristic portions thereof. In some embodiments, each HA polypeptide, fragment thereof, and/or characteristic portion thereof in such a tandem fusion is separated from each other fragment and/or portion by a non-HA polypeptide linker.

Non-HA Polypeptides

In some embodiments, the present invention provides polypeptides whose amino acid sequence does not include a characteristic HA sequence. Such polypeptides are referred to herein as "non-HA polypeptides." In some embodiments, a non-HA polypeptide has an amino acid sequence selected in advance (e.g., via rational design, including for example, introduction of strategic amino acid alterations [additions, deletions, and/or substitutions] as compared with a reference sequence). In some embodiments, a non-HA polypeptide has an amino acid sequence that is determined stochastically and, for example, identified on the basis of the desirable binding characteristics defined herein. Non-HA polypeptides may be binding agents, interfering agents, etc., as described herein.

Production of Polypeptides

Polypeptides (e.g., HA polypeptides and/or non-HA polypeptides), variants thereof, fragments thereof, and/or characteristic portions thereof (and/or nucleic acids encoding any of these) may be produced by any available means.

Polypeptides (including variants, fragments, and/or characteristic portions thereof) may be produced, for example, by utilizing a host cell system engineered to express a polypeptide-encoding nucleic acid.

Any system can be used to produce polypeptides (including variants, fragments, and/or characteristic portions), such as egg, baculovirus, plant, yeast, Madin-Darby Canine Kidney cells (MDCK), or Vero (African green monkey kidney) cells. Alternatively or additionally, polypeptides (including variants, fragments, and/or characteristic portions thereof) can be expressed in cells using recombinant techniques, such as through the use of an expression vector (Sambrook et al., *Molecular Cloning: A Laboratory Manual*, CSHL Press, 1989; incorporated herein by reference).

Alternatively or additionally, polypeptides (including variants, fragments, and/or characteristic portions thereof) can be produced by synthetic means.

Alternatively or additionally, polypeptides (including variants, fragments, and/or characteristic portions thereof), and particularly HA polypeptides, may be produced in the context of intact virus, whether otherwise wild type, attenuated, killed, etc. Polypeptides (including variants, fragments, and/or characteristic portions thereof) may be produced in the context of virus like particles.

In some embodiments, HA polypeptides (including variants, fragments, and/or characteristic portions thereof) can be isolated and/or purified from influenza virus. For example, virus may be grown in eggs, such as embryonated hen eggs, in which case the harvested material is typically allantoic fluid. Alternatively or additionally, influenza virus may be derived from any method using tissue culture to grow the virus. Suitable cell substrates for growing the virus include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

It will be appreciated by those of ordinary skill in the art that polypeptides (including variants, fragments, and/or characteristic portions thereof) may be generated, identified, isolated, and/or produced by culturing cells or organisms that produce the polypeptide (whether alone or as part of a complex, including as part of a virus particle or virus) under conditions that allow ready screening and/or selection of polypeptides capable of binding to umbrella-topology glycans. To give but one example, in some embodiments, it may be useful to produce and/or study a collection of polypeptides (e.g., HA variant polypeptides) under conditions that reveal and/or favor those variants that bind to umbrella topology glycans (e.g., with particular specificity and/or affinity). In some embodiments, such a collection of polypeptides (e.g., HA variant polypeptides) results from evolution in nature. In some embodiments, such a collection of polypeptides (e.g., HA variant polypeptides) results from engineering. In some embodiments, such a collection of polypeptides (e.g., HA variant polypeptides) results from a combination of engineering and natural evolution.

Nucleic Acids

In certain embodiments, the present invention provides nucleic acids which encode an HA polypeptide (including a variant, fragment, and/or characteristic portion thereof). In other embodiments, the invention provides nucleic acids which are complementary to nucleic acids which encode an HA polypeptide (including a variant, fragment, and/or characteristic portion thereof).

In other embodiments, the invention provides nucleic acid molecules which hybridize to nucleic acids encoding an HA polypeptide (including a variant, fragment, and/or characteristic portion thereof). Such nucleic acids can be used, for example, as primers or as probes. To give but a few examples, such nucleic acids can be used as primers in polymerase chain reaction (PCR), as probes for hybridization (including in situ hybridization), and/or as primers for reverse transcription-PCR (RT-PCR).

In certain embodiments, nucleic acids can be DNA or RNA, and can be single stranded or double-stranded. In some embodiments, nucleic acids may include one or more non-natural nucleotides; in other embodiments, nucleic acids include only natural nucleotides.

HA Polypeptide Binding Agents

The invention provides HA polypeptide binding agents. In some embodiments, binding agents are entities that bind to one or more HA polypeptides (including variants, fragments, and/or characteristic portions thereof), as described herein. HA polypeptide binding agents may be of any chemical type. In some embodiments, binding agents are polypeptides (including, e.g., antibodies or antibody fragments). In some embodiments, such binding agents are small molecules. In some embodiments, such binding agents are nucleic acids. In some embodiments, such binding agents are aptamers. In some embodiments, binding agents are polymers; in some embodiments, HA polypeptide binding agents are non-polymeric. In some embodiments, binding agents are carbohydrates. In some embodiments, HA polypeptide binding agents are lectins.

In some embodiments, binding agents bind to H1 HA polypeptides (including variants, fragments, and/or characteristic portions thereof). In some embodiments, binding agents bind to H1 HA polypeptide variants (e.g., fragments and/or characteristic portions thereof) having enhanced human binding and/or infectivity. In some embodiments, an HA polypeptide binding agent binds to an H1 HA polypeptide variant with a greater affinity than it binds to a cognate parent H1 HA polypeptide. In some embodiments, an HA polypeptide binding agent binds to an H1 HA polypeptide enhanced human binding variant with a 2-fold, 3-fold, 4-fold, 5-fold, 10-fold, 15-fold, 20-fold, 50-fold, 100-fold, 500-fold, 1000-fold, or more than 1000-fold greater affinity than it binds to a cognate parent H1 HA polypeptide. In some embodiments, an HA polypeptide binding agent binds to an influenza virus expressing an H1 HA polypeptide enhanced human binding variant with a 2-fold, 3-fold, 4-fold, 5-fold, 10-fold, 15-fold, 20-fold, 50-fold, 100-fold, 500-fold, 1000-fold, or more than 1000-fold greater affinity than it binds to an influenza virus expressing its cognate parent HA polypeptide.

In some embodiments, HA polypeptide binding agents are entities that mimic the structure and/or three-dimensional characteristics of umbrella-topology glycans. In some embodiments, such binding agents are or comprise umbrella-topology glycans. In some embodiments, such binding agents are entities that more closely resemble umbrella-topology glycans than they resemble cone-topology glycans.

In some embodiments, when a binding agent binds to an HA polypeptide (and/or to variants, fragments, and/or characteristic portions thereof), the HA polypeptide is blocked from binding to HA receptors. Thus, in some embodiments, an HA polypeptide binding agent may also function as an "interfering agent," as described in the section below entitled "HA Polypeptide Interfering Agents."

In some embodiments, an HA polypeptide binding agent preferentially binds to a particular HA polypeptide (e.g., variants, fragments, and/or characteristic portions thereof). For example, in some embodiments, a binding agent preferentially binds to H1 HA polypeptides as compared with non-H1 HA polypeptides. In some embodiments, a binding agent binds to an H1 HA polypeptide with a 2-fold, 3-fold, 4-fold, 5-fold, 10-fold, 15-fold, 20-fold, 50-fold, 100-fold, 500-fold, 1000-fold, or more than 1000-fold greater affinity than it binds to a non-H1 HA polypeptide. In some embodiments, a binding agent binds to an H1 HA polypeptide having one or more of the following mutations: Lys145Ser, Lys145Asn, Ile219Lys, Ser186Pro, Ala189Thr, and/or Glu227Ala with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to an H1 HA polypeptide not having one or more of those mutations. In some embodiments, a binding agent binds to an H1 HA polypeptide having a Ile219Lys mutation with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to an H1 HA polypeptide not having that mutation. In some embodiments, a binding agent binds to an H1 HA polypeptide having Ser186Pro, Ala189Thr, and Glu227Ala mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to an H1 HA polypeptide not having those mutations. In some embodiments, a binding agent binds to an H1 HA polypeptide having Lys145Ser or Lys145Asn mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to an H1 HA polypeptide not having those mutations. In some embodiments, a binding agent binds to an H1 HA polypeptide having Lys145Ser/Lys145Asn, Ser186Pro, Ala189Thr, and Glu227Ala mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000- fold greater affinity than it binds to an H1 HA polypeptide not having those mutations. In some embodiments, a binding agent binds to an H1 HA polypeptide having Lys145Ser/Lys145Asn and Ile219Lys mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to an H1 HA polypeptide not having those mutations.

In some embodiments, a binding agent binds to an influenza virus expressing an H1 HA polypeptide with a 2-fold, 3-fold, 4-fold, 5-fold, 10-fold, 15-fold, 20-fold, 50-fold, 100-fold, 500-fold, 1000-fold, or more than 1000-fold greater affinity than it binds to an influenza virus expressing a non-H1 HA polypeptide. In some embodiments, a binding agent binds to influenza virus expressing an H1 HA polypeptide having one or more of the following mutations: Ile219Lys, Ser186Pro, Ala189Thr, and/or Glu227Ala with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to influenza virus expressing an H1 HA polypeptide not having one or more of those mutations. In some embodiments, a binding agent binds to influenza virus expressing an H1 HA polypeptide having a Ile219Lys mutation with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to influenza virus expressing an H1 HA polypeptide not having that mutation. In some embodiments, a binding agent binds to influenza virus expressing an H1 HA polypeptide having Ser186Pro, Ala189Thr, and Glu227Ala mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to influenza virus expressing an H1 HA polypeptide not having those mutations. In some embodiments, a binding agent binds to influenza virus expressing an H1 HA polypeptide having Lys145Ser or Lys145Asn mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to influenza virus expressing an H1 HA polypeptide not having those mutations. In some embodiments, a binding agent binds to influenza virus expressing an H1 HA polypeptide having Lys145Ser/Lys145Asn, Ser186Pro, Ala189Thr, and Glu227Ala mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to influenza virus expressing an H1 HA polypeptide not having those mutations. In some embodiments, a binding agent binds to influenza virus expressing an H1 HA polypeptide having Lys145Ser/Lys145Asn and Ile219Lys mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to influenza virus expressing an H1 HA polypeptide not having those mutations.

In some embodiments, when administered to a subject, binding agents bind to at least about 10%, about 15%, about 20%, about 25%, about 30% about 35%, about 40%, about 45%, about 50%, about 55%, about 60%, about 65%, about 70%, about 75%, about 80%, about 85%, about 90%, about 95%, or more of the HA polypeptides present with the subject (e.g., present within a subject's blood, mucosal tissues, etc.).

In certain embodiments, binding affinity of binding agents to HA polypeptides is assessed over a range of concentrations. Such a strategy provides significantly more information, particularly in multivalent binding assays, than do single-concentration analyses. In some embodiments, for example, binding affinities of binding agents are assessed over concentrations ranging over at least 2-fold, 3-fold, 4-fold, 5-fold, 6-fold, 7-fold, 8-fold, 9-fold, 10-fold, or more than 10-fold.

In some embodiments, binding agents that preferentially bind to H1 HA polypeptides (e.g., variants, fragments, and/or characteristic portions thereof) are useful for various diagnostic and/or surveillance methods, including but not limited to those described in the section below called "Detection of H1-Containing Influenzas"

HA Polypeptide Interfering Agents

The present invention provides interfering agents. In some embodiments, interfering agents are entities that bind to designated targets (e.g., to a particular HA polypeptide and/or to particular glycans, such as umbrella-topology glycans) as described herein. Interfering agents may be of any chemical type. In some embodiments, interfering agents are polypeptides (including, e.g., antibodies or antibody fragments); in some such embodiments, interfering agents are HA polypeptides; in other embodiments, interfering agents are polypeptides whose amino acid sequence does not include an HA characteristic sequence (i.e., "non-HA polypeptides"). In some embodiments, interfering agents are small molecules. In some embodiments, interfering agents are nucleic acids. In some embodiments, interfering agents are aptamers. In some embodiments, interfering agents are polymers; in some embodiments, interfering agents are non-polymeric. In some embodiments, interfering agents are carbohydrates. In some embodiments, interfering agents are lectins.

In some embodiments, interfering agents as described herein bind to one or more HA polypeptides (and/or to variants, fragments, and/or characteristic portions thereof). In some embodiments, interfering agents bind to H1 HA polypeptides. In some embodiments, interfering agents bind to H1 HA polypeptide variants having enhanced human binding and/or infectivity.

In some embodiments, interfering agents compete with umbrella-topology glycans (e.g., on HA receptors) for binding to HA polypeptides (e.g., H1 HA polypeptides), including variants, fragments, and/or characteristic portions thereof). In some embodiments, interfering agents bind to HA polypeptides with a greater affinity than umbrella topology glycans bind to HA polypeptides. In some embodiments, interfering agents bind to HA polypeptides with a 2-fold, 3-fold, 4-fold, 5-fold, 10-fold, 15-fold, 20-fold, 50-fold, 100-fold, 500-fold, 1000-fold, or more than 1000-fold greater affinity than umbrella topology glycans bind to HA polypeptides.

In some embodiments, interfering agents as described herein bind to sialylated glycans having an umbrella-like topology (e.g., on HA receptors). In certain embodiments, interfering agents bind to umbrella-topology glycans with high affinity and/or specificity. In some embodiments, interfering agents show a binding preference for umbrella-topology glycans as compared with cone-topology glycans. In some embodiments, interfering agents compete with HA for binding to glycans on HA receptors. In some embodiments, interfering agents compete with HA for binding to umbrella-topology glycans. In some embodiments, an interfering agent provided herein is an umbrella topology blocking agent. In some embodiments, an interfering agent provided herein is an umbrella topology specific blocking agent. In some embodiments, interfering agents bind to umbrella topology glycan mimics.

In some embodiments, interfering agents compete with HA polypeptides (and/or to variants, fragments, and/or characteristic portions thereof) for binding to umbrella topology glycans (e.g., on HA receptors). In some embodiments, interfering agents bind to umbrella topology glycans with a greater affinity than HA polypeptides bind to umbrella topology glycans. In some embodiments, interfering agents bind to umbrella topology glycans with a 2-fold, 3-fold, 4-fold, 5-fold, 10-fold, 15-fold, 20-fold, 50-fold, 100-fold, 500-fold, 1000-fold, or more than 1000-fold greater affinity than HA polypeptides bind to umbrella topology glycans.

In certain embodiments, binding affinity of interfering agents is assessed over a range of concentrations. Such a strategy provides significantly more information, particularly in multivalent binding assays, than do single-concentration analyses. In some embodiments, for example, binding affinities of interfering agents are assessed over concentrations ranging over at least 2-fold, 3-fold, 4-fold, 5-fold, 6-fold, 7-fold, 8-fold, 9-fold, 10-fold, or more than 10-fold.

In some embodiments, binding of an interfering agent to a target interferes with the ability of an HA polypeptide to bind to an HA receptor. In some embodiments, binding of an interfering agent to a target results in about 40%, about 50%, about 60%, about 70%, about 80%, about 90%, about 95%, about 98%, about 99%, or about 100% reduction in binding of an HA polypeptide to bind to an HA receptor. In some embodiments, interfering agents are useful for treatment and/or prevention of influenza infection, for example, because they block the ability of an HA polypeptide to bind to an HA receptor.

Some particular types of interfering agents are discussed in more detail below.

Interfering Agents that Bind to Glycans

In some embodiments, interfering agents (e.g., HA polypeptides, LSBAs, UTBAs, UTSBAs, etc.) bind to umbrella glycans (and/or to umbrella topology glycan mimics), such as those present on HA receptors. In certain embodiments, interfering agents bind to umbrella topology glycans (and/or to umbrella topology glycan mimics) with high affinity. In some embodiments, interfering agents bind to umbrella topology glycans with greater affinity than they bind to cone topology glycans. In certain embodiments, interfering agents bind to a plurality of different umbrella topology glycans, often with high affinity and/or specificity.

In some embodiments, interfering agents bind to umbrella topology glycans (e.g., long α2-6 sialylated glycans such as, for example, Neu5Acα2-6Galβ1-4GlcNAcβ1-3Galβ1-4GlcNAc-) with high affinity. For example, in some embodiments, interfering agents bind to umbrella topology glycans with an affinity comparable to that observed for a wild type HA that mediates infection of a humans (e.g., H1N1 HA or H3N2 HA). In some embodiments, interfering agents bind to umbrella topology glycans with an affinity that is at least 25%, 30%, 35%, 40%, 45%, 50%, 55%, 60%, 65%, 70%, 75%, 80%, 85%, 90%, 95%, 96%, 97%, 98%, 99%, or 100% of that observed under comparable conditions for a wild type HA that mediates infection of humans. In some embodiments, interfering agents bind to umbrella glycans with an affinity that is greater than that observed under comparable conditions for a wild type HA that mediates infection of humans. In some embodiments, exemplary interfering agents include LSBAs, UTBAs, and/or UTSBAs.

In certain embodiments, interfering agents show high affinity if they show a saturating signal in a multivalent glycan array binding assay such as those described herein. In some embodiments, interfering agents show high affinity if they show a signal above about 400000 or more (e.g., above about 500000, 600000, 700000, 800000, etc.) in such studies. In some embodiments, interfering agents as described herein show saturating binding to umbrella glycans over a concentration range of at least 2 fold, 3 fold, 4 fold, 5 fold or more, and in some embodiments over a concentration range as large as 10 fold or more.

Furthermore, in some embodiments, interfering agents bind to umbrella topology glycans (and/or to umbrella topology glycan mimics) more strongly than they bind to cone topology glycans. In some embodiments, interfering agents bind to umbrella topology glycans with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to cone topology glycans.

In some embodiments, interfering agents bind to α2-6 sialylated glycans; in some embodiments, interfering agents bind preferentially to α2-6 sialylated glycans. In certain embodiments, interfering agents bind to a plurality of different α2-6 sialylated glycans. In some embodiments, interfering agents are not able to bind to α2-3 sialylated glycans, and in other embodiments interfering agents are able to bind to α2-3 sialylated glycans.

In some embodiments, interfering agents bind to receptors found on human upper respiratory epithelial cells. In certain embodiments, interfering agents bind to HA receptors in the bronchus and/or trachea. In some embodiments, interfering agents are not able to bind receptors in the deep lung, and in other embodiments, interfering agents are able to bind receptors in the deep lung.

In some embodiments, interfering agents bind to at least about 10%, about 15%, about 20%, about 25%, about 30% about 35%, about 40%, about 45%, about 50%, about 55%, about 60%, about 65%, about 70%, about 75%, about 80%, about 85%, about 90%, about 95%, or more of the glycans found on HA receptors in human upper respiratory tract tissues (e.g., epithelial cells).

In some embodiments, interfering agents bind to one or more of the glycans illustrated in FIG. 8. In some embodiments, interfering agents bind to multiple glycans illustrated in FIG. 8. In some embodiments, interfering agents bind with high affinity and/or specificity to glycans illustrated in FIG. 8. In some embodiments, interfering agents bind to glycans illustrated in FIG. 8 preferentially as compared with their binding to glycans illustrated in FIG. 7. In some embodiments, interfering agents bind to an oligosaccharide of the following form:

Neu5Acα2-6Sug1-Sug2-Sug3 where:

1. Neu5Ac α2-6 is always or almost always at the non-reducing end;
2. Sug1:
   a. is a hexose (frequently Gal or Glc) or hexosamine (GlcNAc or GalNAc) in α or β configuration (frequently β- for N- and O-linked extension and α- in the case of GalNAcα- that is O-linked to glycoprotein);
   b. no sugars other than Neu5Acα2-6 should be attached to any of the non-reducing positions of Sug1 (except when Sug1 is GalNAcα- that is O-linked to the glycoprotein); and/or
   c. non-sugar moieties such as sulfate, phosphate, guanidium, amine, N-acetyl, etc. can be attached to non-reducing positions (typically 6 position) of Sug1 to improve contacts with HA;
3. Sug2 and/or Sug3:
   a. hexose (frequently Gal or Glc) or hexosamine (GlcNAc or GalNAc) in α or β configuration (frequently β); and/or
   b. sugars (such as Fuc) or non-sugar moieties such as sulfate, phosphate, guanidium, amine, N-acetyl, etc. can be attached to non-reducing positions of Sug2, Sug3, and/or Sug4;
4. Linkage between any two sugars in the oligosaccharide apart from Neu5Acα2-6 linkage can be 1-2, 1-3, 1-4, and/or 1-6 (typically 1-3 or 1-4); and/or
5. Structure where Neu5Acα2-6 is linked GalNAcα that is O-linked to the glycoprotein and additional sugars are linked to the non-reducing end of GalNAcα for example
   i. Neu5Acα2-6(Neu5Acα2-3Galβ1-3)GalNAcα-
   ii. Neu5Acα2-6(Galβ1-3)GalNAcα-

The present invention provides interfering agents with designated binding specificity, and also provides interfering agents with designated binding characteristics with respect to umbrella glycans.

HA Receptors

In some embodiments, interfering agents are entities that are or comprise HA receptors (e.g., fragments and/or characteristic portions thereof). HA interacts with cell surfaces by binding to a glycoprotein receptor. Binding of HA (e.g., H1 HA polypeptides and/or variants, fragments, and/or characteristic portions thereof) to HA receptors is predominantly mediated by N-linked glycans on the HA receptors. Specifically, HA on the surface of flu virus particles recognizes sialylated glycans that are associated with HA receptors on the surface of the cellular host. After recognition and binding, the host cell engulfs the viral cell and the virus is able to replicate and produce many more virus particles to be distributed to neighboring cells. Some crystal structures of exemplary HA-glycan interactions have been identified and are presented in Table 3:

type of linkage of the receptor-bound glycan can affect the conformation of the receptor's HA-binding site, thus affecting the receptor's specificity for different HAs.

For example, the glycan binding pocket of avian HA is narrow. According to the present invention, this pocket binds to the trans conformation of α2-3 sialylated glycans, and/or to cone-topology glycans, whether α2-3 or α2-6 linked.

HA receptors in avian tissues, and also in human deep lung and gastrointestinal (GI) tract tissues are characterized by α2-3 sialylated glycan linkages, and furthermore (according to the present invention), are characterized by glycans, including α2-3 sialylated and/or α2-6 sialylated glycans, which predominantly adopt cone topologies. HA receptors having such cone-topology glycans may be referred to herein as CTHArs.

By contrast, human HA receptors in the bronchus and trachea of the upper respiratory tract are modified by α2-6 sialylated glycans. Unlike the α2-3 motif, the α2-6 motif has an additional degree of conformational freedom due to the C6-C5 bond (Russell et al., *Glycoconj J* 23:85, 2006; incorporated herein by reference). HAs that bind to such α2-6 sialylated glycans have a more open binding pocket to accommodate the diversity of structures arising from this conformational freedom. Moreover, according to the present invention, HAs may need to bind to glycans (e.g., α2-6 sialylated glycans) in an umbrella topology, and particularly may need to bind to such umbrella topology glycans with strong affinity and/or specificity, in order to effectively mediate infection of human upper respiratory tract tissues. HA receptors having umbrella-topology glycans may be referred to herein as UTHArs.

As a result of these spatially restricted glycosylation profiles, humans are not usually infected by viruses containing many wild type swine HAs (e.g., swine H1). Specifically, because the portions of the human respiratory tract that are most likely to encounter virus (i.e., the trachea and bronchi) lack receptors with cone glycans (e.g., α2-3 sialylated glycans, and/or short glycans) and wild type swine HAs typically bind primarily or exclusively to receptors

TABLE 3

Crystal Structures of HA-Glycan Complexes

| Abbreviation (PDB ID) | Virus Strain | Glycan (with assigned coordinates) |
| --- | --- | --- |
| ASI30_H1_23 (1RV0) | A/Swine/Iowa/30 (H1N1) | Neu5Ac |
| ASI30_H1_26 (1RVT) | A/Swine/Iowa/30 (H1N1) | Neu5Acα6Galβ4GlcNAcβ3Galβ4Glc |
| APR34_H1_23 (1RVX) | A/Puerto Rico/8/34 (H1N1) | Neu5Acα3Galβ4GlcNAc |
| APR34_H1_26 (1RVZ) | A/Puerto Rico/8/34 (H1N1) | Neu5Acα6Galβ4GlcNAc |
| ADU63_H3_23 (1MQM) | A/Duck/Ukraine/1/63 (H3N8) | Neu5Acα3Gal |
| ADU63_H3_26 (1MQN) | A/Duck/Ukraine/1/63 (H3N8) | Neu5Acα6Gal |
| AAI68_H3_23 (1HGG) | A/Aichi/2/68 (H3N2) | Neu5Acα3Galβ4Glc |
| ADS97_H5_23 (1JSN) | A/Duck/Singapore/3/97 (H5N3) | Neu5Acα3Galβ3GlcNAc |
| AD S97_H5_26(1JSO) | A/Duck/Singapore/3/97 (H5N3) | Neu5Ac |
| Viet04_H5 (2FK0) | ANietnam/1203/2004 (H5N1) | |

HA-α2-6 sialylated glycan complexes were generated by superimposition of the CA trace of the HA1 subunit of ADU63_H3 and ADS97_H5 and Viet04_H5 on ASI30_H1_26 and APR34_H1_26 (H1). Although the structural complexes of the human A/Aichi/2/68 (H3N2) with α2-6 sialylated glycans are published (Eisen et al., 1997, *Virology*, 232:19), their coordinates were not available in the Protein Data Bank. The SARF2 (http://123d.ncifcrf.gov/sarf2.html) program was used to obtain the structural alignment of the different HA1 subunits for superimposition.

HA receptors are modified by either α2-3 or α2-6 sialylated glycans near the receptor's HA-binding site, and the associated with cone glycans (e.g., α2-3 sialylated glycans, and/or short glycans), humans rarely become infected with swine viruses. Only when in sufficiently close contact with virus that it can access the deep lung and/or gastrointestinal tract receptors having umbrella glycans (e.g., long α2-6 sialylated glycans) do humans become infected.

Lectins

In some embodiments, binding agents provided in accordance with the present invention are lectins. Lectins are sugar-binding proteins which may bind to a soluble carbohydrate or to a carbohydrate moiety which is a part of a glycoconjugate (e.g., a glycopeptide or glycolipid). Lectins typically agglutinate certain animal cells and/or precipitate glycoconjugates by recognizing a particular sugar moiety. For example, SNA-1 is a lectin that has a high affinity for α2-6 sialic acids. As yet another example, polyporus squamosus lectins (PSL1a and PSL1b) have high affinity for binding sialylated glycoconjugates containing Neu5Acα2, 6Galβ1,4Glc/GlcNAc trisaccharide sequences of asparagine-linked glycoproteins. Non-limiting exemplary lectins that may act as binding agents include SNA-1, SNA-1', PSL1a, PSL1b, and polypeptides derived therefrom.

Amino acid sequences of exemplary lectins are provided below:

```
Sambucus Nigra Lectin 1
(Genbank Accession No. U27122):
                                       (SEQ ID NO: 51)
MRLVAKLLYLAVLAICGLGIHGALTHPRVTPPVYPSVSFNLTGADTYEPF

LRALQEKVILGNHTAFDLPVLNPESQVSDSNRFVLVPLTNPSGDTVTLAI

DVVNLYVVAFSSNGKSYFFSGSTAVQRDNLFVDTTQEELNFTGNYTSLER

QVGFGRVYIPLGPKSLDQAISSLRTYTLTAGDTKPLARGLLVVIQMVSEA

ARFRYIELRIRTSITDASEFTPDLLMLSMENNWSSMSSEIQQAQPGGIFA

GVVQLRDERNNSIEVTNFRRLFELTYIAVLLYGCAPVTSSSYSNNAIDAQ

IIKMPVFRGGEYEKVCSVVEVTRRISGWDGLCVDVRYGHYIDGNPVQLRP

CGNECNQLWTFRTDGTIRWLGKCLTASSSVMIYDCNTVPPEATKWVVSID

GTITNPHSGLVLTAPQAAEGTALSLENNIHAARQGWTVGDVEPLVTFIVG

YKQMCLRENGENNFVWLEDCVLNRVQQEWALYGDGTIRVNSNRSLCVTSE

DHEPSDLIVILKCEGSGNQRWVFNTNGTISNPNAKLLMDVAQRDVSLRKI

ILYRPTGNPNQQWITTTHPA

Sambucus Nigra Lectin 1'
(Genbank Accession No. U66191):
                                       (SEQ ID NO: 52)
MKVVATILYLVVLAICGLGIHGAHPTHSAPPTVYPSVSFNLTEANSNEYR

HFLQELRGKVILGSHRAFDLPVLNPESKVSDSDRFVLVRLTNPSRKKVTL

AIDVVTFYVVAFAQNDRSYFFSGSSEVQRENLFVDTTQEDLNFKGDYTSL

EHQVGFGRVYIPLGPKSLAQSISSLSTYKSSAGDNKRLARSLLVVIQMVS

EAARFRYIQLRIQASITDAKEFTPDLLMLSMENKWSSMSSEIQQAQPGGA

FAQVVKLLDQRNHPIDVTNFRRLFQLTSVAVLLHGCPTVTKMPAYIIKMP

VFNGGEDEERCSVVEEVTRRIGGRDGFCAEVKNGDEKDGTPVQLSSCGEQ

SNQQWTFSTDGTIQSLGKCLTTSSSVMIYNCKVVPPESTKWVVSIDGTIT

NPRSGLVLTAPKAAEGTLVSLEKNVHAARQGWIVGNVEPLVTFIVGYEQM

CLETNPGNNDVSLGDCSVKSASKVDQKWALYGDGTIRVNNDRSLCVTSEG

KSSNEPIIILKCLGWANQRWVFNTDGTISNPDSKLVMHVDQNDVPLRKII

LSHPSGTSNQQWIASTHPA

Polyporous squamosus lectin 1a (UniProt Q75WT9)
                                       (SEQ ID NO: 53)
MSFQGHGIYYIASAYVANTRLALSEDSSANKSPDVIISSDAVDPLNNLWL

IEPVGEADTYTVRNAFAGSYMDLAGHAATDGTAIIGYRPTGGDNQKWIIS

QINDVWKIKSKETGTFVTLLNGDGGGTGTVVGWQNITNNTSQNWTFQKLS

QTGANVHATLLACPALRQDFKSYLSDGLYLVLTRDQISSIWQASGLGSTP

WRSEIFDCDDFATVFKGAVAKWGNENFKANGFALLCGLMFGSKSSGAHAY

NWFVERGNFSTVTFFEPQNGTYSANAWDYKAYFGLF

Polyporous squamosus lectin 1b (UniProt Q75WT8)
                                       (SEQ ID NO: 54)
MSFEGHGIYHIPHAHVANIRMALANRGSGQNGTPVIAWDSNNDAFDHMWL

VEPTGEADTYTIHNVSTGTYMDVTASAVADNTPIIGYQRTGNDNQKWIIR

QVQTDGGDRPWKIQCKATGTFATLYSGGGSGTAIVGWRLVNSNGNQDWVF

QKLSQTSVNVHATLLACGATVGQDFKNYLYDGLYLVLPRDRISAIWKASG

LGETARRDGIYDSDEFAMTFKSAAATWGKENFKADGFAILCGMMFGTKAS

TNRHAYNWVVERGSFSTVTFFEPQNGTYSDDAWGYKAYFGLF
```

Interfering Agents that Bind to HA Polypeptides

In some embodiments, interfering agents are entities that bind to HA polypeptides (and/or to variants, fragments, and/or characteristic portions thereof), such as any of the HA polypeptides described herein. In some embodiments, interfering agents are entities that bind to H1 HA polypeptides (and/or to variants, fragments, and/or characteristic portions thereof). In some embodiments, interfering agents bind to H1 HA polypeptides with greater affinity than they bind to non-H1 HA polypeptides. In some embodiments, interfering agents bind to H1 HA polypeptides with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to non-H1 HA polypeptides. In some embodiments, interfering agents bind to H1 HA polypeptides having one or more of the following mutations: Ile219Lys, Ser186Pro, Ala189Thr, and/or Glu227Ala with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to H1 HA polypeptides not having one or more of those mutations. In some embodiments, interfering agents bind to H1 HA polypeptides having a Ile219Lys mutation with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to H1 HA polypeptides not having that mutation. In some embodiments, interfering agents bind to H1 HA polypeptides having Ser186Pro, Ala189Thr, and Glu227Ala mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to H1 HA polypeptides not having those mutations. In some embodiments, interfering agents bind to H1 HA polypeptides having Lys145Ser or Lys145Asn mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to H1 HA polypeptides not having those mutations. In some embodiments, interfering agents bind to H1 HA polypeptides having Lys145Ser/Lys145Asn, Ser186Pro, Ala189Thr, and Glu227Ala mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to H1 HA polypeptides not having those mutations. In some embodiments, interfering agents bind to H1 HA polypeptides having Lys145Ser/Lys145Asn and Ile219Lys mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to H1 HA polypeptides not having those mutations.

In some embodiments, an interfering agent binds to influenza virus expressing an H1 HA polypeptide with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than it binds to an influenza virus expressing a non-H1 HA polypeptide. In some embodiments, interfering agents bind to influenza virus expressing H1 HA polypeptides having one or more of the following mutations: Ile219Lys, Ser186Pro, Ala189Thr, and/or Glu227Ala with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to influenza virus expressing H1 HA polypeptides not having one or more of those mutations. In some embodiments, interfering agents bind to influenza virus expressing H1 HA polypeptides having a Ile219Lys mutation with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to influenza virus expressing H1 HA polypeptides not having that mutation. In some embodiments, interfering agents bind to influenza virus expressing H1 HA polypeptides having Ser186Pro, Ala189Thr, and Glu227Ala mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to influenza virus expressing H1 HA polypeptides not having those mutations. In some embodiments, interfering agents bind to influenza virus expressing H1 HA polypeptides having Lys145Ser or Lys145Asn mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to influenza virus expressing H1 HA polypeptides not having those mutations. In some embodiments, interfering agents bind to influenza virus expressing H1 HA polypeptides having Lys145Ser/Lys145Asn, Ser186Pro, Ala189Thr, and Glu227Ala mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to influenza virus expressing H1 HA polypeptides not having those mutations. In some embodiments, interfering agents bind to influenza virus expressing H1 HA polypeptides having Lys145Ser/Lys145Asn and Ile219Lys mutations with a 2-fold, 3-fold, 4-fold, 5-fold, 6-fold, 7-fold, 8-fold, 9-fold, 10-fold, 20-fold, 50-fold, 100-fold, 500-fold, 1000-fold, or more than 1000-fold greater affinity than they bind to influenza virus expressing H1 HA polypeptides not having those mutations.

Interfering agents having one or more of the binding preferences described herein may be useful as therapeutic agents for treatment and/or prevention of influenza, e.g., H1 HA influenza. In some embodiments, interfering agents having one or more of the binding preferences described herein may be useful as therapeutic agents for treatment and/or prevention of influenza expressing H1 HA polypeptides having one or more of Lys145Ser, Lys145Asn, Ile219Lys, Ser186Pro, Ala189Thr, and/or Glu227Ala mutations. In some embodiments, interfering agents having one or more of the binding preferences described herein may be useful as therapeutic agents for treatment and/or prevention of influenza expressing H1 HA polypeptides having an Ile219Lys mutation. In some embodiments, interfering agents having one or more of the binding preferences described herein may be useful as therapeutic agents for treatment and/or prevention of influenza expressing H1 HA polypeptides having Ile219Lys, Ser186Pro, Ala189Thr, and Glu227Ala mutations. In some embodiments, interfering agents having one or more of the binding preferences described herein may be useful as therapeutic agents for treatment and/or prevention of influenza expressing H1 HA polypeptides having Lys145Ser or Lys145Asn mutations. In some embodiments, interfering agents having one or more of the binding preferences described herein may be useful as therapeutic agents for treatment and/or prevention of influenza expressing H1 HA polypeptides having Lys145Ser/Lys145Asn, Ser186Pro, Ala189Thr, and Glu227Ala mutations. In some embodiments, interfering agents having one or more of the binding preferences described herein may be useful as therapeutic agents for treatment and/or prevention of influenza expressing H1 HA polypeptides having Lys145Ser/Lys145Asn and Ile219Lys mutations.

In some embodiments, when administered to a subject, interfering agents bind to at least about 10%, about 15%, about 20%, about 25%, about 30% about 35%, about 40%, about 45%, about 50%, about 55%, about 60%, about 65%, about 70%, about 75%, about 80%, about 85%, about 90%, about 95%, or more of the HA polypeptides (e.g., of the H1 polypeptides and/or of the H1 polypeptide variants with enhanced human binding and/or infectivity) present with the subject (e.g., present within a subject's blood, mucosal tissues, etc.).

Aptamers

In some embodiments, binding agents provided in accordance with the present invention are aptamers. Aptamer interfering agents can function by binding to umbrella topology glycans and/or HA polypeptides, e.g., H1 HA polypeptides (and/or to variants, fragments, and/or characteristic portions thereof).

Aptamers are macromolecules composed of nucleic acid (e.g., RNA, DNA) that bind tightly to a specific molecular target (e.g., an umbrella topology glycan and/or an HA polypeptide, variant, fragment, and/or characteristic portion thereof). A particular aptamer may be described by a linear nucleotide sequence and is typically about 15-60 nucleotides in length. Without wishing to be bound by any theory, it is contemplated that the chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and small molecules. In addition to high specificity, aptamers have very high affinities for their targets (e.g., affinities in the picomolar to low nanomolar range for proteins). Aptamers are chemically stable and can be boiled or frozen without loss of activity. Because they are synthetic molecules, they are amenable to a variety of modifications, which can optimize their function for particular applications. For example, aptamers can be modified to dramatically reduce their sensitivity to degradation by enzymes in the blood for use in vivo applications. In addition, aptamers can be modified to alter their biodistribution or plasma residence time.

Selection of aptamers that can bind umbrella topology glycans (and/or to umbrella topology glycan mimics) can be achieved through methods known in the art. For example, aptamers can be selected using the SELEX (Systematic Evolution of Ligands by Exponential Enrichment) method (Tuerk, C., and Gold, L., Science 249:505-510 (1990); incorporated herein by reference). In the SELEX method, a large library of nucleic acid molecules (e.g., $10^{15}$ different molecules) is produced and/or screened with a target molecule (e.g., an umbrella topology glycan and/or an HA polypeptide, variant, fragment, and/or characteristic portion thereof). A target molecule is allowed to incubate with the library of nucleotide sequences for a period of time. Several methods, known in the art, can then be used to physically isolate the aptamer target molecules from the unbound molecules in the mixture, which can be discarded. Aptamers with the highest affinity for the target molecule can then be purified away from the target molecule and amplified enzymatically to produce a new library of molecules that is substantially enriched for aptamers that can bind the target molecule. The enriched library can then be used to initiate a new cycle of selection, partitioning, and amplification. After 5-15 cycles of this iterative selection, partitioning and amplification process, the library is reduced to a small number of aptamers that bind tightly to the target molecule. Individual molecules in the mixture can then be isolated, their nucleotide sequences determined, and their properties with respect to binding affinity and specificity measured and compared. Isolated aptamers can then be further refined to eliminate any nucleotides that do not contribute to target binding and/or aptamer structure, thereby producing aptamers truncated to their core binding domain. See Jayasena, S. D. *Clin. Chem.* 45:1628-1650 (1999) for review of aptamer technology; the entire teachings of which are incorporated herein by reference.

Antibodies

In some embodiments, interfering agents are antibodies that recognize umbrella-topology glycans and/or HA polypeptides, e.g., H1 HA polypeptides (and/or to variants, fragments, and/or characteristic portions thereof).

Antibodies may be monoclonal or polyclonal and may be prepared by any of a variety of techniques known to those of ordinary skill in the art (e.g., see Harlow and Lane, Antibodies: A Laboratory *Manual*, Cold Spring Harbor Laboratory, 1988; incorporated herein by reference). For example, antibodies can be produced by cell culture techniques, including the generation of monoclonal antibodies, or via transfection of antibody genes into suitable bacterial or mammalian cell hosts, in order to allow for the production of recombinant antibodies.

Antibodies suitable for the invention include antibodies or fragments of antibodies that bind immunospecifically to any umbrella topology glycan epitope. As used herein, the term "antibodies" is intended to include immunoglobulins and fragments thereof which are specifically reactive to the designated protein or peptide, or fragments thereof. Suitable antibodies include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibody polypeptides for use herein may be of any type (e.g., IgA, IgD, IgE, IgG, IgM).

As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region.

Antibodies can be generated using methods well known in the art. For example, protocols for antibody production are described by Harlow and Lane, *Antibodies: A Laboratory Manual*, (1988). Typically, antibodies can be generated in mouse, rat, guinea pig, hamster, camel, llama, shark, or other appropriate host. Alternatively, antibodies may be made in chickens, producing IgY molecules (Schade et al., (1996) *ALTEX* 13(5):80-85; incorporated herein by reference). In some embodiments, antibodies suitable for the present invention are subhuman primate antibodies. For example, general techniques for raising therapeutically useful antibodies in baboons may be found, for example, in Goldenberg et al., international patent publication No. WO 91/11465 (1991; incorporated herein by reference), and in Losman et al., *Int. J. Cancer* 46: 310 (1990; incorporated herein by reference). In some embodiments, monoclonal antibodies may be prepared using hybridoma methods (Milstein and Cuello, (1983) *Nature* 305(5934):537-40; incorporated herein by reference). In some embodiments, monoclonal antibodies may also be made by recombinant methods (U.S. Pat. No. 4,166,452, 1979; incorporated herein by reference).

In some embodiments, antibodies suitable for the invention may include humanized or human antibodies. Humanized forms of non-human antibodies are chimeric Igs, Ig chains or fragments (such as Fv, Fab, Fab', F(ab')2 or other antigen-binding subsequences of Abs) that contain minimal sequence derived from non-human Ig. Generally, a humanized antibody has one or more amino acid residues introduced from a non-human source. These non-human amino acid residues are often referred to as "import" residues, which are typically taken from an "import" variable domain. Humanization is accomplished by substituting rodent complementarity determining regions (CDRs) or CDR sequences for the corresponding sequences of a human antibody (Riechmann et al., *Nature* 332(6162):323-7, 1988; Verhoeyen et al., *Science.* 239(4847):1534-6, 1988; incorporated herein by reference). Such "humanized" antibodies are chimeric Abs (U.S. Pat. No. 4,816,567, 1989; incorporated herein by reference), wherein substantially less than an intact human variable domain has been substituted by the corresponding sequence from a non-human species. In some embodiments, humanized antibodies are typically human antibodies in which some CDR residues and possibly some FR residues are substituted by residues from analogous sites in rodent Abs. Humanized antibodies include human Igs (recipient antibody) in which residues from a CDR of the recipient are replaced by residues from a CDR of a non-human species (donor antibody) such as mouse, rat or rabbit, having the desired specificity, affinity and capacity. In some instances, corresponding non-human residues replace Fv framework residues of the human Ig. Humanized antibodies may comprise residues that are found neither in the recipient antibody nor in the imported CDR or framework sequences.

In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Riechmann et al., *Nature* 332(6162):323-7, 1988; Verhoeyen et al., *Science.* 239(4847):1534-6, 1988; all of which are incorporated herein by reference).

Human antibodies can also be produced using various techniques, including phage display libraries (Hoogenboom et al., *Mol Immunol.* (1991) 28(9):1027-37; Marks et al., *J Mol Biol.* (1991) 222(3):581-97; all of which are incorporated herein by reference) and the preparation of human monoclonal antibodies (Reisfeld and Sell, 1985, *Cancer Surv.* 4(1):271-90; incorporated herein by reference). Similarly, introducing human Ig genes into transgenic animals in which the endogenous Ig genes have been partially or completely inactivated can be exploited to synthesize human antibodies. Upon challenge, human antibody production is observed, which closely resembles that seen in humans in all respects, including gene rearrangement, assembly, and antibody repertoire (Fishwild et al., High-avidity human IgG kappa monoclonal antibodies from a novel strain of minilocus transgenic mice, *Nat Biotechnol.* 1996 July; 14(7): 845-51; Lonberg et al., Antigen-specific human antibodies from mice comprising four distinct genetic modifications, *Nature* 1994 April 28; 368(6474):856-9; Lonberg and Huszar, Human antibodies from transgenic mice, *Int. Rev. Immunol.* 1995; 13(1):65-93; Marks et al., By-passing immunization: building high affinity human antibodies by chain shuffling. *Biotechnology* (NY). 1992 July; 10(7):779-83; all of which are incorporated herein by reference).

Testing Interfering Agents in Animal Models

The present invention provides methods for testing an interfering agent (e.g., HA polypeptides, LSBAs, USBAs, UTSBAs, umbrella-topology glycans, etc.) in an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, rabbits, and rats. In certain embodiments, an animal host used for the invention is a ferret. In particular, in some embodiments, an animal host is naïve to viral exposure or infection prior to administration of an interfering agent (optionally in a composition). In some embodiments, the animal host is inoculated with, infected with, or otherwise exposed to virus prior to or concurrent with administration of an interfering agent. An animal host used in the practice of the present invention can be inoculated with, infected with, or otherwise exposed to virus by any method known in the art. In some embodiments, an animal host may be inoculated with, infected with, or exposed to virus intranasally.

In some embodiments, a suitable animal host may have a similar distribution of umbrella vs. cone topology glycans and/or α2-6 glycans vs. α2-3 glycans to the distribution found in the human respiratory tract. For example, it is contemplated that a ferret as an animal host may be more representative than a mouse when used as model of disease caused by influenza viruses in humans (Tumpey, et al. Science (2007) 315; 655-659; incorporated herein by reference). Without wishing to be bound any theories, the present invention encompasses the idea that ferrets may have a more similar distribution of glycans in the respiratory tract to those in the human respiratory tract than mouse does to human.

Naïve and/or inoculated animals may be used for any of a variety of studies. For example, such animal models may be used for virus transmission studies as in known in the art. It is contemplated that the use of ferrets in virus transmission studies may serve as a reliable predictor for virus transmission in humans. For example, air transmission of viral influenza from inoculated animals (e.g., ferrets) to naïve animals is known in the art (Tumpey, et al. Science (2007) 315; 655-659; incorporated herein by reference). Virus transmission studies may be used to test interfering agent polypeptides (e.g., HA polypeptides). For example, interfering agents may be administered to a suitable animal host before, during or after virus transmission studies in order to determine the efficacy of said interfering agent in blocking virus binding and/or infectivity in the animal host. Using information gathered from virus transmission studies in an animal host, one may predict the efficacy of an interfering agent in blocking virus binding and/or infectivity in a human host.

Detection of H1-Containing Influenzas

The present invention provides systems, compositions, and methods for detection of influenza. In some embodiments, the invention provides binding agents that preferentially bind to a particular HA polypeptide (and/or to variants, fragments, and/or characteristic portions thereof). For example, in some embodiments, a binding agent preferentially binds to H1 HA polypeptides as compared with non-H1 HA polypeptides, as described in further detail in the section above entitled "HA Polypeptide Binding Agents." In some embodiments, a binding agent preferentially binds to an H1 HA polypeptide having enhanced human binding and/or infectivity as compared with a parent H1 HA polypeptide (e.g., a parent H1 HA influenza strain found on Table 1).

In some embodiments, a binding agent preferentially binds to an H1 HA polypeptide having one or more of the following mutations: Lys145Ser, Lys145Asn, Ile219Lys, Ser186Pro, Ala189Thr, and/or Glu227Ala with as compared with an H1 HA polypeptide not having one or more of those mutations. In some embodiments, a binding agent preferentially binds to an H1 HA polypeptide having an Ile219Lys mutation as compared with an H1 HA polypeptide not having that mutation. In some embodiments, a binding agent preferentially binds to an H1 HA polypeptide having Ser186Pro, Ala189Thr, and Glu227Ala mutations as compared with an H1 HA polypeptide not having those mutations. In some embodiments, a binding agent preferentially binds to an H1 HA polypeptide having Lys145Ser or Lys145Asn mutations as compared with an H1 HA polypeptide not having those mutations. In some embodiments, a binding agent preferentially binds to an H1 HA polypeptide having Lys145Ser/Lys145Asn, Ser186Pro, Ala189Thr, and Glu227Ala mutations as compared with an H1 HA polypeptide not having those mutations. In some embodiments, a binding agent preferentially binds to an H1 HA polypeptide having Lys145Ser/Lys145Asn and Ile219Lys mutations as compared with an H1 HA polypeptide not having those mutations.

In some embodiments, binding agents that preferentially bind to H1 HA polypeptides (e.g., variants, fragments, and/or characteristic portions thereof) are useful for various diagnostic and/or surveillance methods. For example, binding agents that preferentially bind to particular HA polypeptides, such as H1 HA polypeptides, (and/or to variants, fragments, and/or characteristic portions thereof) can be used in assays to determine whether a patient is infected with and/or suffering from infection with an influenza virus. In some embodiments, binding agents that preferentially bind to H1 HA polypeptides (and/or to variants, fragments, and/or characteristic portions thereof) can be used in assays to determine whether a patient is infected with and/or suffering from infection with an H1 influenza virus. In some embodiments, binding agents that preferentially bind to H1 HA polypeptides (and/or to variants, fragments, and/or characteristic portions thereof) can be used in assays to determine whether a patient is infected with and/or suffering from infection with an H1 influenza virus characterized in that the H1 polypeptide shows enhanced human binding and/or infectivity. In some embodiments, binding agents that preferentially bind to particular H1 HA polypeptides (and/or to variants, fragments and/or characteristic portions thereof) can be used to determine whether a patient is infected with and/or suffering from infection with an H1 influenza virus characterized in that its H1 polypeptide has one or more of the following mutations: Lys145Ser, Lys145Asn, Ile219Lys, Ser186Pro, Ala189Thr, and/or Glu227Ala. In some embodiments, binding agents that preferentially bind to H1 HA polypeptides (and/or to variants, fragments, and/or characteristic portions thereof) can be used in assays to determine whether a patient is infected with and/or suffering from infection with an H1 influenza virus characterized in that the H1 polypeptide has an Ile219Lys mutation. In some embodiments, binding agents that preferentially bind to H1 HA polypeptides (and/or to variants, fragments, and/or characteristic portions thereof) can be used in assays to determine whether a patient is infected with and/or suffering from infection with an H1 influenza virus characterized in that the H1 polypeptide has Ser186Pro, Ala189Thr, and/or Glu227Ala mutations. In some embodiments, binding agents that preferentially bind to H1 HA polypeptides (and/or to variants, fragments, and/or characteristic portions thereof) can be used in assays to determine whether a patient is infected with and/or suffering from infection with an H1 influenza virus characterized in that the H1 polypeptide has Lys145Ser or Lys145Asn mutations. In some embodiments, binding agents that preferentially bind to H1 HA polypeptides (and/or to variants, fragments, and/or characteristic portions thereof) can be used in assays to determine whether a patient is infected with and/or suffering from infection with an H1 influenza virus characterized in that the H1 polypeptide has Lys145Ser/Lys145Asn, Ser186Pro, Ala189Thr, and Glu227Ala mutations. In some embodiments, binding agents that preferentially bind to H1 HA polypeptides (and/or to variants, fragments, and/or characteristic portions thereof) can be used in assays to determine whether a patient is infected with and/or suffering from infection with an H1 influenza virus characterized in that the H1 polypeptide has Lys145Ser/Lys145Asn and Ile219Lys mutations.

In some embodiments, binding agents that preferentially bind to HA polypeptides, such as H1 HA polypeptides, (and/or to variants, fragments, and/or characteristic portions thereof) can be used in assays to determine whether a sample contains influenza virus. In some embodiments, binding agents that preferentially bind to H1 HA polypeptides (and/or to variants, fragments, and/or characteristic portions thereof) can be used in assays to determine whether a sample contains an H1 influenza virus. In some embodiments, binding agents that preferentially bind to H1 HA polypeptides (and/or to variants, fragments, and/or characteristic portions thereof) can be used in assays to determine whether a sample contains an H1 influenza virus characterized in that the H1 polypeptide shows enhanced human binding and/or infectivity. In some embodiments, binding agents that preferentially bind to particular H1 HA polypeptides (and/or to variants, fragments and/or characteristic portions thereof) can be used to determine whether a sample contains an H1 influenza virus characterized in that its H1 polypeptide has one or more of the following mutations: Lys145Ser, Lys145Asn, Ile219Lys, Ser186Pro, Ala189Thr, and/or Glu227Ala. In some embodiments, binding agents that preferentially bind to H1 HA polypeptides (and/or to variants, fragments, and/or characteristic portions thereof) can be used in assays to determine whether a sample contains an H1 influenza virus characterized in that the H1 polypeptide has an Ile219Lys mutation. In some embodiments, binding agents that preferentially bind to H1 HA polypeptides (and/or to variants, fragments, and/or characteristic portions thereof) can be used in assays to determine whether a sample contains an H1 influenza virus characterized in that the H1 polypeptide has Ser186Pro, Ala189Thr, and/or Glu227Ala mutations. In some embodiments, binding agents that preferentially bind to H1 HA polypeptides (and/or to variants, fragments, and/or characteristic portions thereof) can be used in assays to determine whether a sample contains an H1 influenza virus characterized in that the H1 polypeptide has Lys145Ser or Lys145Asn mutations. In some embodiments, binding agents that preferentially bind to H1 HA polypeptides (and/or to variants, fragments, and/or characteristic portions thereof) can be used in assays to determine whether a sample contains an H1 influenza virus characterized in that the H1 polypeptide has Lys145Ser/Lys145Asn, Ser186Pro, Ala189Thr, and Glu227Ala mutations. In some embodiments, binding agents that preferentially bind to H1 HA polypeptides (and/or to variants, fragments, and/or characteristic portions thereof) can be used in assays to determine whether a sample contains an H1 influenza virus characterized in that the H1 polypeptide has Lys145Ser/Lys145Asn and Ile219Lys mutations.

The present invention provides systems, compositions, and methods utilizing HA polypeptide binding agents for detecting HA polypeptides (e.g., fragments and/or characteristic portions thereof) in pathological samples, including, but not limited to, blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. The present invention also provides systems, compositions, and methods for detecting HA polypeptides in environmental samples, including, but not limited to, soil, water, and flora. Other samples that have not been listed may also be applicable.

In some embodiments, methods for detecting HA polypeptides involve providing a pathological and/or environmental sample, contacting the sample with an HA polypeptide binding agent, and determining whether the HA polypeptide binding agent binds to the sample relative to a negative control binding agent. In some embodiments, such methods involve a step of processing the sample (e.g., subjecting the sample to one or more purification steps) prior to the step of contacting. In some embodiments, provided HA polypeptide binding agents are labeled with a detectable moiety (e.g., fluorescent, radioactive, chemiluminescent label, etc.). In some embodiments, HA polypeptide binding agents are detectable via immunological methods (e.g., western blotting, ELISA, immunofluorescence, etc.). In some embodiments, HA polypeptide binding agents are immobilized (e.g., to a bead, to a microtiter dish, to an array, to a glycan array, etc.) prior to the step of contacting.

In some embodiments, HA polypeptide binding agents are or comprise umbrella topology glycans (including umbrella topology glycan mimics). In such embodiments, glycans are immobilized to glycan arrays, and the step of contacting involves incubating the glycan array with the sample.

In some embodiments, HA polypeptide binding agents are or comprise antibodies (including antibody fragments, as described herein). In such embodiments, antibodies are immobilized to beads, and the step of contacting involves performing an immunoprecipitation.

Antibodies that bind to HA polypeptides can also be used in virus neutralization tests, in which a sample is treated with antibody specific to HA polypeptides of interest, and tested for its ability to infect cultured cells relative to untreated sample. If virus in that sample contains such HA polypeptides, the antibody will neutralize the virus and prevent it from infecting the cultured cells. Alternatively or additionally, such antibodies can also be used in HA-inhibition tests, in which the HA protein is isolated from a given sample, treated with antibody specific to a particular HA polypeptide or set of HA polypeptides, and tested for its ability to agglutinate erythrocytes relative to untreated sample. If virus in the sample contains such an HA polypeptide, the antibody will neutralize the activity of the HA polypeptide and prevent it from agglutinating erythrocytes (Harlow & Lane, Antibodies: A Laboratory Manual, CSHL Press, 1988; www.who.int/cseresources/publications/influenza/WHO_CDS_CSR_NCS_2002_5/en/index.html; www.who.int/csr/disease/avian_influenza/guidelines/labtests/en/index.html).

In some embodiments, such agents may include nucleic acids that specifically bind to nucleotides that encode particular HA polypeptides and that can be used to specifically detect such HA polypeptides by RT-PCR or in situ hybridization (www.whaint/cseresources/publications/influenza/WHO_CDS_CSR_NCS_2002_5/en/index.html; www.who.int/csr/disease/avian influenza/guidelines/labtests/en/index.html). In certain embodiments, nucleic acids which have been isolated from a sample are amplified prior to detection. In certain embodiments, diagnostic reagents can be detectably labeled.

Kits

The present invention provides kits containing reagents useful for carrying out therapeutic, prophylactic, and/or diagnostic methods in accordance with the invention. Kits contents include, but are not limited to, HA polypeptides, HA polypeptide binding agents, HA polypeptide interfering agents, fragments thereof, variants thereof, and/or characteristic portions thereof. Kits may include nucleic acids (e.g., expression plasmids) encoding HA polypeptides, HA polypeptide binding agents, HA polypeptide interfering agents, fragments thereof, variants thereof, and/or characteristic portions thereof. Mammalian cell lines may also be included with the kits, including but not limited to, Vero and MDCK cell lines.

In certain embodiments, kits for use in accordance with the present invention may include, a reference sample, instructions for processing samples, performing the test, instructions for interpreting the results, buffers and/or other reagents necessary for performing the test. In certain embodiments the kit can comprise a panel of antibodies.

In some embodiments of the present invention, glycan arrays, as discussed below, may be utilized as diagnostics and/or kits.

In certain embodiments, glycan arrays and/or kits are used to perform dose response studies to assess binding of HA polypeptides to umbrella glycans at multiple doses (e.g., as described herein). Such studies give particularly valuable insight into the binding characteristics of tested HA polypeptides, and are particularly useful to assess specific binding. Dose response binding studies of this type find many useful applications. To give but one example, they can be helpful in tracking the evolution of binding characteristics in a related series of HA polypeptide variants, whether the series is generated through natural evolution, intentional engineering, or a combination of the two.

In certain embodiments, glycan arrays and/or kits are used to induce, identify, and/or select binding agents (e.g., HA polypeptides, and/or HA polypeptide variants) having desired binding characteristics. For instance, in some embodiments, glycan arrays and/or kits are used to exert evolutionary (e.g., screening and/or selection) pressure on a population of polypeptide binding agents (e.g., HA polypeptides).

In some embodiments, kits comprise instructions for use.

Glycan Arrays

To rapidly expand the current knowledge of known specific glycan-glycan binding protein (GBP) interactions, the Consortium for Functional Glycomics (CFG; www.functionalglycomics.org), an international collaborative research initiative, has developed glycan arrays comprising several glycan structures that have enabled high throughput screening of GBPs for novel glycan ligand specificities. The glycan arrays comprise both monovalent and polyvalent glycan motifs (i.e., attached to polyacrylamide backbone), and each array comprises 264 glycans with low (10 μM) and high (100 μM) concentrations, and six spots for each concentration (see http://www.functionalglycomics.org/static/consortium/resources/resourcecoreh5.shtml).

Arrays predominantly comprise synthetic glycans that capture the physiological diversity of N- and O-linked glycans. In addition to the synthetic glycans, N-linked glycan mixtures derived from different mammalian glycoproteins are also represented on the array.

As used herein, a glycan "array" refers to a set of one or more glycans, optionally immobilized on a solid support. In some embodiments, an "array" is a collection of glycans present as an organized arrangement or pattern at two or more locations that are physically separated in space. Typically, a glycan array will have at least 4, 8, 16, 24, 48, 96 or several hundred or thousand discrete locations. In general, glycan arrays may have any of a variety of formats. Various different array formats applicable to biomolecules are known in the art. For example, a huge number of protein and/or nucleic acid arrays are well known. Those of ordinary skill in the art will immediately appreciate standard array formats appropriate for glycan arrays of the present invention.

In some embodiments, glycan arrays are present in "microarray" formats. A microarray may typically have sample locations separated by a distance of 50-200 microns or less and immobilized sample in the nano to micromolar range or nano to picogram range. Array formats known in the art include, for example, those in which each discrete sample location has a scale of, for example, ten microns.

In some embodiments, glycan arrays comprise a plurality of glycans spatially immobilized on a support. The present invention provides glycan molecules arrayed on a support. As used herein, "support" refers to any material which is suitable to be used to array glycan molecules. As will be appreciated by those of ordinary skill in the art, any of a wide variety of materials may be employed. To give but a few examples, support materials which may be of use in the invention include hydrophobic membranes, for example, nitrocellulose, PVDF or nylon membranes. Such membranes are well known in the art and can be obtained from, for example, Bio-Rad, Hemel Hempstead, UK.

In some embodiments, the support on which glycans are arrayed may comprise a metal oxide. Suitable metal oxides include, but are not limited to, titanium oxide, tantalum oxide, and aluminum oxide. Examples of such materials may be obtained from Sigma-Aldrich Company Ltd, Fancy Road, Poole, Dorset. BH12 4QH UK. In some embodiments, such a support is or comprises a metal oxide gel. In some embodiments, such a support is or comprises silica gels or aluminum oxide gels (examples of such materials may be obtained from, for example, Merck KGaA, Darmstadt, Germany).

In some embodiments of the invention, glycan arrays are immobilized on a support that can resist change in size or shape during normal use. For example a support may be a glass slide coated with a component material suitable to be used to array glycans. Also, some composite materials can desirable provide solidity to a support.

As demonstrated herein, arrays are useful for the identification and/or characterization of different HA polypeptides and their binding characteristics. In certain embodiments, HA polypeptides are tested on such arrays to assess their ability to bind to umbrella topology glycans (e.g., to $\alpha$2-6 sialylated glycans, and particularly to long $\alpha$2-6 sialylated glycans arranged in an umbrella topology).

Indeed, the present invention provides arrays of HA polypeptide binding agents that are or comprise one or more of umbrella topology glycans, mimics of umbrella topology glycans, $\alpha$2-6 sialylated glycans, and $\alpha$2-3 sialylated glycans, that can be used to characterize HA polypeptide binding capabilities and/or as a diagnostic to detect, for example, human-binding HA polypeptides (e.g., H1 HA polypeptides, as described above). As will be clear to those of ordinary skill in the art, such arrays are useful for characterizing or detecting any HA polypeptides, including for example, those found in natural influenza isolates in addition to those designed and/or prepared by researchers.

In some embodiments, such arrays include glycans representative of about 10%, 15%, 20%, 25%, 30% 35%, 40%, 45%, 50%, 55%, 60%, 65%, 70%, 75%, 80%, 85%, 90% 95%, or more of the glycans (e.g., the umbrella glycans, which will often be α2-6 sialylated glycans, particularly long α2-6 sialylated glycans) found on human HA receptors, and particularly on human upper respiratory tract HA receptors. In some embodiments, arrays include some or all of the glycan structures depicted in FIGS. 5-8. In some embodiments, arrays include at least about 10%, 15%, 20%, 25%, 30% 35%, 40%, 45%, 50%, 55%, 60%, 65%, 70%, 75%, 80%, 85%, 90% 95%, or more of these depicted glycans.

The present invention provides methods for identifying or characterizing HA proteins using glycan arrays. In some embodiments, for example, such methods comprise steps of (1) providing a sample containing HA polypeptide, (2) contacting the sample with a glycan array comprising, and (3) detecting binding of HA polypeptide to one or more glycans on the array.

Suitable sources for samples containing HA polypeptides to be contacted with glycan arrays according to the present invention include, but are not limited to, pathological samples and/or environmental samples, such as those described above.

A wide variety of detection systems suitable for assaying HA polypeptide binding to glycan arrays are known in the art. For example, HA polypeptides can be detectably labeled (directly or indirectly) prior to or after being contacted with the array; binding can then be detected by detection of localized label. In some embodiments, scanning devices can be utilized to examine particular locations on an array.

Alternatively or additionally, binding to arrayed glycans can be measured using, for example, calorimetric, fluorescence, or radioactive detection systems, or other labeling methods, or other methods that do not require labeling. In general, fluorescent detection typically involves directly probing the array with a fluorescent molecule and monitoring fluorescent signals. Alternatively or additionally, arrays can be probed with a molecule that is tagged (for example, with biotin) for indirect fluorescence detection (in this case, by testing for binding of fluorescently-labeled streptavidin). Alternatively or additionally, fluorescence quenching methods can be utilized in which the arrayed glycans are fluorescently labeled and probed with a test molecule (which may or may not be labeled with a different fluorophore). In such embodiments, binding to the array acts to squelch the fluorescence emitted from the arrayed glycan, therefore binding is detected by loss of fluorescent emission. Alternatively or additionally, arrayed glycans can be probed with a live tissue sample that has been grown in the presence of a radioactive substance, yielding a radioactively labeled probe. Binding in such embodiments can be detected by measuring radioactive emission.

Such methods are useful to determine the fact of binding and/or the extent of binding by HA polypeptides to glycan arrays. In some embodiments of the invention, such methods can further be used to identify and/or characterize agents that interfere with or otherwise alter glycan-HA polypeptide interactions.

Methods described below may be useful for identifying whether a molecule thought to be capable of interacting with a carbohydrate can actually do so, or to identify whether a molecule unexpectedly has the capability of interacting with a carbohydrate.

The present invention provides methods of using arrays, for example, to detect a particular agent in a test sample. For instance, such methods may comprise steps of (1) contacting a glycan array with a test sample (e.g., with a sample thought to contain an HA polypeptide, e.g., an H1 HA polypeptide); and, (2) detecting the binding of any agent in the test sample to the array.

Binding to arrays may be utilized, for example, to determine kinetics of interaction between binding agent and glycan. For example, methods for determining interaction kinetics may include steps of (1) contacting a glycan array with the molecule being tested; and, (2) measuring kinetics of interaction between the binding agent and arrayed glycan(s).

The kinetics of interaction of a binding agent with any of the glycans in an array can be measured by real time changes in, for example, colorimetric or fluorescent signals, as detailed above. Such methods may be of particular use in, for example, determining whether a particular binding agent is able to interact with a specific carbohydrate with a higher degree of binding than does a different binding agent interacting with the same carbohydrate.

It will be appreciated, of course, that glycan binding by HA polypeptides can be evaluated on glycan samples or sources not present in an array format per se. For example, HA polypeptides can be bound to tissue samples and/or cell lines to assess their glycan binding characteristics. Appropriate cell lines include, for example, any of a variety of mammalian cell lines, particularly those expressing HA receptors containing umbrella topology glycans (e.g., at least some of which may be α2-6 sialylated glycans, and particularly long α2-6 sialylated glycans). In some embodiments, utilized cell lines express individual glycans with umbrella topology. In some embodiments, utilized cell lines express a diversity of glycans. In some embodiments, cell lines are obtained from clinical isolates; in some they are maintained or manipulated to have a desired glycan distribution and/or prevalence. In some embodiments, tissue samples and/or cell lines express glycans characteristic of mammalian upper respiratory epithelial cells.

Treatment

The present invention provides systems, compositions, and methods to treat (e.g., alleviate, ameliorate, relieve, delay onset of, inhibit progression of, reduce severity of, and/or reduce incidence of one or more symptoms or features of) and/or prevent influenza infection. In some embodiments, interfering agents and/or binding agents such as those described herein may be used for a variety of therapeutic purposes, e.g., treating influenza infection and/or developing vaccines to immunize subjects against influenza infection.

The present invention encompasses the recognition that vaccines and/or therapeutics that successfully prevent, delay onset of, and/or treat infection with influenza strain A/South Carolina/1/1918 and/or A/Swine/Iowa/15/1930 may successfully prevent, delay onset of, and/or treat infection with influenza strain 2009 A/H1N1 (e.g., A/CA/4/2009). Vaccines and/or therapeutics that successfully prevent, delay onset of, and/or treat infection with influenza strain 2009 A/H1N1 (e.g., A/CA/4/2009) may successfully prevent, delay onset of, and/or treat infection with influenza strain A/South Carolina/1/1918 and/or A/Swine/Iowa/15/1930. Thus, in some embodiments, vaccine and/or therapeutic compositions (such as those described in the sections below) comprise one or more of influenza strains A/South Carolina/1/1918, A/Swine/Iowa/15/1930, and/or 2009 A/H1N1 (e.g., A/CA/4/2009). In some embodiments, vaccine and/or therapeutic compositions comprise influenza strains A/South Carolina/1/1918 and A/Swine/Iowa/15/1930. In some embodiments, vaccine and/or therapeutic compositions comprise influenza strains A/South Carolina/1/1918 and 2009 A/H1N1 (e.g., A/CA/4/2009). In some embodiments, vaccine and/or therapeutic compositions comprise influenza strains A/Swine/Iowa/15/1930 and 2009 A/H1N1 (e.g., A/CA/4/2009). In some embodiments, vaccine and/or therapeutic compositions comprise influenza strain A/South Carolina/1/1918. In some embodiments, vaccine and/or therapeutic compositions comprise influenza strain A/Swine/Iowa/15/1930. In some embodiments, vaccine and/or therapeutic compositions comprise influenza strain 2009 A/H1N1 (e.g., A/CA/4/2009).

In some embodiments, vaccine and/or therapeutic compositions (such as those described in the sections below) comprise one or more H1 HA polypeptides present in one or more of influenza strains A/South Carolina/1/1918, A/Swine/Iowa/15/1930, and/or 2009 A/H1N1 (e.g., A/CA/4/2009). In some embodiments, vaccine and/or therapeutic compositions comprise H1 HA polypeptides present in influenza strains A/South Carolina/1/1918 and A/Swine/Iowa/15/1930. In some embodiments, vaccine and/or therapeutic compositions comprise H1 HA polypeptides present in influenza strains A/South Carolina/1/1918 and 2009 A/H1N1 (e.g., A/CA/4/2009). In some embodiments, vaccine and/or therapeutic compositions comprise H1 HA poly-peptides present in influenza strains A/Swine/Iowa/15/1930 and 2009 A/H1N1 (e.g., A/CA/4/2009). In some embodiments, vaccine and/or therapeutic compositions comprise H1 HA polypeptides present in influenza strain A/South Carolina/1/1918. In some embodiments, vaccine and/or therapeutic compositions comprise H1 HA polypeptides present in influenza strain A/Swine/Iowa/15/1930. In some embodiments, vaccine and/or therapeutic compositions comprise H1 HA polypeptides present in influenza strain 2009 A/H1N1 (e.g., A/CA/4/2009).

In some embodiments, methods of vaccination and/or treatment (such as those described in the sections below) involve stratification of a patient population based on prior exposure to influenza strains A/South Carolina/1/1918 and/or A/Swine/Iowa/15/1930. Such methods involve steps of determining whether a patient has been previously exposed to one or both of influenza strains A/South Carolina/1/1918 and/or A/Swine/Iowa/15/1930. Any of a variety of methods can be used to determine whether an individual has been previously exposed to one or both of influenza strains A/South Carolina/1/1918 and/or A/Swine/Iowa/15/1930. To give but a few examples, white blood cells can be isolated from a patient and analyzed to determine whether any 1918- and/or 1930-positive B cells are present. Alternatively or additionally, epidemiological methods can be utilized to determine a probability that a particular patient has or has not been exposed to 1918 and/or 1930 strains.

In some embodiments, if it is determined that a patient has been previously been exposed to one or both of influenza strains A/South Carolina/1/1918 and/or A/Swine/Iowa/15/1930, that patient may receive less concentrated, less potent, and/or less frequent doses of 2009 A/H1N1 (e.g., A/CA/4/2009) vaccines and/or therapeutics. If it is determined that a patient has not been previously been exposed to one or both of influenza strains A/South Carolina/1/1918 and/or A/Swine/Iowa/15/1930, that patient may receive more concentrated, more potent, and/or more frequent doses of 2009 A/H1N1 (e.g., A/CA/4/2009) vaccines and/or therapeutics.

In some embodiments, if it is determined that a patient has been previously been exposed to one or both of influenza strains A/South Carolina/1/1918 and/or A/Swine/Iowa/15/1930, that patient may be vaccinated using a vaccine composition which has demonstrated protection against A/South Carolina/1/1918 and/or A/Swine/Iowa/15/1930. In some embodiments, if it is determined that a patient has been previously been exposed to one or both of influenza strains A/South Carolina/1/1918 and/or A/Swine/Iowa/15/1930, that patient may be treated using a therapeutic composition which has demonstrated therapeutic effect against A/South Carolina/1/1918 and/or A/Swine/Iowa/15/1930.

A. Vaccination

In some embodiments, interfering agents and/or binding agents in accordance with the invention (e.g., entities that bind to HA polypeptides and/or fragments, variants, and/or characteristic portions thereof entities that bind to umbrella-topology glycans) may be utilized for prophylactic applications. In some embodiments, prophylactic applications involve systems and methods for preventing, inhibiting progression of, and/or delaying the onset of influenza infection.

In some embodiments, influenza vaccines are used to prevent and/or delay onset of infection by influenza. In some embodiments, vaccination is tailored to a particular HA polypeptide. For example, vaccine compositions may comprise H1 HA polypeptides and/or variants, fragments, and/or characteristic portions thereof. In some embodiments, it is desirable for vaccine compositions to comprise antigens that have a native conformation, mediate a protective response (e.g., complement activation, virus neutralization, etc.), and/or can induce a strong antibody response.

In some embodiments, interfering agents may be utilized for passive immunization (i.e., immunization wherein antibodies are administered to a subject). In some embodiments, influenza vaccines for passive immunization may comprise antibody interfering agents, such as those described herein. In some embodiments, passive immunization occurs when antibodies are transferred from mother to fetus during pregnancy. In some embodiments, antibodies are administered directly to an individual (e.g., by injection, orally, etc.).

The present invention provides influenza vaccines for active immunization (i.e., immunization wherein microbes, proteins, peptides, epitopes, mimotopes, etc. are administered to a subject). In some embodiments, influenza vaccines may comprise one or more interfering agents and/or binding agents, as described herein.

In some embodiments, vaccines comprise at least one HA polypeptide (and/or to variants, fragments, and/or characteristic portions thereof), e.g., any of the HA polypeptides, variants, fragments, characteristic portions, and/or combinations thereof described herein (e.g., in the section entitled "HA Polypeptides"). In some embodiments, vaccines comprise H1 HA polypeptides (and/or to variants, fragments, and/or characteristic portions thereof). In some embodiments, vaccines comprise H1 HA polypeptides having one or more of the following mutations: Ile219Lys, Ser186Pro, Ala189Thr, and/or Glu227Ala. In some embodiments, vaccines comprise H1 HA polypeptides having an Ile219Lys mutation. In some embodiments, vaccines comprise H1 HA polypeptides having a mutation at amino acid position 219 (e.g., Ile219Lys) and at least one additional amino acid substitution at an amino acid position selected from the group consisting of a 98, 136, 137, 138, 145, 153, 155, 156, 159, 183, 186, 187, 189, 190, 192, 193, 194, 195, 196, 215, 219, 222, 225, 226, 227, and 228. In some embodiments, vaccines comprise H1 HA polypeptides having Ser186Pro, Ala189Thr, and Glu227Ala mutations. In some embodiments, vaccines comprise H1 HA polypeptides having mutations at amino acid positions 186, 189, and 227 (e.g., Ser186Pro, Ala189Thr, and Glu227Ala) and at least one additional amino acid substitution at an amino acid position selected from the group consisting of a 98, 136, 137, 138, 145, 153, 155, 156, 159, 183, 186, 187, 189, 190, 192, 193, 194, 195, 196, 215, 219, 222, 225, 226, 227, and 228. In some embodiments, vaccines comprise live active virus particles comprising one or more of any HA H1 polypeptide described herein, live attenuated virus particles comprising one or more of any HA H1 polypeptide described herein, virus-like particles (VLPs) comprising one or more of any HA H1 polypeptide described herein, subunit vaccines comprising one or more of any HA H1 polypeptide described herein, and/or combinations thereof In some embodiments, vaccines comprise at least one HA polypeptide (and/or to variants, fragments, and/or characteristic portions thereof) and at least one of influenza strains A/South Carolina/1/1918, A/Swine/Iowa/15/1930, and/or 2009 A/H1N1 (e.g., A/CA/4/2009). In some embodiments, vaccines comprise at least one HA polypeptide (and/or to variants, fragments, and/or characteristic portions thereof) and influenza strains A/South Carolina/1/1918 and A/Swine/Iowa/15/1930. In some embodiments, vaccines comprise at least one HA polypeptide (and/or to variants, fragments, and/or characteristic portions thereof) and influenza strains A/South Carolina/1/1918 and 2009 A/H1N1 (e.g., A/CA/4/2009). In some embodiments, vaccines comprise at least one HA polypeptide (and/or to variants, fragments, and/or characteristic portions thereof) and influenza strains A/Swine/Iowa/15/1930 and 2009 A/H1N1 (e.g., A/CA/4/2009). In some embodiments, vaccines comprise at least one HA polypeptide (and/or to variants, fragments, and/or characteristic portions thereof) and influenza strain A/South Carolina/1/1918. In some embodiments, vaccines comprise at least one HA polypeptide (and/or to variants, fragments, and/or characteristic portions thereof) and influenza strain A/Swine/Iowa/15/1930. In some embodiments, vaccines comprise at least one HA polypeptide (and/or to variants, fragments, and/or characteristic portions thereof) and influenza strain 2009 A/H1N1 (e.g., A/CA/4/2009).

In some embodiments, vaccines comprise at least one HA polypeptide (and/or to variants, fragments, and/or characteristic portions thereof) and at least one H1 HA polypeptide present in at least one of influenza strains A/South Carolina/1/1918, A/Swine/Iowa/15/1930, and/or 2009 A/H1N1 (e.g., A/CA/4/2009). In some embodiments, vaccines comprise at least one HA polypeptide (and/or to variants, fragments, and/or characteristic portions thereof) and H1 HA polypeptides present in influenza strains A/South Carolina/1/1918 and A/Swine/Iowa/15/1930. In some embodiments, vaccines comprise at least one HA polypeptide (and/or to variants, fragments, and/or characteristic portions thereof) and H1 HA polypeptides present in influenza strains A/South Carolina/1/1918 and 2009 A/H1N1 (e.g., A/CA/4/2009). In some embodiments, vaccines comprise at least one HA polypeptide (and/or to variants, fragments, and/or characteristic portions thereof) and H1 HA polypeptides present in influenza strains A/Swine/Iowa/15/1930 and 2009 A/H1N1 (e.g., A/CA/4/2009). In some embodiments, vaccines comprise at least one HA polypeptide (and/or to variants, fragments, and/or characteristic portions thereof) and H1 HA polypeptides present in influenza strain A/South Carolina/1/1918. In some embodiments, vaccines comprise at least one HA polypeptide (and/or to variants, fragments, and/or characteristic portions thereof) and H1 HA polypeptides present in influenza strain A/Swine/Iowa/15/1930. In some embodiments, vaccines comprise at least one HA polypeptide (and/or to variants, fragments, and/or characteristic portions thereof) and H1 HA polypeptides present in influenza strain 2009 A/H1N1 (e.g., A/CA/4/2009).

In some embodiments, a vaccine composition comprises at least one adjuvant. Any adjuvant may be used in accordance with the present invention. A large number of adjuvants are known; a useful compendium of many such compounds is prepared by the National Institutes of Health and can be found on the internet (www.niaid.nih.gov/daids/vaccine/pdf/compendium.pdf). See also Allison (1998, *Dev. Biol. Stand.*, 92:3-11; incorporated herein by reference), Unkeless et al. (1998, *Annu. Rev. Immunol.*, 6:251-281; incorporated herein by reference), and Phillips et al. (1992, *Vaccine*, 10:151-158; incorporated herein by reference). Hundreds of different adjuvants are known in the art and could be employed in the practice of the present invention. Exemplary adjuvants that can be utilized in accordance with the invention include, but are not limited to, cytokines, aluminum salts (e.g., aluminum hydroxide, aluminum phosphate, etc.; Baylor et al., *Vaccine*, 20:518, 2002; incorporated herein by reference), gel-type adjuvants (e.g., calcium phosphate, etc.); microbial adjuvants (e.g., immunomodulatory DNA sequences that include CpG motifs; endotoxins such as monophosphoryl lipid A (Ribi et al., 1986, *Immunology and Immunopharmacology of bacterial endotoxins*, Plenum Publ. Corp., NY, p 407, 1986; incorporated herein by reference); exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161, which is incorporated herein by reference), Q57, saponins (e.g., QS21, Ghochikyan et al., *Vaccine*, 24:2275, 2006; incorporated herein by reference), squalene, tetrachlorodecaoxide, CPG 7909 (Cooper et al., *Vaccine*, 22:3136, 2004; incorporated herein by reference), poly[di(carboxylatophenoxy) phosphazene] (PCCP; Payne et al., *Vaccine*, 16:92, 1998; incorporated herein by reference), interferon-γ (Cao et al., *Vaccine*, 10:238, 1992; incorporated herein by reference), block copolymer P1205 (CRL1005; Katz et al., *Vaccine*, 18:2177, 2000; incorporated herein by reference), interleukin-2 (IL-2; Mbwuike et al., *Vaccine*, 8:347, 1990; incorporated herein by reference), polymethyl methacrylate (PMMA; Kreuter et al., *J. Pharm. Sci.*, 70:367, 1981; incorporated herein by reference), etc.

B. Therapy

The present invention provides systems and methods for treating patients suffering from, susceptible to, and/or displaying symptoms of influenza infection. In some embodiments, the invention provides systems and methods useful for stratifying patients suffering from, susceptible to, and/or displaying symptoms of influenza infection.

In some embodiments, interfering agents and/or binding agents in accordance with the invention (e.g., entities that bind to HA polypeptides and/or fragments, variants, and/or characteristic portions thereof entities that bind to umbrella-topology glycans) may be utilized for therapeutic applications.

In some embodiments, therapeutic applications comprise administering a therapeutically effective amount of at least one interfering agent and/or binding agent in accordance with the invention to a subject in need thereof. In some embodiments, administration of interfering agents and/or binding agents to a subject may alleviate, ameliorate, relieve, delay onset of, inhibit progression of, reduce severity of, and/or reduce incidence of one or more signs, symptoms, and/or features of influenza infection.

In some embodiments, administration of interfering agents and/or binding agents reduces the level of influenza virions circulating in a subject (e.g., influenza virions that are capable of infecting new cells). In some embodiments, administration of interfering agents and/or binding agents reduces the level of influenza virions circulating in a subject by about 10%, about 20%, about 30%, about 40%, about 50%, about 60%, about 70%, about 80%, about 90%, about 95%, about 99%, or about 100% relative to non-treated controls.

In some embodiments, interfering agents and/or binding agents may be used in vitro to reduce viral load in a subject. For reducing viral load of a body component, particularly a body component of a patient infected with influenza, a patient's blood is passed through a device comprising interfering agents and/or binding agents bound to a surface or solid support for capturing influenza virions (see, for example, U.S. Pat. Nos. 5,698,390 and 4,692,411; both of which are incorporated herein by reference). Various other devices found in the literature can be used with the subject antibodies to achieve a similar result. A body component can be a biological fluid (e.g., blood, serum, etc.), a tissue, an organ, such as the liver, and the like.

In some embodiments, the "level of influenza virions circulating in a subject" refers to an absolute number of virions circulating in a subject. In some embodiments, the "level of influenza virions circulating in a subject" refers to the number of virions per unit volume (e.g., milliliter, liter, etc.) of the subject's blood. In some embodiments, the "level of influenza virions circulating in a subject" refers to viral load.

In some embodiments, administration of interfering agents and/or binding agents inhibits binding of virus to HA receptors. In some embodiments, administration of interfering agents and/or binding agents inhibits binding of virus to at least one HA receptor by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of interfering agents and/or binding agents kills and/or inactivates influenza virions in a subject. In some embodiments, administration of influenza antibodies kills and/or inactivates about 10%, about 20%, about 30%, about 40%, about 50%, about 60%, about 70%, about 80%, about 90%, about 95%, about 99%, or about 100% of influenza virions in a subject relative to non-treated controls.

In some embodiments, administration of interfering agents and/or binding agents inhibits virus-mediated fusion with a target cell. In some embodiments, administration of interfering agents and/or binding agents inhibits virus-mediated fusion with a target cell by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of interfering agents and/or binding agents inhibits conformational changes of one or more proteins associated with virus entry. In some embodiments, administration of interfering agents and/or binding agents inhibits conformational changes of one or more proteins associated with virus entry by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of interfering agents and/or binding agents results in conformational changes in HA polypeptides and/or HA receptors. For example, administered interfering agents and/or binding agents may bind to HA polypeptides and/or HA receptors, thereby sterically blocking the HA polypeptide's and/or HA receptors' ability to recognize and/or interact with one another. In some embodiments, administered interfering agents and/or binding agents may bind to HA polypeptides and/or HA receptors, thereby changing the three-dimensional conformation of the HA polypeptides and/or HA receptors in such a way that renders HA polypeptides and/or HA receptors incapable of recognizing one another.

In some embodiments, treatment and/or vaccination regimens are particularly tailored for the individual being treated and/or vaccinated. As described above, the present invention provides systems, compositions, and methods useful for determining whether a patient is infected with H1 HA influenza or non-H1 HA influenza. Such methods can be utilized to stratify patients into treatment and/or vaccination categories. In some embodiments, such methods may be advantageous because the treatment and/or vaccination is tailored to the particular individual being treated and/or vaccinated. To give but one particular example, if a patient is classified as being infected with H1 HA influenza, therapies that are useful for treatment of H1 HA influenza can be administered to the patient, and therapies that are not useful for treatment of H1 HA influenza will not be administered. This avoids or reduces the risk of adverse reactions from administering therapeutics that are not needed. Such methods eliminate the expense of treating and/or vaccinating patients who would not benefit from such treatment and/or vaccination.

C. Pharmaceutical Compositions

In some embodiments, the present invention provides for pharmaceutical compositions including interfering agents and/or binding agents, as described herein. For example, in some embodiments, interfering agent and/or binding agent polypeptides (e.g., HA polypeptides, polypeptides that bind to HA polypeptides, variants thereof, and/or fragments thereof), nucleic acids encoding such polypeptides, characteristic or biologically active fragments of such polypeptides or nucleic acids, antibodies that bind to and/or compete with such polypeptides or fragments, small molecules that interact with or compete with such polypeptides or with glycans that bind to them, etc. are included in pharmaceutical compositions. In some embodiments, interfering agents and/or binding agents that are not polypeptides, e.g., that are small molecules, umbrella topology glycans and mimics thereof, carbohydrates, aptamers, polymers, nucleic acids, etc., are included in pharmaceutical compositions.

The invention encompasses treatment and/or prophylaxis of influenza infections by administration of such pharmaceutical compositions. In some embodiments, pharmaceutical compositions are administered to a subject suffering from or susceptible to an influenza infection. In some embodiments, a subject is considered to be suffering from an influenza infection in the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent.

In some embodiments, subjects suffering from or susceptible to influenza infection are tested for antibodies that recognize HA polypeptides prior to, during, or after administration of pharmaceutical compositions. In some embodiments, subjects having such antibodies are not administered pharmaceutical compositions comprising HA polypeptides. In some embodiments, an appropriate dose of pharmaceutical composition and/or binding agent is selected based on detection (or lack thereof) of such antibodies.

In some embodiments, selection of a particular subject for treatment and/or vaccination, particular binding agent or composition for administration, and/or particular dose or regimen for administration, is memorialized, for example in a written, printed, or electronic storage form.

Compositions provided herein may be administered prior to or after development of one or more symptoms of influenza infection.

The present invention encompasses treatment and/or prevention (e.g., vaccination) of influenza infections by administration of HA polypeptides, interfering agents, and/or binding agents described herein. In some embodiments, treatment of influenza infections according to the present invention is accomplished by administration of a vaccine. To date, although significant accomplishments have been made in the development of influenza vaccines, there is room for further improvement. The present invention provides vaccines comprising HA polypeptides, interfering agents, and/or binding agents. To give but a few examples, vaccines may comprise interfering agents that bind to umbrella glycans (e.g., α2-6 linked umbrella glycans such as, for example, long α2-6 sialylated glycans), binding agents that bind to HA polypeptides, and/or combinations thereof. In some embodiments, a composition is substantially free of agents that preferentially bind to non-umbrella topology glycans. In some such embodiments, pharmaceutical compositions contain not more than 50%, 40%, 30%, 20%, 10%, 5%, or 1% of an agent that binds to HA receptor glycans other than umbrella topology glycans.

In some embodiments, the present invention provides for vaccines and the administration of these vaccines to a human subject (e.g., to an individual suffering from or susceptible to influenza infection). In certain embodiments, vaccines are compositions comprising one or more of the following: (1) inactivated virus, (2) live attenuated influenza virus, for example, replication-defective virus, (3) interfering agent (e.g., HA polypeptides, LSBAs, UTBAs, UTBSAs, etc.), (4) nucleic acid encoding interfering agent polypeptides (e.g., HA polypeptides) and/or or characteristic or biologically active portions thereof, (5) DNA vector that encodes an interfering agent polypeptide (e.g., HA polypeptide) or characteristic or biologically active portion thereof, (6) binding agents (e.g., entities that bind to HA polypeptides), (7) nucleic acid encoding binding agent polypeptides and/or characteristic or biologically active portions thereof, (8) DNA vector that encodes a binding agent polypeptide and/or characteristic or biologically active portion thereof, (9) expression system, for example, cells expressing one or more HA polypeptides to be used as antigens, and/or (10) virus-like particles.

Thus, in some embodiments, the present invention provides inactivated flu vaccines. In certain embodiments, inactivated flu vaccines comprise one of three types of antigen preparation: inactivated whole virus, sub-virions where purified virus particles are disrupted with detergents or other reagents to solubilize the lipid envelope ("split" vaccine) or purified HA polypeptide ("subunit" vaccine). In certain embodiments, virus can be inactivated by treatment with formaldehyde, beta-propiolactone, ether, ether with detergent (such as TWEEN-80), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., *Textbook of Influenza*, Blackwell Science, Malden, M A, 1998; incorporated herein by reference). To assess the potency of the vaccine, the single radial immunodiffusion (SRD) test can be used (Schild et al., *Bull. World Health Organ.*, 52:43-50 & 223-31, 1975; Mostow et al., *J. Clin. Microbiol.*, 2:531, 1975; incorporated herein by reference).

In some embodiments, the present invention provides virus-like particles (VLPs) that are useful for vaccines. In general, VLPs comprise multiple copies of a protein antigen that, when assembled together, mimic the conformation of a native virus. In some embodiments, VLPs contain repetitive high density displays of influenza virus surface proteins (e.g., HA polypeptides in accordance with the present invention) which present conformational epitopes that can elicit strong T cell and/or B cell immune responses. Since VLPs do not contain any viral genetic material, they may be safer than attenuated viruses in vaccine compositions. VLPs can be produced in a variety of cell culture systems including mammalian cell lines, insect cell lines, yeast, plant cells, etc. For a general discussion of VLPs, see, e.g., published PCT applications WO 02/000885, WO 05/020889, WO 06/108226, WO 07/130327, WO 07/130330, WO 08/005777, WO 08/040060, WO 08/054535, WO 08/061243, WO 08/094197, WO 08/094200, WO 08/148104, WO 09/009876, WO 09/012489, WO 10/006452, and US patent application publication 2005/0009008, all of which are incorporated herein by reference.

In some embodiments, a VLP in accordance with the invention is a specialized VLP called a lipoparticle. In general, lipoparticles are stable, highly purified, homogeneous VLPs that are engineered to contain high concentrations of a conformationally intact membrane protein of interest. In some embodiments, lipoparticles in accordance with the present invention contain influenza envelope proteins and/or other influenza antigens.

The present invention also provides live, attenuated flu vaccines, and methods for attenuation are well known in the art. In certain embodiments, attenuation is achieved through the use of reverse genetics, such as site-directed mutagenesis.

In some embodiments, influenza virus for use in vaccines is grown in eggs, for example, in embryonated hen eggs, in which case the harvested material is allantoic fluid. Alternatively or additionally, influenza virus may be derived from any method using tissue culture to grow the virus. Suitable cell substrates for growing the virus include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

In some embodiments, vaccines further comprise one or more adjuvants. Any adjuvant may be used in accordance with the present invention. A large number of adjuvants are known; a useful compendium of many such compounds is prepared by the National Institutes of Health and can be found on the internet (www.niaid.nih.gov/daids/vaccine/pdf/compendium.pdf). See also Allison (1998, *Dev. Biol. Stand.,* 92:3-11; incorporated herein by reference), Unkeless et al. (1998, *Annu. Rev. Immunol.,* 6:251-281; incorporated herein by reference), and Phillips et al. (1992, *Vaccine,* 10:151-158; incorporated herein by reference). Hundreds of different adjuvants are known in the art and could be employed in the practice of the present invention. For example, aluminum salts (e.g., aluminum hydroxide, aluminum phosphate, etc., Baylor et al., *Vaccine,* 20:S18, 2002) and monophosphoryl lipid A (MPL; Ribi et al., (1986, *Immunology and Immunopharmacology of bacterial endotoxins,* Plenum Publ. Corp., NY, p 407, 1986) can be used as adjuvants in human vaccines. Alternatively or additionally, exemplary adjuvants that can be utilized in accordance with the invention include cytokines, calcium phosphate, microbial adjuvants (e.g., immunomodulatory DNA sequences that include CpG motifs; endotoxins such as monophosphoryl lipid A (Ribi et al., 1986, *Immunology and Immunopharmacology of bacterial endotoxins,* Plenum Publ. Corp., NY, p 407, 1986; incorporated herein by reference); exotoxins such as cholera toxin, *E. coli* heat labile toxin, and pertussis toxin; muramyl dipeptide, etc.); oil-emulsion and emulsifier-based adjuvants (e.g., Freund's Adjuvant, SAF, etc.); particulate adjuvants (e.g., liposomes, biodegradable microspheres, etc.); synthetic adjuvants (e.g., nonionic block copolymers, muramyl peptide analogues, polyphosphazene, synthetic polynucleotides, etc.); polymers (e.g., polyphosphazenes; described in U.S. Pat. No. 5,500,161, which is incorporated herein by reference), Q57, squalene, and/or tetrachlorodecaoxide.

Alternatively or additionally, new compounds are currently being tested as adjuvants in human vaccines, such as MF59 (Chiron Corp., http://www.chiron.com/investors/pressreleases/2005/051028.html), CPG 7909 (Cooper et al., *Vaccine,* 22:3136, 2004; incorporated herein by reference), and saponins, such as QS21 (Ghochikyan et al., *Vaccine,* 24:2275, 2006; incorporated herein by reference).

Additionally, some adjuvants are known in the art to enhance the immunogenicity of influenza vaccines, such as poly[di(carboxylatophenoxy)phosphazene] (PCCP; Payne et al., *Vaccine,* 16:92, 1998; incorporated herein by reference), interferon-γ (Cao et al., *Vaccine,* 10:238, 1992; incorporated herein by reference), block copolymer P1205 (CRL1005; Katz et al., *Vaccine,* 18:2177, 2000; incorporated herein by reference), interleukin-2 (IL-2; Mbwuike et al., *Vaccine,* 8:347, 1990; incorporated herein by reference), and polymethyl methacrylate (PMMA; Kreuter et al., *J. Pharm. Sci.,* 70:367, 1981; incorporated herein by reference).

In some embodiments, pharmaceutical compositions do not include adjuvants (e.g., provided compositions are essentially free of adjuvants). In some embodiments, pharmaceutical compositions do not include an alum adjuvant (e.g., provided compositions are essentially free of alum).

The present invention provides other therapeutic compositions useful in the treatment and/or vaccination of viral infections. In some embodiments, treatment and/or vaccination is accomplished by administration of an agent that interferes with expression or activity of an HA polypeptide.

In some embodiments, the present invention provides pharmaceutical compositions comprising antibodies or other agents related to provided polypeptides, interfering agents, and/or binding agents. For example, the invention provides compositions containing antibodies recognize virus particles containing a particular HA polypeptide (e.g., an HA polypeptide that binds to umbrella glycans), nucleic acids (such as nucleic acid sequences complementary to HA sequences, which can be used for RNAi), glycans that compete for binding to HA receptors, small molecules or glycomometics that compete the glycan-HA polypeptide interaction, or any combination thereof. In some embodiments, collections of different agents, having diverse structures are utilized. In some embodiments, therapeutic compositions comprise one or more multivalent agents. In some embodiments, treatment comprises urgent administration shortly after exposure or suspicion of exposure.

In general, a pharmaceutical composition will include a therapeutic agent in addition to one or more inactive agents such as a sterile, biocompatible carrier including, but not limited to, sterile water, saline, buffered saline, or dextrose solution. Alternatively or additionally, a composition may comprise a pharmaceutically acceptable excipient, which, as used herein, includes any and all solvents, dispersion media, diluents, or other liquid vehicles, dispersion or suspension aids, disintegrating agents, surface active agents, isotonic agents, thickening or emulsifying agents, preservatives, buffering agents, solid binders, granulating agents, lubricants, coloring agents, sweetening agents, flavoring agents, perfuming agents, and the like, as suited to the particular dosage form desired. Remington's *The Science and Practice of Pharmacy*, 21st Edition, A. R. Gennaro, (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component of the pharmaceutical composition, its use is contemplated to be within the scope of this invention.

In certain embodiments, a pharmaceutical composition will include a therapeutic agent that is encapsulated, trapped, or bound within a lipid vesicle, a bioavailable and/or biocompatible and/or biodegradable matrix, or other microparticle.

In some embodiments, a provided pharmaceutical composition will include an HA polypeptide, interfering agent, and/or binding agent that is not aggregated. For example, in some embodiments, less than 1%, 2%, 5%, 10%, 20%, or 30%, by dry weight or number, of an HA polypeptide, interfering agent, and/or binding agent is present in an aggregate.

In some embodiments, a provided pharmaceutical composition will include an HA polypeptide, interfering agent, and/or binding agent that is not denatured. For example, in some embodiments, less than 1%, 2%, 5%, 10%, 20%, or 30%, by dry weight or number, of an HA polypeptide, interfering agent, and/or binding agent administered is denatured.

In some embodiments, a provided pharmaceutical composition will include an HA polypeptide, interfering agent, and/or binding agent that is not inactive. For example, in some embodiments, less than 1%, 2%, 5%, 10%, 20%, or 30%, by dry weight or number, of an HA polypeptide, interfering agent, and/or binding agent administered is inactive.

In some embodiments, pharmaceutical compositions are formulated to reduce immunogenicity of provided HA polypeptide, interfering agent, and/or binding agent. For example, in some embodiments, a provided HA polypeptide, interfering agent, and/or binding agent is associated with (e.g., bound to) an agent, such as polyethylene glycol and/or carboxymethyl cellulose, that masks its immunogenicity. In some embodiments, a provided HA polypeptide, interfering agent, and/or binding agent has additional glycosylation that reduces immunogenicity.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such a CREMOPHOR®, alcohols, oils, modified oils, glycols, polysorbates, cyclodextrins, polymers, and/or combinations thereof Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Dosage forms for topical and/or transdermal administration of a compound in accordance with this invention may include ointments, pastes, creams, lotions, gels, powders, solutions, sprays, inhalants and/or patches. Generally, the active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, the rate may be controlled by either providing a rate controlling membrane and/or by dispersing the compound in a polymer matrix and/or gel.

General considerations in the formulation and manufacture of pharmaceutical agents may be found, for example, in *Remington's Pharmaceutical Sciences*, 19th ed., Mack Publishing Co., Easton, Pa., 1995; incorporated herein by reference.

The present invention provides kits for administration of pharmaceutical compositions. For example, in some embodiments, the invention provides a kit comprising at least one dose of an HA polypeptide, HA polypeptide binding agent, HA polypeptide interfering agent, fragment thereof, variant thereof, and/or characteristic portion thereof. In some embodiments, the invention provides a kit comprising an initial unit dose and a subsequent unit dose of a binding agent. In some such embodiments, the initial unit dose is greater than the subsequent unit dose or wherein the two doses are equal.

In some embodiments, kits comprise at least one component of a delivery device, e.g., an inhaler. In some such embodiments, the invention provides a kit comprising at least one component of a delivery device, e.g., an inhaler and a dose of an HA polypeptide, HA polypeptide binding agent, HA polypeptide interfering agent, fragment thereof, variant thereof, and/or characteristic portion thereof. In some embodiments, kits comprise instructions for use.

D. Administration

Pharmaceutical compositions can be administered to any subject (e.g., any animal) in need thereof, including humans. Pharmaceutical compositions may be administered either alone or in combination with one or more other therapeutic agents including, but not limited to, vaccines and/or antibodies. By "in combination with," it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of the pharmaceutical compositions in combination with agents that may improve their bioavailability, reduce or modify their metabolism, inhibit their excretion, or modify their distribution within the body. Although the pharmaceutical compositions of the present invention can be used for treatment and/or vaccination of any subject (e.g., any animal) in need thereof, they are most preferably used in the treatment and/or vaccination of humans. In some embodiments, pharmaceutical compositions and/or binding agents are administered in combination with one or more of an anti-viral agent (e.g., Oseltamivir [tamiflu], Zanamavir [Releza], etc.) and/or a sialidase.

Pharmaceutical compositions may be administered using any amount and any route of administration effective for treatment and/or vaccination. The exact amount required will vary from subject to subject, depending on the species, age, and general condition of the subject, the severity of the infection, the particular composition, its mode of administration, its mode of activity, and the like. Pharmaceutical compositions are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and/or vaccinated and the severity of the disorder; the activity of the specific vaccine composition employed; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed; and like factors, well known in the medical arts.

Pharmaceutical compositions of the present invention may be administered by any route. In some embodiments, pharmaceutical compositions of the present invention are administered by a variety of routes, including oral (PO), intravenous (IV), intramuscular (IM), intra-arterial, intramedullary, intrathecal, subcutaneous (S Q), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

In general, the most appropriate route of administration will depend upon a variety of factors including the nature of the agent being administered (e.g., its stability upon administration), the condition of the subject (e.g., whether the subject is able to tolerate a particular mode of administration), etc. In specific embodiments, pharmaceutical compositions may be administered intranasally. In specific embodiments, pharmaceutical compositions may be administered by intratracheal instillation. In specific embodiments, pharmaceutical compositions may be administered by bronchial instillation. In specific embodiments, pharmaceutical compositions may be administered by inhalation. In specific embodiments, pharmaceutical compositions may be administered as a nasal spray. In specific embodiments, pharmaceutical compositions may be administered mucosally. In specific embodiments, pharmaceutical compositions may be administered orally. In specific embodiments, pharmaceutical compositions may be administered by intravenous injection. In specific embodiments, pharmaceutical compositions may be administered by intramuscular injection. In specific embodiments, pharmaceutical compositions may be administered by subcutaneous injection. At present the oral or nasal spray or aerosol route (e.g., by inhalation) is most commonly used to deliver therapeutic agents directly to the lungs and respiratory system. However, the invention encompasses the delivery of a pharmaceutical composition by any appropriate route taking into consideration likely advances in the sciences of drug delivery.

In some embodiments, preparations for inhaled or aerosol delivery comprise a plurality of particles. In some embodiments, such preparations have a mean particle size of 4, 5, 6, 7, 8, 9, 10, 11, 12, or 13 microns. In some embodiments, preparations for inhaled or aerosol delivery are formulated as a dry powder. In some embodiments, preparations for inhaled or aerosol delivery are formulated as a wet powder, for example through inclusion of a wetting agent. In some embodiments, the wetting agent is selected from the group consisting of water, saline, or other liquid of physiological pH.

In some embodiments, compositions are administered as drops to the nasal or buccal cavity. In some embodiments, a dose may comprise a plurality of drops (e.g., 1-100, 1-50, 1-20, 1-10, 1-5, etc.).

In some embodiments, compositions are administered using a device that delivers a metered dosage of a pharmaceutical composition.

Pharmaceutical compositions may be administered in any dose appropriate to achieve a desired outcome. In some embodiments, the desired outcome is reduction in intensity, severity, and/or frequency, and/or delay of onset of one or more symptoms of influenza infection.

In some embodiments, pharmaceutical compositions are formulated to administer a dose of an HA polypeptide (e.g., variant, fragment, and/or characteristic portion thereof) effective to compete with influenza HA for binding to umbrella topology glycans. In some embodiments, such binding by influenza HA is reduced after administration of one or more doses of a composition as compared with its level absent such administration. In some embodiments, pharmaceutical compositions are formulated to administer a dose of HA polypeptide effective to saturate at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more than 99% of HA binding sites (e.g., HA binding sites containing umbrella topology glycans) present in the subject (e.g., in the respiratory tract of the subject) receiving the composition.

In some embodiments, pharmaceutical compositions are formulated to administer a dose of an interfering agent (e.g., umbrella topology glycan mimic) effective to compete with HA receptors for binding to HA polypeptides (e.g., on the surface of influenza virus particles). In some embodiments, binding of influenza HA polypeptides to HA receptors is reduced after administration of one or more doses of a composition as compared with its level absent such administration. In some embodiments, pharmaceutical compositions are formulated to administer a dose of an interfering agent effective to saturate at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more than 99% of HA binding sites (e.g., HA binding sites containing umbrella topology glycans) present in the subject (e.g., in the respiratory tract of the subject) receiving the composition.

In certain embodiments, pharmaceutical compositions may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of a therapeutic agent per subject body weight per day to obtain a desired therapeutic effect. A desired dosage may be delivered to a subject only once. A desired dosage may be delivered more than three times per day, three times per day, two times per day, once per day, every other day, every third day, every week, every two weeks, every three weeks, every four weeks, every two months, every six months, every twelve months, every two years, every three years, every four years, every five years, every 10 years, or every 20 years. In certain embodiments, the desired dosage may be delivered using multiple administrations (e.g., two, three, four, five, six, seven, eight, nine, ten, eleven, twelve, thirteen, fourteen, fifteen, or more administrations).

It will be appreciated that compositions in accordance with the present invention can be employed in combination therapies. The particular combination of therapies (e.g., therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an agent useful for treating, preventing, and/or delaying the onset of influenza infection may be administered concurrently with another agent useful for treating, preventing, and/or delaying the onset of influenza infection), or they may achieve different effects (e.g., control of any adverse effects). The invention encompasses delivery of pharmaceutical compositions in combination with agents that may improve their bioavailability, reduce and/or modify their metabolism, inhibit their excretion, and/or modify their distribution within the body.

Pharmaceutical compositions in accordance with the present invention may be administered either alone or in combination with one or more other therapeutic agents. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In will be appreciated that therapeutically active agents utilized in combination may be administered together in a single composition or administered separately in different compositions. In general, each agent will be administered at a dose and/or on a time schedule determined for that agent.

In general, it is expected that agents utilized in combination with be utilized at levels that do not exceed the levels at which they are utilized individually. In some embodiments, the levels utilized in combination will be lower than those utilized individually.

In some embodiments, pharmaceutical compositions are administered in combination with one or more of an antiviral agent (e.g., Oseltamivir [tamiflu], Zanamavir [Releza], etc.) and/or a sialidase.

EXEMPLIFICATION

Example 1

Glycan Binding Specificity of 2009 A/H1N1 HA

The present inventors have characterized glycan binding specificity of 2009 A/H1N1 HA, which infects primarily swine, and identified mutant forms of H1 HA that would lead to its human adaptation for efficient airborne human-to-human transmission that is characteristic of HAs from both the seasonal and pandemic influenza A H1N1 viruses. Although several 2009 A/H1N1 strains have been isolated and sequenced, there are few intragenic variations among these. Thus, the present inventors utilized HA from a representative 2009 A/H1N1 virus, i.e., A/California/0409 (henceforth referred to as CA/04).

Materials and Methods

Binding of CA/04 Hemagglutinin to Human Respiratory Tissues

Formalin-fixed and paraffin-embedded normal human tracheal tissue sections and human alveolar tissue sections were purchased from US Biological and US Biomax respectively. Tissue sections were deparaffinized, rehydrated and pre-blocked with 1% BSA in PBS for 30 minutes at room temperature (RT). HA-antibody pre-complexes were generated by incubating 20 µg/ml of recombinant CA/04 HA protein with primary (mouse anti 6×His tag, Abcam) and secondary (Alexa Fluor 488 goat anti mouse IgG, Molecular Probes) antibodies in a ratio of 4:2:1, respectively, for 20 minutes on ice. Tissue binding studies were performed by incubating tissue sections with the diluted HA-antibody complexes for 3 hours at RT. To visualize cell nuclei, sections were counterstained with propidium iodide (Invitrogen; 1:100 in TBST) for 20 minutes at RT. In the case of sialidase pretreatment, tissue sections were incubated with 0.2 units of Sialidase A (recombinant from *Arthrobacter ureafaciens*, Prozyme) for 3 hours at 37° C. prior to incubation with the proteins. Sections were then washed and viewed under a Zeiss LSM510 laser scanning confocal microscope.

Dose Dependent Direct Receptor Binding of CA/04 HA

The receptor specificity of recombinantly expressed Ca/04 HA was investigated using a panel of glycans comprising of both α2-3 and α2-6 sialylated glycans. The wells of streptavidin-coated high binding capacity 384-well plates (Pierce) were incubated with 50 µl of 2.4 µM biotinylated glycans overnight at 4° C. The glycans included were 3'-SLN, 3'-SLN-LN, 3'SLN-LN-LN, 6'-SLN and 6'SLN-LN (LN corresponds to lactosamine (Galβ1-4GlcNAc) and 3'SLN and 6'SLN respectively correspond to Neu5Acα2-3 and Neu5Acα2-6 linked to LN) and were obtained from the Consortium of Functional Glycomics (www.functionalglycomics.org) through their resource request program. A stock solution of HA complex was prepared by incubating appropriate amounts of HA protein, primary antibody (mouse anti 6×His tag IgG, Abcam) and secondary antibody (HRP conjugated goat anti mouse IgG, Santacruz Biotechnology) in the ratio 4:2:1, respectively, on ice for 20 minutes. Appropriate amounts of precomplexed stock HA were diluted to 250 µl with 1% BSA in PBS. 50 µl of precomplexed HA was added to each of the glycan-coated wells and incubated at room temperature for 2 hours followed by three washes with PBST (PBS+0.1% Tween-20) and three washes with PBS. The binding signal was determined based on HRP activity using Amplex Red Peroxidase Assay (Invitrogen) according to the manufacturer's instructions. Appropriate negative controls were included.

Results

Glycan Binding Properties of 2009 A/H1N1 HA

A dose-dependent binding of HA to representative human and avian receptors on a biotin-strepatividin based glycan array platform permitted quantification using an apparent binding constant $K_d{'}$ (Srinivasan et al., 2008, *Proc. Natl. Acad. Sci. U.S.A.*, 105:2800-05; incorporated herein by reference). The parameter $K_d{'}$ can be calculated by fitting the binding data (over a range of HA concentrations) using the Hill equation for multivalent binding (Srinivasan et al., 2008, *Proc. Natl. Acad. Sci. U S. A.*, 105:2800-05; incorporated herein by reference). The trimeric HA unit comprises of three HA monomers (with one RBS per monomer). The spatial arrangement of the biotinylated glycans in the wells of the streptavidin plate array favors binding to only one of the three HA monomers in the trimeric HA unit. Therefore in order to specifically enhance the multivalency in the HA-glycan interactions, the recombinant HA is pre-complexed with the primary and secondary antibodies as described previously (Srinivasan et al., 2008, *Proc. Natl. Acad. Sci. U.S.A.*, 105:2800-05; and Stevens et al., 2006, *Nat. Rev. Microbiol.*, 4:857-64; both of which are incorporated herein by reference). The identical spatial arrangement of 4 trimeric HA units in the precomplex relative to the glycans on the array platform, homogenizes the avidity effects across different HAs and hence permits quantitative comparison between glycan binding strengths of different HAs.

Figure 9A:
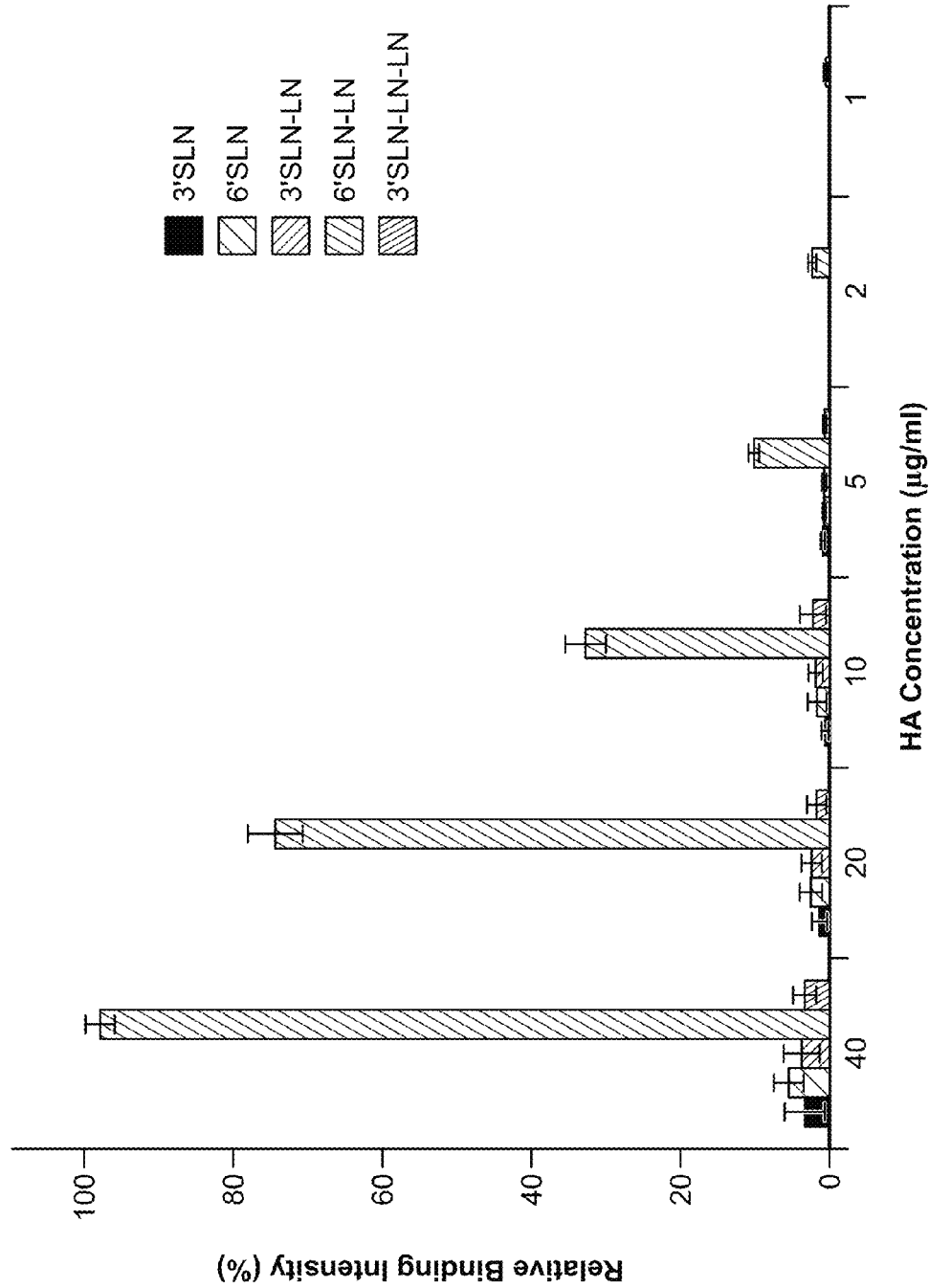
Figure 9B:
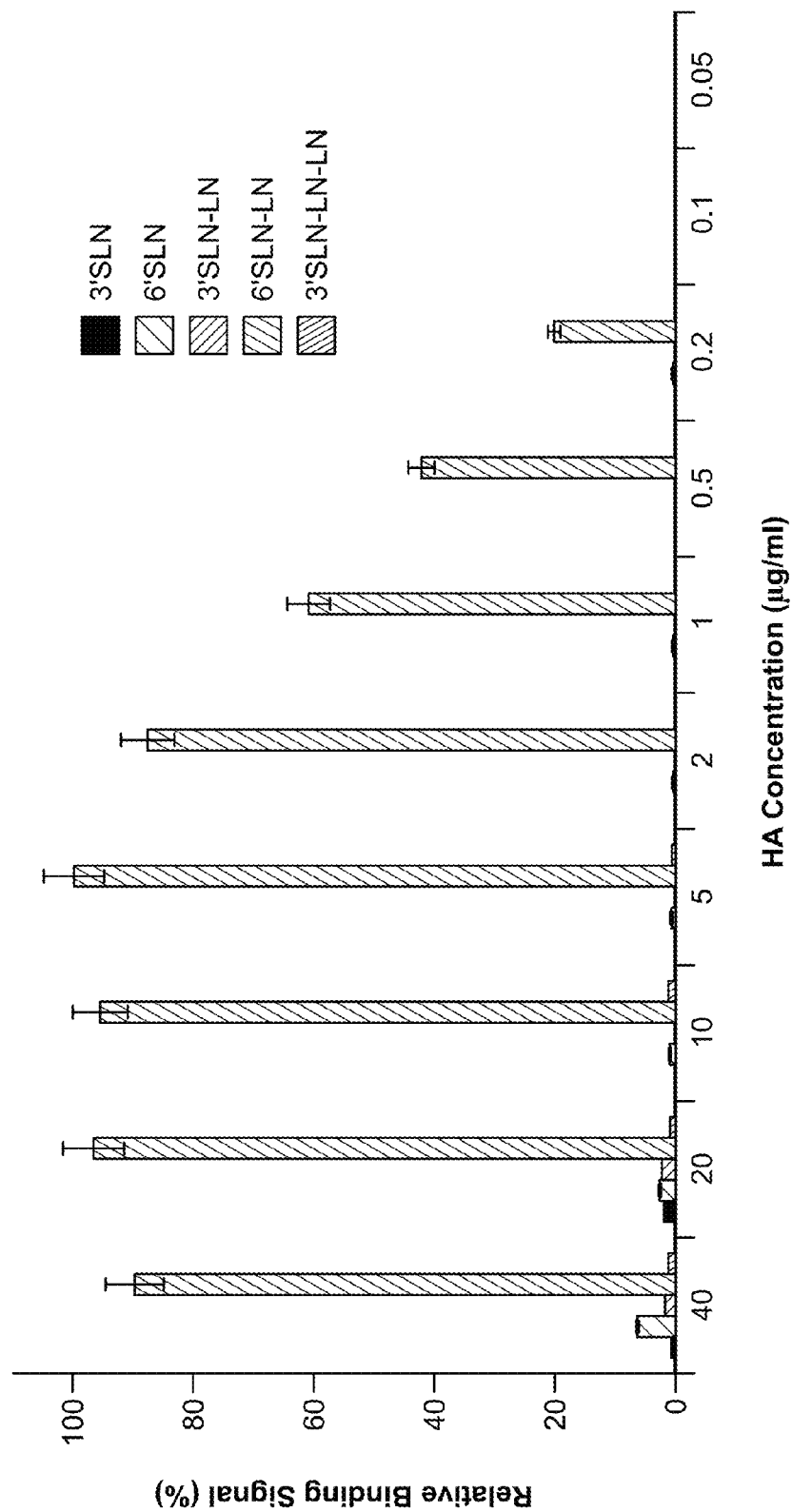

Glycan binding properties of the 2009 A/H1N1 HA were examined using dose-dependent direct receptor binding (Srinivasan et al., 2008, *Proc Natl Acad Sci USA*, 105:2800-5; incorporated herein by reference) and human lung tissue binding (Chandrasekaran et al., 2008, *Nat Biotechnol*, 26:107-13; incorporated herein by reference) assays. These assays were performed with CA/04 HA that was recombinantly expressed using a construct that was designed to produce a soluble protein as described previously (Chandrasekaran et al., 2008, *Nat Biotechnol*, 26:107-13; incorporated herein by reference). In a direct glycan receptor-binding assay, CA/04 HA exhibited a dose-dependent binding to only a single α2-6 glycan (6'SLN-LN) and only minimal binding to α2-3 glycans (FIG. 9A). While the binding pattern of Cal/04 HA is similar to that of HA from the 1918 pandemic influenza A virus (A/South Carolina/1/1918; or SC18), the binding affinity of CA/04 HA is lower than that of SC18 HA (FIG. 9B).

Examining the tissue binding of CA/04 HA indicates that it binds uniformly to the apical surface of the human tracheal (representative upper respiratory) tissue sections (FIG. 10). This binding pattern correlates with the predominant distribution of α2-6 sialylated glycans on the apical surface of the tracheal tissue (Chandrasekaran et al., 2008, *Nat Biotechnol*, 26:107-13; incorporated herein by reference) and the α2-6 binding of CA/04 HA in the direct binding assay. Although CA/04 shows some binding to alveolus, it is not as extensive as the tracheal binding consistent with the minimal α2-3 binding observed in the direct binding assay.

Based on the above data, it is clear that while the A/2009 H1N1 HA has a similar binding selectivity of the pandemic SC18 HA, its α2-6 binding affinity is substantially lower than that of SC18 HA. It was demonstrated previously (Tumpey et al., 2007, *Science*, 315:655-59; incorporated herein by reference) that the efficiency of airborne transmission (e.g., using a ferret animal model, which is an established animal model for influenza A virus transmission in humans) correlates with the α2-6 binding affinity of the viral HA. In fact, a single amino acid mutation in HA of the efficiently transmitting SC18 virus led to a virus (NY18) that transmitted inefficiently. The α2-6 binding affinity of NY18 HA was substantially lower than that of SC18 HA (Srinivasan et al., 2008, *Proc Natl Acad Sci USA*, 105:2800-5; incorporated herein by reference). In a similar fashion the substantially lower α2-6 binding affinity of CA/04 HA than that of SC18 HA indicates that this virus has not yet fully adapted to the human host for efficient airborne human-to-human transmission. Consistent with this conclusion, the lower human receptor-binding strength of CA04 HA correlated with the lower observed efficiency of transmission of the CA04 virus in ferrets, as compared with highly transmissible SC18 (see, e.g., Tumpey et al., 2007, *Science*, 315:655-59; and Maines et al., 2009, *Science*, 325:484-87; both of which are incorporated herein by reference). Similar results were also obtained in mice (Maines et al., 2009, *Science*, 325:484-87; incorporated herein by reference).

Structural Analysis of 2009 A/H1N1 HA

The receptor-binding site (RBS) of the 2009 A (H1N1) HAs (Soundararajan et al., 2009, *Nat Biotechnol*, 27:510-3; incorporated herein by reference), used in this study and those from SC18 and the recent seasonal influenza H1N1 viruses was compared (FIG. 11). The similarity in the binding pattern between CA/04 HA and SC18 HA could potentially arise from the majority of "similar or analogous" RBS residues between these HAs including Asp190 and Asp225, which are "hallmark" amino acids of human adapted H1N1 HAs that make optimal contacts with the α2-6 glycans. Differences in RBS between SC18 and CA/04 HA occur at positions 145, 186, 189, 219 and 227. CA/04 HA has a unique Lys145 which provides an additional anchoring contact for the sialic acid (Soundararajan et al., 2009, *Nat Biotechnol*, 27:510-3; incorporated herein by reference). Residues at 186, 187 189 are positioned to form an interaction network with Asp190 (Soundararajan et al., 2009, *Nat Biotechnol*, 27:510-3; incorporated herein by reference). In the case of SC18 HA, this network involves oxygen atoms of Thr187, Thr189 and Asp190 (Srinivasan et al., 2008, *Proc Natl Acad Sci USA*, 105:2800-5; and Gamblin et al., 2004, *Science*, 303, 1838-42; both of which are incorporated herein by reference). In a similar fashion, in the case of CA/04 HA, the oxygen atoms of Ser186, Thr187 and Asp190 could potentially form this network. Residues 219 and 227 in turn influence the orientation of residue 186.

Figure 12:
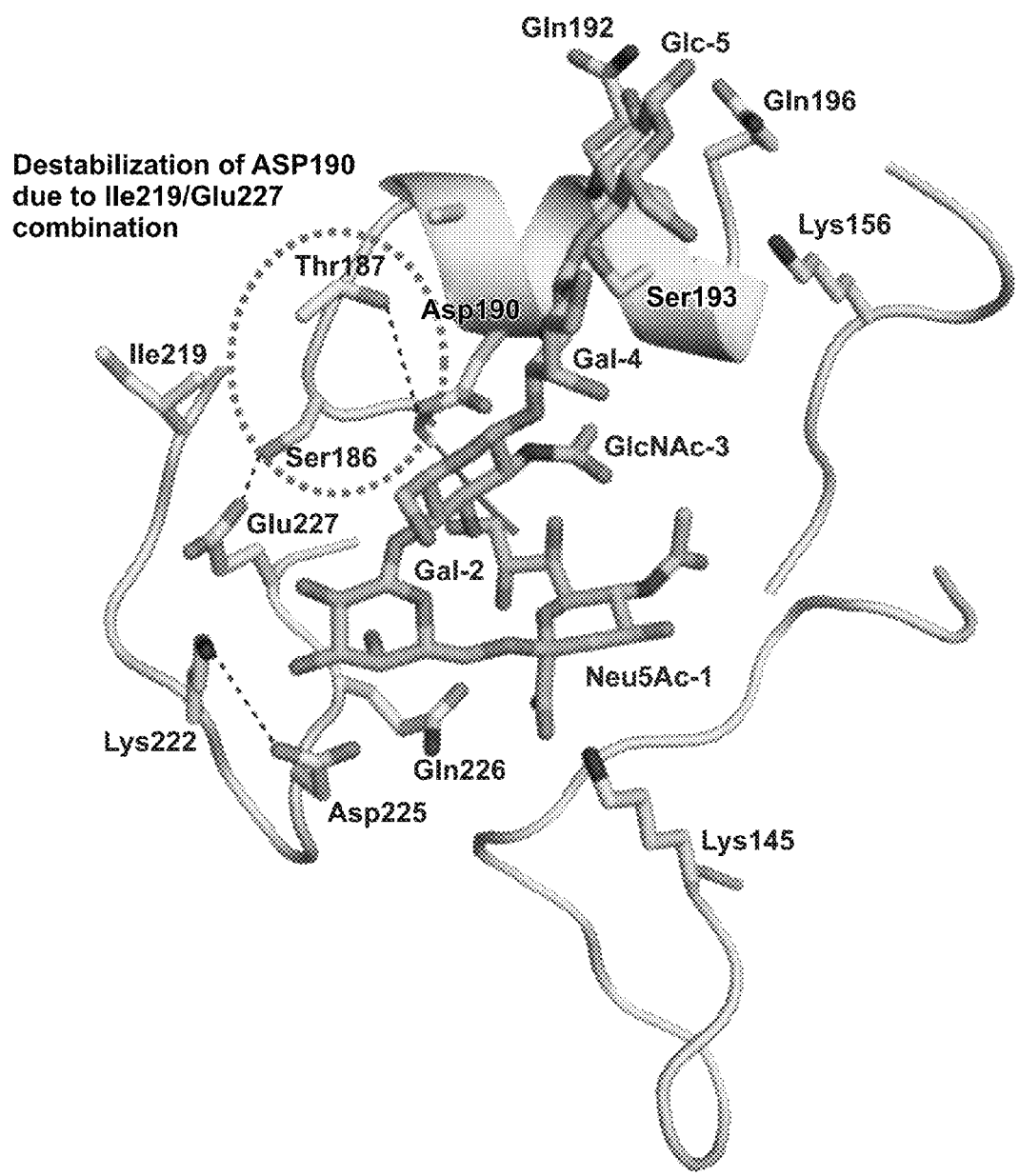

Comparison of residues 219 and 227 (FIG. 11) reveals that either both amino acids are hydrophobic such as Ala219 and Ala227 (as observed in SC18 HA) or they are charged residues such as Lys219 and Glu227 (as observed in the seasonal influenza HAs). The present invention encompasses the recognition that 2009 A(H1N1) HAs have a unique combination of Ile219 and Glu227 that results in a set of interactions that is neither fully hydrophobic nor fully charged. This combination could destabilize the hydrophobic or ionic network of residues at 186, 219 and 227 thereby disrupting optimal contacts with α2-6 sialylated glycans (FIG. 12). Analysis of the RBS of the 2009 A(H1N1) HA offers an explanation for the lower α2-6 binding affinity of CA/04 HA as compared to SC18 HA despite the similar binding pattern (FIG. 9).

Structural analysis (FIG. 12) offers an explanation for the lower affinity due to a combination of amino acids in the RBS that is unique to 2009 A/H1N1 HAs. The present invention encompasses the recognition that mutations in the RBS might fix the issue of positioning the Asp190 for optimal contact with α2-6 glycans and hence increase the affinity for α2-6 binding. According to the present invention, possible combinations of mutations that would fix this issue include:

Ile219→Lys: This would make the network of interactions between the residue positions 219, 222, 225, 227 substantially (if not entirely) ionic which in turn would permit positioning of Ser186 for making interactions with Asp190 that in turn would position Asp190 for making contact with α2-6. This part of the network of interactions in the mutant HA is similar to that observed in recent seasonal influenza H1N1 HAs.

Ser186→Pro/Ala189→Thr/Glu227→Ala: This would make the network of interactions between residue positions 186, 219 and 227 hydrophobic and the Thr189 in the mutant HA along with Thr187 would be positioned for making interactions with Asp190 which in turn would position Asp190 for making contacts with α2-6. This part of the network of interactions in the mutant HA is similar to that observed for SC18.

Both combinations of mutations listed above lead to a unique HA that is unlike any of the recent seasonal influenza H1N1 HAs as well as unlike SC18 HA.

Discussion

In early 2009, a novel strain of a H1N1 influenza virus (referred to as 2009 H1N1) originated from a North American triple reassortant swine H1 virus. The global health threat posed by this virus subsequently led the WHO to categorize this strain as a pandemic (WHO, 2009, *Weekly Epid. Rec.*, 84:249-57; incorporated herein by reference). Based on extensive sequence and structural analysis of the key 2009 H1N1 influenza viral proteins, the present inventors investigated properties of the virus including glycan-receptor binding of the viral hemagglutinin (HA), drug resistance, virulence and transmissibility (see, e.g., Results above Soundararajan et al., 2009, *Nat. Biotechnol.*, 27:510-13; incorporated herein by reference). In contrast to the results presented above in Example 1, which demonstrated that CA/04 HA binds preferentially to α2-6 glycans (as opposed to α2-3 glycans), Childs et al. (2009, *Nat. Biotechnol.*, 27:797-99; incorporated herein by reference) subsequently reported that the 2009 H1N1 virus bound to both α2→3- (avian receptors) and α2→6-(human receptors) linked sialylated glycans in the context of a lipid-based glycan array platform.

Analysis of whole viruses on glycan array platforms, as reported by Childs et al., presents several challenges in understanding subtle differences in binding arising from amino acid substitutions in the glycan receptor-binding site (RBS) of HA. For example, one commonly used method to measure viral titer is based on the ability of the virus to agglutinate red blood cells (RBCs), a property mediated by the binding of viral HA to sialylated glycan receptors on the RBC surface. However, use of this method to compare mutant strains with altered glycan-receptor binding properties to one another or to a reference wild type (WT) strain is complicated by the fact that the same hemagglutination titer of the WT and mutant form of a virus may not correspond to the same number of viral particles. This issue can be circumvented to an extent by using directly labeled viruses (Kumari et al., 2007, *Virol. J.*, 4:42; incorporated herein by reference) or by adjusting the viral titer based on equivalent concentrations of viral protein (e.g., using gel electrophoresis), as reported by Childs et al.

Studies that have been published after the data and conclusions presented in Example 1 focus on qualitative characterization (typically at a high virus or HA concentration). These studies have been designed such that binding signals can be observed for the maximum number of glycans on the array (see, e.g., Childs et al., 2009, *Nat. Biotechnol.*, 27:797-99; and Hua et al., 2010, *PLoS Currents: Influenza*; both of which are incorporated herein by reference). These studies, while offering a vague idea of the number of avian and human receptors that bind to a given HA or virus, are not suitable to quantify and compare binding strength (or affinity) of HA-glycan interactions. In contrast, the present inventors obtained quantitative information by designing assays that analyze binding over a range of HA concentrations and measuring the approach to saturation by taking into account avidity and/or cooperativity effects.

In summary, the present inventors have characterized HA-glycan receptor binding properties of 2009 H1N1. The inventors demonstrated that HA from a representative 2009 H1N1 virus (A/California/04/09 or "CA04") bound specifically to human receptors on a glycan array platform and on human upper respiratory epithelia and showed no observable binding to avian receptors (see Results above and Maines et al., 2009, *Science*, 325:484-87; incorporated herein by reference). The binding strength of CA04 HA to the human receptor, however, was substantially lower than that of HA from the prototypic 1918 H1N1 pandemic, A/South Carolina/1/1918 ("SC18") (see Results above and Maines et al., 2009, *Science*, 325:484-87; incorporated herein by reference). The lower human receptor-binding strength of CA04 HA correlated with the lower observed efficiency of transmission of the CA04 virus (see Results above and Maines et al., 2009, *Science*, 325:484-87; incorporated herein by reference), as compared with highly transmissible SC18) in ferrets (see Tumpey et al., 2007, *Science*, 315:655-59; incorporated herein by reference). The lack of observable binding by CA04 HA to avian receptors is consistent with recent glycan microarray analysis of 2009 H1N1 HAs (Hua et al., 2010, *PLoS Currents: Influenza*; incorporated herein by reference) but is in contrast to the observations in the report by Childs et al. using whole viruses. Without wishing to be bound by any particular theory, these differences may be attributed to differences in the presentation of HA (e.g., as a recombinant protein as against on a whole virus) and glycan receptors in the different array platforms (see Childs et al.).

Example 2

Comparison of 2009 A/H1N1 Isolates with 1918 and 1930 Pandemic Strain Isolates

In 1918 and 1930, strains of H1 influenza viruses emerged that showed enhanced human infectivity as compared with their parent strains. Each of these strains led to a pandemic of influenza infections in humans.

The present inventors have compared binding and/or sequence characteristics of the A/South Carolina/1/1918 and A/Swine/Iowa/15/1930 strains with a representative 2009 A/H1N1 strain, A/California/0409 (CA/04). The present invention encompasses the recognition that similar results would be obtained for other 2009 A/H1N1 strains. The present invention demonstrates that 2009 A/H1N1 shares significant similarities with both the A/South Carolina/1/1918 and A/Swine/Iowa/15/1930 strains, and particularly with the 1918 strain (FIG. 4A-C). This finding implies, among other things, that (1) immunization against the A/South Carolina/1/1918 and A/Swine/Iowa/15/1930 strains, and particularly against the 1918 strain, might provide some cross-reactive protection against 2009 A/H1N1; and/or (2) individuals previously exposed to the A/South Carolina/1/1918 and A/Swine/Iowa/15/1930 strains, and particularly to the 1918 strain, (a) might be less susceptible to infection, and therefore, might demonstrate a lesser need of vaccination and/or treatment than individuals not previously exposed; (b) might require less concentrated, less potent, and/or less frequent dosage of vaccine and/or therapeutic compositions; and/or (c) might be primed due to the previous exposure and likely to achieve successful vaccination.

Example 3

Binding Characteristics of H1 HA Polypeptides

Those of ordinary skill in the art, after reading the present specification, will appreciate that techniques described herein may be used to analyze or determine binding characteristics of H1 polypeptides from any source. Table 4 below provides sequences of various H1 HA polypeptides from a variety of strains. Some of the sequences presented in Table 4 correspond to the HA1 region (e.g., which contains all or part of the glycan receptor binding site). Any number of additional H1 HA polypeptide sequences can be accessed from public databases, including, but not limited to, the GISAID Influenza portal database (http://platform.gisaid.org/dante-cms/live/struktur.j-dante?aid=1131) and/or the NCBI Flu database (http://www.ncbi.nlm.nih.gov/genomes/FLU/FLU.html).

TABLE 4

Sequences of Exemplary H1 HA Polypeptides

| Strain | H1 HA Sequence |
| --- | --- |
| A/Aichi/8/09 (HA1 only) | DTICIGYHANNSTDTVDTVLEKNVTVTHSVNLLENSHNG KLCLLKGIAPLQLGNCSVAGWILGNPECELLISKESWSYI VEKPNPENGTCYPGHFAEYEELREQLSSVSSFERFEIFPKE SSWPNHTVTGVSASCSHNGESSFYRNLLWLTGKNGLYP NLSKSYANNKEKEVLVLWGVHHPPNIAAQKTLYHTENA YVSVVSSHYSRKFTPEIAKRPKVRDQEGRINYYWTLLEP GDTIIFEANGNLIAPRYAFALSRGFGSGIINSNAPMDKCD AKCQTPQGAINSSLPFQNVHPVTIGECPKYVRSAKLRMV TGLRNIPSIQSR (SEQ ID NO: 55) |
| A/Aichi/9/2009 (HA1 only) | DTICIGYHANNSTDTVDTVLEKNVTVTHSVNLLENSHNG KLCLLKGIAPLQLGNCSVAGWILGNPECELLISKESWSYI VEKPNPENGTCYPGHFADYEELREQLSSVSSFERFEIFPK ESSWPNHTVTGVSASCSHNGENSFYRNLLWLTGKNGLY PNLSKSYANNKEKEVLVLWGVHHPPNIADQKALYHTEN AYVSVVSSHYSRKFTPEIAKRPKVRDQEGRINYYWTLLE PGDTIIFEANGNLIAPRYAFALSRGFGSGIINSNAPMDKCD AKCQTPQGAINSSLPFQNVHPVTIGECPKYVRSAKLRMV TGLRNIPSIQSR (SEQ ID NO: 56) |
| A/Aichi/37/09 (HA1 only) | DTICIGYHANNSTDTVDTVLEKNVTVTHSVNLLENSHNG KLCLLKGIAPLQLGNCSVAGWILGNPECELLISKESWSYI VEKPNPENGTCYPGHFADYEELREQLSSVSSFERFEIFPK ESSWPNHTVTGVSASCSHNGENSFYRNLLWLTGKNGLY PNLSKSYANNKEKEVLVLWGVHHPPNIADQKTLYHTEN AYVSVVSSHYSRKFTPEIAKRPKVRDQEGRINYYWPLLE PGDTIIFEANGNLIAPRYAFALSRGFGSGIINSNAPMDKCD AKCQTPQGAINSSLPFQNVHPVTIGECPKYVRSAKLRMV TGLRNIPSIQSR (SEQ ID NO: 57) |
| A/Brisbane/59/2007 (HA1 only) | DTICIGYHANNSTDTVDTVLEKNVTVTHSVNLLENSHNG KLCLLKGIAPLQLGNCSVAGWILGNPECELLISKESWSYI VEKPNPENGTCYPGHFADYEELREQLSSVSSFERFEIFPK ESSWPNHTVTGVSASCSHNGESSFYRNLLWLTGKNGLY PNLSKSYANNKEKEVLVLWGVHHPPNIGDQKALYHTEN AYVSVVSSHYSRKFTPEIAKRPKVRDQEGRINYYWTLLE PGDTIIFEANGNLIAPRYAFALSRGFGSGIINSNAPMDKCD AKCQTPQGAINSSLPFQNVHPVTIGECPKYVRSAKLRMV TGLRNIPSIQSR (SEQ ID NO: 58) |

TABLE 4-continued

Sequences of Exemplary H1 HA Polypeptides

| Strain | H1 HA Sequence |
|---|---|
| A/Washington/1/09 | MKVKLLVLLCTFTATYADTICIGYHANNSTDTVDTVLEK<br>NVTVTHSVNLLENSHNGKLCLLKGIAPLQLGNCSVAGWI<br>LGNPECELLISKESWSYIVEKPNPENGTCYPGHFADYEEL<br>REQLSSVSSFERFEIFPKESSWPNHTVTGVSASCSHNGESS<br>FYRNLLWLTGKNGLYPNLSKSYANNKEKEVLVLWGVH<br>HPPNIVXQKTLYRTENAYVSVVSSHYSRKFTPEIAKRPK<br>VRDQEGRINYYWTLLEPGDTIIFEANGNLIAPRYAFALSR<br>GFGSGIINSNAPMDKCDAKCQTPQGAINSSLPFQNVHPV<br>TIGECPKYVRSAKLRMVTGLRNIPSIQSRGLFGAIAGFIEG<br>GWTGMVDGWYGYHHQNEQGSGYAADQKSTQNAINGI<br>TNKVNSVIEKMNTQFTAVGKEFNKLERRMENLNKKVD<br>DGFIDIWTYNAELLVLLENERTLDFHDSNVKNLYEKVKS<br>QLKNNAKEIGNGCFEFYHKCNDECMESVKNGTY<br>(SEQ ID NO: 59) |
| A/Canterbury/106/2004 | MKVKLLVLLCTFTATYADTICIGYHANNSTDTVDTVLEK<br>NVTVTHSVNLLEDSHNGKLCLLKGIAPLQLGNCSVAGWI<br>LGNPECELLISKESWSYIVEKPNPENGTCYPGHFADYEEL<br>REQLSSVSSFERFEIFPKESSWPNHTVTGVSASCSHNGKS<br>SFYKNLLWLTGKNGLYPNLSKSYANNKEKEVLVLWGV<br>HHPPNIGDQKALYHTENAYVSVVSSHYSRKFTPEIAKRP<br>KVRDQEGRINYYWTLLEPGDTIIFEANGNLIAPRYAFALS<br>RGFGSGIINSNAPMDECDAKCQTPQGAINSSLPFQNVHPV<br>TIGECPKYVRSAKLRMVTGLRNIPSIQSRGLFGAIAGFIEG<br>GWTGMVDGWYGYHHQNEQGSGYAADQKSTQNAINGI<br>TNKVNSVIEKMNTQFTAVGKEFNKLERRMENLNKKVD<br>DGFIDIWTYNAELLVLLENERTLDFHDSNVKNLYEKVKS<br>QLKNNAKEIGNGCFEFYHKCNDECMESVKNGTYDYPKY<br>SEESKLNREKIDGVKLESMGVYQILAIYSTVASSLVLLVS<br>LGAISFWMCSNGSLQCRICI (SEQ ID NO: 60) |
| A/New York/212/2001 | MKAKLLVLLCTFTATYADTICIGYHANNSTDTVDTVLEK<br>NVTVTHSVNLLEDSHNGKLCLLKGIAPLQLGNCSVAGWI<br>LGNPECELLISKESWSYIVETPNPENGTCYPGYFADYEEL<br>REQLSSVSSFERFEIFPKGSSWPNHTVTGVSASCSHNGKS<br>SFYRNLLWLTGKNGLYPNLSMSYVNNKEKEVLVLWGV<br>HHPPNIGDQRALYHTENAYVSVVSSHYSRRFTPEIAKRP<br>KVRDQEGRINYYWTLLEPGDTIIFEANGNLIAPWYAFAL<br>SRGFGSGIITSNAPMDECDAKCQTPQGAINSSLPFQNVHP<br>VTIGECPKYVRSAKLRMVTGLRNIPSIQSRGLFGAIAGFIE<br>GGWTGMVDGWYGYHHQNEQGSGYAADQKSTQNAING<br>ITNKVNSVIEKMNTQFTAVGKEFNKLERRMENLNKKVD<br>DGFLDIWTYNAELLVLLENERTLDFHDSNVKNLYEKVK<br>SQLKNNAKEIGNGCFEFYHKCNDECMESVKNGTYDYPK<br>YSEESKLNREKIDGVKLESMGVYQILAIYSTVASSLVLLV<br>SLGAISFWMCSNGSLQCRICI (SEQ ID NO: 61) |
| A/New York/307/2001 | KAKLLVLLCTFTATYADTICIGYHANNSTDTVDTVLEKN<br>VTVTHSVNLLEDSHNGKLCRLKGTAPLQLGNCSIAGWIL<br>GNPECESLFSKESWSYIAETPNPKNGTCYPGYFADYEEL<br>REQLSSVSSFERFEIFPKDSSWPNHTVTKGVTASCSHNGK<br>SSFYKNLLWLTEKNGLYPNLSKSYVNKKGKEVLVLWG<br>VHHPSNMGDQRAIYHKENAYVSVLSSHYSRRFTPEIAKR<br>PKVRDQEGRINYYWTLLEPGDTIIFEANGNLIAPWYAFA<br>LSRGFGSGIIISNASMGECDAKCQTPQGAINSSLPFQNVH<br>PVTIGECPKYVRSTKLRMVTGLRNVPSIQSRGLFGAIAGF<br>IEGGWTGMIDGWYGYHHQNEQGSGYAADQKSTQNAIN<br>GITNKVNSIIEKMNTQFTAVGKEFNRLERRMENLNKKVD<br>DGFLDIWTYNAELLVLLENERTLDFHDSNVKDLYEKVK<br>TQLKNNAKEIGNGCFEFYHKCNNECMESVKNGTYDYPK<br>YSKESKLNREKIDGVKLESMGVYQILAIYSTVASSLVLLV<br>SLGAISFWMCSNGSLQCRICI (SEQ ID NO: 62) |
| A/Taiwan/117/1996 | MKAKLLVLLCAFTATYADTICIGHHANNSTDTVDTVLE<br>KNVTVTHSVNLLEDSHNGKLCRLKGTAPLQLGNCSVAG<br>WILGNPECESLFSKESWSYIAETPNPENGTCYPGYFADYE<br>ELREQLSSVSSFERFEIFPKESSWPNHTVTKGVTASCSHN<br>GKSSFYKNLLWLTGKNGLYPNLSKSYVNHKEKEVLVL<br>WGVHHPSNIRDQRAIYHTENAYVSVVSSHYSRRFTPEIA<br>KRPKVRDQEGRINYYWTLLEPGDTIIFEANGNLIAPWYA<br>FALSRGFGSGIITSNASMGECDAKCQTPQGAINSSLPFQN<br>VHPVTIGECPKYVRSTKLRMVTGLRNIPSIQSRGLFGAIA<br>GFIEGGWTGMIDGWYGYHHQNEQGSGYAADQKSTQNA<br>INGI (SEQ ID NO: 63) |

TABLE 4-continued

Sequences of Exemplary H1 HA Polypeptides

| Strain | H1 HA Sequence |
|---|---|
| A/Brazil/099/01 | DTICIGYHANNSTDTVDTVLEKNVTVTHSVNLLEDSHNG<br>KLCLLKGIAPLQLGNCSVAGWILGNPECELLISKESWSYI<br>VETPNPENGTCYPGYFADYEELREQLSSVSSFERFEIFPKE<br>SSWPNHTVTGVSASCSHNGKSSFYRNLLWLTGKNGLYP<br>NLSKSYANNKEKEVLVLWGVHHPPNIGDQRALYHTENA<br>YVSVVSSHYSRRFTPEIAKRPKVRDQEGRINYYWTLLEP<br>GDTIIFEANGNLIAPRYAFALSRGFGSGIITSNAPMDECDA<br>KCQTPQGAINSSLPFQNVHPITIGECPKYVRSAKLRMVTG<br>LRNIPSIQS (SEQ ID NO: 64) |

Binding characteristics of these strains may be assessed, for example with respect to umbrella-topology glycans and/or with respect to cone-topology glycans. Binding characteristics may be assessed with respect to, for example, α2-6 sialylated glycans and/or with respect to α2-3 sialylated glycans. In some embodiments, binding characteristics are assessed with respect to at least long α2-6 sialylated glycans (e.g., 6'SLN-LN glycans).

Those of ordinary skill in the art, after reading the present specification, will appreciate that any H1 polypeptide listed in Table 4 that shows appropriate glycan binding characteristics and/or appropriate human infectivity (e.g., not human pandemic infectivity) may be used as a reference against which "enhanced" human binding H1 HA polypeptides are compared. Comparably, any H1 polypeptide listed in Table 4 that shows appropriate glycan binding characteristics (e.g., extensive binding to umbrella-topology glycans and/or preference for umbrella-topology glycans as compared with cone-topology glycans) and/or appropriate human infectivity (e.g., human pandemic infectivity) may be used as a comparator to confirm "enhanced" human binding of a particular H1 HA polypeptide (e.g., a particular H1 HA polypeptide variant).

Example 4

Receptor Binding Properties of Mutated 2009 H1N1 Influenza A Virus HA

Materials and Methods

Cloning, Baculovirus Synthesis, Expression and Purification of HA

Briefly, recombinant baculoviruses with WT or mutant HA genes, respectively, were used to infect (MOI=1) suspension cultures of Sf9 cells (Invitrogen, Carlsbad, Calif.) cultured in BD Baculogold Max-XP SFM (BD Biosciences, San Jose, Calif.). Infection was monitored and the conditioned media was harvested 3-4 days post-infection. Soluble HA from the harvested conditioned media was purified using Nickel affinity chromatography (HisTrap HP columns, GE Healthcare, Piscataway, N.J.). Eluting fractions containing HA were pooled, concentrated and buffer exchanged into 1×PBS pH 8.0 (Gibco) using 100K MWCO spin columns (Millipore, Billerica, Mass.). Purified protein was quantified using BCA method (Pierce).

Homology Based Structural Modeling of CA/04 and Mutants

Using the SWISS-MODEL web-based automated homology modeling platform (http://swissmodel.expasy.org/), homology structural models of CA04, CA04M1 and CA04M2 were constructed. The template structure chosen by SWISS-MODEL was that of a recently solved crystal structure of 2009 H1N1 HA (PDB ID: 3LZG). The starting pose of the HA-human receptor complex was obtained by superimposing the modeled HA structure with the co-crystal structure of 1918 H1N1 HA with human receptor (PDB ID: 2WRG). The starting structural complex was subject to energy minimization (500 steps of steepest descent followed by 500 steps of conjugate gradient). The AMBER force-field was used to assign potentials and charges. The default version of AMBER was that provided with the Discover module of InsightII molecular modeling suite (Accelrys, San Diego, Calif.).

Binding of Recombinant WT and Mutant CA04 HAs to Human Tracheal Tissue Sections

Paraffinized human tracheal (US Biological) tissue sections were deparaffinized, rehydrated and incubated with 1% BSA in PBS for 30 minutes to prevent non-specific binding. HA was pre-complexed with primary antibody (mouse anti 6×His tag, Abcam) and secondary antibody (Alexa fluor 488 goat anti mouse, Invitrogen) in a molar ratio of 4:2:1, respectively, for 20 minutes on ice. Tissue binding was performed over different HA concentrations by diluting the pre-complexed HA in 1% BSA-PBS. Tissue sections were then incubated with the HA-antibody complexes for 3 hours at room temperature (RT). Tissue sections were counterstained by propidium iodide (Invitrogen; 1:100 in TBST). Tissue sections were mounted and then viewed under a confocal microscope (Zeiss LSM510 laser scanning confocal microscopy). In the case of sialidase pretreatment, tissue sections were incubated with 0.2 units of Sialidase A (recombinant from *Arthrobacter ureafaciens*, Prozyme) for 3 hours at 37° C. prior to incubation with the proteins. This enzyme has been demonstrated to cleave the terminal Neu5Ac from both Neu5Acα2→3Gal and Neu5Acα2→6Gal motifs.

Dose Dependent Direct Binding of WT and Mutant CA04 HAs

To investigate the multivalent HA-glycan interactions a streptavidin plate array comprising representative biotinylated α2→3 and α2→6 sialylated glycans as described previously (Srinivasan et al., 2008, *Proc. Natl. Acad. Sci. U S. A.*, 105:2800-05; incorporated herein by reference) (FIG. 14). 3'SLN, 3'SLN-LN, 3'SLN-LN-LN are representative avian receptors. 6'SLN and 6'SLN-LN are representative human receptors. Biotinylated glycans were obtained from the Consortium of Functional Glycomics through their resource request program. Streptavidin-coated High Binding Capacity 384-well plates (Pierce) were loaded to the full capacity of each well by incubating the well with 50 μl of 2.4 μM of biotinylated glycans overnight at 4° C. Excess glycans were removed through extensive washing with PBS. The trimeric HA unit comprises of three HA monomers (and hence three RBS, one for each monomer). The spatial arrangement of the biotinylated glycans in the wells of the streptavidin plate array favors binding to only one of the three HA monomers in the trimeric HA unit. Therefore in order to specifically enhance the multivalency in the HA-glycan interactions, the recombinant HA proteins were pre-complexed with the primary and secondary antibodies in the ratio of 4:2:1 (HA:primary:secondary). The identical arrangement of 4 trimeric HA units in the precomplex for all the HAs permits comparison between their glycan binding affinities.

A stock solution containing appropriate amounts of histidine-tagged HA protein, primary antibody (Mouse anti 6×His tag IgG) and secondary antibody (HRP conjugated goat anti Mouse IgG (Santacruz Biotechnology) in the ratio 4:2:1, respectively, and incubated on ice for 20 minutes. Appropriate amounts of precomplexed stock HA were diluted to 250 µl with 1% BSA in PBS. 50 µl of precomplexed HA was added to each of the glycan-coated wells and incubated at room temperature for 2 hours followed by the above wash steps. The binding signal was determined based on HRP activity using Amplex Red Peroxidase Assay (Invitrogen, CA) according to the manufacturer's instructions. The experiments were done in triplicate. Minimal binding signals were observed in the negative controls including binding of precomplexed unit to wells without glycans and binding of the antibodies alone to the wells with glycans. The binding parameters, cooperativity (n) and apparent binding constant ($K_d'$), for H2 HA-glycan binding were calculated by fitting the average signal value (from the triplicate analysis) and the HA concentration to the linearized form of the Hill equation:

$$\log\left(\frac{y}{1-y}\right) = n * \log([HA]) - \log(K_d')$$

where y is the fractional saturation (average binding signal/maximum observed binding signal). The theoretical y values calculated using the Hill equation:

$$y = \frac{[HA]^n}{[HA]^n + K_d'}$$

Figure 15A:
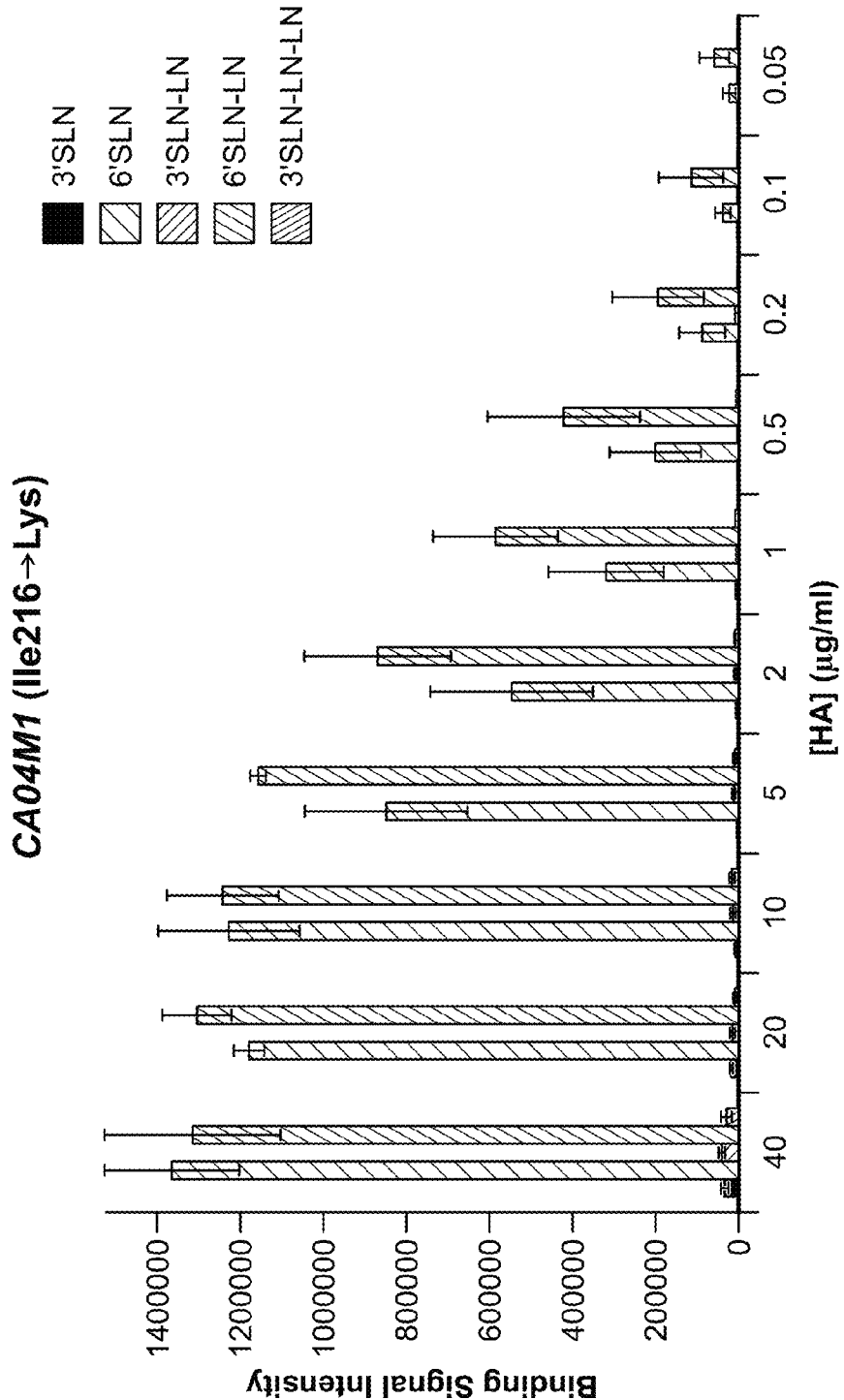
Figure 15B:
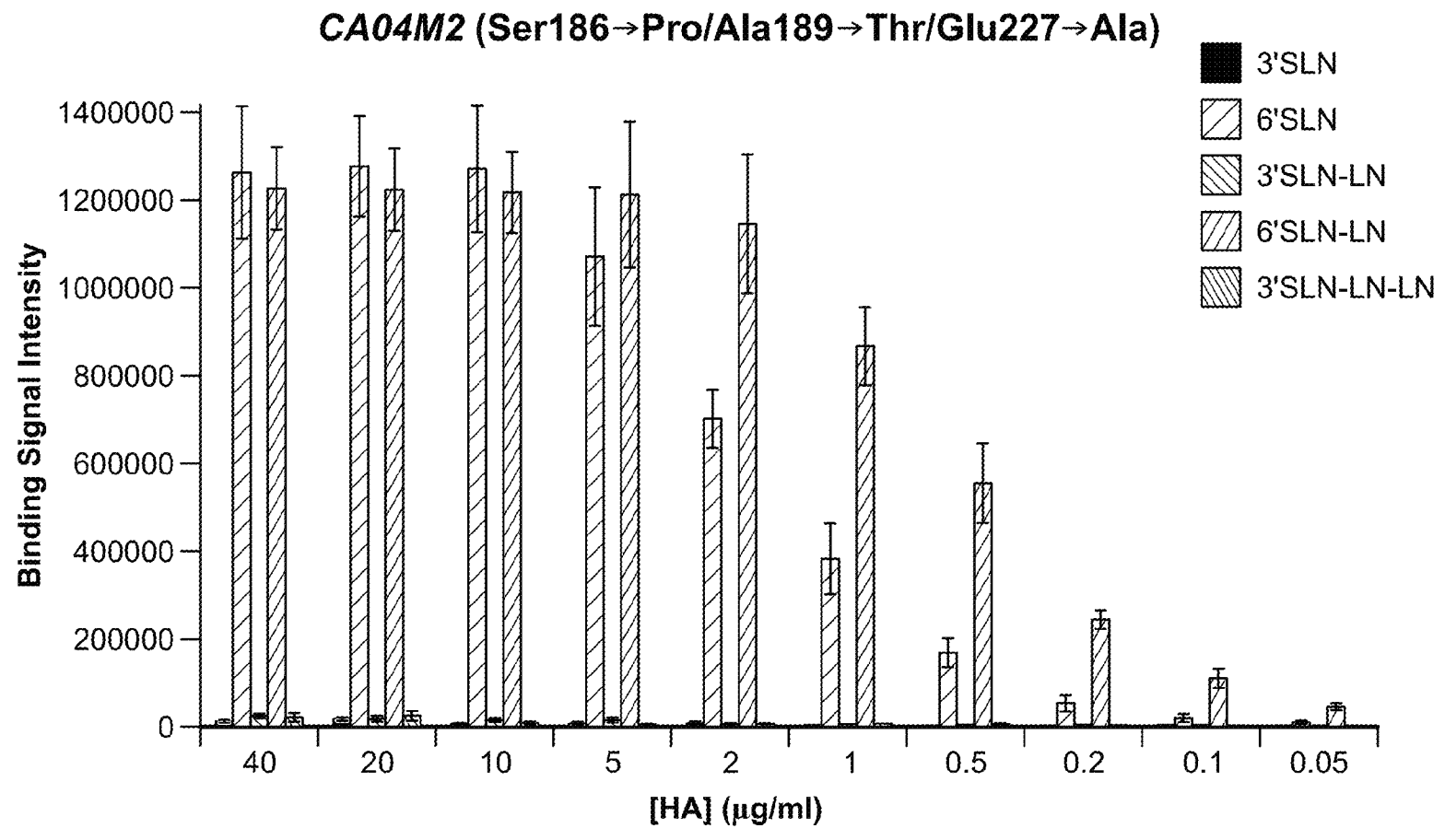
Figure 15C:
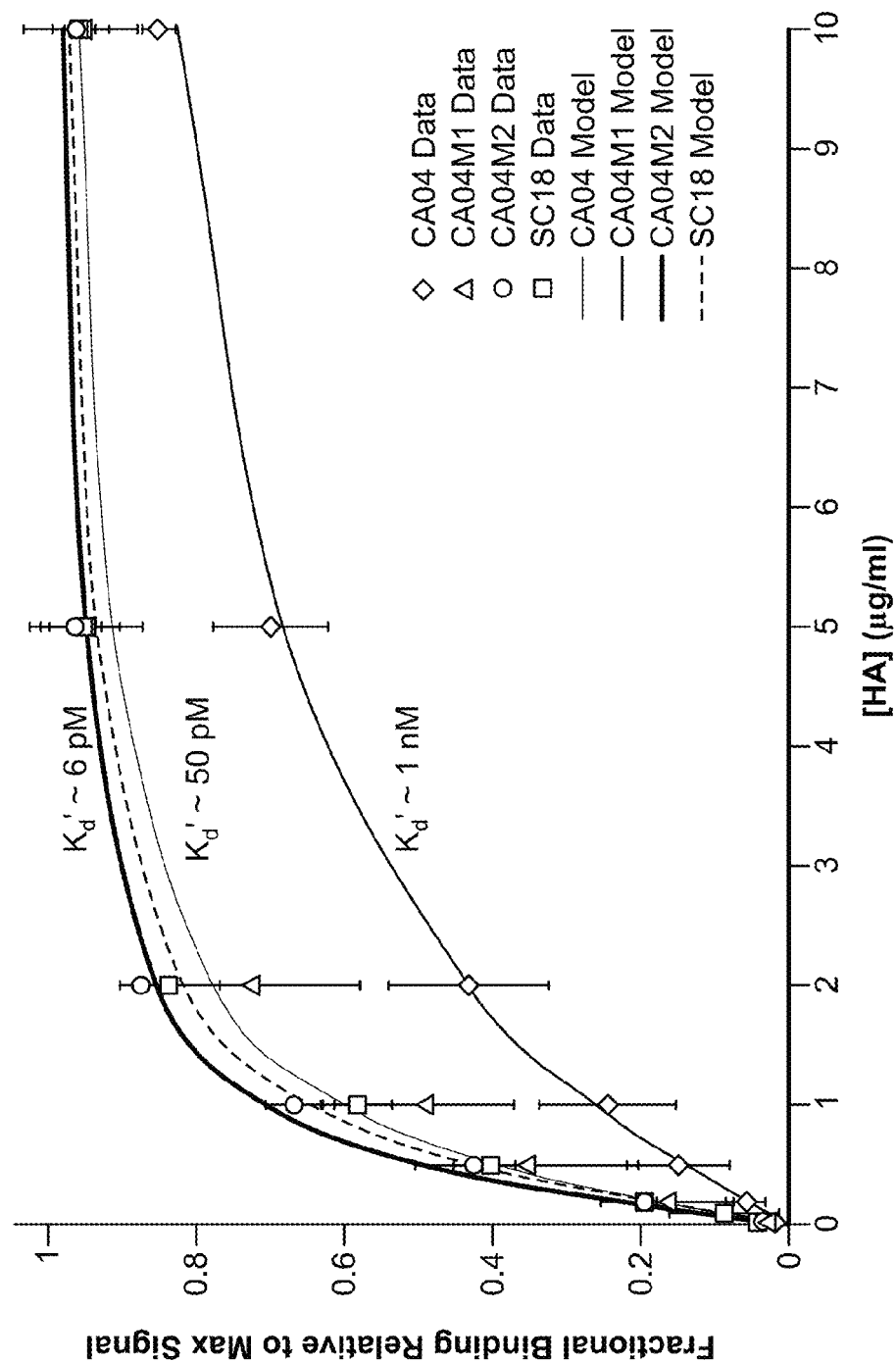
Figure 15D:
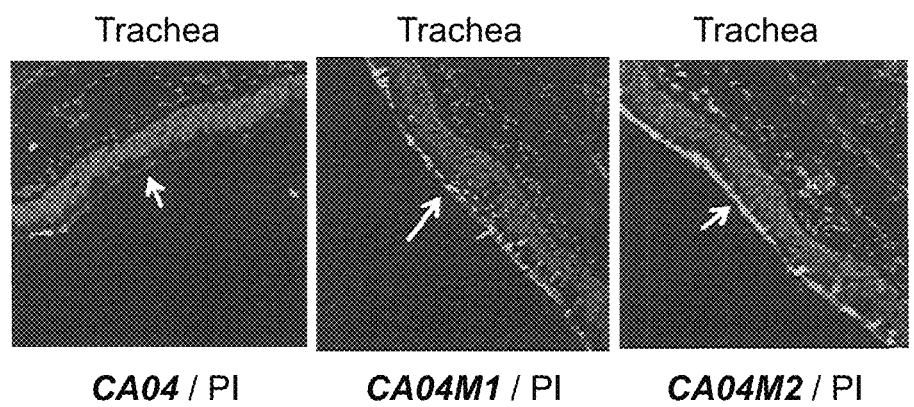
Figure 16:
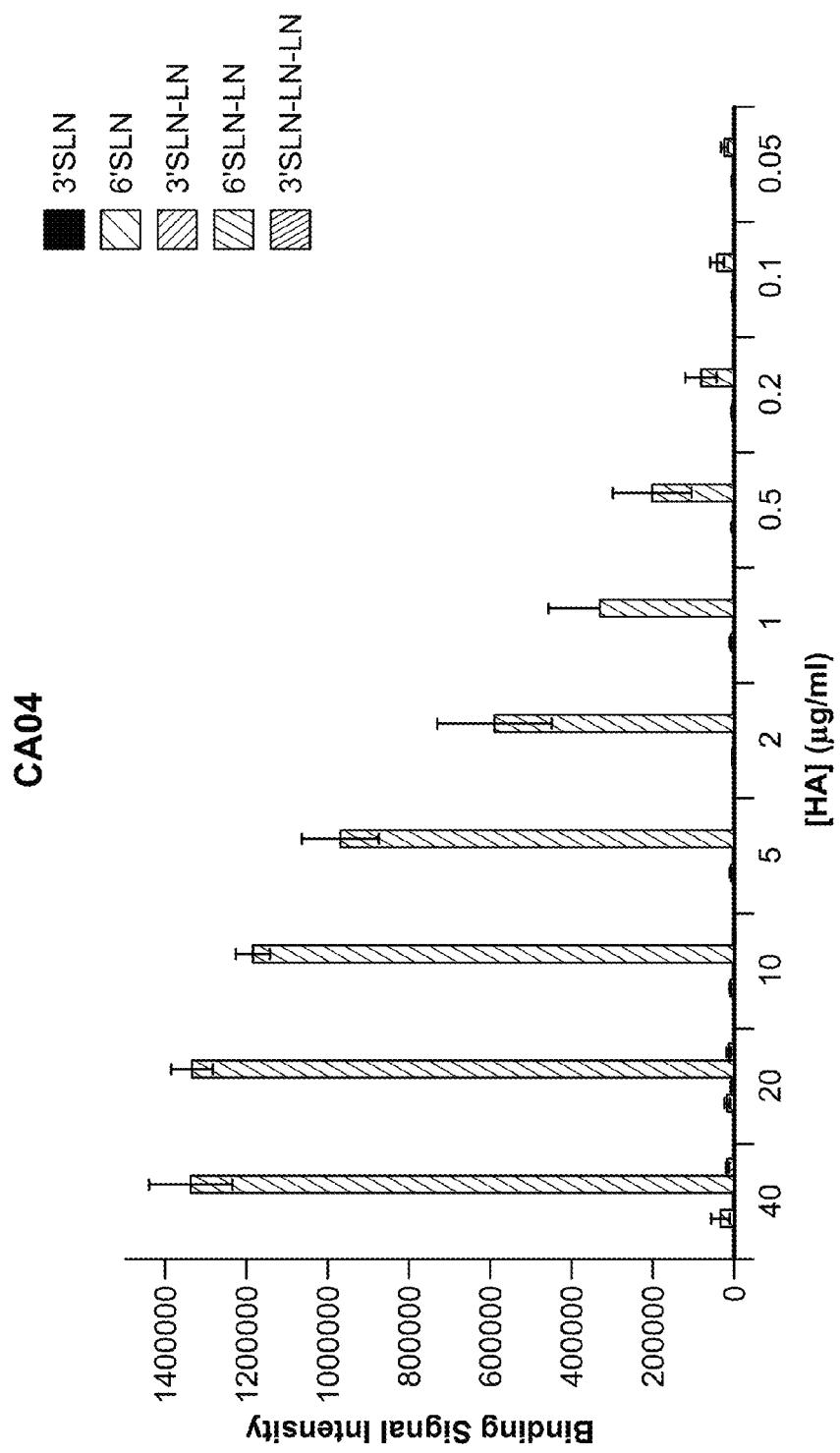
FIG. 16: Dose-dependent direct glycan array binding of CA04 HA in comparison with the natural variants CA04M3 (Asp225Glu), CA04M4 (Asp225Asn) and CA04M5 (Asp225Gly) HAs. Also shown in the bottom panel are the binding curves of these HAs to the representative human receptor (6'SLN-LN) along with the binding strengths quantified using $K_d'$. Although CA04M3 and CA04M4 show same the human receptor binding specificity of CA04, the binding strength of CA04M4>CA04>>CA04M3 HA. CA04M5, on the other hand, shows dose-dependent binding to human receptors at dramatically lower signal values and to avian receptors as well. These observations suggest that length (as compared to polarity) of the side chain at position 225 might influence human-receptor binding.
Figure 16:
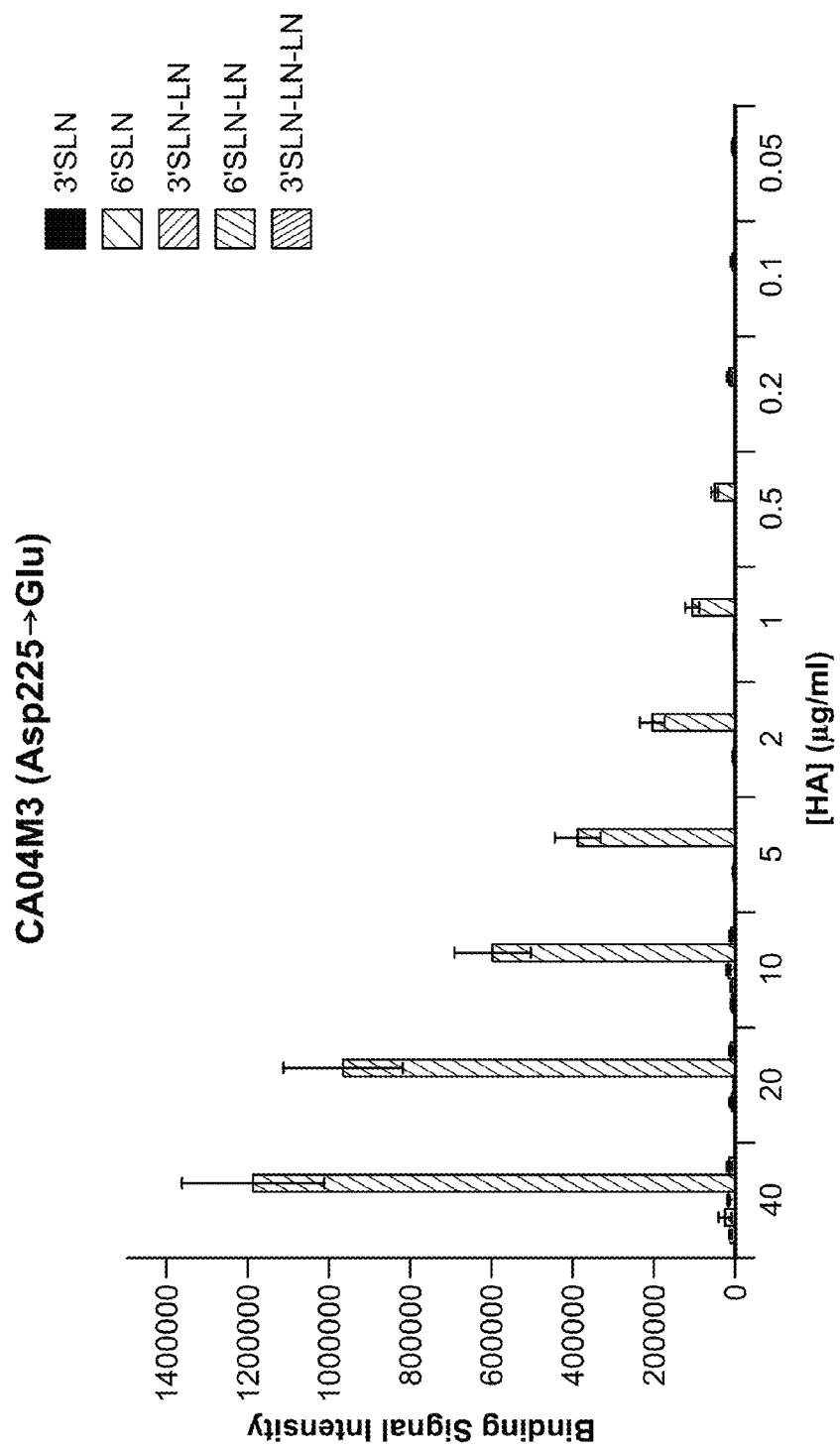
Figure 16:
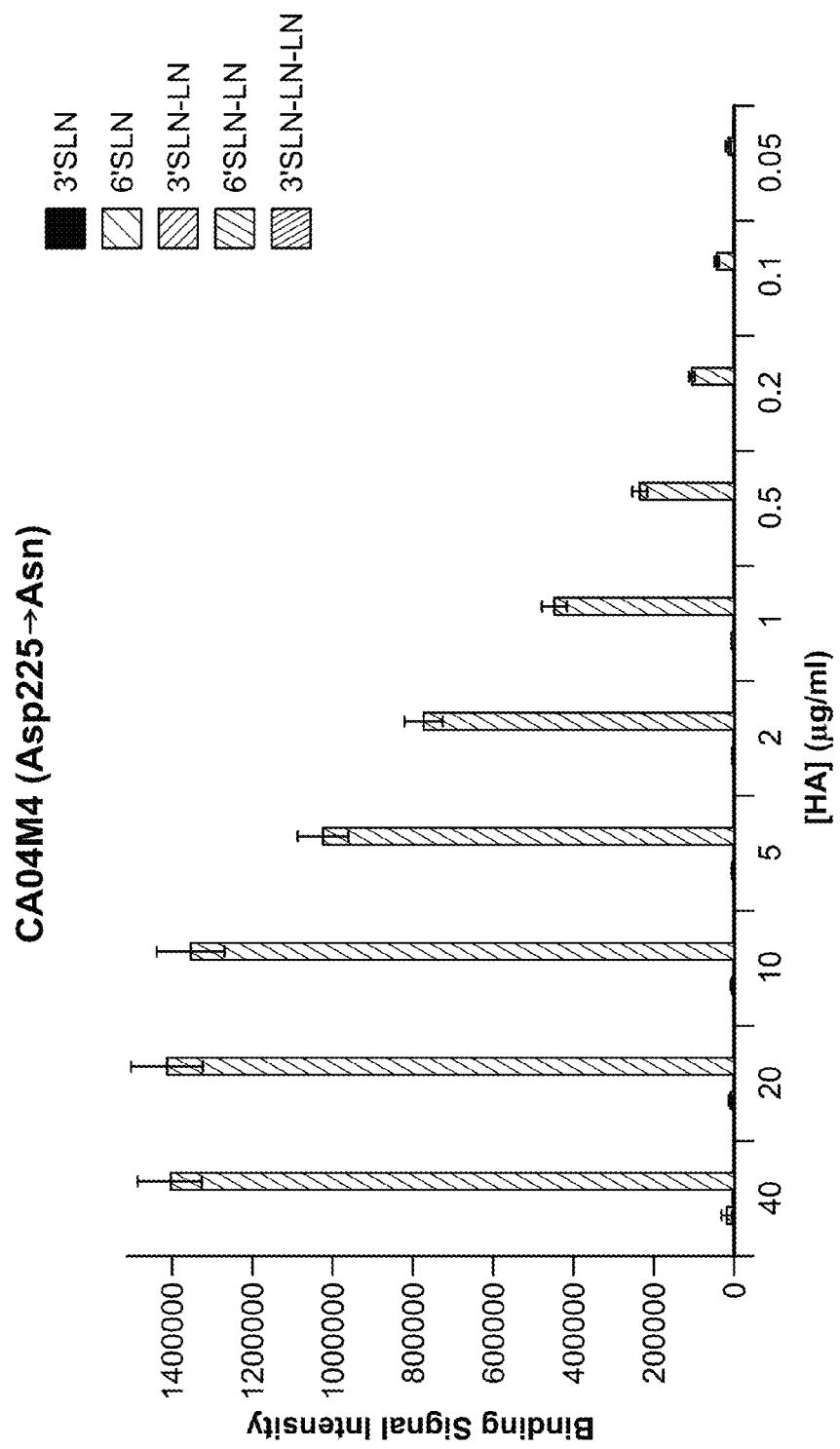
Figure 16:
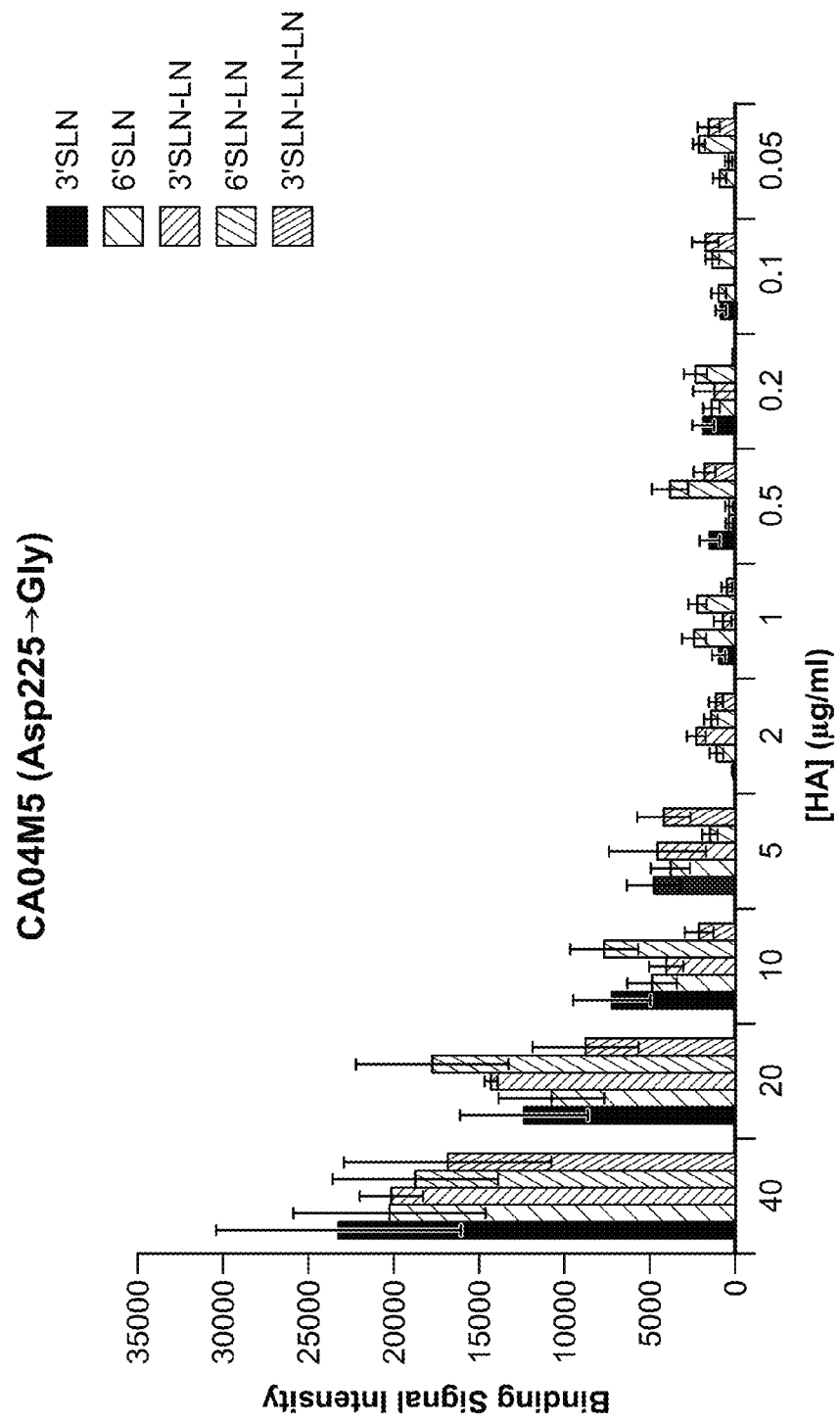
Figure 16:
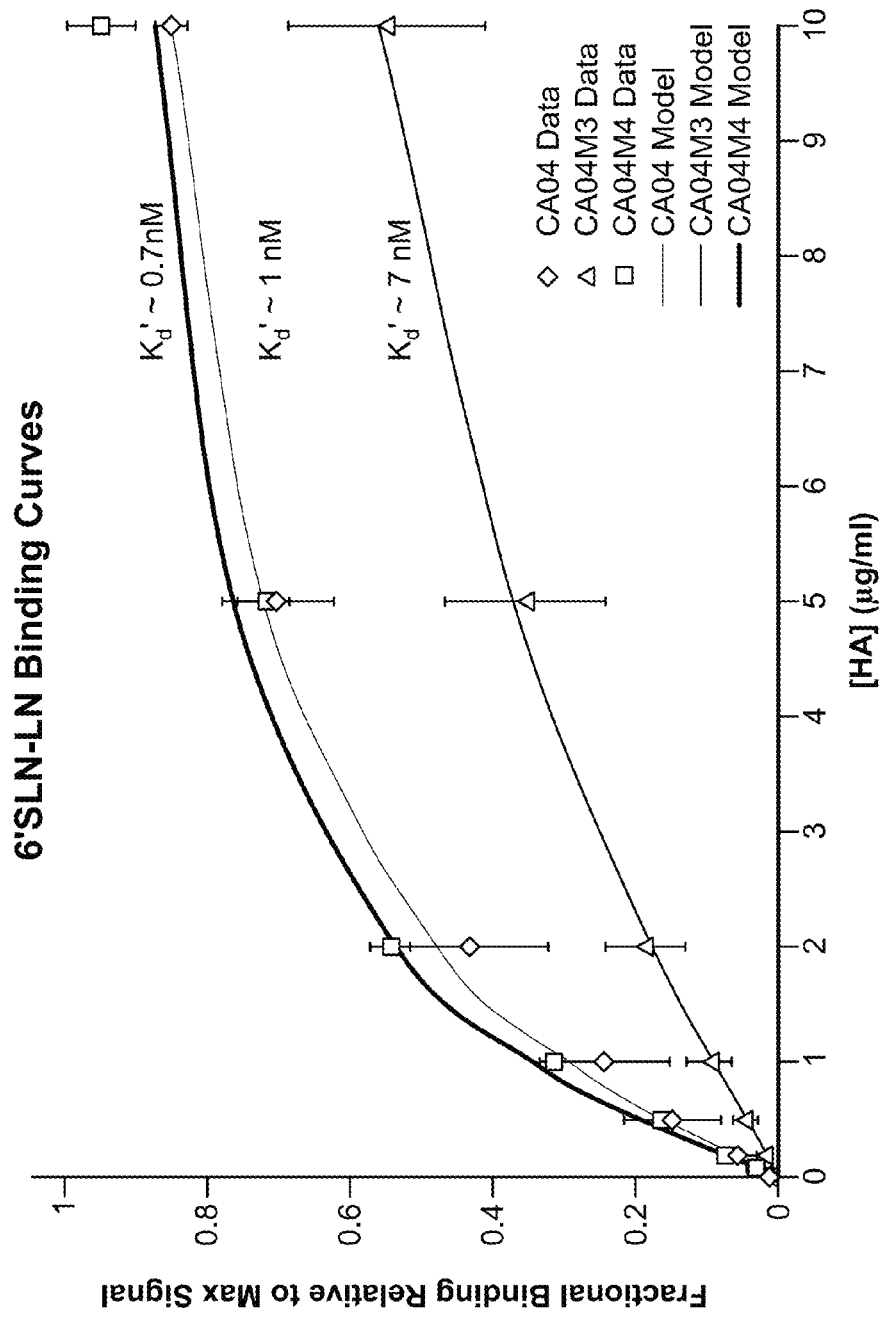

(for the set of n and $K_d'$ parameters) were plotted against the varying concentration of HA to obtain the binding curves for the representative human receptor (6' SLN-LN) in FIG. 15D and FIG. 16.

Results

CA04M1 (Ile219→Lys) and CA04M2 (Ser186→Pro+ Ala189→Thr+Glu227→Ala)

Figure 13A:
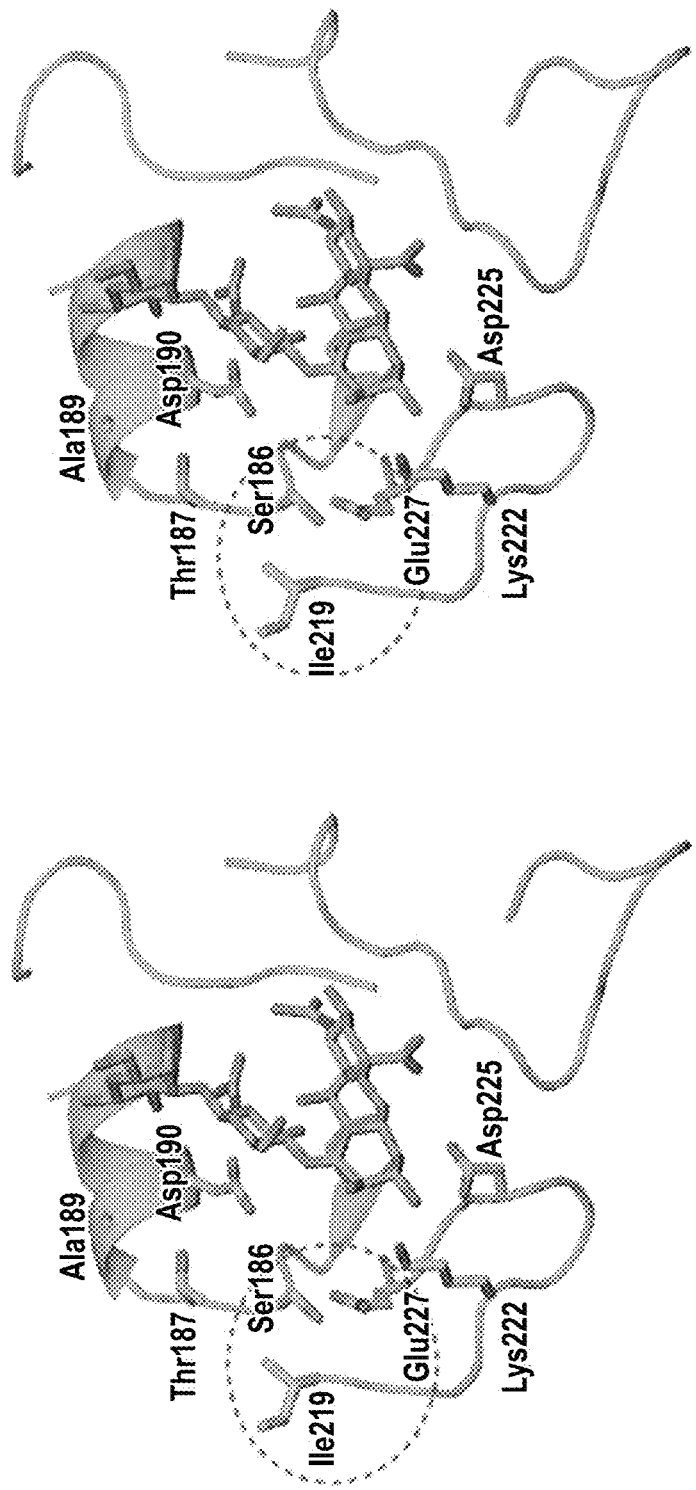
Figure 13B:
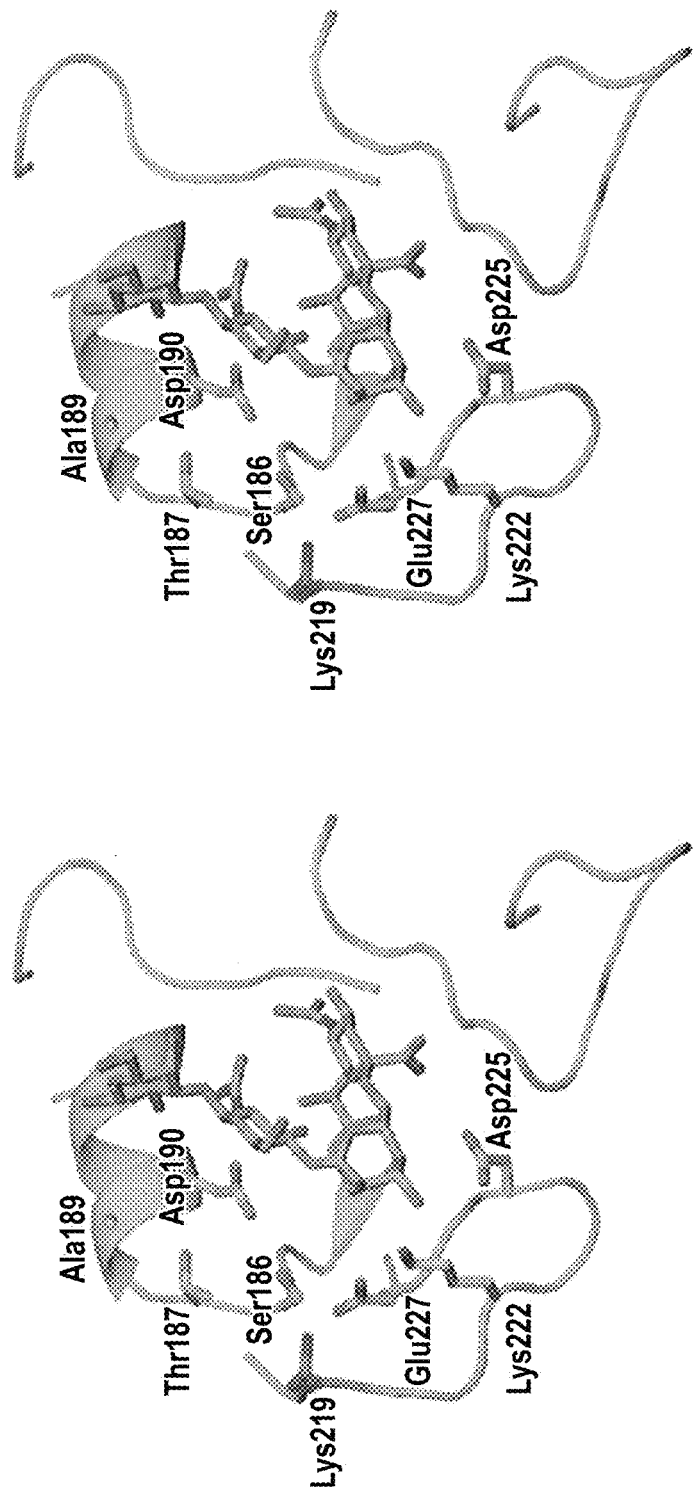
Figure 13C:
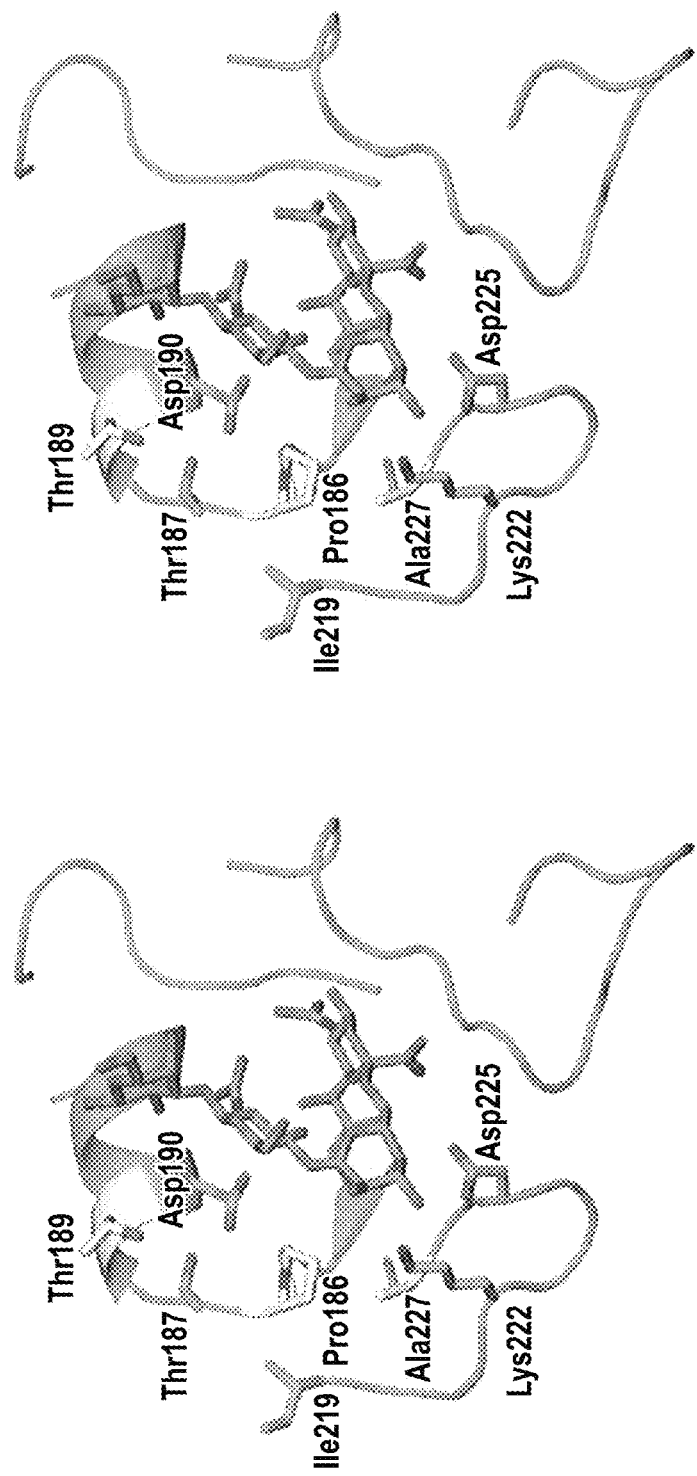
Figure 13D:
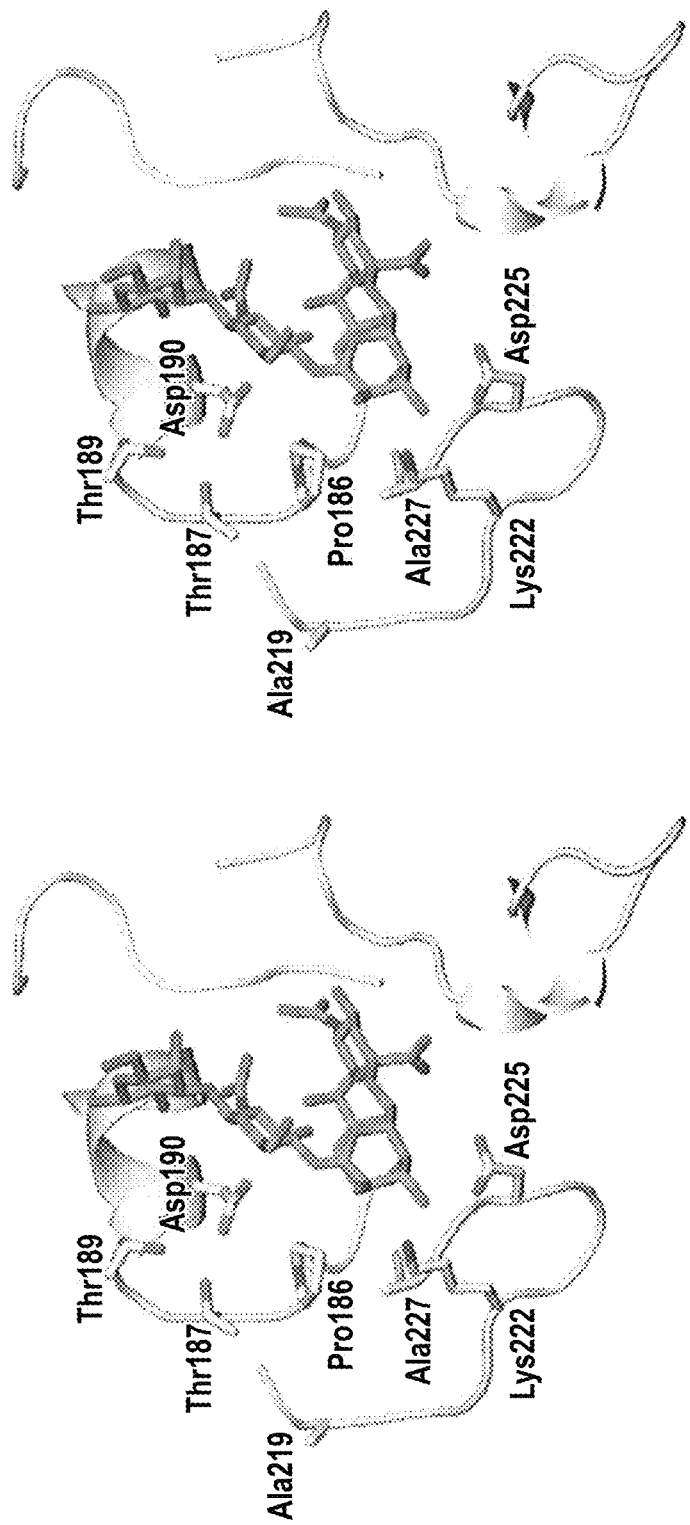

In Example 1, the sequence and structure of the RBS of CA04 was compared with that of highly transmissible human-adapted H1N1 HAs. In Example 1, the inventors predicted that a mismatch in the inter-residue interaction between Ile219 (hydrophobic) and Glu227 (ionic) in CA04 HA potentially disrupts its optimal contact with the human receptors which is in turn responsible for lowering the binding strength (FIG. 13A) (see Maines et al., 2009, Science, 325:484-87; incorporated herein by reference). Without wishing to be bound by any one particular theory, this mismatch may explain the inability of the natural variants to substantially improve human receptor-binding strength despite acquiring mutations at Asp225 in the RBS. As explained in Example 1, the present inventors provided the insight that fixing this mismatched combination would improve the human receptor binding strength of 2009 H1N1 HA. As presented in Example 1, structural analysis of the RBS of CA04 HA indicated two possible ways of fixing this mismatch. The first possibility involved a single Ile219→Lys mutation (CA04M1) that would make the Lys219-Glu227 interaction ionic (FIG. 13B) similar to that observed in RBS of seasonal H1N1 influenza viruses (Maines et al., 2009, Science, 325:484-87; incorporated herein by reference). The second possibility involved three amino acid changes, Ser186→Pro/Ala189→Thr/Glu227→Ala (CA04M2) (FIG. 13C) that would make the interactions hydrophobic similar to that observed in the RBS of SC18 HA (FIG. 13D). The present inventors confirmed that the prediction described in Example 1 was accurate by recombinantly expressing the CA04M1 and CA04M2 mutants and quantifying their respective glycan receptor binding strengths by analyzing them (in their pre-complexed state) using the dose-dependent glycan array analysis.

CA04M1 and CA04M2 showed specific binding to both the representative human receptors (6'SLN and 6'SLN-LN; FIG. 14) on the array (only minimal binding signals to avian receptors were observed at the higher concentrations of 20-40 µg/ml) (FIG. 15A,B). The binding strength of CA04M1 ($K_d'$ ~50 picomolar (pM)) and CA04M2 ($K_d'$ ~6 pM) to 6'SLN-LN is significantly higher than that of CA04 HA (and the natural variants at the 225 position) and is in the same range as that of SC18 HA (FIG. 15C). The differences in the human receptor binding strengths of CA04, CA04M1 and CA04M2 HAs were also reflected in their staining of the apical surface of the human tracheal tissue section, which predominantly expresses human receptors and is a target for efficient viral transmission by respiratory droplets (see, e.g., Srinivasan et al., 2008, Proc. Natl. Acad. Sci. U.S.A., 105: 2800-05; and Chandrasekaran et al., 2008, Nat. Biotechnol., 26:107-13; both of which are incorporated herein by reference). In comparison to CA04 HA, both CA04M1 and CA04M2 HAs show more intense staining of the apical surface of the human tracheal tissue sections (FIG. 15D). Thus, as predicted in Example 1, both of CA04M1 and CA04M2 HAs improved human HA receptor binding strength.

In contrast to the qualitative binding assays described by Childs et al., the present inventors performed dose-dependent binding assays with recombinant HAs which are able to quantify the differences in the relative glycan receptor-binding strengths of WT and mutant HAs. Using such assays, the present inventors have demonstrated mutants of CA04 HA (CA04M1 and CA04M2) that have significantly higher human receptor binding strength as compared to WT HA. These results validated the prediction presented in Example 1, i.e., that fixing mismatched molecular interactions in the RBS of 2009 H1N1 HA substantially increases its human receptor binding strength. The present invention encompasses the recognition that qualitative binding assays would have likely missed identification of these mutants.

The present invention encompasses the recognition that mutant 2009 H1N1 HAs that exhibit increased human receptor binding strength would be likely to promote enhanced human transmission of 2009 H1N1 strains. Indeed, human receptor-binding strength has been shown to correlate with human-to-human transmissibility of the 1918 pandemic H1N1 virus (Srinivasan et al., 2008, Proc. Natl. Acad. Sci. U S A., 105:2800-05; and Tumpey et al., 2007, Science, 315:655-59; both of which are incorporated herein by reference). In addition, the present invention encompasses the recognition that such mutant HAs can be useful for the production of vaccines and/or therapeutics as described herein.

CA04M3 (Asp225→Glu), CA04M4 (Asp225→Asn), and CA04M5 (Asp225→Gly)

Recent isolates of the 2009 H1N1 viruses have acquired mutations in the RBS of HA thereby raising concern regarding the potential evolution of a more virulent and transmissible strain (Melidou et al., May 20, 2010, Virus Res.; incorporated herein by reference). Notably, Asp225, which is involved in human receptor binding (Srinivasan et al., 2008, *Proc. Natl. Acad. Sci. U S. A.*, 105:2800-05; incorporated herein by reference), has mutated into Glu, Asn or Gly. Monitoring such mutations in the glycan receptor-binding site (RBS) of hemagglutinin (HA) may be useful to assess their impact on the human-to-human transmissibility of the 2009 H1N1 viruses. Qualitative assessment of the binding specificity of at the 225 mutants showed that their binding properties are similar to the WT HA (Hua et al., 2010, *PLoS Currents: Influenza*; incorporated herein by reference). In contrast, the present inventors have carried out quantitative analyses of the effect of Asp225 mutations generated in the context of CA04 HA on the human receptor-binding strength using a dose-dependent glycan array binding analysis (FIG. 16).

The present inventors' analysis demonstrates that the binding specificity to the representative human receptor (6'SLN-LN; FIG. 14) is the same between Asp225→Glu (CA04M3) and Asp225→Asn (CA04M4) mutants, consistent with the results obtained in the previous study (Hua et al., 2010, *PLoS Currents: Influenza*; incorporated herein by reference). However there were differences in their human receptor binding strengths where CA04M4 ($K_d'$ ~0.7 nanomolar (nM))>CA04 ($K_d'$~1 nM)>>CA04M3 ($K_d'$~7 nM). The Asp225→Gly (CA04M5) mutant showed a dramatically reduced dose-dependent binding to human receptors and also bound to avian receptors. The binding of CA04M5 mutant to representative avian receptors is in agreement with the previous studies (Hua et al., 2010, *PLoS Currents: Influenza*; incorporated herein by reference). Transmission studies are carried out in ferret and mouse essentially as described in Example 1 and in Maines et al. (2009, *Science*, 325:484-87; both of which are incorporated herein by reference) to confirm these results. Taken together, none of the mutants with the natural amino acid substitutions at the 225 position show substantially improved human receptor binding strength over the WT HA.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

---

We claim:

1. A method of detecting an H1 HA influenza hemagglutinin ("HA") polypeptide variant in a sample, the method comprising steps of:
   contacting a patient sample with a binding agent specific for an H1 HA influenza hemagglutinin ("HA") polypeptide variant whose amino acid sequence:
   i) shows at least 90% identity with a reference wild type H1 HA polypeptide that is the HA from A/California/04/2009 strain (SEQ ID NO: 46);
   ii) includes a sequence substitution relative to the reference at each of the following positions:

| Position (corresponding to wild type H3 HA) | Amino acid residue in reference |
|---|---|
| 186 | Ser |
| 189 | Ala |
| 219 | Ile |
| 227 | Glu | iii) differs from that of each of ADA76, A/duck/Alberta/35/76 (H1N1) (SEQ ID NO: 23); ASI30, A/Swine/Iowa/30 (H1N1) (SEQ ID NO: 24); APR34, A/Puerto Rico/8/34 (H1N1) (SEQ ID NO: 25); ASC18, A/South Carolina/1/18 (H1N1) (SEQ ID NO: 26); AT91, A/Texas/36/91 (H1N1) (SEQ ID NO: 27); ANY18, A/New York/1/18 (H1N1) (SEQ ID NO: 28); ADU63, A/Duck/Ukraine/1/63 (H3N8) (SEQ ID NO: 29); AAI68, A/Aichi/2/68 (H3N2) (SEQ ID NO: 30); AM99, A/Moscow/10/99 (H3N2) (SEQ ID NO: 31); ADS97, A/Duck/Singapore/3/97 (H5N3) (SEQ ID NO: 32); Viet04, A/Vietnam/1203/2004 (H5N1) (SEQ ID NO: 33); and
   detecting binding in the sample.

2. The method of claim 1, where in the sample is or comprises one or more of blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver.

3. The method of claim 1, wherein the sample is from a patient who has previously been exposed to one or more viruses showing similarity with 2009 A/H1N1.

4. A method of detecting influenza, the method comprising steps of:
   contacting an environmental sample with a binding agent specific for an H1 HA influenza hemagglutinin ("HA") polypeptide variant whose amino acid sequence:
   i) shows at least 90% identity with a reference wild type H1 HA polypeptide that is the HA from A/California/04/2009 strain (SEQ ID NO: 46);
   ii) includes a sequence substitution relative to the reference at each of the following positions:

| Position (corresponding to wild type H3 HA) | Amino acid residue in reference |
|---|---|
| 186 | Ser |
| 189 | Ala |
| 219 | Ile |
| 227 | Glu | iii) differs from that of each of ADA76, A/duck/Alberta/35/76 (H1N1) (SEQ ID NO: 23); ASI30, A/Swine/Iowa/30 (H1N1) (SEQ ID NO: 24); APR34, A/Puerto Rico/8/34 (H1N1) (SEQ ID NO: 25); ASC18, A/South Carolina/1/18 (H1N1) (SEQ ID NO: 26); AT91, A/Texas/36/91 (H1N1) (SEQ ID NO: 27); ANY18, A/New York/1/18 (H1N1) (SEQ ID NO: 28); ADU63, A/Duck/Ukraine/1/63 (H3N8) (SEQ ID NO: 29); AAI68, A/Aichi/2/68 (H3N2) (SEQ ID NO: 30); AM99, A/Moscow/10/99 (H3N2) (SEQ ID NO: 31); ADS97, A/Duck/Singapore/3/97 (H5N3) (SEQ ID NO: 32); Viet04, A/Vietnam/1203/2004 (H5N1) (SEQ ID NO: 33); and
   detecting binding of the binding agent to the sample.

5. The method of claim 4, wherein the environmental sample is or comprises one or more of soil, water and flora.

* * * * *

SEQUENCE LISTING

```
<160> NUMBER OF SEQ ID NOS: 64

<210> SEQ ID NO 1
<211> LENGTH: 323
<212> TYPE: PRT
<213> ORGANISM: Artificial sequence
<220> FEATURE:
<223> OTHER INFORMATION: Influenza virus

<400> SEQUENCE: 1

Glu Asn Gly Thr Cys Tyr Pro Gly Glu Phe Ile Asp Tyr Glu Glu Leu
1               5                   10                  15

Arg Glu Gln Leu Ser Ser Ile Ser Ser Phe Glu Lys Phe Glu Ile Phe
                20                  25                  30

Pro Lys Ala Ser Ser Trp Pro Asn His Glu Thr Thr Lys Gly Val Thr
            35                  40                  45

Ala Ala Cys Ser Tyr Ser Gly Ala Ser Ser Phe Tyr Arg Asn Leu Leu
        50                  55                  60

Trp Ile Thr Lys Lys Gly Thr Ser Tyr Pro Lys Leu Ser Lys Ser Tyr
65                  70                  75                  80

Thr Asn Asn Lys Gly Lys Glu Val Leu Val Leu Trp Gly Val His His
                85                  90                  95

Pro Pro Ser Val Ser Glu Gln Gln Ser Leu Tyr Gln Asn Ala Asp Ala
            100                 105                 110

Tyr Val Ser Val Gly Ser Ser Lys Tyr Asn Arg Arg Phe Ala Pro Glu
        115                 120                 125

Ile Ala Ala Arg Pro Glu Val Arg Gly Gln Ala Gly Arg Met Asn Tyr
    130                 135                 140

Tyr Trp Thr Leu Leu Asp Gln Gly Asp Thr Ile Thr Phe Glu Ala Thr
145                 150                 155                 160

Gly Asn Leu Ile Ala Pro Trp Tyr Ala Phe Ala Leu Asn Lys Gly Ser
                165                 170                 175
```

```
Asp Ser Gly Ile Ile Thr Ser Asp Ala Pro Val His Asn Cys Asp Thr
            180                 185                 190

Arg Cys Gln Thr Pro His Gly Ala Leu Asn Ser Ser Leu Pro Phe Gln
        195                 200                 205

Asn Val His Pro Ile Thr Ile Gly Glu Cys Pro Lys Tyr Val Lys Ser
    210                 215                 220

Thr Lys Leu Arg Met Ala Thr Gly Leu Arg Asn Val Pro Ser Ile Gln
225                 230                 235                 240

Ser Arg Gly Leu Phe Gly Ala Ile Ala Gly Phe Ile Glu Gly Gly Trp
                245                 250                 255

Thr Gly Met Ile Asp Gly Trp Tyr Gly Tyr His His Gln Asn Glu Gln
            260                 265                 270

Gly Ser Gly Tyr Ala Ala Asp Gln Lys Ser Thr Gln Asn Ala Ile Asp
        275                 280                 285

Gly Ile Thr Ser Lys Val Asn Ser Val Ile Glu Lys Met Asn Thr Gln
    290                 295                 300

Phe Thr Ala Val Gly Lys Glu Phe Asn Asn Leu Glu Arg Arg Ile Glu
305                 310                 315                 320

Asn Leu Asn

<210> SEQ ID NO 2
<211> LENGTH: 323
<212> TYPE: PRT
<213> ORGANISM: Artificial sequence
<220> FEATURE:
<223> OTHER INFORMATION: Influenza virus

<400> SEQUENCE: 2

Glu Asn Gly Thr Cys Tyr Pro Gly Asp Phe Ile Asp Tyr Glu Glu Leu
1               5                   10                  15

Arg Glu Gln Leu Ser Ser Val Ser Ser Phe Glu Lys Phe Glu Ile Phe
                20                  25                  30

Pro Lys Thr Ser Ser Trp Pro Asn His Glu Thr Thr Lys Gly Val Thr
            35                  40                  45

Ala Ala Cys Ser Tyr Ala Gly Ala Ser Ser Phe Tyr Arg Asn Leu Leu
        50                  55                  60

Trp Leu Thr Lys Lys Gly Ser Ser Tyr Pro Lys Leu Ser Lys Ser Tyr
65                  70                  75                  80

Val Asn Asn Lys Gly Lys Glu Val Leu Val Leu Trp Gly Val His His
                85                  90                  95

Pro Pro Thr Gly Thr Asp Gln Gln Ser Leu Tyr Gln Asn Ala Asp Ala
            100                 105                 110

Tyr Val Ser Val Gly Ser Ser Lys Tyr Asn Arg Arg Phe Thr Pro Glu
        115                 120                 125

Ile Ala Ala Arg Pro Lys Val Arg Asp Gln Ala Gly Arg Met Asn Tyr
    130                 135                 140

Tyr Trp Thr Leu Leu Glu Pro Gly Asp Thr Ile Thr Phe Glu Ala Thr
145                 150                 155                 160

Gly Asn Leu Ile Ala Pro Trp Tyr Ala Phe Ala Leu Asn Arg Gly Ser
                165                 170                 175

Gly Ser Gly Ile Ile Thr Ser Asp Ala Pro Val His Asp Cys Asn Thr
            180                 185                 190

Lys Cys Gln Thr Pro His Gly Ala Ile Asn Ser Ser Leu Pro Phe Gln
        195                 200                 205

Asn Ile His Pro Val Thr Ile Gly Glu Cys Pro Lys Tyr Val Arg Ser
```

```
            210                 215                 220
Thr Lys Leu Arg Met Ala Thr Gly Leu Arg Asn Ile Pro Ser Ile Gln
225                 230                 235                 240

Ser Arg Gly Leu Phe Gly Ala Ile Ala Gly Phe Ile Glu Gly Gly Trp
                245                 250                 255

Thr Gly Met Ile Asp Gly Trp Tyr Gly Tyr His His Gln Asn Glu Gln
                260                 265                 270

Gly Ser Gly Tyr Ala Ala Asp Gln Lys Ser Thr Gln Asn Ala Ile Asp
            275                 280                 285

Gly Ile Thr Asn Lys Val Asn Ser Val Ile Glu Lys Met Asn Thr Gln
            290                 295                 300

Phe Thr Ala Val Gly Lys Glu Phe Asn Asn Leu Glu Arg Arg Ile Glu
305                 310                 315                 320

Asn Leu Asn

<210> SEQ ID NO 3
<211> LENGTH: 322
<212> TYPE: PRT
<213> ORGANISM: Artificial sequence
<220> FEATURE:
<223> OTHER INFORMATION: Influenza virus

<400> SEQUENCE: 3

Glu Asn Gly Thr Cys Tyr Pro Gly Tyr Phe Ala Asp Tyr Glu Glu Leu
1               5                   10                  15

Arg Glu Gln Leu Ser Ser Val Ser Ser Phe Glu Arg Phe Glu Ile Phe
                20                  25                  30

Pro Lys Glu Ser Ser Trp Pro Asn His Thr Val Thr Gly Val Ser Ala
            35                  40                  45

Ser Cys Ser His Asn Gly Lys Ser Ser Phe Tyr Arg Asn Leu Leu Trp
        50                  55                  60

Leu Thr Gly Lys Asn Gly Leu Tyr Pro Asn Leu Ser Lys Ser Tyr Val
65                  70                  75                  80

Asn Asn Lys Glu Lys Glu Val Leu Val Leu Trp Gly Val His His Pro
                85                  90                  95

Pro Asn Ile Gly Asp Gln Arg Ala Leu Tyr His Thr Glu Asn Ala Tyr
            100                 105                 110

Val Ser Val Val Ser Ser His Tyr Ser Arg Arg Phe Thr Pro Glu Ile
        115                 120                 125

Ala Lys Arg Pro Lys Val Arg Asp Gln Glu Gly Arg Ile Asn Tyr Tyr
    130                 135                 140

Trp Thr Leu Leu Glu Pro Gly Asp Thr Ile Ile Phe Glu Ala Asn Gly
145                 150                 155                 160

Asn Leu Ile Ala Pro Trp Tyr Ala Phe Ala Leu Ser Arg Gly Phe Gly
                165                 170                 175

Ser Gly Ile Ile Thr Ser Asn Ala Pro Met Asp Glu Cys Asp Ala Lys
            180                 185                 190

Cys Gln Thr Pro Gln Gly Ala Ile Asn Ser Ser Leu Pro Phe Gln Asn
        195                 200                 205

Val His Pro Val Thr Ile Gly Glu Cys Pro Lys Tyr Val Arg Ser Ala
    210                 215                 220

Lys Leu Arg Met Val Thr Gly Leu Arg Asn Ile Pro Ser Ile Gln Ser
225                 230                 235                 240

Arg Gly Leu Phe Gly Ala Ile Ala Gly Phe Ile Glu Gly Gly Trp Thr
                245                 250                 255
```

```
Gly Met Val Asp Gly Trp Tyr Gly Tyr His His Gln Asn Glu Gln Gly
            260                 265                 270

Ser Gly Tyr Ala Ala Asp Gln Lys Ser Thr Gln Asn Ala Ile Asn Gly
            275                 280                 285

Ile Thr Asn Lys Val Asn Ser Val Ile Glu Lys Met Asn Thr Gln Phe
            290                 295                 300

Thr Ala Val Gly Lys Glu Phe Asn Lys Leu Glu Arg Arg Met Glu Asn
305                 310                 315                 320

Leu Asn
```

<210> SEQ ID NO 4
<211> LENGTH: 321
<212> TYPE: PRT
<213> ORGANISM: Artificial sequence
<220> FEATURE:
<223> OTHER INFORMATION: Influenza virus

<400> SEQUENCE: 4

```
Ala Asn Gly Leu Cys Tyr Pro Gly Ser Phe Asn Asp Tyr Glu Glu Leu
1               5                   10                  15

Lys His Leu Leu Thr Ser Val Thr His Phe Glu Lys Val Lys Ile Leu
            20                  25                  30

Pro Arg Asp Gln Trp Thr Gln His Thr Thr Thr Gly Gly Ser Arg Ala
            35                  40                  45

Cys Ala Val Ser Gly Asn Pro Ser Phe Phe Arg Asn Met Val Trp Leu
        50                  55                  60

Thr Glu Lys Gly Ser Asn Tyr Pro Ile Ala Lys Arg Ser Tyr Asn Asn
65                  70                  75                  80

Thr Ser Gly Lys Gln Met Leu Val Ile Trp Gly Ile His His Pro Asn
            85                  90                  95

Asp Asp Thr Glu Gln Arg Thr Leu Tyr Gln Asn Val Gly Thr Tyr Val
            100                 105                 110

Ser Val Gly Thr Ser Thr Leu Asn Lys Arg Ser Ile Pro Glu Ile Ala
        115                 120                 125

Thr Arg Pro Lys Val Asn Gly Gln Gly Gly Arg Met Glu Phe Ser Trp
130                 135                 140

Thr Leu Leu Glu Thr Trp Asp Val Ile Asn Phe Glu Ser Thr Gly Asn
145                 150                 155                 160

Leu Ile Ala Pro Glu Tyr Gly Phe Lys Ile Ser Lys Arg Gly Ser Ser
            165                 170                 175

Gly Ile Met Lys Thr Glu Lys Thr Leu Glu Asn Cys Glu Thr Lys Cys
            180                 185                 190

Gln Thr Pro Leu Gly Ala Ile Asn Thr Thr Leu Pro Phe His Asn Ile
        195                 200                 205

His Pro Leu Thr Ile Gly Glu Cys Pro Lys Tyr Val Lys Ser Asp Arg
210                 215                 220

Leu Val Leu Ala Thr Gly Leu Arg Asn Val Pro Gln Ile Glu Ser Arg
225                 230                 235                 240

Gly Leu Phe Gly Ala Ile Ala Gly Phe Ile Glu Gly Gly Trp Gln Gly
            245                 250                 255

Met Val Asp Gly Trp Tyr Gly Tyr His His Ser Asn Asp Gln Gly Ser
            260                 265                 270

Gly Tyr Ala Ala Asp Lys Glu Ser Thr Gln Lys Ala Ile Asp Gly Ile
        275                 280                 285
```

```
Thr Asn Lys Val Asn Ser Val Ile Glu Lys Met Asn Thr Gln Phe Glu
    290                 295                 300

Ala Val Gly Lys Glu Phe Asn Asn Leu Glu Arg Arg Leu Glu Asn Leu
305                 310                 315                 320

Asn

<210> SEQ ID NO 5
<211> LENGTH: 321
<212> TYPE: PRT
<213> ORGANISM: Artificial sequence
<220> FEATURE:
<223> OTHER INFORMATION: Influenza virus

<400> SEQUENCE: 5

Arg Asp Gly Leu Cys Tyr Pro Gly Ser Phe Asn Asp Tyr Glu Glu Leu
1               5                   10                  15

Lys His Leu Leu Ser Ser Val Lys His Phe Glu Lys Val Lys Ile Leu
            20                  25                  30

Pro Lys Asp Arg Trp Thr Gln His Thr Thr Thr Gly Gly Ser Arg Ala
        35                  40                  45

Cys Ala Val Ser Gly Asn Pro Ser Phe Phe Arg Asn Met Val Trp Leu
50                  55                  60

Thr Glu Lys Gly Ser Asn Tyr Pro Val Ala Lys Gly Ser Tyr Asn Asn
65                  70                  75                  80

Thr Ser Gly Glu Gln Met Leu Ile Ile Trp Gly Val His His Pro Asn
                85                  90                  95

Asp Glu Lys Glu Gln Arg Thr Leu Tyr Gln Asn Val Gly Thr Tyr Val
            100                 105                 110

Ser Val Gly Thr Ser Thr Leu Asn Lys Arg Ser Thr Pro Asp Ile Ala
        115                 120                 125

Thr Arg Pro Lys Val Asn Gly Leu Gly Ser Arg Met Glu Phe Ser Trp
130                 135                 140

Thr Leu Leu Asp Met Trp Asp Thr Ile Asn Phe Glu Ser Thr Gly Asn
145                 150                 155                 160

Leu Ile Ala Pro Glu Tyr Gly Phe Lys Ile Ser Lys Arg Gly Ser Ser
                165                 170                 175

Gly Ile Met Lys Thr Glu Gly Thr Leu Glu Asn Cys Glu Thr Lys Cys
            180                 185                 190

Gln Thr Pro Leu Gly Ala Ile Asn Thr Thr Leu Pro Phe His Asn Val
        195                 200                 205

His Pro Leu Thr Ile Gly Glu Cys Pro Lys Tyr Val Lys Ser Glu Lys
210                 215                 220

Leu Val Leu Ala Thr Gly Leu Arg Asn Val Pro Gln Ile Glu Ser Arg
225                 230                 235                 240

Gly Leu Phe Gly Ala Ile Ala Gly Phe Ile Glu Gly Gly Trp Gln Gly
                245                 250                 255

Met Ile Asp Gly Trp Tyr Gly Tyr His His Ser Asn Asp Gln Gly Ser
            260                 265                 270

Gly Tyr Ala Ala Asp Lys Glu Ser Thr Gln Lys Ala Phe Asp Gly Ile
        275                 280                 285

Thr Asn Lys Val Asn Ser Val Ile Glu Lys Met Asn Thr Gln Phe Glu
290                 295                 300

Ala Val Gly Lys Glu Phe Ser Asn Leu Glu Arg Arg Leu Glu Asn Leu
305                 310                 315                 320

Asn
```

<210> SEQ ID NO 6
<211> LENGTH: 317
<212> TYPE: PRT
<213> ORGANISM: Artificial sequence
<220> FEATURE:
<223> OTHER INFORMATION: Influenza virus

<400> SEQUENCE: 6

```
Phe Ser Asn Cys Tyr Pro Tyr Asp Ile Pro Asp Tyr Ala Ser Leu Arg
1               5                   10                  15

Ser Leu Val Ala Ser Ser Gly Thr Leu Glu Phe Ile Thr Glu Gly Phe
            20                  25                  30

Thr Trp Thr Gly Val Thr Gln Asn Gly Gly Ser Ser Ala Cys Lys Arg
        35                  40                  45

Gly Pro Ala Asn Gly Phe Phe Ser Arg Leu Asn Trp Leu Thr Lys Ser
    50                  55                  60

Glu Ser Ala Tyr Pro Val Leu Asn Val Thr Met Pro Asn Asn Asp Asn
65                  70                  75                  80

Phe Asp Lys Leu Tyr Ile Trp Gly Val His His Pro Ser Thr Asn Gln
                85                  90                  95

Glu Gln Thr Asp Leu Tyr Val Gln Ala Ser Gly Arg Val Thr Val Ser
            100                 105                 110

Thr Arg Arg Ser Gln Gln Thr Ile Ile Pro Asn Ile Gly Ser Arg Pro
        115                 120                 125

Trp Val Arg Gly Gln Pro Gly Arg Ile Ser Ile Tyr Trp Thr Ile Val
    130                 135                 140

Lys Pro Gly Asp Val Leu Val Ile Asn Ser Asn Gly Asn Leu Ile Ala
145                 150                 155                 160

Pro Arg Gly Tyr Phe Lys Met Arg Thr Gly Lys Ser Ser Ile Met Arg
                165                 170                 175

Ser Asp Ala Pro Ile Asp Thr Cys Ile Ser Glu Cys Ile Thr Pro Asn
            180                 185                 190

Gly Ser Ile Pro Asn Asp Lys Pro Phe Gln Asn Val Asn Lys Ile Thr
        195                 200                 205

Tyr Gly Ala Cys Pro Lys Tyr Val Lys Gln Asn Thr Leu Lys Leu Ala
    210                 215                 220

Thr Gly Met Arg Asn Val Pro Gly Lys Gln Thr Arg Gly Leu Phe Gly
225                 230                 235                 240

Ala Ile Ala Gly Phe Ile Glu Asn Gly Trp Glu Gly Met Ile Asp Gly
                245                 250                 255

Trp Tyr Gly Phe Arg His Gln Asn Ser Glu Gly Thr Gly Gln Ala Ala
            260                 265                 270

Asp Leu Lys Ser Thr Gln Ala Ala Ile Asp Gln Ile Asn Arg Lys Leu
        275                 280                 285

Asn Arg Val Ile Glu Lys Thr Asn Glu Lys Phe His Gln Ile Glu Lys
    290                 295                 300

Glu Phe Ser Glu Val Glu Gly Arg Ile Gln Asp Leu Glu
305                 310                 315
```

<210> SEQ ID NO 7
<211> LENGTH: 317
<212> TYPE: PRT
<213> ORGANISM: Artificial sequence
<220> FEATURE:
<223> OTHER INFORMATION: Influenza virus

<400> SEQUENCE: 7

Phe Ser Asn Cys Tyr Pro Tyr Asp Val Pro Asp Tyr Ala Ser Leu Arg
1               5                   10                  15

Ser Leu Val Ala Ser Ser Gly Thr Leu Glu Phe Ile Thr Glu Gly Phe
            20                  25                  30

Thr Trp Thr Gly Val Thr Gln Asn Gly Gly Ser Asn Ala Cys Lys Arg
        35                  40                  45

Gly Pro Gly Ser Gly Phe Phe Ser Arg Leu Asn Trp Leu Thr Lys Ser
    50                  55                  60

Gly Ser Thr Tyr Pro Val Leu Asn Val Thr Met Pro Asn Asn Asp Asn
65                  70                  75                  80

Phe Asp Lys Leu Tyr Ile Trp Gly Ile His His Pro Ser Thr Asn Gln
                85                  90                  95

Glu Gln Thr Ser Leu Tyr Val Gln Ala Ser Gly Arg Val Thr Val Ser
            100                 105                 110

Thr Arg Arg Ser Gln Gln Thr Ile Ile Pro Asn Ile Gly Ser Arg Pro
        115                 120                 125

Trp Val Arg Gly Leu Ser Ser Arg Ile Ser Ile Tyr Trp Thr Ile Val
    130                 135                 140

Lys Pro Gly Asp Val Leu Val Ile Asn Ser Asn Gly Asn Leu Ile Ala
145                 150                 155                 160

Pro Arg Gly Tyr Phe Lys Met Arg Thr Gly Lys Ser Ser Ile Met Arg
                165                 170                 175

Ser Asp Ala Pro Ile Asp Thr Cys Ile Ser Glu Cys Ile Thr Pro Asn
            180                 185                 190

Gly Ser Ile Pro Asn Asp Lys Pro Phe Gln Asn Val Asn Lys Ile Thr
        195                 200                 205

Tyr Gly Ala Cys Pro Lys Tyr Val Lys Gln Asn Thr Leu Lys Leu Ala
    210                 215                 220

Thr Gly Met Arg Asn Val Pro Glu Lys Gln Thr Arg Gly Leu Phe Gly
225                 230                 235                 240

Ala Ile Ala Gly Phe Ile Glu Asn Gly Trp Glu Gly Met Ile Asp Gly
                245                 250                 255

Trp Tyr Gly Phe Arg His Gln Asn Ser Glu Gly Thr Gly Gln Ala Ala
            260                 265                 270

Asp Leu Lys Ser Thr Gln Ala Ala Ile Asp Gln Ile Asn Gly Lys Leu
        275                 280                 285

Asn Arg Val Ile Glu Lys Thr Asn Glu Lys Phe His Gln Ile Glu Lys
    290                 295                 300

Glu Phe Ser Glu Val Glu Gly Arg Ile Gln Asp Leu Glu
305                 310                 315

<210> SEQ ID NO 8
<211> LENGTH: 317
<212> TYPE: PRT
<213> ORGANISM: Artificial sequence
<220> FEATURE:
<223> OTHER INFORMATION: Influenza virus

<400> SEQUENCE: 8

Tyr Ser Asn Cys Tyr Pro Tyr Asp Val Pro Asp Tyr Ala Ser Leu Arg
1               5                   10                  15

Ser Leu Val Ala Ser Ser Gly Thr Leu Glu Phe Asn Asn Glu Ser Phe
            20                  25                  30

Asn Trp Ala Gly Val Thr Gln Asn Gly Thr Ser Ser Ala Cys Lys Arg

```
                35                  40                  45
Arg Ser Asn Lys Ser Phe Phe Ser Arg Leu Asn Trp Leu Thr His Leu
 50                  55                  60

Lys Tyr Lys Tyr Pro Ala Leu Asn Val Thr Met Pro Asn Asn Glu Lys
 65                  70                  75                  80

Phe Asp Lys Leu Tyr Ile Trp Gly Val His His Pro Val Thr Asp Ser
                     85                  90                  95

Asp Gln Ile Ser Leu Tyr Ala Gln Ala Ser Gly Arg Ile Thr Val Ser
                100                 105                 110

Thr Lys Arg Ser Gln Gln Thr Val Ile Pro Asn Ile Gly Tyr Arg Pro
            115                 120                 125

Arg Val Arg Asp Ile Ser Ser Arg Ile Ser Ile Tyr Trp Thr Ile Val
130                 135                 140

Lys Pro Gly Asp Ile Leu Leu Ile Asn Ser Thr Gly Asn Leu Ile Ala
145                 150                 155                 160

Pro Arg Gly Tyr Phe Lys Ile Arg Ser Gly Lys Ser Ser Ile Met Arg
                    165                 170                 175

Ser Asp Ala Pro Ile Gly Lys Cys Asn Ser Glu Cys Ile Thr Pro Asn
                180                 185                 190

Gly Ser Ile Pro Asn Asp Lys Pro Phe Gln Asn Val Asn Arg Ile Thr
            195                 200                 205

Tyr Gly Ala Cys Pro Arg Tyr Val Lys Gln Asn Thr Leu Lys Leu Ala
210                 215                 220

Thr Gly Met Arg Asn Val Pro Glu Lys Gln Thr Arg Gly Ile Phe Gly
225                 230                 235                 240

Ala Ile Ala Gly Phe Ile Glu Asn Gly Trp Glu Gly Met Val Asp Gly
                    245                 250                 255

Trp Tyr Gly Phe Arg His Gln Asn Ser Glu Gly Thr Gly Gln Ala Ala
                260                 265                 270

Asp Leu Lys Ser Thr Gln Ala Ala Ile Asn Gln Ile Asn Gly Lys Leu
            275                 280                 285

Asn Arg Leu Ile Gly Lys Thr Asn Glu Lys Phe His Gln Ile Glu Lys
290                 295                 300

Glu Phe Ser Glu Val Glu Gly Arg Ile Gln Asp Leu Glu
305                 310                 315

<210> SEQ ID NO 9
<211> LENGTH: 319
<212> TYPE: PRT
<213> ORGANISM: Artificial sequence
<220> FEATURE:
<223> OTHER INFORMATION: Influenza virus

<400> SEQUENCE: 9

Val Asp Thr Cys Tyr Pro Phe Asp Val Pro Asp Tyr Gln Ser Leu Arg
 1               5                  10                  15

Ser Ile Leu Ala Asn Asn Gly Lys Phe Glu Phe Ile Ala Glu Glu Phe
                20                  25                  30

Gln Trp Asn Thr Val Lys Gln Asn Gly Lys Ser Gly Ala Cys Lys Arg
            35                  40                  45

Ala Asn Val Asn Asp Phe Phe Asn Arg Leu Asn Trp Leu Thr Lys Ser
 50                  55                  60

Asn Gly Asp Ala Tyr Pro Leu Gln Asn Leu Thr Lys Val Asn Asn Gly
 65                  70                  75                  80

Asp Tyr Ala Arg Leu Tyr Ile Trp Gly Val His His Pro Ser Thr Asp
```

```
                85              90               95
Thr Glu Gln Thr Asp Leu Tyr Lys Asn Asn Pro Gly Arg Val Thr Val
            100             105             110
Ser Thr Lys Thr Ser Gln Thr Ser Val Val Pro Asn Ile Gly Ser Arg
            115             120             125
Pro Trp Val Arg Gly Gln Ser Gly Arg Ile Ser Phe Tyr Trp Thr Ile
            130             135             140
Val Asp Pro Gly Asp Ile Ile Val Phe Asn Thr Ile Gly Asn Leu Ile
145             150             155             160
Ala Pro Arg Gly His Tyr Lys Leu Asn Ser Gln Lys Ser Thr Ile
            165             170             175
Leu Asn Thr Ala Val Pro Ile Gly Ser Cys Val Ser Lys Cys His Thr
            180             185             190
Asp Arg Gly Ser Ile Thr Thr Thr Lys Pro Phe Gln Asn Ile Ser Arg
            195             200             205
Ile Ser Ile Gly Asp Cys Pro Lys Tyr Val Lys Gln Gly Ser Leu Lys
            210             215             220
Leu Ala Thr Gly Met Arg Asn Ile Pro Glu Lys Ala Thr Arg Gly Leu
225             230             235             240
Phe Gly Ala Ile Ala Gly Phe Ile Glu Asn Gly Trp Gln Gly Leu Ile
            245             250             255
Asp Gly Trp Tyr Gly Phe Arg His Gln Asn Ala Glu Gly Thr Gly Thr
            260             265             270
Ala Ala Asp Leu Lys Ser Thr Gln Ala Ala Ile Asp Gln Ile Asn Gly
            275             280             285
Lys Leu Asn Arg Leu Ile Glu Lys Thr Asn Glu Lys Tyr His Gln Ile
            290             295             300
Glu Lys Glu Phe Glu Gln Val Glu Gly Arg Ile Gln Asp Leu Glu
305             310             315

<210> SEQ ID NO 10
<211> LENGTH: 327
<212> TYPE: PRT
<213> ORGANISM: Artificial sequence
<220> FEATURE:
<223> OTHER INFORMATION: Influenza virus

<400> SEQUENCE: 10

Val Asn Asp Leu Cys Tyr Pro Gly Asp Phe Asn Asp Tyr Glu Glu Leu
1               5               10              15
Lys His Leu Leu Ser Arg Ile Asn His Phe Glu Lys Ile Gln Ile Ile
            20              25              30
Pro Lys Ser Ser Trp Ser Ser His Glu Ala Ser Leu Gly Val Ser Ser
            35              40              45
Ala Cys Pro Tyr Gln Gly Lys Ser Ser Phe Phe Arg Asn Val Val Trp
50              55              60
Leu Ile Lys Lys Asn Ser Thr Tyr Pro Thr Ile Lys Arg Ser Tyr Asn
65              70              75              80
Asn Thr Asn Gln Glu Asp Leu Leu Val Leu Trp Gly Ile His His Pro
            85              90              95
Asn Asp Ala Ala Glu Gln Thr Lys Leu Tyr Gln Asn Pro Thr Thr Tyr
            100             105             110
Ile Ser Val Gly Thr Ser Thr Leu Asn Gln Arg Leu Val Pro Arg Ile
            115             120             125
Ala Thr Arg Ser Lys Val Asn Gly Gln Ser Gly Arg Met Glu Phe Phe
```

-continued

```
            130                 135                 140
Trp Thr Ile Leu Lys Pro Asn Asp Ala Ile Asn Phe Glu Ser Asn Gly
145                 150                 155                 160

Asn Phe Ile Ala Pro Glu Tyr Ala Tyr Lys Ile Val Lys Lys Gly Asp
                165                 170                 175

Ser Thr Ile Met Lys Ser Glu Leu Glu Tyr Gly Asn Cys Asn Thr Lys
                180                 185                 190

Cys Gln Thr Pro Met Gly Ala Ile Asn Ser Ser Met Pro Phe His Asn
                195                 200                 205

Ile His Pro Leu Thr Ile Gly Glu Cys Pro Lys Tyr Val Lys Ser Asn
                210                 215                 220

Arg Leu Val Leu Ala Thr Gly Leu Arg Asn Ser Pro Gln Arg Glu Arg
225                 230                 235                 240

Arg Arg Arg Lys Lys Arg Gly Leu Phe Gly Ala Ile Ala Gly Phe Ile
                245                 250                 255

Glu Gly Gly Trp Gln Gly Met Val Asp Gly Trp Tyr Gly Tyr His His
                260                 265                 270

Ser Asn Glu Gln Gly Ser Gly Tyr Ala Ala Asp Lys Glu Ser Thr Gln
                275                 280                 285

Lys Ala Ile Asp Gly Val Thr Asn Lys Val Asn Ser Ile Ile Asp Lys
                290                 295                 300

Met Asn Thr Gln Phe Glu Ala Val Gly Arg Glu Phe Asn Asn Leu Glu
305                 310                 315                 320

Arg Arg Ile Glu Asn Leu Asn
                325
```

<210> SEQ ID NO 11
<211> LENGTH: 326
<212> TYPE: PRT
<213> ORGANISM: Artificial sequence
<220> FEATURE:
<223> OTHER INFORMATION: Influenza virus

<400> SEQUENCE: 11

```
Ala Asn Asp Leu Cys Tyr Pro Gly Asp Phe Asn Asp Tyr Glu Glu Leu
1               5                   10                  15

Lys His Leu Leu Ser Arg Ile Asn His Phe Glu Lys Ile Gln Ile Ile
                20                  25                  30

Pro Lys Asn Ser Trp Ser Ser His Glu Ala Ser Leu Gly Val Ser Ser
                35                  40                  45

Ala Cys Pro Tyr Gln Gly Lys Ser Ser Phe Phe Arg Asn Val Val Trp
50                  55                  60

Leu Ile Lys Lys Asn Asn Ala Tyr Pro Thr Ile Lys Arg Ser Tyr Asn
65                  70                  75                  80

Asn Thr Asn Gln Glu Asp Leu Leu Val Leu Trp Gly Ile His His Pro
                85                  90                  95

Asn Asp Ala Ala Glu Gln Thr Arg Leu Tyr Gln Asn Pro Thr Thr Tyr
                100                 105                 110

Ile Ser Val Gly Thr Ser Thr Leu Asn Gln Arg Leu Val Pro Lys Ile
                115                 120                 125

Ala Thr Arg Ser Lys Val Asn Gly Gln Asn Gly Arg Met Glu Phe Phe
                130                 135                 140

Trp Thr Ile Leu Lys Pro Asn Asp Ala Ile Asn Phe Glu Ser Asn Gly
145                 150                 155                 160

Asn Phe Ile Ala Pro Glu Tyr Ala Tyr Lys Ile Val Lys Lys Gly Asp
```

```
                 165                 170                 175
Ser Ala Ile Met Lys Ser Glu Leu Glu Tyr Gly Asn Cys Asn Thr Lys
                180                 185                 190

Cys Gln Thr Pro Met Gly Ala Ile Asn Ser Ser Met Pro Phe His Asn
            195                 200                 205

Ile His Pro Leu Thr Ile Gly Glu Cys Pro Lys Tyr Val Lys Ser Asn
        210                 215                 220

Arg Leu Val Leu Ala Thr Gly Leu Arg Asn Ser Pro Gln Arg Glu Arg
225                 230                 235                 240

Arg Arg Lys Lys Arg Gly Leu Phe Gly Ala Ile Ala Gly Phe Ile Glu
                245                 250                 255

Gly Gly Trp Gln Gly Met Val Asp Gly Trp Tyr Gly Tyr His His Ser
                260                 265                 270

Asn Glu Gln Gly Ser Gly Tyr Ala Ala Asp Lys Glu Ser Thr Gln Lys
                275                 280                 285

Ala Ile Asp Gly Val Thr Asn Lys Val Asn Ser Ile Ile Asp Lys Met
            290                 295                 300

Asn Thr Gln Phe Glu Ala Val Gly Arg Glu Phe Asn Asn Leu Glu Arg
305                 310                 315                 320

Arg Ile Glu Asn Leu Asn
                325

<210> SEQ ID NO 12
<211> LENGTH: 324
<212> TYPE: PRT
<213> ORGANISM: Artificial sequence
<220> FEATURE:
<223> OTHER INFORMATION: Influenza virus

<400> SEQUENCE: 12

Gln Asn Gly Ile Cys Tyr Pro Gly Thr Leu Asn Glu Ile Glu Glu Leu
1               5                   10                  15

Lys Ala Leu Ile Gly Ser Gly Glu Arg Ile Glu Arg Phe Glu Met Phe
                20                  25                  30

Pro Lys Ser Thr Trp Ser Gly Val Asn Thr Asn Asn Gly Val Thr Arg
            35                  40                  45

Ala Cys Pro Asp Asn Ser Gly Ser Ser Phe Tyr Arg Asn Leu Leu Trp
        50                  55                  60

Ile Thr Lys Thr Asn Ser Ala Ala Tyr Pro Val Ile Lys Gly Thr Tyr
65                  70                  75                  80

Asn Asn Thr Gly Asn Gln Pro Ile Leu Tyr Phe Trp Gly Val His His
                85                  90                  95

Pro Pro Asp Thr Asn Ala Gln Asn Asn Leu Tyr Gly Ser Gly Asp Arg
            100                 105                 110

Tyr Val Arg Met Gly Thr Glu Ser Met Asn Phe Ala Lys Gly Pro Glu
        115                 120                 125

Ile Ser Ala Arg Pro Val Val Asn Gly Gln Arg Gly Arg Ile Asp Tyr
    130                 135                 140

Tyr Trp Ser Val Leu Lys Pro Gly Glu Thr Leu Asn Val Glu Ser Asn
145                 150                 155                 160

Gly Asn Leu Ile Ala Pro Trp Tyr Ala Tyr Lys Phe Val Ser Thr Asn
                165                 170                 175

Ser Lys Gly Ala Val Phe Lys Ser Asn Leu Pro Ile Glu Asn Cys Asp
            180                 185                 190

Ala Thr Cys Gln Thr Ile Ala Gly Val Leu Arg Thr Asn Lys Thr Phe
```

```
                195                 200                 205

Gln Asn Val Ser Pro Leu Trp Ile Gly Lys Cys Pro Lys Tyr Val Lys
    210                 215                 220

Ser Glu Ser Leu Arg Leu Ala Thr Gly Leu Arg Asn Val Pro Gln Ile
225                 230                 235                 240

Ala Thr Arg Gly Leu Phe Gly Ala Ile Ala Gly Phe Ile Glu Gly Gly
                245                 250                 255

Trp Thr Gly Leu Val Asp Gly Trp Tyr Gly Tyr His His Glu Asn Ser
            260                 265                 270

Gln Gly Ser Gly Tyr Ala Ala Asp Arg Glu Ser Thr Gln Lys Ala Ile
        275                 280                 285

Asp Gly Ile Thr Asn Lys Val Asn Ser Ile Ile Asp Lys Met Asn Thr
    290                 295                 300

Gln Phe Glu Ala Val Asp His Glu Phe Ser Asn Leu Glu Arg Arg Ile
305                 310                 315                 320

Asp Asn Met Asn

<210> SEQ ID NO 13
<211> LENGTH: 319
<212> TYPE: PRT
<213> ORGANISM: Artificial sequence
<220> FEATURE:
<223> OTHER INFORMATION: Influenza virus

<400> SEQUENCE: 13

Ser Asp Val Cys Tyr Pro Gly Lys Phe Val Asn Glu Glu Ala Leu Arg
1               5                   10                  15

Gln Ile Leu Arg Glu Ser Gly Gly Ile Asn Lys Glu Thr Met Gly Phe
            20                  25                  30

Thr Tyr Ser Gly Ile Arg Thr Asn Gly Ala Thr Ser Thr Cys Arg Arg
        35                  40                  45

Ser Gly Ser Ser Phe Tyr Ala Glu Met Lys Trp Leu Leu Ser Asn Thr
    50                  55                  60

Asp Asn Ala Ala Phe Pro Gln Met Thr Lys Ser Tyr Lys Asn Thr Arg
65                  70                  75                  80

Lys Asp Pro Ala Leu Ile Ile Trp Gly Ile His His Ser Gly Ser Thr
                85                  90                  95

Thr Glu Gln Thr Lys Leu Tyr Gly Ser Gly Asn Lys Leu Ile Thr Val
            100                 105                 110

Glu Ser Ser Asn Tyr Gln Gln Ser Phe Val Pro Ser Pro Gly Ala Arg
        115                 120                 125

Pro Lys Val Asp Gly Gln Ser Gly Arg Ile Asp Phe His Trp Leu Met
    130                 135                 140

Leu Asn Pro Asn Asp Thr Ile Thr Phe Ser Phe Asn Gly Ala Phe Ile
145                 150                 155                 160

Ala Pro Asp Arg Ala Ser Phe Leu Arg Gly Lys Ser Met Gly Ile Gln
                165                 170                 175

Ser Gly Val Gln Val Asp Asp Asn Cys Glu Gly Asp Cys Tyr His Ser
            180                 185                 190

Gly Gly Thr Ile Ile Ser Asn Leu Pro Phe Gln Asn Ile Asn Ser Arg
        195                 200                 205

Ala Val Gly Lys Cys Pro Arg Tyr Val Lys Gln Glu Ser Leu Met Leu
    210                 215                 220

Ala Thr Gly Met Lys Asn Val Pro Glu Ile Pro Lys Gly Arg Gly Leu
225                 230                 235                 240
```

Phe Gly Ala Ile Ala Gly Phe Ile Glu Asn Gly Trp Glu Gly Leu Ile
                245                 250                 255

Asp Gly Trp Tyr Gly Phe Arg His Gln Asn Ala Gln Gly Glu Gly Thr
            260                 265                 270

Ala Ala Asp Tyr Lys Ser Thr Gln Ser Ala Ile Asp Gln Ile Thr Gly
        275                 280                 285

Lys Leu Asn Arg Leu Ile Glu Lys Thr Asn Gln Gln Phe Glu Leu Ile
    290                 295                 300

Asp Asn Glu Phe Thr Glu Val Glu Lys Gln Ile Gly Asn Val Ile
305                 310                 315

<210> SEQ ID NO 14
<211> LENGTH: 323
<212> TYPE: PRT
<213> ORGANISM: Artificial sequence
<220> FEATURE:
<223> OTHER INFORMATION: Influenza virus

<400> SEQUENCE: 14

Pro Glu Gly Met Cys Tyr Pro Gly Ser Val Glu Asn Leu Glu Glu Leu
1               5                   10                  15

Arg Phe Val Phe Ser Ser Ala Ala Ser Tyr Lys Arg Ile Arg Leu Phe
            20                  25                  30

Asp Tyr Ser Arg Trp Asn Val Thr Arg Ser Gly Thr Ser Lys Ala Cys
        35                  40                  45

Asn Ala Ser Thr Gly Gly Gln Ser Phe Tyr Arg Ser Ile Asn Trp Leu
    50                  55                  60

Thr Lys Lys Lys Pro Asp Thr Tyr Asp Phe Asn Glu Gly Ala Tyr Val
65                  70                  75                  80

Asn Asn Glu Asp Gly Asp Ile Ile Phe Leu Trp Gly Ile His His Pro
                85                  90                  95

Pro Asp Thr Lys Glu Gln Thr Thr Leu Tyr Lys Asn Ala Asn Thr Leu
            100                 105                 110

Ser Ser Val Thr Thr Asn Thr Ile Asn Arg Ser Phe Gln Pro Asn Ile
        115                 120                 125

Gly Pro Arg Pro Leu Val Arg Gly Gln Gln Gly Arg Met Asp Tyr Tyr
    130                 135                 140

Trp Gly Ile Leu Lys Arg Gly Glu Thr Leu Lys Ile Arg Thr Asn Gly
145                 150                 155                 160

Asn Leu Ile Ala Pro Glu Phe Gly Tyr Leu Leu Lys Gly Glu Ser Tyr
                165                 170                 175

Gly Arg Ile Ile Gln Asn Glu Asp Ile Pro Ile Gly Asn Cys Asn Thr
            180                 185                 190

Lys Cys Gln Thr Tyr Ala Gly Ala Ile Asn Ser Ser Lys Pro Phe Gln
        195                 200                 205

Asn Ala Ser Arg His Tyr Met Gly Glu Cys Pro Lys Tyr Val Lys Lys
    210                 215                 220

Ala Ser Leu Arg Leu Ala Val Gly Leu Arg Asn Thr Pro Ser Val Glu
225                 230                 235                 240

Pro Arg Gly Leu Phe Gly Ala Ile Ala Gly Phe Ile Glu Gly Gly Trp
                245                 250                 255

Ser Gly Met Ile Asp Gly Trp Tyr Gly Phe His His Ser Asn Ser Glu
            260                 265                 270

Gly Thr Gly Met Ala Ala Asp Gln Lys Ser Thr Gln Glu Ala Ile Asp
        275                 280                 285

```
Lys Ile Thr Asn Lys Val Asn Ile Val Asp Lys Met Asn Arg Glu
            290                 295                 300

Phe Glu Val Val Asn His Glu Phe Ser Glu Val Lys Arg Ile Asn
305                 310                 315                 320

Met Ile Asn

<210> SEQ ID NO 15
<211> LENGTH: 316
<212> TYPE: PRT
<213> ORGANISM: Artificial sequence
<220> FEATURE:
<223> OTHER INFORMATION: Influenza virus

<400> SEQUENCE: 15

Val Asn Gly Thr Cys Tyr Pro Gly Asn Val Glu Asn Leu Glu Leu
1               5                   10                  15

Arg Thr Leu Phe Ser Ser Ala Ser Ser Tyr Gln Arg Ile Gln Ile Phe
                20                  25                  30

Pro Asp Thr Ile Trp Asn Val Thr Tyr Thr Gly Thr Ser Lys Ala Cys
            35                  40                  45

Ser Gly Ser Phe Tyr Arg Ser Met Arg Trp Leu Thr Gln Lys Ser Gly
    50                  55                  60

Ser Tyr Pro Val Gln Asp Ala Gln Tyr Thr Asn Asn Arg Glu Lys Ser
65                  70                  75                  80

Ile Leu Phe Val Trp Gly Ile His His Pro Pro Thr Asp Thr Ala Gln
                85                  90                  95

Thr Asn Leu Tyr Ile Asn Thr Asp Thr Thr Thr Ser Val Thr Thr Glu
            100                 105                 110

Asp Leu Asn Arg Ile Phe Lys Pro Val Ile Gly Pro Arg Pro Leu Val
            115                 120                 125

Asn Gly Leu Gln Gly Arg Ile Asn Tyr Tyr Trp Ser Val Leu Lys Pro
130                 135                 140

Gly Gln Thr Leu Arg Val Arg Ser Asn Gly Asn Leu Ile Ala Pro Trp
145                 150                 155                 160

Tyr Gly His Val Leu Ser Gly Gly Ser His Gly Arg Ile Leu Lys Thr
                165                 170                 175

Asp Leu Asn Ser Gly Asn Cys Val Val Gln Cys Gln Thr Glu Lys Gly
            180                 185                 190

Gly Leu Asn Ser Thr Leu Pro Phe His Asn Ile Ser Lys Tyr Ala Phe
            195                 200                 205

Gly Ile Cys Pro Lys Tyr Val Arg Val Lys Ser Leu Lys Leu Ala Val
        210                 215                 220

Gly Leu Arg Asn Val Pro Ala Arg Ser Asn Arg Gly Leu Phe Gly Ala
225                 230                 235                 240

Ile Ala Gly Phe Ile Glu Gly Gly Trp Pro Gly Leu Val Ala Gly Trp
                245                 250                 255

Tyr Gly Phe Gln His Ser Asn Asp Gln Gly Val Gly Met Ala Ala Asp
            260                 265                 270

Arg Asp Ser Thr Gln Arg Ala Ile Asp Lys Ile Thr Ser Lys Val Asn
            275                 280                 285

Asn Ile Val Asp Lys Met Asn Lys Gln Tyr Glu Ile Ile Asp His Glu
        290                 295                 300

Phe Ser Glu Val Glu Thr Arg Leu Asn His Ile Asn
305                 310                 315
```

```
<210> SEQ ID NO 16
<211> LENGTH: 321
<212> TYPE: PRT
<213> ORGANISM: Artificial sequence
<220> FEATURE:
<223> OTHER INFORMATION: Influenza virus

<400> SEQUENCE: 16

Ile Ala Tyr Cys Tyr Pro Gly Ala Thr Val Asn Glu Glu Ala Leu Arg
1               5                   10                  15

Gln Lys Ile Met Glu Ser Gly Gly Ile Asp Lys Ile Ser Thr Gly Phe
            20                  25                  30

Thr Tyr Gly Ser Ser Ile Asn Ser Ala Gly Thr Thr Arg Ser Cys Met
        35                  40                  45

Arg Ser Gly Gly Asn Ser Phe Tyr Ala Glu Leu Lys Trp Leu Val Ser
    50                  55                  60

Lys Asn Lys Gly Gln Asn Phe Pro Gln Thr Ala Asn Thr Tyr Arg Asn
65                  70                  75                  80

Thr Asp Ser Ala Glu His Leu Ile Ile Trp Gly Ile His His Pro Ser
                85                  90                  95

Ser Thr Gln Glu Lys Asn Asp Leu Tyr Gly Thr Gln Ser Leu Ser Ile
            100                 105                 110

Ser Val Gly Ser Ser Thr Tyr Gln Asn Asn Phe Val Pro Val Val Gly
        115                 120                 125

Ala Arg Pro Gln Val Asn Gly Gln Ser Gly Arg Ile Asp Phe His Trp
    130                 135                 140

Thr Met Val Gln Pro Gly Asp Asn Ile Thr Phe Ser His Asn Gly Gly
145                 150                 155                 160

Leu Ile Ala Pro Ser Arg Val Ser Lys Leu Lys Gly Arg Gly Leu Gly
                165                 170                 175

Ile Gln Ser Gly Ala Ser Val Asp Asn Asp Cys Glu Ser Lys Cys Phe
            180                 185                 190

Trp Lys Gly Gly Ser Ile Asn Thr Lys Leu Pro Phe Gln Asn Leu Ser
        195                 200                 205

Pro Arg Thr Val Gly Gln Cys Pro Lys Tyr Val Asn Lys Lys Ser Leu
    210                 215                 220

Leu Leu Ala Thr Gly Met Arg Asn Val Pro Glu Val Val Gln Gly Arg
225                 230                 235                 240

Gly Leu Phe Gly Ala Ile Ala Gly Phe Ile Glu Asn Gly Trp Glu Gly
                245                 250                 255

Met Val Asp Gly Trp Tyr Gly Phe Arg His Gln Asn Ala Gln Gly Thr
            260                 265                 270

Gly Gln Ala Ala Asp Tyr Lys Ser Thr Gln Ala Ala Ile Asp Gln Ile
        275                 280                 285

Thr Gly Lys Leu Asn Arg Leu Ile Glu Lys Thr Asn Thr Glu Phe Glu
    290                 295                 300

Ser Ile Glu Ser Glu Phe Ser Glu Ile Glu His Gln Ile Gly Asn Val
305                 310                 315                 320

Ile

<210> SEQ ID NO 17
<211> LENGTH: 321
<212> TYPE: PRT
<213> ORGANISM: Artificial sequence
<220> FEATURE:
<223> OTHER INFORMATION: Influenza virus
```

<400> SEQUENCE: 17

```
Thr Asn Gly Ile Cys Tyr Pro Thr Leu Glu Asn Glu Glu Glu Leu Arg
1               5                   10                  15

Leu Lys Phe Ser Gly Val Leu Glu Phe Ser Lys Phe Glu Ala Phe Thr
                20                  25                  30

Ser Asn Gly Trp Gly Ala Val Asn Ser Gly Ala Gly Val Thr Ala Ala
            35                  40                  45

Cys Lys Phe Gly Ser Ser Asn Ser Phe Phe Arg Asn Met Ile Trp Leu
50                  55                  60

Ile His Gln Ser Gly Thr Tyr Pro Val Ile Arg Arg Thr Phe Asn Asn
65                  70                  75                  80

Thr Lys Gly Arg Asp Val Leu Val Val Trp Gly Val His His Pro Ala
                85                  90                  95

Thr Leu Lys Glu His Gln Asp Leu Tyr Lys Lys Asp Ser Ser Tyr Val
            100                 105                 110

Ala Val Asp Ser Glu Ser Tyr Asn Arg Arg Phe Thr Pro Glu Ile Ser
        115                 120                 125

Thr Arg Pro Lys Val Asn Gly Gln Ala Gly Arg His Thr Phe Tyr Trp
130                 135                 140

Thr Ile Val Lys Pro Gly Glu Ala Ile Thr Phe Glu Ser Asn Gly Ala
145                 150                 155                 160

Phe Leu Ala Pro Arg Tyr Ala Phe Glu Leu Val Ser Leu Gly Asn Gly
                165                 170                 175

Lys Leu Phe Arg Ser Asp Leu Asn Ile Glu Ser Cys Ser Thr Lys Cys
            180                 185                 190

Gln Ser Glu Ile Gly Gly Ile Asn Thr Asn Arg Ser Phe His Asn Val
        195                 200                 205

His Arg Asn Thr Ile Gly Asp Cys Pro Lys Tyr Val Asn Val Lys Ser
210                 215                 220

Leu Lys Leu Ala Thr Gly Leu Arg Asn Val Pro Ala Ile Ala Thr Arg
225                 230                 235                 240

Gly Leu Phe Gly Ala Ile Ala Gly Phe Ile Glu Gly Gly Trp Pro Gly
                245                 250                 255

Leu Ile Asn Gly Trp Tyr Gly Phe Gln His Arg Asn Glu Glu Gly Thr
            260                 265                 270

Gly Ile Ala Ala Asp Lys Glu Ser Thr Gln Lys Ala Ile Asp Gln Ile
        275                 280                 285

Thr Ser Lys Val Asn Asn Ile Val Asp Arg Met Asn Thr Asn Phe Glu
290                 295                 300

Ser Val Gln His Glu Phe Ser Glu Ile Glu Glu Arg Ile Asn Gln Leu
305                 310                 315                 320

Ser
```

<210> SEQ ID NO 18
<211> LENGTH: 321
<212> TYPE: PRT
<213> ORGANISM: Artificial sequence
<220> FEATURE:
<223> OTHER INFORMATION: Influenza virus

<400> SEQUENCE: 18

```
Met Glu Gly Val Cys Tyr Pro Gly Ser Ile Glu Asn Gln Glu Glu Leu
1               5                   10                  15

Arg Ser Leu Phe Ser Ser Ile Lys Lys Tyr Glu Arg Val Lys Met Phe
```

```
                    20                  25                  30

Asp Phe Thr Lys Trp Asn Val Thr Tyr Thr Gly Thr Ser Arg Ala Cys
                35                  40                  45

Asn Asn Thr Ser Asn Arg Gly Ser Phe Tyr Arg Ser Met Arg Trp Leu
 50                  55                  60

Thr Leu Lys Ser Gly Gln Phe Pro Val Gln Thr Asp Glu Tyr Lys Asn
 65                  70                  75                  80

Thr Arg Asp Ser Asp Ile Leu Phe Thr Trp Ala Ile His His Pro Pro
                85                  90                  95

Thr Ser Ala Glu Gln Val Gln Leu Tyr Lys Asn Pro Asp Thr Leu Ser
                100                 105                 110

Ser Val Thr Thr Asp Glu Ile Asn Arg Ser Phe Lys Pro Asn Ile Gly
                115                 120                 125

Pro Arg Pro Leu Val Arg Gly Gln Gln Gly Arg Met Asp Tyr Tyr Trp
                130                 135                 140

Ala Val Leu Lys Pro Gly Gln Thr Val Lys Ile Gln Thr Asn Gly Asn
145                 150                 155                 160

Leu Ile Ala Pro Glu Tyr Gly His Leu Ile Thr Gly Lys Ser His Gly
                165                 170                 175

Arg Ile Leu Lys Asn Asn Leu Pro Val Gly Gln Cys Val Thr Glu Cys
                180                 185                 190

Gln Leu Asn Glu Gly Val Met Asn Thr Ser Lys Pro Phe Gln Asn Thr
                195                 200                 205

Ser Lys His Tyr Ile Gly Lys Cys Pro Lys Tyr Ile Pro Ser Gly Ser
                210                 215                 220

Leu Lys Leu Ala Ile Gly Leu Arg Asn Val Pro Gln Val Gln Asn Arg
225                 230                 235                 240

Gly Leu Phe Gly Ala Ile Ala Gly Phe Ile Glu Gly Gly Trp Pro Gly
                245                 250                 255

Leu Val Ala Gly Trp Tyr Gly Phe Gln His Gln Asn Ala Glu Gly Thr
                260                 265                 270

Gly Met Ala Ala Asp Arg Asp Ser Thr Gln Lys Ala Ile Asp Asn Met
                275                 280                 285

Gln Asn Lys Leu Asn Asn Val Ile Asp Lys Met Asn Lys Gln Phe Glu
                290                 295                 300

Val Val Asn His Glu Phe Ser Glu Val Glu Ser Arg Ile Asn Met Ile
305                 310                 315                 320

Asn

<210> SEQ ID NO 19
<211> LENGTH: 321
<212> TYPE: PRT
<213> ORGANISM: Artificial sequence
<220> FEATURE:
<223> OTHER INFORMATION: Influenza virus

<400> SEQUENCE: 19

Pro His Gly Leu Cys Tyr Pro Gly Glu Leu Asn Asn Asn Gly Glu Leu
1                5                   10                  15

Arg His Leu Phe Ser Gly Ile Arg Ser Phe Ser Arg Thr Glu Leu Ile
                20                  25                  30

Pro Pro Thr Ser Trp Gly Glu Val Leu Asp Gly Ala Thr Ser Ala Cys
                35                  40                  45

Arg Asp Asp Lys Gly Thr Asn Ser Phe Tyr Arg Asn Leu Val Trp Phe
 50                  55                  60
```

Val Lys Lys Asn Asn Arg Tyr Pro Val Ile Ser Lys Thr Tyr Asn Asn
65                  70                  75                  80

Thr Thr Gly Arg Asp Val Leu Val Leu Trp Gly Ile His His Pro Val
            85                  90                  95

Ser Val Glu Glu Thr Lys Thr Leu Tyr Val Asn Ser Asp Pro Tyr Thr
        100                 105                 110

Leu Val Ser Thr Lys Ser Trp Ser Glu Lys Tyr Lys Leu Glu Thr Gly
    115                 120                 125

Val Arg Pro Gly Tyr Asn Gly Gln Arg Ser Trp Met Lys Ile Tyr Trp
130                 135                 140

Ser Leu Leu His Pro Gly Glu Met Ile Thr Phe Glu Ser Asn Gly Gly
145                 150                 155                 160

Leu Leu Ala Pro Arg Tyr Gly Tyr Ile Ile Glu Glu Tyr Gly Lys Gly
                165                 170                 175

Arg Ile Phe Gln Ser Arg Ile Arg Met Ser Lys Cys Asn Thr Lys Cys
            180                 185                 190

Gln Thr Ser Val Gly Gly Ile Asn Thr Asn Arg Thr Phe Gln Asn Ile
        195                 200                 205

Asp Lys Asn Ala Leu Gly Asp Cys Pro Lys Tyr Ile Lys Ser Gly Gln
210                 215                 220

Leu Lys Leu Ala Thr Gly Leu Arg Asn Val Pro Ala Ile Asp Asn Arg
225                 230                 235                 240

Gly Leu Leu Gly Ala Ile Ala Gly Phe Ile Glu Gly Gly Trp Pro Gly
                245                 250                 255

Leu Ile Asn Gly Trp Tyr Gly Phe Gln His Gln Asn Glu Gln Gly Thr
            260                 265                 270

Gly Ile Ala Ala Asp Lys Glu Ser Thr Gln Lys Ala Ile Asp Gln Ile
        275                 280                 285

Thr Thr Lys Ile Asn Asn Ile Ile Asp Lys Met Asn Gly Asn Tyr Asp
290                 295                 300

Ser Ile Arg Gly Glu Phe Asn Gln Val Glu Lys Arg Ile Asn Met Leu
305                 310                 315                 320

Ala

<210> SEQ ID NO 20
<211> LENGTH: 319
<212> TYPE: PRT
<213> ORGANISM: Artificial sequence
<220> FEATURE:
<223> OTHER INFORMATION: Influenza virus

<400> SEQUENCE: 20

Val Asp Thr Cys Tyr Pro Phe Asp Val Pro Asp Tyr Gln Ser Leu Arg
1               5                   10                  15

Ser Ile Leu Ala Ser Ser Gly Ser Leu Glu Phe Ile Ala Glu Gln Phe
            20                  25                  30

Thr Trp Asn Gly Val Lys Val Asp Gly Ser Ser Ser Ala Cys Leu Arg
        35                  40                  45

Gly Gly Arg Asn Ser Phe Phe Ser Arg Leu Asn Trp Leu Thr Lys Glu
    50                  55                  60

Thr Asn Gly Asn Tyr Gly Pro Ile Asn Val Thr Lys Glu Asn Thr Gly
65                  70                  75                  80

Ser Tyr Val Arg Leu Tyr Leu Trp Gly Val His His Pro Ser Ser Asp
                85                  90                  95

-continued

```
Asn Glu Gln Thr Asp Leu Tyr Lys Val Ala Thr Gly Arg Val Thr Val
                100                 105                 110

Ser Thr Arg Ser Asp Gln Ile Ser Ile Val Pro Asn Ile Gly Ser Arg
        115                 120                 125

Pro Arg Val Arg Asn Gln Ser Gly Arg Ile Ser Ile Tyr Trp Thr Leu
    130                 135                 140

Val Asn Pro Gly Asp Ser Ile Ile Phe Asn Ser Ile Gly Asn Leu Ile
145                 150                 155                 160

Ala Pro Arg Gly His Tyr Lys Ile Ser Lys Ser Thr Lys Ser Thr Val
                165                 170                 175

Leu Lys Ser Asp Lys Arg Ile Gly Ser Cys Thr Ser Pro Cys Leu Thr
        180                 185                 190

Asp Lys Gly Ser Ile Gln Ser Asp Lys Pro Phe Gln Asn Val Ser Arg
    195                 200                 205

Ile Ala Ile Gly Asn Cys Pro Lys Tyr Val Lys Gln Gly Ser Leu Met
210                 215                 220

Leu Ala Thr Gly Met Arg Asn Ile Pro Gly Lys Gln Ala Lys Gly Leu
225                 230                 235                 240

Phe Gly Ala Ile Ala Gly Phe Ile Glu Asn Gly Trp Gln Gly Leu Ile
                245                 250                 255

Asp Gly Trp Tyr Gly Phe Arg His Gln Asn Ala Glu Gly Thr Gly Thr
        260                 265                 270

Ala Ala Asp Leu Lys Ser Thr Gln Ala Ala Ile Asp Gln Ile Asn Gly
    275                 280                 285

Lys Leu Asn Arg Leu Ile Glu Lys Thr Asn Glu Lys Tyr His Gln Ile
290                 295                 300

Glu Lys Glu Phe Glu Gln Val Glu Gly Arg Ile Gln Asp Leu Glu
305                 310                 315

<210> SEQ ID NO 21
<211> LENGTH: 329
<212> TYPE: PRT
<213> ORGANISM: Artificial sequence
<220> FEATURE:
<223> OTHER INFORMATION: Influenza virus

<400> SEQUENCE: 21

Ser Asp Ile Cys Tyr Pro Gly Lys Phe Thr Asn Glu Glu Ala Leu Arg
1               5                   10                  15

Gln Ile Ile Arg Glu Ser Gly Gly Ile Asp Lys Glu Pro Met Gly Phe
            20                  25                  30

Arg Tyr Ser Gly Ile Lys Thr Asp Gly Ala Thr Ser Ala Cys Lys Arg
        35                  40                  45

Thr Val Ser Ser Phe Tyr Ser Glu Met Lys Trp Leu Leu Ser Ser Lys
    50                  55                  60

Ala Asn Gln Val Phe Pro Gln Leu Asn Gln Thr Tyr Arg Asn Asn Arg
65                  70                  75                  80

Lys Glu Pro Ala Leu Ile Val Trp Gly Val His His Ser Ser Ser Leu
                85                  90                  95

Asp Glu Gln Asn Lys Leu Tyr Gly Ala Gly Asn Lys Leu Ile Thr Val
            100                 105                 110

Gly Ser Ser Lys Tyr Gln Gln Ser Phe Ser Pro Ser Pro Gly Asp Arg
        115                 120                 125

Pro Lys Val Asn Gly Gln Ala Gly Arg Ile Asp Phe His Trp Met Leu
    130                 135                 140
```

```
Leu Asp Pro Gly Asp Thr Val Thr Phe Thr Phe Asn Gly Ala Phe Ile
145                 150                 155                 160

Ala Pro Asp Arg Ala Thr Phe Leu Arg Ser Asn Ala Pro Ser Gly Val
                165                 170                 175

Glu Tyr Asn Gly Lys Ser Leu Gly Ile Gln Ser Asp Ala Gln Ile Asp
            180                 185                 190

Glu Ser Cys Glu Gly Glu Cys Phe Tyr Ser Gly Gly Thr Ile Asn Ser
        195                 200                 205

Pro Leu Pro Phe Gln Asn Ile Asp Ser Trp Ala Val Gly Arg Cys Pro
    210                 215                 220

Arg Tyr Val Lys Gln Ser Ser Leu Pro Leu Ala Leu Gly Met Lys Asn
225                 230                 235                 240

Val Pro Glu Lys Ile His Thr Arg Gly Leu Phe Gly Ala Ile Ala Gly
                245                 250                 255

Phe Ile Glu Asn Gly Trp Glu Gly Leu Ile Asp Gly Trp Tyr Gly Phe
            260                 265                 270

Arg His Gln Asn Ala Gln Gly Gln Gly Thr Ala Ala Asp Tyr Lys Ser
        275                 280                 285

Thr Gln Ala Ala Ile Asp Gln Ile Thr Gly Lys Leu Asn Arg Leu Ile
    290                 295                 300

Glu Lys Thr Asn Thr Gln Phe Glu Leu Ile Asp Asn Glu Phe Thr Glu
305                 310                 315                 320

Val Glu Gln Gln Ile Gly Asn Val Ile
                325
```

```
<210> SEQ ID NO 22
<211> LENGTH: 320
<212> TYPE: PRT
<213> ORGANISM: Artificial sequence
<220> FEATURE:
<223> OTHER INFORMATION: Influenza virus

<400> SEQUENCE: 22

Pro Asn Lys Leu Cys Phe Pro Gly Glu Leu Asp Asn Gly Glu Leu
1               5                   10                  15

Arg His Leu Phe Ser Gly Val Asn Ser Phe Ser Arg Thr Glu Leu Ile
                20                  25                  30

Ser Pro Asn Lys Trp Gly Asp Ile Leu Asp Gly Val Thr Ala Ser Cys
            35                  40                  45

Arg Asp Asn Gly Ala Ser Ser Phe Tyr Arg Asn Leu Val Trp Ile Val
    50                  55                  60

Lys Asn Lys Asn Gly Lys Tyr Pro Val Ile Lys Gly Asp Tyr Asn Asn
65                  70                  75                  80

Thr Thr Gly Arg Asp Val Leu Val Leu Trp Gly Ile His His Pro Asp
                85                  90                  95

Thr Glu Thr Thr Ala Ile Asn Leu Tyr Ala Ser Lys Asn Pro Tyr Thr
            100                 105                 110

Leu Val Ser Thr Lys Glu Trp Ser Lys Arg Tyr Glu Leu Glu Ile Gly
    115                 120                 125

Thr Arg Ile Gly Asp Gly Gln Arg Ser Trp Met Lys Leu Tyr Trp His
130                 135                 140

Leu Met Arg Pro Gly Glu Arg Ile Met Phe Glu Ser Asn Gly Gly Leu
                150                 155                 160

Ile Ala Pro Arg Tyr Gly Tyr Ile Ile Glu Lys Tyr Gly Thr Gly Arg
            165                 170                 175
```

```
Ile Phe Gln Ser Gly Val Arg Met Ala Lys Cys Asn Thr Lys Cys Gln
            180                 185                 190

Thr Ser Leu Gly Gly Ile Asn Thr Asn Lys Thr Phe Gln Asn Ile Glu
        195                 200                 205

Arg Asn Ala Leu Gly Asp Cys Pro Lys Tyr Ile Lys Ser Gly Gln Leu
    210                 215                 220

Lys Leu Ala Thr Gly Leu Arg Asn Val Pro Ser Val Gly Glu Arg Gly
225                 230                 235                 240

Leu Phe Gly Ala Ile Ala Gly Phe Ile Glu Gly Gly Trp Pro Gly Leu
                245                 250                 255

Ile Asn Gly Trp Tyr Gly Phe Gln His Gln Asn Glu Gln Gly Thr Gly
            260                 265                 270

Ile Ala Ala Asp Lys Ala Ser Thr Gln Lys Ala Ile Asp Glu Ile Thr
        275                 280                 285

Thr Lys Ile Asn Asn Ile Ile Glu Lys Met Asn Gly Asn Tyr Asp Ser
    290                 295                 300

Ile Arg Gly Glu Phe Asn Gln Val Glu Lys Arg Ile Asn Met Leu Ala
305                 310                 315                 320

<210> SEQ ID NO 23
<211> LENGTH: 164
<212> TYPE: PRT
<213> ORGANISM: Artificial sequence
<220> FEATURE:
<223> OTHER INFORMATION: Influenza virus

<400> SEQUENCE: 23

Ser Tyr Ile Ile Glu Thr Ser Asn Ser Glu Asn Gly Thr Cys Tyr Pro
1               5                   10                  15

Gly Glu Phe Ile Asp Tyr Glu Glu Leu Arg Glu Gln Leu Ser Ser Ile
            20                  25                  30

Ser Ser Phe Glu Lys Phe Glu Ile Phe Pro Lys Ala Ser Ser Trp Pro
        35                  40                  45

Asn His Glu Thr Thr Lys Gly Val Thr Ala Ala Cys Ser Tyr Ser Gly
    50                  55                  60

Ala Ser Ser Phe Tyr Arg Asn Leu Leu Trp Ile Thr Lys Lys Gly Thr
65                  70                  75                  80

Ser Tyr Pro Lys Leu Ser Lys Ser Tyr Thr Asn Asn Lys Gly Lys Glu
                85                  90                  95

Val Leu Val Leu Trp Gly Val His His Pro Pro Ser Val Ser Glu Gln
            100                 105                 110

Gln Ser Leu Tyr Gln Asn Ala Asp Ala Tyr Val Ser Val Gly Ser Ser
        115                 120                 125

Lys Tyr Asn Arg Arg Phe Ala Pro Glu Ile Ala Ala Arg Pro Glu Val
    130                 135                 140

Arg Gly Gln Ala Gly Arg Met Asn Tyr Tyr Trp Thr Leu Leu Asp Gln
145                 150                 155                 160

Gly Asp Thr Ile

<210> SEQ ID NO 24
<211> LENGTH: 164
<212> TYPE: PRT
<213> ORGANISM: Artificial sequence
<220> FEATURE:
<223> OTHER INFORMATION: Influenza virus

<400> SEQUENCE: 24
```

```
Ser Tyr Ile Val Glu Thr Ser Asn Ser Asp Asn Gly Thr Cys Tyr Pro
1               5                   10                  15

Gly Asp Phe Ile Asp Tyr Glu Glu Leu Arg Glu Gln Leu Ser Ser Val
                20                  25                  30

Ser Ser Phe Glu Lys Phe Glu Ile Phe Pro Lys Thr Ser Ser Trp Pro
            35                  40                  45

Asn His Glu Thr Thr Arg Gly Val Thr Ala Ala Cys Pro Tyr Ala Gly
        50                  55                  60

Ala Ser Ser Phe Tyr Arg Asn Leu Leu Trp Leu Val Lys Lys Gly Asn
65                  70                  75                  80

Ser Tyr Pro Lys Leu Ser Lys Ser Tyr Val Asn Asn Lys Gly Lys Glu
                85                  90                  95

Val Leu Val Leu Trp Gly Val His His Pro Pro Thr Ser Thr Asp Gln
                100                 105                 110

Gln Ser Leu Tyr Gln Asn Ala Asp Ala Tyr Val Ser Val Gly Ser Ser
            115                 120                 125

Lys Tyr Asp Arg Arg Phe Thr Pro Glu Ile Ala Ala Arg Pro Lys Val
                130                 135                 140

Arg Gly Gln Ala Gly Arg Met Asn Tyr Tyr Trp Thr Leu Leu Glu Pro
145                 150                 155                 160

Gly Asp Thr Ile

<210> SEQ ID NO 25
<211> LENGTH: 163
<212> TYPE: PRT
<213> ORGANISM: Artificial sequence
<220> FEATURE:
<223> OTHER INFORMATION: Influenza virus

<400> SEQUENCE: 25

Ser Tyr Ile Val Glu Thr Pro Asn Ser Glu Asn Gly Ile Cys Tyr Pro
1               5                   10                  15

Gly Asp Phe Ile Asp Tyr Glu Glu Leu Arg Glu Gln Leu Ser Ser Val
                20                  25                  30

Ser Ser Phe Glu Arg Phe Glu Ile Phe Pro Lys Glu Ser Ser Trp Pro
            35                  40                  45

Asn His Asn Thr Asn Gly Val Thr Ala Ala Cys Ser His Glu Gly Lys
        50                  55                  60

Ser Ser Phe Tyr Arg Asn Leu Leu Trp Leu Thr Glu Lys Glu Gly Ser
65                  70                  75                  80

Tyr Pro Lys Leu Lys Asn Ser Tyr Val Asn Lys Lys Gly Lys Glu Val
                85                  90                  95

Leu Val Leu Trp Gly Ile His His Pro Pro Asn Ser Lys Glu Gln Gln
                100                 105                 110

Asn Leu Tyr Gln Asn Glu Asn Ala Tyr Val Ser Val Val Thr Ser Asn
            115                 120                 125

Tyr Asn Arg Arg Phe Thr Pro Glu Ile Ala Glu Arg Pro Lys Val Arg
                130                 135                 140

Asp Gln Ala Gly Arg Met Asn Tyr Tyr Trp Thr Leu Leu Lys Pro Gly
145                 150                 155                 160

Asp Thr Ile

<210> SEQ ID NO 26
<211> LENGTH: 164
<212> TYPE: PRT
<213> ORGANISM: Artificial sequence
```

```
<220> FEATURE:
<223> OTHER INFORMATION: Influenza virus

<400> SEQUENCE: 26

Ser Tyr Ile Val Glu Thr Ser Asn Ser Glu Asn Gly Thr Cys Tyr Pro
1               5                   10                  15

Gly Asp Phe Ile Asp Tyr Glu Glu Leu Arg Glu Gln Leu Ser Ser Val
                20                  25                  30

Ser Ser Phe Glu Lys Phe Glu Ile Phe Pro Lys Thr Ser Ser Trp Pro
            35                  40                  45

Asn His Glu Thr Thr Lys Gly Val Thr Ala Ala Cys Ser Tyr Ala Gly
        50                  55                  60

Ala Ser Ser Phe Tyr Arg Asn Leu Leu Trp Leu Thr Lys Lys Gly Ser
65                  70                  75                  80

Ser Tyr Pro Lys Leu Ser Lys Ser Tyr Val Asn Asn Lys Gly Lys Glu
                85                  90                  95

Val Leu Val Leu Trp Gly Val His His Pro Pro Thr Gly Thr Asp Gln
            100                 105                 110

Gln Ser Leu Tyr Gln Asn Ala Asp Ala Tyr Val Ser Val Gly Ser Ser
        115                 120                 125

Lys Tyr Asn Arg Arg Phe Thr Pro Glu Ile Ala Ala Arg Pro Lys Val
    130                 135                 140

Arg Asp Gln Ala Gly Arg Met Asn Tyr Tyr Trp Thr Leu Leu Glu Pro
145                 150                 155                 160

Gly Asp Thr Ile

<210> SEQ ID NO 27
<211> LENGTH: 164
<212> TYPE: PRT
<213> ORGANISM: Artificial sequence
<220> FEATURE:
<223> OTHER INFORMATION: Influenza virus

<400> SEQUENCE: 27

Ser Tyr Ile Ala Glu Thr Pro Asn Pro Glu Asn Gly Thr Cys Tyr Pro
1               5                   10                  15

Gly Tyr Phe Ala Asp Tyr Glu Glu Leu Arg Glu Gln Leu Ser Ser Val
                20                  25                  30

Ser Ser Phe Glu Arg Phe Glu Ile Phe Pro Lys Glu Ser Ser Trp Pro
            35                  40                  45

Asn His Thr Val Thr Lys Gly Val Thr Thr Ser Cys Ser His Asn Gly
        50                  55                  60

Lys Ser Ser Phe Tyr Arg Asn Leu Leu Trp Leu Thr Lys Lys Asn Gly
65                  70                  75                  80

Leu Tyr Pro Asn Val Ser Lys Ser Tyr Val Asn Asn Lys Glu Lys Glu
                85                  90                  95

Val Leu Val Leu Trp Gly Val His His Pro Ser Asn Ile Gly Asp Gln
            100                 105                 110

Arg Ala Ile Tyr His Thr Glu Asn Ala Tyr Val Ser Val Val Ser Ser
        115                 120                 125

His Tyr Ser Arg Arg Phe Thr Pro Glu Ile Ala Lys Arg Pro Lys Val
    130                 135                 140

Arg Asp Gln Glu Gly Arg Ile Asn Tyr Tyr Trp Thr Leu Leu Glu Pro
145                 150                 155                 160

Gly Asp Thr Ile
```

```
<210> SEQ ID NO 28
<211> LENGTH: 164
<212> TYPE: PRT
<213> ORGANISM: Artificial sequence
<220> FEATURE:
<223> OTHER INFORMATION: Influenza virus

<400> SEQUENCE: 28

Ser Tyr Ile Val Glu Thr Ser Asn Ser Glu Asn Gly Thr Cys Tyr Pro
1               5                   10                  15

Gly Asp Phe Ile Asp Tyr Glu Glu Leu Arg Glu Gln Leu Ser Ser Val
                20                  25                  30

Ser Ser Phe Glu Lys Phe Glu Ile Phe Pro Lys Thr Ser Ser Trp Pro
            35                  40                  45

Asn His Glu Thr Thr Lys Gly Val Thr Ala Ala Cys Ser Tyr Ala Gly
        50                  55                  60

Ala Ser Ser Phe Tyr Arg Asn Leu Leu Trp Leu Thr Lys Lys Gly Ser
65                  70                  75                  80

Ser Tyr Pro Lys Leu Ser Lys Ser Tyr Val Asn Asn Lys Gly Lys Glu
                85                  90                  95

Val Leu Val Leu Trp Gly Val His His Pro Pro Thr Gly Thr Asp Gln
            100                 105                 110

Gln Ser Leu Tyr Gln Asn Ala Asp Ala Tyr Val Ser Val Gly Ser Ser
        115                 120                 125

Lys Tyr Asn Arg Arg Phe Thr Pro Glu Ile Ala Ala Arg Pro Lys Val
    130                 135                 140

Arg Gly Gln Ala Gly Arg Met Asn Tyr Tyr Trp Thr Leu Leu Glu Pro
145                 150                 155                 160

Gly Asp Thr Ile

<210> SEQ ID NO 29
<211> LENGTH: 159
<212> TYPE: PRT
<213> ORGANISM: Artificial sequence
<220> FEATURE:
<223> OTHER INFORMATION: Influenza virus

<400> SEQUENCE: 29

Asp Leu Phe Val Glu Arg Ser Asn Ala Phe Ser Asn Cys Tyr Pro Tyr
1               5                   10                  15

Asp Ile Pro Asp Tyr Ala Ser Leu Arg Ser Leu Val Ala Ser Ser Gly
                20                  25                  30

Thr Leu Glu Phe Ile Thr Glu Gly Phe Thr Trp Thr Gly Val Thr Gln
            35                  40                  45

Asn Gly Gly Ser Ser Ala Cys Lys Arg Gly Pro Ala Asn Gly Phe Phe
        50                  55                  60

Ser Arg Leu Asn Trp Leu Thr Lys Ser Glu Ser Ala Tyr Pro Val Leu
65                  70                  75                  80

Asn Val Thr Met Pro Asn Asn Asp Asn Phe Asp Lys Leu Tyr Ile Trp
                85                  90                  95

Gly Val His His Pro Ser Thr Asn Gln Glu Gln Thr Asn Leu Tyr Val
            100                 105                 110

Gln Ala Ser Gly Arg Val Thr Val Ser Thr Arg Arg Ser Gln Gln Thr
        115                 120                 125

Ile Ile Pro Asn Ile Gly Ser Arg Pro Trp Val Arg Gly Gln Pro Gly
    130                 135                 140
```

Arg Ile Ser Ile Tyr Trp Thr Ile Val Lys Pro Gly Asp Val Leu
145                 150                 155

<210> SEQ ID NO 30
<211> LENGTH: 159
<212> TYPE: PRT
<213> ORGANISM: Artificial sequence
<220> FEATURE:
<223> OTHER INFORMATION: Influenza virus

<400> SEQUENCE: 30

Asp Leu Phe Val Glu Arg Ser Lys Ala Phe Ser Asn Cys Tyr Pro Tyr
1               5                   10                  15

Asp Val Pro Asp Tyr Ala Ser Leu Arg Ser Leu Val Ala Ser Ser Gly
                20                  25                  30

Thr Leu Glu Phe Ile Thr Glu Gly Phe Thr Trp Thr Gly Val Thr Gln
            35                  40                  45

Asn Gly Gly Ser Asn Ala Cys Lys Arg Gly Pro Gly Ser Gly Phe Phe
        50                  55                  60

Ser Arg Leu Asn Trp Leu Thr Lys Ser Gly Ser Thr Tyr Pro Val Leu
65                  70                  75                  80

Asn Val Thr Met Pro Asn Asn Asp Asn Phe Asp Lys Leu Tyr Ile Trp
                85                  90                  95

Gly Ile His His Pro Ser Thr Asn Gln Glu Gln Thr Ser Leu Tyr Val
            100                 105                 110

Gln Ala Ser Gly Arg Val Thr Val Ser Thr Arg Arg Ser Gln Gln Thr
        115                 120                 125

Ile Ile Pro Asn Ile Gly Ser Arg Pro Trp Val Arg Gly Leu Ser Ser
    130                 135                 140

Arg Ile Ser Ile Tyr Trp Thr Ile Val Lys Pro Gly Asp Val Leu
145                 150                 155

<210> SEQ ID NO 31
<211> LENGTH: 159
<212> TYPE: PRT
<213> ORGANISM: Artificial sequence
<220> FEATURE:
<223> OTHER INFORMATION: Influenza virus

<400> SEQUENCE: 31

Asp Leu Phe Val Glu Arg Ser Lys Ala Tyr Ser Asn Cys Tyr Pro Tyr
1               5                   10

```
Arg Ile Ser Ile Tyr Trp Thr Ile Val Lys Pro Gly Asp Ile Leu
145                 150                 155
```

<210> SEQ ID NO 32
<211> LENGTH: 163
<212> TYPE: PRT
<213> ORGANISM: Artificial sequence
<220> FEATURE:
<223> OTHER INFORMATION: Influenza virus

<400> SEQUENCE: 32

```
Ser Tyr Ile Val Glu Lys Asp Asn Pro Val Asn Gly Leu Cys Tyr Pro
1               5                   10                  15

Glu Asn Phe Asn Asp Tyr Glu Glu Leu Lys His Leu Leu Ser Ser Thr
            20                  25                  30

Asn His Phe Glu Lys Ile Arg Ile Ile Pro Arg Ser Ser Trp Ser Asn
        35                  40                  45

His Asp Ala Ser Ser Gly Val Ser Ser Ala Cys Pro Tyr Asn Gly Arg
    50                  55                  60

Ser Ser Phe Phe Arg Asn Val Val Trp Leu Ile Lys Lys Asn Asn Ala
65                  70                  75                  80

Tyr Pro Thr Ile Lys Arg Ser Tyr Asn Asn Thr Asn Gln Glu Asp Leu
                85                  90                  95

Leu Ile Leu Trp Gly Ile His His Pro Asn Asp Ala Ala Glu Gln Thr
            100                 105                 110

Lys Leu Tyr Gln Asn Pro Thr Thr Tyr Val Ser Val Gly Thr Ser Thr
        115                 120                 125

Leu Asn Gln Arg Ser Val Pro Glu Ile Ala Thr Arg Pro Lys Val Asn
    130                 135                 140

Gly Gln Ser Gly Arg Met Glu Phe Phe Trp Thr Ile Leu Lys Pro Asn
145                 150                 155                 160

Asp Ala Ile
```

<210> SEQ ID NO 33
<211> LENGTH: 163
<212> TYPE: PRT
<213> ORGANISM: Artificial sequence
<220> FEATURE:
<223> OTHER INFORMATION: Influenza virus

<400> SEQUENCE: 33

```
Ser Tyr Ile Val Glu Lys Ala Asn Pro Val Asn Asp Leu Cys Tyr Pro
1               5                   10                  15

Gly Asp Phe Asn Asp Tyr Glu Glu Leu Lys His Leu Leu Ser Arg Ile
            20                  25                  30

Asn His Phe Glu Lys Ile Gln Ile Ile Pro Lys Ser Ser Trp Ser Ser
        35                  40                  45

His Glu Ala Ser Leu Gly Val Ser Ser Ala Cys Pro Tyr Gln Gly Lys
    50                  55                  60

Ser Ser Phe Phe Arg Asn Val Val Trp Leu Ile Lys Lys Asn Ser Thr
65                  70                  75                  80

Tyr Pro Thr Ile Lys Arg Ser Tyr Asn Asn Thr Asn Gln Glu Asp Leu
                85                  90                  95

Leu Val Leu Trp Gly Ile His His Pro Asn Asp Ala Ala Glu Gln Thr
            100                 105                 110

Lys Leu Tyr Gln Asn Pro Thr Thr Tyr Ile Ser Val Gly Thr Ser Thr
        115                 120                 125
```

```
Leu Asn Gln Arg Leu Val Pro Arg Ile Ala Thr Arg Ser Lys Val Asn
            130                 135                 140
Gly Gln Ser Gly Arg Met Glu Phe Phe Trp Thr Ile Leu Lys Pro Asn
145                 150                 155                 160
Asp Ala Ile

<210> SEQ ID NO 34
<211> LENGTH: 566
<212> TYPE: PRT
<213> ORGANISM: Artificial sequence
<220> FEATURE:
<223> OTHER INFORMATION: Influenza virus

<400> SEQUENCE: 34

Met Lys Ala Ile Leu Val Val Leu Leu Tyr Thr Phe Ala Thr Ala Asn
1               5                   10                  15
Ala Asp Thr Leu Cys Ile Gly Tyr His Ala Asn Asn Ser Thr Asp Thr
            20                  25                  30
Val Asp Thr Val Leu Glu Lys Asn Val Thr Val Thr His Ser Val Asn
        35                  40                  45
Leu Leu Glu Asp Lys His Asn Gly Lys Leu Cys Lys Leu Arg Gly Val
    50                  55                  60
Ala Pro Leu His Leu Gly Lys Cys Asn Ile Ala Gly Trp Ile Leu Gly
65                  70                  75                  80
Asn Pro Glu Cys Glu Ser Leu Ser Thr Ala Ser Ser Trp Ser Tyr Ile
                85                  90                  95
Val Glu Thr Pro Ser Ser Asp Asn Gly Thr Cys Tyr Pro Gly Asp Phe
            100                 105                 110
Ile Asp Tyr Glu Glu Leu Arg Glu Gln Leu Ser Ser Val Ser Ser Phe
        115                 120                 125
Glu Arg Phe Glu Ile Phe Pro Lys Thr Ser Ser Trp Pro Asn His Asp
    130                 135                 140
Ser Asn Lys Gly Val Thr Ala Ala Cys Pro His Ala Gly Ala Lys Ser
145                 150                 155                 160
Phe Tyr Lys Asn Leu Ile Trp Leu Val Lys Lys Gly Asn Ser Tyr Pro
                165                 170                 175
Lys Leu Ser Lys Ser Tyr Ile Asn Asp Lys Gly Lys Glu Val Leu Val
            180                 185                 190
Leu Trp Gly Ile His His Pro Ser Thr Ser Ala Asp Gln Gln Ser Leu
        195                 200                 205
Tyr Gln Asn Ala Asp Thr Tyr Val Phe Val Gly Ser Ser Arg Tyr Ser
    210                 215                 220
Lys Lys Phe Lys Pro Glu Ile Ala Ile Arg Pro Lys Val Arg Asp Gln
225                 230                 235                 240
Glu Gly Arg Met Asn Tyr Tyr Trp Thr Leu Val Glu Pro Gly Asp Lys
                245                 250                 255
Ile Thr Phe Glu Ala Thr Gly Asn Leu Val Val Pro Arg Tyr Ala Phe
            260                 265                 270
Ala Met Glu Arg Asn Ala Gly Ser Gly Ile Ile Ile Ser Asp Thr Pro
        275                 280                 285
Val His Asp Cys Asn Thr Thr Cys Gln Thr Pro Lys Gly Ala Ile Asn
    290                 295                 300
Thr Ser Leu Pro Phe Gln Asn Ile His Pro Ile Thr Ile Gly Lys Cys
305                 310                 315                 320
```

```
Pro Lys Tyr Val Lys Ser Thr Lys Leu Arg Leu Ala Thr Gly Leu Arg
            325                 330                 335

Asn Ile Pro Ser Ile Gln Ser Arg Gly Leu Phe Gly Ala Ile Ala Gly
        340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 35
<211> LENGTH: 566
<212> TYPE: PRT
<213> ORGANISM: Artificial sequence
<220> FEATURE:
<223> OTHER INFORMATION: Influenza virus

<400> SEQUENCE: 35

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110
```

-continued

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Thr Tyr Val Phe Val Gly Ser Ser Arg Tyr Ser
            210                 215                 220

Lys Lys Phe Lys Pro Glu Ile Ala Lys Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val

```
                    530                 535                 540
Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 36
<211> LENGTH: 566
<212> TYPE: PRT
<213> ORGANISM: Artificial sequence
<220> FEATURE:
<223> OTHER INFORMATION: Influenza virus

<400> SEQUENCE: 36

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Pro Thr Ser Thr Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Ala Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
```

```
                    325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Val Asp Gly Trp Tyr Gly Tyr
            355                 360                 365
His His Gln Asn Glu Gln Gly Ser Gly Tyr Ala Ala Asp Leu Lys Ser
            370                 375                 380
Thr Gln Asn Ala Ile Asp Glu Ile Thr Asn Lys Val Asn Ser Val Ile
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
            435                 440                 445
Glu Arg Thr Leu Asp Tyr His Asp Ser Asn Val Lys Asn Leu Tyr Glu
            450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
                485                 490                 495
Lys Asn Gly Thr Tyr Asp Tyr Pro Lys Tyr Ser Glu Glu Ala Lys Leu
            500                 505                 510
Asn Arg Glu Glu Ile Asp Gly Val Lys Leu Glu Ser Thr Arg Ile Tyr
            515                 520                 525
Gln Ile Leu Ala Ile Tyr Ser Thr Val Ala Ser Ser Leu Val Leu Val
            530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 37
<211> LENGTH: 566
<212> TYPE: PRT
<213> ORGANISM: Artificial sequence
<220> FEATURE:
<223> OTHER INFORMATION: Influenza virus

<400> SEQUENCE: 37

Met Glu Ala Arg Leu Leu Val Leu Leu Cys Ala Phe Ala Ala Thr Asn
1               5                   10                  15
Ala Asp Thr Ile Cys Ile Gly Tyr His Ala Asn Asn Ser Thr Asp Thr
            20                  25                  30
Val Asp Thr Val Leu Glu Lys Asn Val Thr Val Thr His Ser Val Asn
        35                  40                  45
Leu Leu Glu Asp Ser His Asn Gly Lys Leu Cys Lys Leu Lys Gly Ile
    50                  55                  60
Ala Pro Leu Gln Leu Gly Lys Cys Asn Ile Ala Gly Trp Leu Leu Gly
65                  70                  75                  80
Asn Pro Glu Cys Asp Leu Leu Leu Thr Ala Ser Ser Trp Ser Tyr Ile
                85                  90                  95
Val Glu Thr Ser Asn Ser Glu Asn Gly Thr Cys Tyr Pro Gly Asp Phe
            100                 105                 110
Ile Asp Tyr Glu Glu Leu Arg Glu Gln Leu Ser Ser Val Ser Ser Phe
```

-continued

```
            115                 120                 125
Glu Lys Phe Glu Ile Phe Pro Lys Thr Ser Ser Trp Pro Asn His Glu
130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Thr Gly Thr Asp Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
        275                 280                 285

Val His Asp Cys Asn Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540
```

-continued

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 38
<211> LENGTH: 565
<212> TYPE: PRT
<213> ORGANISM: Artificial sequence
<220> FEATURE:
<223> OTHER INFORMATION: Influenza virus

<400> SEQUENCE: 38

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Thr Thr Gly Val Ser Ala Ser Cys Ser His Asn Gly Glu Ser Ser Phe
145                 150                 155                 160

Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Lys Glu Asn Ala Tyr Val Ser Val Ser Ser His Tyr Ser Arg
210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Glu Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

```
Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 39
<211> LENGTH: 565
<212> TYPE: PRT
<213> ORGANISM: Artificial sequence
<220> FEATURE:
<223> OTHER INFORMATION: Influenza virus

<400> SEQUENCE: 39

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asn Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125
```

```
Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540
```

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 40
<211> LENGTH: 326
<212> TYPE: PRT
<213> ORGANISM: Artificial sequence
<220> FEATURE:
<223> OTHER INFORMATION: Influenza virus

<400> SEQUENCE: 40

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
50                  55                  60

Pro Glu Cys Glu Leu Leu Ile Ser Lys Glu Ser Trp Ser Tyr Ile Val
65                  70                  75                  80

Glu Lys Pro Asn Pro Glu Asn Gly Thr Cys Tyr Pro Gly His Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Glu Asn Ser Phe Tyr
130                 135                 140

Arg Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
                165                 170                 175

Gly Val His His Pro Pro Asn Ile Ala Asp Gln Lys Ala Leu Tyr His
            180                 185                 190

Thr Glu Asn Ala Tyr Val Ser Val Val Ser Ser His Tyr Ser Arg Lys
        195                 200                 205

Phe Thr Pro Glu Ile Ala Lys Arg Pro Lys Val Arg Asp Gln Glu Gly
210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Arg Tyr Ala Phe Ala Leu
                245                 250                 255

Ser Arg Gly Phe Gly Ser Gly Ile Ile Asn Ser Asn Ala Pro Met Asp
            260                 265                 270

Lys Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
290                 295                 300

Tyr Val Arg Ser Ala Lys Leu Arg Met Val Thr Gly Leu Arg Asn Ile
305                 310                 315                 320

Pro Ser Ile Gln Ser Arg
            325

<210> SEQ ID NO 41
<211> LENGTH: 326
<212> TYPE: PRT
<213> ORGANISM: Artificial sequence
<220> FEATURE:
<223> OTHER INFORMATION: Influenza virus

<400> SEQUENCE: 41

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
50                  55                  60

Pro Glu Cys Glu Leu Leu Ile Ser Lys Glu Ser Trp Ser Tyr Ile Val
65                  70                  75                  80

Glu Lys Pro Asn Pro Glu Asn Gly Thr Cys Tyr Pro Gly His Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Glu Ser Ser Phe Tyr
130                 135                 140

Arg Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
                165                 170                 175

Gly Val His His Pro Pro Asn Ile Gly Asp Gln Lys Ala Leu Tyr His
            180                 185                 190

Thr Glu Asn Ala Tyr Val Ser Val Val Ser Ser His Tyr Ser Arg Lys
        195                 200                 205

Phe Thr Pro Glu Ile Ala Lys Arg Pro Lys Val Arg Asp Gln Glu Gly
210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Arg Tyr Ala Phe Ala Leu
                245                 250                 255

Ser Arg Gly Phe Gly Ser Gly Ile Ile Asn Ser Asn Ala Pro Met Asp
            260                 265                 270

Lys Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
290                 295                 300

Tyr Val Arg Ser Ala Lys Leu Arg Met Val Thr Gly Leu Arg Asn Ile
305                 310                 315                 320

Pro Ser Ile Gln Ser Arg
                325
```

<210> SEQ ID NO 42
<211> LENGTH: 327
<212> TYPE: PRT
<213> ORGANISM: Artificial sequence
<220> FEATURE:

<223> OTHER INFORMATION: Influenza virus

<400> SEQUENCE: 42

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
50                  55                  60

Pro Glu Cys Glu Ser Leu Ser Thr Ala Ser Ser Trp Ser Tyr Ile Val
65                  70                  75                  80

Glu Thr Pro Ser Ser Asp Asn G

```
Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Lys Leu Lys Gly Ile
 50                  55                  60

Ala Pro Leu Gln Leu Gly Lys Cys Asn Ile Ala Gly Trp Leu Leu Gly
 65                  70                  75                  80

Asn Pro Glu Cys Asp Leu Leu Leu Thr Ala Ser Ser Trp Ser Tyr Ile
            85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Lys Phe Glu Ile Phe Pro Lys Thr Ser Ser Trp Pro Asn His Glu
            130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
            165                 170                 175

Lys Leu Ser Lys Ser Tyr Val Asn Asn Lys Gly Lys Glu Val Leu Val
            180                 185                 190

Leu Trp Gly Val His His Pro Pro Thr Gly Thr Asp Gln Gln Ser Leu
            195                 200                 205

Tyr Gln Asn Ala Asp Ala Tyr Val Ser Val Gly Ser Ser Lys Tyr Asn
 210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
            245                 250                 255

Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
            275                 280                 285

Val His Asp Cys Asn Thr Lys Cys Gln Thr Pro His Gly Ala Ile Asn
            290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
            325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
            370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
            405                 410                 415

Leu Glu Arg Arg Ile Glu Asn Leu Asn Lys Lys Val Asp Asp Gly Phe
            420                 425                 430
```

```
Leu Asp Ile Trp Thr Tyr Asn Ala Glu Leu Leu Val Leu Leu Glu Asn
            435                 440                 445

Glu Arg Thr Leu Asp Phe His Asp Ser Asn Val Arg Asn Leu Tyr Glu
        450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 44
<211> LENGTH: 566
<212> TYPE: PRT
<213> ORGANISM: Artificial sequence
<220> FEATURE:
<223> OTHER INFORMATION: Influenza virus
<220> FEATURE:
<221> NAME/KEY: MISC_FEATURE
<222> LOCATION: (77)..(78)
<223> OTHER INFORMATION: X = any amino acid

<400> SEQUENCE: 44

Met Lys Ala Ile Leu Leu Val Leu Leu Cys Ala Phe Ala Ala Thr Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Gly Gly Ile
    50                  55                  60

Ala Pro Leu Gln Leu Gly Lys Cys Asn Ile Ala Gly Xaa Xaa Leu Gly
65                  70                  75                  80

Asn Pro Glu Cys Asp Leu Leu Leu Thr Val Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Arg Gly Val Thr Ala Ala Cys Pro Tyr Ala Gly Ala Ser Ser
145                 150                 155                 160

Phe Tyr Arg Asn Leu Leu Trp Leu Val Lys Lys Glu Asn Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Pro Thr Ser Thr Asp Gln Gln Ser Leu
        195                 200                 205
```

Tyr Gln Asn Ala Asp Ala Tyr Val Ser Val Gly Ser Ser Lys Tyr Asp
    210                 215                 220

Arg Arg Phe Thr Pro Glu Ile Ala Ala Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Val Ala Pro Arg Tyr Ala Phe
            260                 265                 270

Ala Leu Asn Arg Gly Ser Glu Ser Gly Ile Ile Thr Ser Asp Ala Pro
        275                 280                 285

Val His Asp Cys Asp Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Lys Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Leu Ile Asp Gly Trp Tyr Gly Tyr
        355                 360                 365

His His Gln Asn Gly Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Val Val Gly Lys Glu Phe Asn Asn
                405                 410                 415

Leu Glu Arg Arg Ile Lys Asn Leu Asn Lys Lys Val Asp Asp Gly Phe
            420                 425                 430

Leu Asp Val Trp Thr Tyr Asn Ala Glu Met Leu Val Leu Leu Glu Asn
        435                 440                 445

Glu Arg Thr Leu Asp Phe His Asp Ser Asn Val Lys Asn Leu Tyr Glu
    450                 455                 460

Lys Ala Arg Ser Gln Leu Arg Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Met Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 45
<211> LENGTH: 566
<212> TYPE: PRT
<213> ORGANISM: Artificial sequence
<220> FEATURE:
<223> OTHER INFORMATION: Influenza virus

<400> SEQUENCE: 45

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
        50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
        130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Thr Tyr Val Phe Val Gly Ser Ser Arg Tyr Ser
        210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
        290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
        370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415
```

-continued

```
Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 46
<211> LENGTH: 566
<212> TYPE: PRT
<213> ORGANISM: Artificial sequence
<220> FEATURE:
<223> OTHER INFORMATION: Influenza virus

<400> SEQUENCE: 46

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
        50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205
```

Tyr Gln Asn Ala Asp Thr Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
            245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
        450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 47
<211> LENGTH: 566
<212> TYPE: PRT
<213> ORGANISM: Artificial sequence
<220> FEATURE:
<223> OTHER INFORMATION: Influenza virus

<400> SEQUENCE: 47

```
Met Lys Ala Ile Leu Val Val Leu Leu Tyr Thr Phe Ala Thr Ala Asn
 1               5                  10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
 50                  55                  60

Ala Pro Leu His Leu Lys Cys Asn Ile Ala Gly Trp Ile Leu Gly
 65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Met Ser Ser Phe
            115                 120                 125

Glu Arg Phe Glu Ile Phe Pro Lys Thr Ser Ser Trp Pro Asn His Asp
        130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Leu Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
```

```
                    420                 425                 430
Leu Asp Ile Trp Thr Tyr Asn Ala Glu Leu Leu Val Leu Leu Glu Asn
                435                 440                 445
Glu Arg Thr Leu Asp Tyr His Asp Ser Asn Val Lys Asn Leu Tyr Glu
    450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
                485                 490                 495
Lys Asn Gly Thr Tyr Asp Tyr Pro Lys Tyr Ser Glu Glu Ala Lys Leu
                500                 505                 510
Asn Arg Glu Glu Ile Asp Gly Val Lys Leu Glu Ser Thr Arg Ile Tyr
            515                 520                 525
Gln Ile Leu Ala Ile Tyr Ser Thr Val Ala Ser Ser Leu Val Leu Val
        530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 48
<211> LENGTH: 566
<212> TYPE: PRT
<213> ORGANISM: Artificial sequence
<220> FEATURE:
<223> OTHER INFORMATION: Influenza virus

<400> SEQUENCE: 48

Met Lys Ala Ile Leu Val Val Leu Leu Tyr Thr Phe Ala Thr Ala Asn
1               5                   10                  15
Ala Asp Thr Leu Cys Ile Gly Tyr His Ala Asn Asn Ser Thr Asp Thr
                20                  25                  30
Val Asp Thr Val Leu Glu Lys Asn Val Thr Val Thr His Ser Val Asn
            35                  40                  45
Leu Leu Glu Asp Lys His Asn Gly Lys Leu Cys Lys Leu Arg Gly Val
        50                  55                  60
Ala Pro Leu His Leu Gly Lys Cys Asn Ile Ala Gly Trp Ile Leu Gly
65                  70                  75                  80
Asn Pro Glu Cys Glu Ser Leu Ser Thr Ala Ser Ser Trp Ser Tyr Ile
                85                  90                  95
Val Glu Thr Ser Ser Ser Asp Asn Gly Thr Cys Tyr Pro Gly Asp Phe
                100                 105                 110
Ile Asp Tyr Glu Glu Leu Arg Glu Gln Leu Ser Ser Val Ser Ser Phe
            115                 120                 125
Glu Arg Phe Glu Ile Phe Pro Lys Thr Ser Ser Trp Pro Asn His Asp
        130                 135                 140
Ser Asn Lys Gly Val Thr Ala Ala Cys Pro His Ala Gly Ala Lys Ser
145                 150                 155                 160
Phe Tyr Lys Asn Leu Ile Trp Leu Val Lys Lys Gly Asn Ser Tyr Pro
                165                 170                 175
Lys Leu Ser Lys Ser Tyr Ile Asn Asp Lys Gly Lys Glu Val Leu Val
                180                 185                 190
Leu Trp Gly Ile His His Pro Ser Thr Ser Ala Asp Gln Gln Ser Leu
            195                 200                 205
Tyr Gln Asn Ala Asp Ala Tyr Val Phe Val Gly Ser Ser Arg Tyr Ser
```

210                 215                 220
Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 49
<211> LENGTH: 566
<212> TYPE: PRT
<213> ORGANISM: Artificial sequence
<220> FEATURE:
<223> OTHER INFORMATION: Influenza virus

<400> SEQUENCE: 49

Met Glu Ala Arg Leu Leu Val Leu Leu Cys Ala Phe Ala Ala Thr Asn

```
  1               5                  10                 15
Ala Asp Thr Ile Cys Ile Gly Tyr His Ala Asn Asn Ser Thr Asp Thr
                 20                 25                 30

Val Asp Thr Val Leu Glu Lys Asn Val Thr Val Thr His Ser Val Asn
                 35                 40                 45

Leu Leu Glu Asp Ser His Asn Gly Lys Leu Cys Leu Lys Gly Ile
50                    55                 60

Ala Pro Leu Gln Leu Gly Lys Cys Asn Ile Ala Gly Trp Leu Leu Gly
65                    70                 75                 80

Asn Pro Glu Cys Asp Leu Leu Leu Thr Ala Ser Ser Trp Ser Tyr Ile
                 85                 90                 95

Val Glu Thr Ser Asn Ser Glu Asn Gly Thr Cys Tyr Pro Gly Asp Phe
                 100                105                110

Ile Asp Tyr Glu Glu Leu Arg Glu Gln Leu Ser Ser Val Ser Ser Phe
                 115                120                125

Glu Lys Phe Glu Ile Phe Pro Lys Thr Ser Ser Trp Pro Asn His Glu
                 130                135                140

Thr Thr Lys Gly Val Thr Ala Ala Cys Ser Tyr Ala Gly Ala Ser Ser
145                   150                155                160

Phe Tyr Arg Asn Leu Leu Trp Leu Thr Lys Lys Gly Ser Ser Tyr Pro
                 165                170                175

Lys Leu Ser Lys Ser Tyr Val Asn Asn Lys Gly Lys Glu Val Leu Val
                 180                185                190

Leu Trp Gly Val His His Pro Pro Thr Gly Thr Asp Gln Gln Ser Leu
                 195                200                205

Tyr Gln Asn Ala Asp Ala Tyr Val Ser Val Gly Ser Ser Lys Tyr Asn
                 210                215                220

Arg Arg Phe Thr Pro Glu Ile Ala Ala Arg Pro Lys Val Arg Asp Gln
225                   230                235                240

Ala Gly Arg Met Asn Tyr Tyr Trp Thr Leu Leu Glu Pro Gly Asp Thr
                 245                250                255

Ile Thr Phe Glu Ala Thr Gly Asn Leu Ile Ala Pro Trp Tyr Ala Phe
                 260                265                270

Ala Leu Asn Arg Gly Ser Gly Ser Gly Ile Ile Thr Ser Asp Ala Pro
                 275                280                285

Val His Asp Cys Asn Thr Lys Cys Gln Thr Pro His Gly Ala Ile Asn
                 290                295                300

Ser Ser Leu Pro Phe Gln Asn Ile His Pro Val Thr Ile Gly Glu Cys
305                   310                315                320

Pro Lys Tyr Val Arg Ser Thr Lys Leu Arg Met Ala Thr Gly Leu Arg
                 325                330                335

Asn Ile Pro Ser Ile Gln Ser Arg Gly Leu Phe Gly Ala Ile Ala Gly
                 340                345                350

Phe Ile Glu Gly Gly Trp Thr Gly Met Ile Asp Gly Trp Tyr Gly Tyr
                 355                360                365

His His Gln Asn Glu Gln Gly Ser Gly Tyr Ala Ala Asp Gln Lys Ser
                 370                375                380

Thr Gln Asn Ala Ile Asp Gly Ile Thr Asn Lys Val Asn Ser Val Ile
385                   390                395                400

Glu Lys Met Asn Thr Gln Phe Thr Ala Val Gly Lys Glu Phe Asn Asn
                 405                410                415

Leu Glu Arg Arg Ile Glu Asn Leu Asn Lys Lys Val Asp Asp Gly Phe
                 420                425                430
```

-continued

```
Leu Asp Ile Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
                500                 505                 510

Asn Arg Glu Glu Ile Asp Gly Val Lys Leu Glu Ser Met Gly Val Tyr
                515                 520                 525

Gln Ile Leu Ala Ile Tyr Ser Thr Val Ala Ser Ser Leu Val Leu Leu
                530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 50
<211> LENGTH: 566
<212> TYPE: PRT
<213> ORGANISM: Artificial sequence
<220> FEATURE:
<223> OTHER INFORMATION: Influenza virus
<220> FEATURE:
<221> NAME/KEY: MISC_FEATURE
<222> LOCATION: (77)..(78)
<223> OTHER INFORMATION: X = any amino acid

<400> SEQUENCE: 50

Met Lys Ala Ile Leu Val Leu Leu Cys Ala Phe Ala Ala Thr Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Gly Gly Ile
    50                  55                  60

Ala Pro Leu Gln Leu Gly Lys Cys Asn Ile Ala Gly Xaa Xaa Leu Gly
65                  70                  75                  80

Asn Pro Glu Cys Asp Leu Leu Leu Thr Val Ser Ser Trp Ser Tyr Ile
                85                  90                  95

Val Glu Thr Ser Asn Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Lys Phe Glu Ile Phe Pro Lys Thr Ser Ser Trp Pro Asn His Glu
    130                 135                 140

Thr Thr Arg Gly Val Thr Ala Ala Cys Pro Tyr Ala Gly Ala Ser Ser
145                 150                 155                 160

Phe Tyr Arg Asn Leu Leu Trp Leu Val Lys Lys Glu Asn Ser Tyr Pro
                165                 170                 175

Lys Leu Ser Lys Ser Tyr Val Asn Asn Lys Gly Lys Glu Val Leu Val
                180                 185                 190

Leu Trp Gly Val His His Pro Pro Thr Ser Thr Asp Gln Gln Ser Leu
```

```
                195                 200                 205
Tyr Gln Asn Ala Asp Ala Tyr Val Ser Val Gly Ser Ser Lys Tyr Asp
    210                 215                 220
Arg Arg Phe Thr Pro Glu Ile Ala Ala Arg Pro Lys Val Arg Gly Gln
225                 230                 235                 240
Ala Gly Arg Met Asn Tyr Tyr Trp Thr Leu Leu Glu Pro Gly Asp Thr
                245                 250                 255
Ile Thr Phe Glu Ala Thr Gly Asn Leu Val Ala Pro Arg Tyr Ala Phe
            260                 265                 270
Ala Leu Asn Arg Gly Ser Glu Ser Gly Ile Ile Thr Ser Asp Ala Pro
        275                 280                 285
Val His Asp Cys Asp Thr Lys Cys Gln Thr Pro His Gly Ala Ile Asn
    290                 295                 300
Ser Ser Leu Pro Phe Gln Asn Ile His Pro Val Thr Ile Gly Glu Cys
305                 310                 315                 320
Pro Lys Tyr Val Lys Ser Thr Lys Leu Arg Met Val Thr Gly Leu Arg
                325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Leu Ile Asp Gly Trp Tyr Gly Tyr
        355                 360                 365
His His Gln Asn Gly Gln Gly Ser Gly Tyr Ala Ala Asp Gln Lys Ser
    370                 375                 380
Thr Gln Asn Ala Ile Asp Gly Ile Thr Asn Lys Val Asn Ser Val Ile
385                 390                 395                 400
Glu Lys Met Asn Thr Gln Phe Thr Val Val Gly Lys Glu Phe Asn Asn
                405                 410                 415
Leu Glu Arg Arg Ile Lys Asn Leu Asn Lys Lys Val Asp Asp Gly Phe
            420                 425                 430
Leu Asp Val Trp Thr Tyr Asn Ala Glu Met Leu Val Leu Leu Glu Asn
        435                 440                 445
Glu Arg Thr Leu Asp Phe His Asp Ser Asn Val Lys Asn Leu Tyr Glu
    450                 455                 460
Lys Ala Arg Ser Gln Leu Arg Asn Asn Ala Lys Glu Ile Gly Asn Gly
465                 470                 475                 480
Cys Phe Glu Phe Tyr His Lys Cys Asp Asp Ala Cys Met Glu Ser Val
                485                 490                 495
Arg Asn Gly Thr Tyr Asp Tyr Pro Lys Tyr Ser Glu Glu Ser Lys Leu
            500                 505                 510
Asn Arg Glu Glu Ile Asp Gly Val Lys Leu Glu Ser Met Met Val Tyr
        515                 520                 525
Gln Ile Leu Ala Ile Tyr Ser Thr Val Ala Ser Ser Leu Val Leu Leu
    530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 51
<211> LENGTH: 570
<212> TYPE: PRT
<213> ORGANISM: Artificial sequence
<220> FEATURE:
<223> OTHER INFORMATION: Influenza virus
```

```
<400> SEQUENCE: 51

Met Arg Leu Val Ala Lys Leu Leu Tyr Leu Ala Val Leu Ala Ile Cys
1               5                   10                  15

Gly Leu Gly Ile His Gly Ala Leu Thr His Pro Arg Val Thr Pro Pro
            20                  25                  30

Val Tyr Pro Ser Val Ser Phe Asn Leu Thr Gly Ala Asp Thr Tyr Glu
            35                  40                  45

Pro Phe Leu Arg Ala Leu Gln Glu Lys Val Ile Leu Gly Asn His Thr
    50                  55                  60

Ala Phe Asp Leu Pro Val Leu Asn Pro Glu Ser Gln Val Ser Asp Ser
65                  70                  75                  80

Asn Arg Phe Val Leu Val Pro Leu Thr Asn Pro Ser Gly Asp Thr Val
                85                  90                  95

Thr Leu Ala Ile Asp Val Val Asn Leu Tyr Val Val Ala Phe Ser Ser
                100                 105                 110

Asn Gly Lys Ser Tyr Phe Phe Ser Gly Ser Thr Ala Val Gln Arg Asp
            115                 120                 125

Asn Leu Phe Val Asp Thr Thr Gln Glu Glu Leu Asn Phe Thr Gly Asn
    130                 135                 140

Tyr Thr Ser Leu Glu Arg Gln Val Gly Phe Gly Arg Val Tyr Ile Pro
145                 150                 155                 160

Leu Gly Pro Lys Ser Leu Asp Gln Ala Ile Ser Ser Leu Arg Thr Tyr
                165                 170                 175

Thr Leu Thr Ala Gly Asp Thr Lys Pro Leu Ala Arg Gly Leu Leu Val
                180                 185                 190

Val Ile Gln Met Val Ser Glu Ala Ala Arg Phe Arg Tyr Ile Glu Leu
            195                 200                 205

Arg Ile Arg Thr Ser Ile Thr Asp Ala Ser Glu Phe Thr Pro Asp Leu
    210                 215                 220

Leu Met Leu Ser Met Glu Asn Asn Trp Ser Ser Met Ser Ser Glu Ile
225                 230                 235                 240

Gln Gln Ala Gln Pro Gly Gly Ile Phe Ala Gly Val Val Gln Leu Arg
                245                 250                 255

Asp Glu Arg Asn Asn Ser Ile Glu Val Thr Asn Phe Arg Arg Leu Phe
            260                 265                 270

Glu Leu Thr Tyr Ile Ala Val Leu Leu Tyr Gly Cys Ala Pro Val Thr
    275                 280                 285

Ser Ser Ser Tyr Ser Asn Asn Ala Ile Asp Ala Gln Ile Ile Lys Met
290                 295                 300

Pro Val Phe Arg Gly Gly Glu Tyr Glu Lys Val Cys Ser Val Val Glu
305                 310                 315                 320

Val Thr Arg Arg Ile Ser Gly Trp Asp Gly Leu Cys Val Asp Val Arg
                325                 330                 335

Tyr Gly His Tyr Ile Asp Gly Asn Pro Val Gln Leu Arg Pro Cys Gly
            340                 345                 350

Asn Glu Cys Asn Gln Leu Trp Thr Phe Arg Thr Asp Gly Thr Ile Arg
    355                 360                 365

Trp Leu Gly Lys Cys Leu Thr Ala Ser Ser Ser Val Met Ile Tyr Asp
370                 375                 380

Cys Asn Thr Val Pro Pro Glu Ala Thr Lys Trp Val Val Ser Ile Asp
385                 390                 395                 400

Gly Thr Ile Thr Asn Pro His Ser Gly Leu Val Leu Thr Ala Pro Gln
                405                 410                 415
```

```
Ala Ala Glu Gly Thr Ala Leu Ser Leu Glu Asn Asn Ile His Ala Ala
            420                 425                 430

Arg Gln Gly Trp Thr Val Gly Asp Val Glu Pro Leu Val Thr Phe Ile
            435                 440                 445

Val Gly Tyr Lys Gln Met Cys Leu Arg Glu Asn Gly Glu Asn Asn Phe
450                 455                 460

Val Trp Leu Glu Asp Cys Val Leu Asn Arg Val Gln Gln Glu Trp Ala
465                 470                 475                 480

Leu Tyr Gly Asp Gly Thr Ile Arg Val Asn Ser Asn Arg Ser Leu Cys
            485                 490                 495

Val Thr Ser Glu Asp His Glu Pro Ser Asp Leu Ile Val Ile Leu Lys
            500                 505                 510

Cys Glu Gly Ser Gly Asn Gln Arg Trp Val Phe Asn Thr Asn Gly Thr
            515                 520                 525

Ile Ser Asn Pro Asn Ala Lys Leu Leu Met Asp Val Ala Gln Arg Asp
            530                 535                 540

Val Ser Leu Arg Lys Ile Ile Leu Tyr Arg Pro Thr Gly Asn Pro Asn
545                 550                 555                 560

Gln Gln Trp Ile Thr Thr Thr His Pro Ala
            565                 570

<210> SEQ ID NO 52
<211> LENGTH: 569
<212> TYPE: PRT
<213> ORGANISM: Artificial sequence
<220> FEATURE:
<223> OTHER INFORMATION: Influenza virus

<400> SEQUENCE: 52

Met Lys Val Val Ala Thr Ile Leu Tyr Leu Val Val Leu Ala Ile Cys
1               5                   10                  15

Gly Leu Gly Ile His Gly Ala His Pro Thr His Ser Ala Pro Pro Thr
            20                  25                  30

Val Tyr Pro Ser Val Ser Phe Asn Leu Thr Glu Ala Asn Ser Asn Glu
            35                  40                  45

Tyr Arg His Phe Leu Gln Glu Leu Arg Gly Lys Val Ile Leu Gly Ser
50                  55                  60

His Arg Ala Phe Asp Leu Pro Val Leu Asn Pro Glu Ser Lys Val Ser
65                  70                  75                  80

Asp Ser Asp Arg Phe Val Leu Val Arg Leu Thr Asn Pro Ser Arg Lys
            85                  90                  95

Lys Val Thr Leu Ala Ile Asp Val Val Thr Phe Tyr Val Val Ala Phe
            100                 105                 110

Ala Gln Asn Asp Arg Ser Tyr Phe Phe Ser Gly Ser Ser Glu Val Gln
            115                 120                 125

Arg Glu Asn Leu Phe Val Asp Thr Thr Gln Glu Asp Leu Asn Phe Lys
            130                 135                 140

Gly Asp Tyr Thr Ser Leu Glu His Gln Val Gly Phe Gly Arg Val Tyr
145                 150                 155                 160

Ile Pro Leu Gly Pro Lys Ser Leu Ala Gln Ser Ile Ser Ser Leu Ser
            165                 170                 175

Thr Tyr Lys Ser Ser Ala Gly Asp Asn Lys Arg Leu Ala Arg Ser Leu
            180                 185                 190

Leu Val Val Ile Gln Met Val Ser Glu Ala Ala Arg Phe Arg Tyr Ile
            195                 200                 205
```

Gln Leu Arg Ile Gln Ala Ser Ile Thr Asp Ala Lys Glu Phe Thr Pro
    210             215                 220

Asp Leu Leu Met Leu Ser Met Glu Asn Lys Trp Ser Ser Met Ser Ser
225                 230                 235                 240

Glu Ile Gln Gln Ala Gln Pro Gly Gly Ala Phe Ala Gln Val Val Lys
                245                 250                 255

Leu Leu Asp Gln Arg Asn His Pro Ile Asp Val Thr Asn Phe Arg Arg
            260                 265                 270

Leu Phe Gln Leu Thr Ser Val Ala Val Leu Leu His Gly Cys Pro Thr
        275                 280                 285

Val Thr Lys Met Pro Ala Tyr Ile Ile Lys Met Pro Val Phe Asn Gly
    290                 295                 300

Gly Glu Asp Glu Glu Arg Cys Ser Val Glu Glu Val Thr Arg Arg
305                 310                 315                 320

Ile Gly Gly Arg Asp Gly Phe Cys Ala Glu Val Lys Asn Gly Asp Glu
                325                 330                 335

Lys Asp Gly Thr Pro Val Gln Leu Ser Ser Cys Gly Glu Gln Ser Asn
            340                 345                 350

Gln Gln Trp Thr Phe Ser Thr Asp Gly Thr Ile Gln Ser Leu Gly Lys
        355                 360                 365

Cys Leu Thr Thr Ser Ser Val Met Ile Tyr Asn Cys Lys Val Val
370                 375                 380

Pro Pro Glu Ser Thr Lys Trp Val Val Ser Ile Asp Gly Thr Ile Thr
385                 390                 395                 400

Asn Pro Arg Ser Gly Leu Val Leu Thr Ala Pro Lys Ala Ala Glu Gly
                405                 410                 415

Thr Leu Val Ser Leu Glu Lys Asn Val His Ala Ala Arg Gln Gly Trp
            420                 425                 430

Ile Val Gly Asn Val Glu Pro Leu Val Thr Phe Ile Val Gly Tyr Glu
        435                 440                 445

Gln Met Cys Leu Glu Thr Asn Pro Gly Asn Asn Asp Val Ser Leu Gly
    450                 455                 460

Asp Cys Ser Val Lys Ser Ala Ser Lys Val Asp Gln Lys Trp Ala Leu
465                 470                 475                 480

Tyr Gly Asp Gly Thr Ile Arg Val Asn Asn Asp Arg Ser Leu Cys Val
                485                 490                 495

Thr Ser Glu Gly Lys Ser Ser Asn Glu Pro Ile Ile Ile Leu Lys Cys
            500                 505                 510

Leu Gly Trp Ala Asn Gln Arg Trp Val Phe Asn Thr Asp Gly Thr Ile
        515                 520                 525

Ser Asn Pro Asp Ser Lys Leu Val Met His Val Asp Gln Asn Asp Val
    530                 535                 540

Pro Leu Arg Lys Ile Ile Leu Ser His Pro Ser Gly Thr Ser Asn Gln
545                 550                 555                 560

Gln Trp Ile Ala Ser Thr His Pro Ala
                565

<210> SEQ ID NO 53
<211> LENGTH: 286
<212> TYPE: PRT
<213> ORGANISM: Artificial sequence
<220> FEATURE:
<223> OTHER INFORMATION: Influenza virus

<400> SEQUENCE: 53

-continued

Met Ser Phe Gln Gly His Gly Ile Tyr Tyr Ile Ala Ser Ala Tyr Val
1               5                   10                  15

Ala Asn Thr Arg Leu Ala Leu Ser Glu Asp Ser Ser Ala Asn Lys Ser
            20                  25                  30

Pro Asp Val Ile Ile Ser Ser Asp Ala Val Asp Pro Leu Asn Asn Leu
        35                  40                  45

Trp Leu Ile Glu Pro Val Gly Glu Ala Asp Thr Tyr Thr Val Arg Asn
    50                  55                  60

Ala Phe Ala Gly Ser Tyr Met Asp Leu Ala Gly His Ala Ala Thr Asp
65                  70                  75                  80

Gly Thr Ala Ile Ile Gly Tyr Arg Pro Thr Gly Asp Asn Gln Lys
                85                  90                  95

Trp Ile Ile Ser Gln Ile Asn Asp Val Trp Lys Ile Lys Ser Lys Glu
            100                 105                 110

Thr Gly Thr Phe Val Thr Leu Leu Asn Gly Asp Gly Gly Thr Gly
            115                 120                 125

Thr Val Val Gly Trp Gln Asn Ile Thr Asn Asn Thr Ser Gln Asn Trp
    130                 135                 140

Thr Phe Gln Lys Leu Ser Gln Thr Gly Ala Asn Val His Ala Thr Leu
145                 150                 155                 160

Leu Ala Cys Pro Ala Leu Arg Gln Asp Phe Lys Ser Tyr Leu Ser Asp
                165                 170                 175

Gly Leu Tyr Leu Val Leu Thr Arg Asp Gln Ile Ser Ser Ile Trp Gln
            180                 185                 190

Ala Ser Gly Leu Gly Ser Thr Pro Trp Arg Ser Glu Ile Phe Asp Cys
            195                 200                 205

Asp Asp Phe Ala Thr Val Phe Lys Gly Ala Val Ala Lys Trp Gly Asn
    210                 215                 220

Glu Asn Phe Lys Ala Asn Gly Phe Ala Leu Leu Cys Gly Leu Met Phe
225                 230                 235                 240

Gly Ser Lys Ser Ser Gly Ala His Ala Tyr Asn Trp Phe Val Glu Arg
                245                 250                 255

Gly Asn Phe Ser Thr Val Thr Phe Phe Glu Pro Gln Asn Gly Thr Tyr
            260                 265                 270

Ser Ala Asn Ala Trp Asp Tyr Lys Ala Tyr Phe Gly Leu Phe
            275                 280                 285

<210> SEQ ID NO 54
<211> LENGTH: 292
<212> TYPE: PRT
<213> ORGANISM: Artificial sequence
<220> FEATURE:
<223> OTHER INFORMATION: Influenza virus

<400> SEQUENCE: 54

Met Ser Phe Glu Gly His Gly Ile Tyr His Ile Pro His Ala His Val
1               5                   10                  15

Ala Asn Ile Arg Met Ala Leu Ala Asn Arg Gly Ser Gly Gln Asn Gly
            20                  25                  30

Thr Pro Val Ile Ala Trp Asp Ser Asn Asn Asp Ala Phe Asp His Met
        35                  40                  45

Trp Leu Val Glu Pro Thr Gly Glu Ala Asp Thr Tyr Thr Ile His Asn
    50                  55                  60

Val Ser Thr Gly Thr Tyr Met Asp Val Thr Ala Ser Ala Val Ala Asp
65                  70                  75                  80

```
Asn Thr Pro Ile Ile Gly Tyr Gln Arg Thr Gly Asn Asp Asn Gln Lys
                85                  90                  95

Trp Ile Ile Arg Gln Val Gln Thr Asp Gly Gly Asp Arg Pro Trp Lys
            100                 105                 110

Ile Gln Cys Lys Ala Thr Gly Thr Phe Ala Thr Leu Tyr Ser Gly Gly
        115                 120                 125

Gly Ser Gly Thr Ala Ile Val Gly Trp Arg Leu Val Asn Ser Asn Gly
    130                 135                 140

Asn Gln Asp Trp Val Phe Gln Lys Leu Ser Gln Thr Ser Val Asn Val
145                 150                 155                 160

His Ala Thr Leu Leu Ala Cys Gly Ala Thr Val Gly Gln Asp Phe Lys
                165                 170                 175

Asn Tyr Leu Tyr Asp Gly Leu Tyr Leu Val Leu Pro Arg Asp Arg Ile
            180                 185                 190

Ser Ala Ile Trp Lys Ala Ser Gly Leu Gly Glu Thr Ala Arg Arg Asp
        195                 200                 205

Gly Ile Tyr Asp Ser Asp Glu Phe Ala Met Thr Phe Lys Ser Ala Ala
    210                 215                 220

Ala Thr Trp Gly Lys Glu Asn Phe Lys Ala Asp Gly Phe Ala Ile Leu
225                 230                 235                 240

Cys Gly Met Met Phe Gly Thr Lys Ala Ser Thr Asn Arg His Ala Tyr
                245                 250                 255

Asn Trp Val Val Glu Arg Gly Ser Phe Ser Thr Val Thr Phe Phe Glu
            260                 265                 270

Pro Gln Asn Gly Thr Tyr Ser Asp Asp Ala Trp Gly Tyr Lys Ala Tyr
        275                 280                 285

Phe Gly Leu Phe
    290

<210> SEQ ID NO 55
<211> LENGTH: 326
<212> TYPE: PRT
<213> ORGANISM: Artificial sequence
<220> FEATURE:
<223> OTHER INFORMATION: Influenza virus

<400> SEQUENCE: 55

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
    50                  55                  60

Pro Glu Cys Glu Leu Leu Ile Ser Lys Glu Ser Trp Ser Tyr Ile Val
65                  70                  75                  80

Glu Lys Pro Asn Pro Glu Asn Gly Thr Cys Tyr Pro Gly His Phe Ala
                85                  90                  95

Glu Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Glu Ser Ser Phe Tyr
    130                 135                 140
```

```
Arg Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
                165                 170                 175

Gly Val His His Pro Pro Asn Ile Ala Ala Gln Lys Thr Leu Tyr His
            180                 185                 190

Thr Glu Asn Ala Tyr Val Ser Val Ser Ser His Tyr Ser Arg Lys
        195                 200                 205

Phe Thr Pro Glu Ile Ala Lys Arg Pro Lys Val Arg Asp Gln Glu Gly
210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Arg Tyr Ala Phe Ala Leu
                245                 250                 255

Ser Arg Gly Phe Gly Ser Gly Ile Ile Asn Ser Asn Ala Pro Met Asp
            260                 265                 270

Lys Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
        290                 295                 300

Tyr Val Arg Ser Ala Lys Leu Arg Met Val Thr Gly Leu Arg Asn Ile
305                 310                 315                 320

Pro Ser Ile Gln Ser Arg
            325

<210> SEQ ID NO 56
<211> LENGTH: 326
<212> TYPE: PRT
<213> ORGANISM: Artificial sequence
<220> FEATURE:
<223> OTHER INFORMATION: Influenza virus

<400> SEQUENCE: 56

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asn Ser His Asn Gly Lys Leu Cys Leu Leu Lys Gly Ile Ala
            35                  40                  45

Pro Leu Gln Leu Gly Asn Cys Ser Val Ala Gly Trp Ile Leu Gly Asn
        50                  55                  60

Pro Glu Cys Glu Leu Leu Ile Ser Lys Glu Ser Trp Ser Tyr Ile Val
65                  70                  75                  80

Glu Lys Pro Asn Pro Glu Asn Gly Thr Cys Tyr Pro Gly His Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Glu Asn Ser Phe Tyr
    130                 135                 140

Arg Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
                165                 170                 175
```

```
Gly Val His His Pro Pro Asn Ile Ala Asp Gln Lys Ala Leu Tyr His
                180                 185                 190

Thr Glu Asn Ala Tyr Val Ser Val Ser Ser His Tyr Ser Arg Lys
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Arg Tyr Ala Phe Ala Leu
                245                 250                 255

Ser Arg Gly Phe Gly Ser Gly Ile Ile Asn Ser Asn Ala Pro Met Asp
                260                 265                 270

Lys Cys Asp Ala Lys Cys Gln Thr Pro Gln Gly Ala Ile Asn Ser Ser
                275                 280                 285

Leu Pro Phe Gln Asn Val His Pro Val Thr Ile Gly Glu Cys Pro Lys
                290                 295                 300

Tyr Val Arg Ser Ala Lys Leu Arg Met Val Thr Gly Leu Arg Asn Ile
305                 310                 315                 320

Pro Ser Ile Gln Ser Arg
                325

<210> SEQ ID NO 57
<211> LENGTH: 326
<212> TYPE: PRT
<213> ORGANISM: Artificial sequence
<220> FEATURE:
<223> OTHER INFORMATION: Influenza virus

<400> SEQUENCE: 57

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asn Ser His Asn Gly Lys Leu Cys Leu Leu Lys Gly Ile Ala
                35                  40                  45

Pro Leu Gln Leu Gly Asn Cys Ser Val Ala Gly Trp Ile Leu Gly Asn
    50                  55                  60

Pro Glu Cys Glu Leu Leu Ile Ser Lys Glu Ser Trp Ser Tyr Ile Val
65                  70                  75                  80

Glu Lys Pro Asn Pro Glu Asn Gly Thr Cys Tyr Pro Gly His Phe Ala
                85                  90                  95

Asp Tyr Glu Glu Leu Arg Glu Gln Leu Ser Ser Val Ser Ser Phe Glu
                100                 105                 110

Arg Phe Glu Ile Phe Pro Lys Glu Ser Ser Trp Pro Asn His Thr Val
            115                 120                 125

Thr Gly Val Ser Ala Ser Cys Ser His Asn Gly Glu Asn Ser Phe Tyr
    130                 135                 140

Arg Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
                165                 170                 175

Gly Val His His Pro Pro Asn Ile Ala Asp Gln Lys Thr Leu Tyr His
                180                 185                 190

Thr Glu Asn Ala Tyr Val Ser Val Val Ser Ser His Tyr Ser Arg Lys
        195                 200                 205
```

```
Phe Thr Pro Glu Ile Ala Lys Arg Pro Lys Val Arg Asp Gln Glu Gly
            210                 215                 220

Arg Ile Asn Tyr Tyr Trp Pro Leu Leu Glu Pro Gly Asp Thr Ile Ile
225                 230                 235                 240

Phe Glu Ala Asn Gly Asn Leu Ile Ala Pro Arg Tyr Ala Phe Ala Leu
            245                 250                 255

Ser Arg Gly Phe Gly Ser Gly Ile Ile Asn Ser Asn Ala Pro Met Asp
            260                 265                 270

Lys Cys Asp Ala Lys Cys Gln Thr Pro Gln Gly Ala Ile Asn Ser Ser
            275                 280                 285

Leu Pro Phe Gln Asn Val His Pro Val Thr Ile Gly Glu Cys Pro Lys
            290                 295                 300

Tyr Val Arg Ser Ala Lys Leu Arg Met Val Thr Gly Leu Arg Asn Ile
305                 310                 315                 320

Pro Ser Ile Gln Ser Arg
                325

<210> SEQ ID NO 58
<211> LENGTH: 326
<212> TYPE: PRT
<213> ORGANISM: Artificial sequence
<220> FEATURE:
<223> OTHER INFORMATION: Influenza virus

<400> SEQUENCE: 58

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Ser His Asn Gly Lys Leu Cys Leu Leu Lys Gly Ile Ala
            35                  40                  45

Pro Leu Gln Leu Gly Asn Cys Ser Val Ala Gly Trp Ile Leu Gly Asn
            50                  55                  60

Pro Glu Cys Glu Leu Leu Ile Ser Lys Glu Ser Trp Ser Tyr Ile Val
65                  70                  75                  80

Glu Lys Pro Asn Pro Glu Asn Gly Thr Cys Tyr Pro Gly His Phe Ala
            85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
            115                 120                 125

Thr Gly Val Ser Ala Ser Cys Ser His Asn Gly Glu Ser Ser Phe Tyr
130                 135                 140

Arg Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
            165                 170                 175

Gly Val His His Pro Asn Ile Gly Asp Gln Lys Ala Leu Tyr His
            180                 185                 190

Thr Glu Asn Ala Tyr Val Ser Val Ser Ser His Tyr Ser Arg Lys
            195                 200                 205

Phe Thr Pro Glu Ile Ala Lys Arg Pro Lys Val Arg Asp Gln Glu Gly
            210                 215                 220

Arg Ile Asn Tyr Tyr Trp Thr Leu Leu Glu Pro Gly Asp Thr Ile Ile
225                 230                 235                 240
```

-continued

```
Phe Glu Ala Asn Gly Asn Leu Ile Ala Pro Arg Tyr Ala Phe Ala Leu
                245                 250                 255

Ser Arg Gly Phe Gly Ser Gly Ile Ile Asn Ser Asn Ala Pro Met Asp
            260                 265                 270

Lys Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg
                325

<210> SEQ ID NO 59
<211> LENGTH: 500
<212> TYPE: PRT
<213> ORGANISM: Artificial sequence
<220> FEATURE:
<223> OTHER INFORMATION: Influenza virus
<220> FEATURE:
<221> NAME/KEY: MISC_FEATURE
<222> LOCATION: (203)..(203)
<223> OTHER INFORMATION: X = amy amino acid

<400> SEQUENCE: 59

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Val Xaa Gln Lys Thr Leu Tyr
        195                 200                 205

Arg Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
```

```
                245                 250                 255
Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr
            500

<210> SEQ ID NO 60
<211> LENGTH: 565
<212> TYPE: PRT
<213> ORGANISM: Artificial sequence
<220> FEATURE:
<223> OTHER INFORMATION: Influenza virus

<400> SEQUENCE: 60

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
```

```
                100                 105                 110
Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
            130                 135                 140

Val Thr Gly Val Ser Ala Ser Cys Ser His Asn Gly Lys Ser Ser Phe
145                 150                 155                 160

Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
            195                 200                 205

His Thr Glu Asn Ala Tyr Val Ser Val Val Ser Ser His Tyr Ser Arg
            210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
                260                 265                 270

Leu Ser Arg Gly Phe Gly Ser Gly Ile Ile Asn Ser Asn Ala Pro Met
            275                 280                 285

Asp Glu Cys Asp Ala Lys Cys Gln Thr Pro Gln Gly Ala Ile Asn Ser
            290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
            450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
            515                 520                 525
```

```
Ile Leu Ala Ile Tyr Ser Thr Val Ala Ser Ser Leu Val Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 61
<211> LENGTH: 565
<212> TYPE: PRT
<213> ORGANISM: Artificial sequence
<220> FEATURE:
<223> OTHER INFORMATION: Influenza virus

<400> SEQUENCE: 61

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Gly Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Met Ser Tyr Val Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320
```

```
Lys Tyr Val Arg Ser Ala Lys Leu Arg Met Val Thr Gly Leu Arg Asn
            325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 62
<211> LENGTH: 565
<212> TYPE: PRT
<213> ORGANISM: Artificial sequence
<220> FEATURE:
<223> OTHER INFORMATION: Influenza virus

<400> SEQUENCE: 62

Lys Ala Lys Leu Leu Val Leu Leu Cys Thr Phe Thr Ala Thr Tyr Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45

Leu Glu Asp Ser His Asn Gly Lys Leu Cys Arg Leu Lys Gly Thr Ala
    50                  55                  60

Pro Leu Gln Leu Gly Asn Cys Ser Ile Ala Gly Trp Ile Leu Gly Asn
65                  70                  75                  80

Pro Glu Cys Glu Ser Leu Phe Ser Lys Glu Ser Trp Ser Tyr Ile Ala
                85                  90                  95

Glu Thr Pro Asn Pro Lys Asn Gly Thr Cys Tyr Pro Gly Tyr Phe Ala
            100                 105                 110
```

```
Asp Tyr Glu Glu Leu Arg Glu Gln Leu Ser Ser Val Ser Ser Phe Glu
            115                 120                 125

Arg Phe Glu Ile Phe Pro Lys Asp Ser Ser Trp Pro Asn His Thr Val
130                 135                 140

Thr Lys Gly Val Thr Ala Ser Cys Ser His Asn Gly Lys Ser Ser Phe
145                 150                 155                 160

Tyr Lys Asn Leu Leu Trp Leu Thr Glu Lys Asn Gly Leu Tyr Pro Asn
                165                 170                 175

Leu Ser Lys Ser Tyr Val Asn Lys Lys Gly Lys Glu Val Leu Val Leu
            180                 185                 190

Trp Gly Val His His Pro Ser Asn Met Gly Asp Gln Arg Ala Ile Tyr
            195                 200                 205

His Lys Glu Asn Ala Tyr Val Ser Val Leu Ser Ser His Tyr Ser Arg
            210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Ile Ser Asn Ala Ser Met
            275                 280                 285

Gly Glu Cys Asp Ala Lys Cys Gln Thr Pro Gln Gly Ala Ile Asn Ser
            290                 295                 300

Ser Leu Pro Phe Gln Asn Val His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Val Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Ser Ile Ile Glu
385                 390                 395                 400

Lys Met Asn Thr Gln Phe Thr Ala Val Gly Lys Glu Phe Asn Arg Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asp Leu Tyr Glu Lys
450                 455                 460

Val Lys Thr Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Lys Glu Ser Lys Leu Asn
            500                 505                 510

Arg Glu Lys Ile Asp Gly Val Lys Leu Glu Ser Met Gly Val Tyr Gln
            515                 520                 525
```

```
Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 63
<211> LENGTH: 392
<212> TYPE: PRT
<213> ORGANISM: Artificial sequence
<220> FEATURE:
<223> OTHER INFORMATION: Influenza virus

<400> SEQUENCE: 63

Met Lys Ala Lys Leu Leu Val Leu Leu Cys Ala Phe Thr Ala Thr Tyr
1               5                   10                  15

Ala Asp Thr Ile Cys Ile Gly His His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Thr
50                  55                  60

Ala Pro Leu Gln Leu Gly Asn Cys Ser Val Ala Gly Trp Ile Leu Gly
65                  70                  75                  80

Asn Pro Glu Cys Glu Ser Leu Phe Ser Lys Glu Ser Trp Ser Tyr Ile
                85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Lys Gly Val Thr Ala Ser Cys Ser His Asn Gly Lys Ser Ser
145                 150                 155                 160

Phe Tyr Lys Asn Leu Leu Trp Leu Thr Gly Lys Asn Gly Leu Tyr Pro
                165                 170                 175

Asn Leu Ser Lys Ser Tyr Val Asn His Lys Glu Lys Glu Val Leu Val
            180                 185                 190

Leu Trp Gly Val His His Pro Ser Asn Ile Arg Asp Gln Arg Ala Ile
        195                 200                 205

Tyr His Thr Glu Asn Ala Tyr Val Ser Val Val Ser Ser His Tyr Ser
210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Gly Glu Cys Asp Ala Lys Cys Gln Thr Pro Gln Gly Ala Ile Asn
290                 295                 300

Ser Ser Leu Pro Phe Gln Asn Val His Pro Val Thr Ile Gly Glu Cys
305                 310                 315                 320
```

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
        370                 375                 380

Thr Gln Asn Ala Ile Asn Gly Ile
385                 390

<210> SEQ ID NO 64
<211> LENGTH: 325
<212> TYPE: PRT
<213> ORGANISM: Artificial sequence
<220> FEATURE:
<223> OTHER INFORMATION: Influenza virus

<400> SEQUENCE: 64

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
    50                  55                  60

Pro Glu Cys Glu Leu Leu Ile Ser Lys Glu Ser Trp Ser Tyr Ile Val
65                  70                  75                  80

Glu Thr Pro Asn Pro Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Lys Ser Ser Phe Tyr
    130                 135                 140

Arg Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
                165                 170                 175

Gly Val His His Pro Pro Asn Ile Gly Asp Gln Arg Ala Leu Tyr His
            180                 185                 190

Thr Glu Asn Ala Tyr Val Ser Val Val Ser Ser His Tyr Ser Arg Arg
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Arg Tyr Ala Phe Ala Leu
                245                 250                 255

Ser Arg Gly Phe Gly Ser Gly Ile Ile Thr Ser Asn Ala Pro Met Asp
            260                 265                 270

Glu Cys Asp Ala Lys Cys Gln Thr Pro Gln Gly Ala Ile Asn Ser Ser
        275                 280                 285

```
Leu Pro Phe Gln Asn Val His Pro Ile Thr Ile Gly Glu Cys Pro Lys
    290                 295                 300
Tyr Val Arg Ser Ala Lys Leu Arg Met Val Thr Gly Leu Arg Asn Ile
305                 310                 315                 320
Pro Ser Ile Gln Ser
                325
```